(12) United States Patent
Rosenfeld et al.

(10) Patent No.: US 7,454,359 B2
(45) Date of Patent: *Nov. 18, 2008

(54) SYSTEM AND METHOD FOR DISPLAYING A HEALTH STATUS OF HOSPITALIZED PATIENTS

(75) Inventors: Brian A. Rosenfeld, Baltimore, MD (US); Michael Breslow, Lutherville, MD (US)

(73) Assignee: VISICU, Inc., Baltimore, MD (US)

( * ) Notice: Subject to any disclaimer, the term of this patent is extended or adjusted under 35 U.S.C. 154(b) by 498 days.

This patent is subject to a terminal disclaimer.

(21) Appl. No.: 11/096,189

(22) Filed: Mar. 31, 2005

(65) Prior Publication Data

US 2005/0187796 A1 Aug. 25, 2005
US 2006/0161459 A9 Jul. 20, 2006

Related U.S. Application Data

(63) Continuation-in-part of application No. 10/946,548, filed on Sep. 21, 2004, now Pat. No. 7,256,708, and a continuation-in-part of application No. 10/654,668, filed on Sep. 4, 2003, which is a continuation of application No. 09/443,072, filed on Nov. 18, 1999, now Pat. No. 6,804,656.

(60) Provisional application No. 60/141,520, filed on Jun. 23, 1999.

(51) Int. Cl.
 *G06Q 10/00* (2006.01)
(52) U.S. Cl. ............................. 705/2; 705/3; 600/300
(58) Field of Classification Search ................ 705/2–3; 600/300
See application file for complete search history.

(56) References Cited

U.S. PATENT DOCUMENTS 3,646,606 A * 2/1972 Buxton et al. ............... 600/483
4,365,199 A 12/1982 McNair (Continued)

FOREIGN PATENT DOCUMENTS

WO      WO 98/29790      7/1998

(Continued)

OTHER PUBLICATIONS

Terry Ann Capuano et al. Remote Telemetry, Jul. 1995, Nursing Management, vol. 26, No. 7, p. 26.*

(Continued)

*Primary Examiner*—Robert W Morgan
(74) *Attorney, Agent, or Firm*—Roberts Mardula & Wertheim LLC

(57) ABSTRACT

A system and method for displaying a health status of hospitalized patients. Patient data associated with hospitalized patients is selected according to display rules. A display module selects selected patient data, applies display rules to the selected patient data, and displays the selected patient data. A smart alert module generates and applies patient specific rules to other selected patient data elements. If a patient-specific rule for a hospitalized patient has been contravened, an alert is issued from the remote command center. Graphical attributes may be assigned to patients for whom an alert has been issued and to selected patient data elements that fall outside of an acceptable range. The graphical attributes determine how selected patient data appear on a display screen.

84 Claims, 67 Drawing Sheets

U.S. PATENT DOCUMENTS

| | | | |
|---|---|---|---|
| 4,489,387 | A | 12/1984 | Lamb et al. |
| 4,731,725 | A | 3/1988 | Suto et al. |
| 4,838,275 | A | 6/1989 | Lee |
| 4,852,570 | A | 8/1989 | Levine |
| 4,878,175 | A | 10/1989 | Norden-Paul et al. |
| 5,255,187 | A | 10/1993 | Sorensen |
| 5,321,800 | A | 6/1994 | Lesser |
| 5,348,008 | A | 9/1994 | Bornn et al. |
| 5,544,649 | A | 8/1996 | David et al. |
| 5,544,661 | A | 8/1996 | Davis et al. |
| 5,574,828 | A | 11/1996 | Hayward et al. |
| 5,576,952 | A | 11/1996 | Stutman et al. |
| 5,619,991 | A | 4/1997 | Sloane |
| 5,678,562 | A | 10/1997 | Sellers |
| 5,701,894 | A | 12/1997 | Cherry et al. |
| 5,715,449 | A | 2/1998 | Peters, Jr. et al. |
| 5,724,580 | A | 3/1998 | Levin et al. |
| 5,729,204 | A | 3/1998 | Fackler et al. |
| 5,772,585 | A | 6/1998 | Lavin |
| 5,812,983 | A | 9/1998 | Kumagai |
| 5,822,544 | A | 10/1998 | Chaco et al. |
| 5,823,948 | A | 10/1998 | Ross, Jr. et al. |
| 5,832,450 | A | 11/1998 | Myers et al. |
| 5,839,438 | A | 11/1998 | Graettinger et al. |
| 5,842,978 | A | 12/1998 | Levy |
| 5,867,821 | A | 2/1999 | Ballantyne et al. |
| 5,868,669 | A | 2/1999 | Iliff |
| 5,899,855 | A | 5/1999 | Brown |
| 5,942,986 | A | 8/1999 | Shabot et al. |
| 5,987,519 | A | 11/1999 | Peifer et al. |
| 6,024,699 | A | 2/2000 | Surwit et al. |
| 6,093,146 | A | 7/2000 | Filangeri |
| 6,102,856 | A | 8/2000 | Groff et al. |
| 6,154,668 | A | 11/2000 | Pedersen et al. |
| 6,168,563 | B1 | 1/2001 | Brown |
| 6,215,403 | B1 | 4/2001 | Chan et al. |
| 6,225,901 | B1 | 5/2001 | Kail, IV |
| 6,230,142 | B1 | 5/2001 | Benigno et al. |
| 6,234,964 | B1 | 5/2001 | Iliff |
| 6,238,338 | B1 | 5/2001 | DeLuca et al. |
| 6,245,013 | B1 | 6/2001 | Minoz et al. |
| 6,254,536 | B1 | 7/2001 | DeVito |
| 6,278,999 | B1 | 8/2001 | Knapp |
| 6,292,698 | B1 | 9/2001 | Duffin et al. |
| 6,304,788 | B1 | 10/2001 | Eady et al. |
| 6,315,719 | B1 | 11/2001 | Rode et al. |
| 6,364,834 | B1 | 4/2002 | Reuss et al. |
| 6,385,589 | B1 | 5/2002 | Trusheim et al. |
| 6,398,728 | B1 | 6/2002 | Bardy |
| 6,442,433 | B1 | 8/2002 | Linberg |
| 6,533,724 | B2 | 3/2003 | McNair |
| 6,741,264 | B1 | 5/2004 | Lesser |
| 6,835,176 | B2 | 12/2004 | McNair |
| 6,893,396 | B2 | 5/2005 | Schulze et al. |
| 2002/0002473 | A1 | 1/2002 | Schrier et al. |
| 2002/0177758 | A1 | 11/2002 | Schoenberg et al. |
| 2002/0177759 | A1 | 11/2002 | Schoenberg et al. |
| 2002/0187483 | A1 | 12/2002 | Hoffman et al. |
| 2002/0193667 | A1 | 12/2002 | McNair |
| 2003/0036687 | A1 | 2/2003 | Schoenberg et al. |
| 2004/0030578 | A1 | 2/2004 | Cross et al. |
| 2004/0063031 | A1 | 4/2004 | Gallucci et al. |
| 2004/0078366 | A1 | 4/2004 | Crooks et al. |
| 2004/0193451 | A1 | 9/2004 | McNair |
| 2004/0197813 | A1 | 10/2004 | Hoffman et al. |
| 2004/0199333 | A1 | 10/2004 | Hoffman et al. |
| 2004/0225201 | A1 | 11/2004 | McNair |
| 2004/0236604 | A1 | 11/2004 | McNair |
| 2005/0027563 | A1 | 2/2005 | Fackler et al. |
| 2005/0049891 | A1 | 3/2005 | Wilson |
| 2005/0060191 | A1 | 3/2005 | Parkins et al. |
| 2005/0075794 | A1 | 4/2005 | Hoffman et al. |
| 2005/0075904 | A1 | 4/2005 | Wagner et al. |
| 2005/0076060 | A1 | 4/2005 | Finn et al. |
| 2005/0125098 | A1 | 6/2005 | Wang et al. |
| 2005/0125256 | A1 | 6/2005 | Schoenberg et al. |
| 2005/0206518 | A1 | 9/2005 | Welch et al. |
| 2005/0228241 | A1 | 10/2005 | McNair |
| 2005/0251418 | A1 | 11/2005 | Fox, Jr. et al. |
| 2005/0267351 | A1 | 12/2005 | Humphrey et al. |
| 2005/0283062 | A1 | 12/2005 | Hoffman et al. |
| 2006/0031018 | A1 | 2/2006 | Bush et al. |
| 2006/0036542 | A1 | 2/2006 | McNair |

FOREIGN PATENT DOCUMENTS

| | | |
|---|---|---|
| WO | WO 99/13766 | 3/1999 |
| WO | 00/79466 A2 | 12/2000 |

OTHER PUBLICATIONS

Cantrell, Mark. "Nurses Keep Watch from miles away or at the bedside." Nursing Spectrum, Jan. 2005 (4 pages).

Angus, D.C., et al. "Caring for the critically ill patient. Current and projected workforce requirements for care of the critically ill and patients with pulmonary disease: can we meet the requirements of an aging population?" (abstract) JAMA, Dec. 6, 2000; 284(21): 2762-70.

CELI, Leo Anthony, et al. "The eICU: It's Not Just Telemedicine." Crit. Care Med. 2001, vol. 29, No. 8 (Suppl.).

Hanson, C.W. 3rd, et al. "Effects of an organized critical care service on outcomes and resource utilization: a cohort study." (abstract) Crit. Care Med. Feb. 1999; 27(2):270-4.

Manthous, C.A., et al. "Effects of a medical intensivist on patient care in a community teaching hospital." (abstract) Mayo Clin. Proc. May 1997; 72(5):391-9.

Pronovost, P.J., et al. "Organizational characteristics of intensive care units related to outcomes of abdominal aortic surgery." (abstract) JAMA. Apr. 14, 1999; 281(14):1310-7.

Pronovost, Peter J., et al. "Physician Staffing Patterns and Clinical Outcomes in Critically Ill Patients: A Systematic Review." JAMA. Nov. 6, 2002; 288(17):2151-62.

"Remote Control." Modern Healthcare, Feb. 25, 2002 (4 pages).

Breslow, Michael J., et al. "Technology Strategies to Improve ICU Practice." Seminars in Anesthesia 24: 59-70, 2005.

Breslow, Michael J. "Remote ICU Care Programs: Current Status." J. Crit. Care: 22, 66-76, 2007.

Hetherington, Laurel Traynowicz; "High tech meets high touch: telemedicine's contribution to patient wellness"; Spring, 1998; Nursing Administration Quarterly, vol. 22, No. 3.

Tsien, Christine L., "TrendFinder: Automated Detection of Alarmable Trends", Department of Electrical Engineering and Computer Science, Massachusetts Institute of Technology, Massachusetts; Jun. 2000.

Hosseinzadeh, Abolfazl, "A Rule-Based System for Vital Sign Monitoring in Intensive Care", Department of Electrical Engineering, McGill University, Montreal; Nov. 1993.

Aukburg, S.J. et al., "Automation of Physiological Data Presentation and Alarms in the Post Anesthesia Care Unit." In Symposium on Computer Applications in Medical Care, Nov. 5-8, 1989, Washington, DC; pp. 580-582.

Benis, A. M. et al., "Improved Detection of Adverse Cardiovascular Trends with the Use of a Two-Variable Computer Alarm" *Critical Care Medicine*, vol. 8, No. 2, Jun. 1980: 341-344.

Bierman, M. l. et al., "Pulse Oximetry in the Postoperative Care of Cardiac Surgical Patients; A Randomized Controlled Trial." *Chest*, vol. 102, No. 5, Nov. 1992: 1367-1370.

Bradshaw, K. E., "Computerized Alerting System Warns of Life-Threatening Events." In Symposium on Computer Application in Medical Care, Oct. 25-26, 1986, Washington, DC; pp. 403-409.

Chizeck, H. J., "Modeling, Simulation and Control in a Data Rich Environment." In Symposium on Computer Applications in Medical Care, Oct. 25-26, 1986, Washington, DC; pp. 65-69.

Coiera, E., "Intelligent Monitoring and Control of Dynamic Physiological Systems." *Artificial Intelligence in Medicine*, vol. 5, 1993: pp. 1-8.

Colvin, J. R. et al., "Microcomputer-Controlled Administration of Vasodilators Following Cardiac Surgery: Technical Considerations." *J. Cardiothoracic Anesthesia*, vol. 3, No. 1, Feb. 1989: pp. 10-15.

Coplin, W. M. et al., "Accuracy of Continuous Jugular Bulb Oximetry in the Intensive Care Unit." Neurosurgery, vol. 42, No. 3, Mar. 1998: 533-540.

Crew, A. D. et al., "Preliminary Clinical Trials of a Computer-Based Cardiac Arrest Alarm." Intensive Care Med, vol. 17, 1991: 359-364.

Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Guedes de Oliveira, P. et al., "The Role of Computer Based Techniques in Patient Monitoring: Technical Note." *Acta Neuorchir*, vol. 55, 1992 (Suppl.): 18-20.

Hahnel, J. et al., "Can a Clinician Predict the Technical Equipment a Patient will Need During Intensive Care Unit Treatment? An Approach to Standardize and Redesign the Intensive Care Unit Workstation." J *Clinical Monitoring*, vol. 8, No. 1, Jan. 1992:1-6.

Hall, G. L. & P.B. Colditz, "Continuous Physiological Monitoring: An Integrated System for Use in Neonatal Intensive Care." *Australian Physical & Engineering Sciences in Medicine*, vol. 18, No. 3, 1995; 139-142.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Irazuzta, Jose, "Monitoring in Pediatric Intensive Care." *Indian J. Pediatrics*, vol. 60, 1993: 55-65.

Jans, R. et al., "A Low Cost ECG Central Station for Intensive Care." *Australian Physical &Engineering Sciences in Medicine*, vol. 13, No. 1, 1990: 31-35.

Jastremski, M. et al., "A Model for Technology Assessment as Applied to Closed Loop Infusion Systems" *Critical Care Medicine*, vol. 23, No. 10, Oct. 1995: 1745-1755.

Klass, M. A. & E. Y. Cheng, "Early Response to Pulse Oximetry Alarms with Telemetry." *J. Monitoring*, vol. 10, No. 3, May 1994: 178-180.

Koski, E. M. J. et al., "A Knowledge-Based Alarm System for Monitoring Cardiac Operated Patients—Assessment of Clinical Performance." *International J Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International J. Clinical Monitoring and Computing*, vol. 8, 1992: 289-293.

Laffel, G. et al., "Using Control Charts to Analyze Serial Patient-Related Data." *Quality Management in Health Care*, vol. 3, No. 1, Fall 1994: 70-77.

L'Estrange, P. R. et al., "A Microcomputer System for Physiological Data Collection and Analysis." *Australian Dental Journal*, vol. 3 8, No. 5, Oct. 1993: 400-405.

M. de Beer, N. A. et al., "Clinical Evaluation of a Method for Automatic Detection and Removal of Artifacts in Auditory Evoked Potential Monitoring." J *Clinical Monitoring*, vol. 11, No. 6, Nov. 1995: 381-391.

Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.

Makivirta, A. & E. M. J. Koski, "Alarm-Inducing Variability in Cardiac Postoperative Data and the Effects of Prealarm Delay." Critical Care Medicine, vol. 8, No. 6, May 1994: 153-162.

Martin, J. F., "Closed-Loop Control of Arterial Pressure During Cardiac Surgery." J. *Clinical Monitoring*, vol. 8, No. 3, Jul. 1992: 252-253.

Meyer, C., "Visions of Tomorrow's ICU." *American J. Nursing*, Apr. 1993: 27-31.

Nenov, V. I. et al., "Computer Applications in the Intensive Care Unit." *Neurosurgery Clinics of North America*, vol. 5, No. 4, Oct. 1994: 811-827.

Nobel, J. J., "Physiologic Monitoring Systems, Acute Care." *Pediatric Emergency Care*, vol. 8, No. 4, Aug. 1992: 235-237.

Orr, J. A. & Westenskow, D. R., "A Breathing Circuit Alarm System Based on Neural Networks." *J. Clinical Monitoring*, vol. 10, No. 2, Mar. 1994: 101-109.

Pappert, D. et al., "Preliminary Evaluation of a New Continuous Intra-Arterial Blood Gas Monitoring Device." *Acta Anaesthesiologica Scandinavica*, Suppl. 107, vol. 39, 1995: 67-70.

Rampil, I. J., "Intelligent Detection of Artifact." *The Automated Anesthesia Record and Alarm Systems*, Chapter 17, 1987: 175-190.

Runciman, W. B. et al., "The Pulse Oximeter: Applications and Limitations—An Analysis of 2000 Incident Reports." *Anaesthesia and Intensive Care*, vol. 2 1, No. 5, Oct. 1993: 543-550.

Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.

Sanklecha, M., "The Pulse Oximeter." *Indian J. Pediatrics*, vol. 60, No. 3, 1993: 469-470.

Schnapp, L. M. & N. J. Cohen, "Pulse Oximetry; Uses and Abuses." *Chest*, vol. 98, No. 5, Nov. 1990: 1244-1250.

Simpson, R. L., "Automating the ICU: Facing the Realities." *Nursing Management*, vol. 23, No. 3, Mar. 1992: 24-26.

Sittig, D. F. & M. Factor, "Physiological Trend Detection and Artifact Rejection: A Parallel Implementation of a Multi-State Kalman Filtering Algorithm." In Symposium on Computer Applications in Medical Care, Nov. 5-8, 1989, Washington, DC; pp. 569-574.

Stoodley, K. D. C. et al., "Problems in the Development of a Computerized Ward Monitoring System for a Pediatric Intensive Care Unit." *International J Clinical Monitoring and Computing*, vol. 8, 1992: 281-287.

Sukavaara, T. et al., "A Knowledge-based Alarm System for Monitoring Cardiac Operated Patients—Technical Construction and Evaluation." *International J. Clinical Monitoring and Computing*, vol. 10, 1993: 117-126.

Szaflarski, N. L., "Emerging Technology in Critical Care: Continuous Intra-Arterial Blood Gas Monitoring." *American J. Critical Care*, vol. 5, No. 1, Jan. 1996: 55-65.

Uckun, S., "Intelligent Systems in Patient Monitoring and Therapy Management." *International J. Clinical Monitoring and Computing*, vol. 11, 1994: 241-253.

Webb, R. K., "Medical Decision Making and Decision Analysis." *Anesthesia and Intensive Care*, vol. 16, No. 1, Feb. 1988: 107-109.

Yien, H. et al., "Spectral Analysis of Systemic Arterial Pressure and Heart Rate Signals as a Prognostic Tool for the Prediction of Patient Outcome in the Intensive Care Unit." *Critical Care Medicine*, vol. 25, No. 2, 1997: 258-266.

Tsien, Christine L. and James Fackler, "Poor Prognosis for Existing Monitors in the Intensive Care Unit" *Critical Care Medicine*, vol. 25, No. 4, 1997: 614-619.

Tsien, Christine L.. "Reducing False Alarms in the Intensive Care Unit: A Systematic Comparison of Four Algorithms" Proceedings *AMIA* Symposium, 1997. pp. 9-14 (unnumbered).

Tsien, Christine L. "Reducing False Alarms in the Intensive Care Unit: A Systematic Comparison of Four Algorithms" Proceedings Annual *AMIA* Fall Symposium (1997), p. 894.

Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R. Cohen, and M. R. Berthold, Eds.; Springer-Verlag, London, UK; pp. 111-121.

Zhao, Ruilin, "A Model-Based Expert System for Interpretation of Hemodynamic Data from ICU Patients." Department of Electrical Engineering and Computer Science, Massachusetts Institute of Technology; May 18, 1997 (pp. 1-121).

Editors: M. Michael Shabot and Reed M. Gardner, Computers and Medicine: Decision Support Systems in Critical Care, 1994, Springer-Verlag New York, Inc. New York.

Gilad J. Kuperman, M.D. and Reed M. Gardner, Ph.D, The Help System: A Snapshot in Time, 1988, Dept. of Biophysics, LDS Hospital, Salt Lake City, Utah.

Project Leaders: Benoit Dawant, Ph.D. and John A. Morris, Jr. M.D., Vanderbilt University Simon Project Website, 2004, Vanderbilt University, Nashville, Tennessee.

Greg Borzo, Web Technology: Coming Soon to a Hospital Near You, American Medical News, Nov. 18, 1996, American Medical Association www.amednews.com.

Abstract: J.E. Gray, C. Safran, R.B. Davis, G. Pomilio-Weitzner, J.E. Stewart, L. Zaccagnini and D. Pursley, Baby Care Link: Using the Internet and Telemedicine to Improve Care for High-risk Infants, Dec. 2000, Pediatrics, vol. 106, No. 6, pp. 1318-1324.

Abstract: Ray Duncan and Jeffrey J. Pomerance, Computer Assistance in Delivery of Patient Care in a Neonatal Intensive Care Unit, The Use of Computers in Perinatal Medicine, Chapter 19, pp. 337-351, 1982, Praeger Publishers, New York, NY.

Abstract: Ray Duncan, MD, Computer Assisted Care in the Neonatal Intensive Care Unit, Proceedings of the 17th Annual Symposium on Computer Applications in Medical Care, Nov. 1993, p. 929, American Medical Informatics Association.

Abstract: Metnitz PG, Laback P. Popow C, Laback 0, Lenz K, Hiesmayr M, Computer assisted data analysis in intensive care: the ICDEV project—development of a scientific database system for intensive care (Intensive Care Data Evaluation Project), International Journal of Clinical Monitoring and Computing, 1995, vol. 12, No. 3, pp. 147-159.

Abstract: Paul H. Peristein, MD, Neil K. Edwards, MS, Harry D. Atherton, MS, James M. Sutherland, MD, Computer Assisted Newborn Intensive Care, Pediatrics, Apr. 1976, vol. 57, No. 4, pp. 494-501.

Abstract: Edward H. Shortliffe, MD, PHD, Computer Programs to Support Clinical Decision Making, Jama, Jul. 3, 1987, vol. 258, No. 1, pp. 61-66.

Abstract: Merz U, Peschgens t, Budde r, Kretzschmann F, Homchen H V, Computer-assisted monitoring in the neonatal intensive care unit [German], Klin Padiatr, Nov./Dec. 1995, vol. 207, No. 6, pp. 331-333.

Abstract: Charles Safran, MD, Francois Herrman, MD, David Rind, MD, Hollis B. Kowaloff, BA, Howard L. Bleich, MD, and Warner V. Slack, MD, Computer-Based Support for Clinical Decision Making, M.D. Computing, 1990, vol. 7, No. 5, pp. 319-322.

Abstract: Reed M. Gardner, PHD, Computerized Management of Intensive Care Patients, M.D. Computing, 1986, vol. 3, No. 1, pp. 36-51.

Abstract: F. John Lewis; Steven Deller; Michael Quinn; Benjamin Lee; Raymond Will; and John Raines, Continuous Patient Monitoring with a Small Digital Computer, Computers and Biomedical Research, 1972, vol. 5, pp. 411-428.

Abstract: N. Fumai, C. Collet, M. Petroni, K. Roger, A. Lam, E. Saab, A.'S. Malowany, F. A. Carnevale, R. D. Gottesman, Database Design of an Intensive Care Unit Patient Data Management System, Proceedings of the Fourth Annual IEEE Symposium on Computer-Based Medical Systems, May 12, 1991, pp. 78-85, IEEE Computer Society Press, Los Alamitos, CA.

Abstract: George Hripcsak; Paul D. Clayton; Robert A. Jenders; James J. Cimino; and Stephen B. Johnson, Design of a Clinical Event Monitor, Computers and Biomedical Research, Jun. 1996, vol. 29, No. 3, pp. 194-221.

Abstract: David M. Rind, MD; Roger Davis, SCD; and Charles Safran, MD, Designing Studies of Computer-Based Alerts and Reminders, MD Computing, 1995, vol. 12, No. 2, pp. 122-126.

Abstract: Dwayne R. Westenkow, PHD, Automating Patient Care with Closed-Loop Control, M.D. Computing, 1986, vol. 3, No. 2, pp. 14-20.

Abstract: Snowden S, Brownlee KG, Dear P R, An expert system to assist neonatal intensive care, I Med Eng Technol Mar.-Apr. 1997;21(2):67-73, vol. 21, No. 2, pp. 67-73.

Abstract: A. Aifredo Morales, Engr., MS, James Gray, MD, MS, Charles Safran, MD, An Application Server Approach for Integration of Clinical Systems, Proceedings of the AMIA 1999 Annual Symposium, 1999, AMIA.

Abstract: Kang Wang, PHD; Isaac Kohane, MD, PHD; Karen L. Bradshaw, BS; James Facider, MD, A Real Time Patient Monitoring System on the World Wide Web, Proceedings of the 1996 AMIA Annual Fall Symposium, Nov. 1996, pp. 729-732, Hanley and Belfus, Inc.

Abstract: Michael Factor, David H. Gelernter, Craig E. Kolb, Perry L. Miller and Dean F. Sittig, Real-Time Data Fusion in the Intensive Care Unit, IEEE Computer, Nov. 1991, pp. 45-53.

Editor: Judy G. Ozbolt, Ph.D., A Conference of the American Medical Informatics Association, Symposium on Computer Applications in Medical Care, Nov. 5-9, 1994, Hanley & Belfus, Inc. Medical Publishers, Philadelphia, PA.

W. Hsueh-Fen Young, Reed M. Gardner, Thomas D. East and Kristi Turner, Computerized Ventilator Data Selection: Artifact Rejection and Data Reduction, Int'l Journal of Clinical Monitoring and Computing 1997, 14: 165-176, Kluwer Academic Publishers, Netherlands.

Randolph A. Miller, M.D. and Reed M. Gardner, Ph.D., Summary Recommendations for Responsible Monitoring and Regulation of Clinical Software Systems, Annals of Internal Medicine, Nov. 1997, vol. 127, No. 9.

Reed M. Gardner, T. Allan Pryor and Homer R. Warner, The HELP Hospital Information System: Update 1998, Intl Journal of Medical Informatics 1999, vol. 54, pp. 169-182, Elsevier Science Ireland Ltd., Ireland.

Martin Spikoff, Systems Aid Rural Health Delivery, QIPhysician. com, Sep. 2003.

Abstract: Jerome P. Kassirer, MD, The Next Transformation in the Delivery of Health Care (Editorial), NEJM, Jan. 5, 1995, vol. 332, No. 1, pp. 52-54.

Abstract: Lorene S. Avila; M. Michael Shabot, Keys to the successful implementation of an ICU patient data management system, International Journal of Clinical Monitoring and Computing, 1988, vol. 5, pp. 15-25.

Abstract: Reed M. Gardner, MD; M. Michael Shabot, MD, Computerized ICU Data Management: Pitfalls and Promises, International Journal of Clinical Monitoring and Computing, 1990, vol. 7, pp. 99-105.

Karl W. Thomas, M.D., Charles S. Dayton, B.S., R.Ph., and Michael W. Peterson, M.D., Evolution of Internet-Based Clinical Decision Support Systems, Journal of Medical Internet Research 1999, vol. 1, University of Iowa, Iowa City, Iowa.

Abstract: C. J. McDonald, Protocol-Based Computer Reminders, The Quality of Care and The Non-Perfectability of Man, The New England Journal of Medicine, Dec. 9, 1976, vol. 295, No. 24, 1351-1355.

Abstract: T.D. East, A.H. Morris, C.J. Wallace, T.P. Clemmer, J.F. Orme, Jr., L.K. Weaver, S. Henderson and D.F. Sittig, A Strategy for Development of Computerized Critical Decision Support Systems, Intl Journal of Clinical Monitoring and Computing, 1991-92, vol. 8, No. 4, 263-269.

Dr. Ramana Reddy and Dr. V. "Juggy" Jagannathan, Secure Collaboration Technology for Rural Clinical Telemedicine, National Library of Medicine, Oct. 8, 1996 Press Release, West Virginia University, West Virginia.

West Virginia University Research Corporation, Secure Collaboration Technology for Rural Clinical Telemedicine: Final Report, National Library of Medicine.

Martin J. Tobin, M.D., Principles and Practice of Intensive Care Monitoring, 1998, McGraw-Hill Inc.

Peter J. Haug, Reed M. Gardner, and R. Scott Evans, "Hospital-Based Decision Support" in *Clinical Decision Support Systems: Theory and Practice*, ETA S. Berner [ed.], 1999, Springer-Verlag New York, Inc., New York, NY, pp. 77-103.

Clement J. McDonald, M.D. and William M. Tierney, M.D., Computer-Stored Medical Records: Their Future Role in Medical Practice, JAMA, Jun. 17, 1988, pp. 3433-3440, vol. 259, No. 23.

Gilad J. Kuperman, Reed M. Gardner, and T. Allan Pryor, Help: A Dynamic Hospital Information System, 1991, Springer-Verlag New York, Inc., New York, NY.

M. Michael Shabot, M.D., Mark Lobue, B.S., and Jeannie Chen, Pharm.D., Wireless Clinical Alerts for Physiologic, Laboratory and Medication Data, Department of Enterprise Information Services, Surgery and Pharmacy Cedars-Sinai Health System, Los Angeles, CA.

Chaoxin Sima, Ravi Raman, Ramana Reddy, William Hunt and Sumitra Reddy, Vital Signs Services for Secure Telemedicine Applications, Concurrent Engineering Research Center, West Virginia University, Morgantown, WV.

Dickey Seidlitz Johnson, Jane Ranzenberger, Ruth D. Herbert, Reed M. Gardner, and Terry P. Clemmer, A Computerized Alert Program for Acutely Ill Patients, Journal of Nursing Administration, Jun. 1980, pp. 26-35.

Reed M. Gardner, Ph.D., Blair J. West, M.S., T. Allan Pryor, Ph.D., Keith G Larsen, R.Ph., Homer R Warner, M.D., Terry P Clemmer, M.D., James F. Orme, Jr. M.D., Computer-Based ICU Data Acquisition as an Aid to Clinical Decision-Making, Critical Care Medicine, 1982, pp. 823-830, vol. 10, No. 12, The Williams & Wilkins Co.

Reed M. Gardner and Terry P. Clemmer, Computerized Protocols Applied to Acute Patient Care, 1977, Mediad Inc., Tarrytown, NY.

Karen E. Bradshaw, Reed M. Gardner, and T. Allan Pryor, Development of a Computerized Laboratory Alerting System, Computers and Biomedical Research 22, 575-587, 1989, Academic Press, Inc.

Terry P. Clemmer and Reed M. Gardner, Medical Informatics in the Intensive Care Unit: State of the Art 1991, International Journal of Clinical Monitoring and Computing 8: 237-250, 1992, Kluwer Academic Publishers, Netherlands.

Reed M. Gardner, Ph.D., David V. Ostler, and O. Hank Duffy, M.D., Computers in the Emergency Room, Internal Medicine for the Specialist, vol. 8, No. 3, Mar. 1987.

Dean F. Sittig, Nathan L. Pace, Reed M. Gardner, Eduardo Beck, and Alan H. Morris, Implementation of a Computerized Patient Advice System Using the HELP Clinical Information System, Computers and Biomedical Research 22, 474-487, 1989, Academic Press Inc.

P. D. Clayton, R. Scott Evans, T. Pryor, R. M. Gardner, P. J. Haug, O. B. Wigertz, and H. R. Warner, Bringing HELP to the Clinical Laboratory—Use of an Expert System to Provide Automatic Interpretation of Laboratory Data, Ann Clin Biochem 1987; 24: Supplement.

D. F. Sittig, Ph.D., R. M. Gardner, Ph.D., N. L. Pace, M.D., M. Bombino, M. D., and A. H. Morris, M.D., Compas: A Computerized Patient Advice System to Direct Ventilatory Care, Medical Informatics 88: Computers in Clinical Medicine, Sep. 13-15, 1988, British Medical Informatics Society, London.

Karen E. Bradshaw, Ph.D., Dean F. Sittig, Ph.D., Reed M. Gardner, Ph.D., T. Alllan Pryor, Ph.D., and Marge Budd, M.S., Improving Efficiency and Quality in a Computerized ICU, 1988 SCAMC, Inc.

Dean F. Sittig, Ph.D., C. Gregory Elliott, M.D., C. Jane Wallace, R.N., B.S.N., Polly Bailey, R.N., Reed M. Gardner, Ph.D., Computerized Screening for Identification of Adult Respiration Distress Syndrome (ARDS) Patients, 1988 SCAMC, Inc.

R. Scott Evans, Ph.D., Reed M. Gardner, Ph.D., John P. Burke, M.D., Stanley L. Pestotnik, R.P.H., Robert A. Larsen, M.D., David C. Classen, M.D., and Paul D. Clayton, Ph.D., A Computerized Approach to Monitor Prophylactic Antibiotics, 1987, SCAMC, Inc.

Susan Henderson, B.A., Thomas D. East, Ph.D., Alan H. Morris, M.D., Reed M. Gardner, Ph.D., Performance evaluation of computerized clinical protocols for management of arterial hypoxemia in ARDS patients, LDS Hospital, and University of Utah, Salt Lake City, UT.

Thomas D. East, Ph.D., Susan Henderson, B.A., Alan H. Morris, M.D., Reed M. Gardner, Ph.D., Implementation Issues and Challenges for Computerized Clinical Protocols for Management of Mechanical Ventilation in ARDS Patients, LDS Hospital, Salt Lake City, UT.

C. Gregory Elliott, M.D., Deon Simmons, R.R.T., C. Duwayne Schmidt, M.D., Kip Enger, B.S., C.R.T.T., Loren Greenway, B.S., R.R.T., and Reed M. Gardner, Ph.D., Computer-Assisted Medical Direction of Respiratory Care, Respiratory Management, vol. 19, No. 2.

H. Keller and CH. Trendelenburg, Data Presentation Interpretation, Clinical Biochemistry Principles, Methods, Applications, Walter-deGruyter & Co., 1989.

Reed M. Gardner, Ph.D., Karen W. Hollingsworth, R.N., M.S, C.C. R.N., ECG and Pressure Monitoring: How to Obtain Optimal Results, 295-305.

Reed M. Gardner, Ph.D., Dean F. Sittig, M.S., Marge C. Budd, R.N., M.S., Computers in the Intensive Care Unit: Match or Mismatch?, 248-259.

Emmanuel Furst, Ph.D., Cardiovascular Technology, The Journal of Cardiovascular Nursing, Nov. 1989, 68-78.

Dean F. Sittig, Reed M. Gardner, Nathan L. Pace, Alan H. Morris, and Eduardo Beck, Computerized Management of Patient Care in a Complex, Controlled Clinical Trial in the Intensive Care Unit, Computer Methods and Programs in Biomedicine 30, 1989, 77-84.

Karen E. Bradshaw, Ph.D., Dean F. Sittig, Ph.D., Reed M. Gardner, Ph.D., T. Allan Pryor, Ph.D., and Marge Budd, R.N., M.S., Computer-Based Data Entry for Nurses in the ICU, Clinical Computing, Nov. 1988.

Robert A. Larsen, M.D., R. Scott Evans, Ph.D., John P. Burke, M.D., Stanley L. Pestonik, R.Ph., Reed M. Gardner, Ph.D., David C. Classen, M.D., Improved Perioperative Antibiotic Use and Reduced Surgical Wound Infections Through Use of Computer Decision Analysis, Computer Applications for Surgical Prophylaxis/Larsen et al.

R. M. Gardner, Computers in the ICU and Surgery-Keeping Real-Time Patient Records for Decision-Making.

Thomas D. East, Ph.D., Alan H. Morris, M.D., Terry Clemmer, M.D., James F. Orme, M.D., C. Jane Wallace, B.S.N., Susan Henderson, B.A., Dean F. Sittig, Ph.D., Reed M. Gardner, Ph.D., Development of Computerized Critical Care Protocols—A Strategy That Really Works!, 1990 LDS Hospital, Salt Lake City, UT.

R. Scott Evans, Ph.D., John P. Burke, M.D., Stanley L. Pestonik, R.Ph., David C. Classen, M.D., Ronald L. Menlove, Ph.D., and Reed M. Gardner, Ph.D., Prediction of Hospital Inflections and Selection of Antibiotics Using an Automated Hospital Database, 1990, SCAMC, Inc. 663-667.

Susan E. Henderson, B.A., Robert O. Crapo, M.D., Thomas D. East, Ph.D., Alan H. Morris, M.D., C. Jane Wallace, R.N., Reed M. Gardner, Ph.D., Computerized Clinical Protocols in an Intensive Care Unit: How Well are They Followed?, 1990, SCAMC, Inc., LDS Hospital, Salt Lake City, UT.

Reed M. Gardner, PHD, Russell K. Hulse, RPH, MBA, Keith G. Larsen, RPH, Assessing The Effectiveness Of A Computerized Pharmacy System, 1990, SCAMC, Inc., 668-672.

Reed M. Gardner, "Patient-Monitoring Systems", *Medical Informatics: Computer Applications in Health Care*, E.H. Shortliffe and L.E. Perrealt (eds.), G. Wiederhold and L.M. Fagan (assoc. eds.) (Reading, MA: Addison-Wesley, 1990.

Reed M. Gardner, Olaf K. Golubjatnikov, R. Myron Laub, Julie T. Jacobson, and R. Scott Evans, Computer-Critiqued Blood Ordering Using the HELP System, Computers and Biomedical Research 23, 514-528, 1990, Academic Press, Inc.

Karen E. Tate, Ph.D., Reed M. Gard'ner, Ph.D., and Lindell K. Weaver, M.D., A Computerized Laboratory Alerting System, Clinical Computing, 1990, vol. 7, No. 5, 296-301.

Dean F. Sittig, Reed M. Gardner, Alan H. Morris, and C. Jane Wallace, Clinical Evaluation of Computer-Based Respiratory Care Algorithms, International Journal of Clinical Monitoring and Computing 7, 1990, 177-185, Kluwer Academic Publishers, Netherlands.

R. Scott Evans, Stanley L. Pestotnilc, John P. Burke, Reed M. Gardner, Robert A. Larsen, and David C. Classen, Reducing Tile Duration Of Prophylactic Antibiotic Use Through Computer Monitoring Of Surgical Patients, DICP, The Annals of Pharmacotherapy, Apr. 1990, vol. 24, 351-354, Harvey Whitney Books Company, Cincinnati, OH.

Reed M. Gardner, and M. Michael Shabot, Computerized ICU Data Management: Pitfalls and Promises, International Journal of Clinical Monitoring and Computing 7: 99-105, 1990, Kluwer Academic Publishers, Netherlands.

Stanley L. Pestotnik, R.PH., R. Scott Evans, PH.D., John P. Burke, M.D., Reed M. Gardner, PH.D., David C. Classen, M.D., Therapeutic Antibiotic Monitoring: Surveillance Using a Computerized Expert System, The American Journal of Medicine, Jan. 1990, vol. 88, 43-48.

Gil Kuperman, MD, Brent James, MD, MSTAT, Julie Jacobsen, MT (ASCP), Reed M. Gardner, PHD, Continuous Quality Improvement Applied To Medical Care: Experiences At LDS Hospital, Medical Decision Making, Oct. -Dec. 1991, 60-65, vol. 11, No. 4.

Susan Henderson, Robert O. Crapo, C. Jane Wallace, Thomas D. East, Alan H. Morris, & Reed M. Gardner, Performance Of Computerized Protocols For The Management Of Arterial Oxygenation In An Intensive Care Unit, International Journal of Clinical Monitoring and Computing 8, 1992, 271-180, Kluwer Academic Publishers, Netherlands.

Reed M. Gardner, Ph.D., William L. Hawley, Thomas D. East, Ph.D., Thomas A. Oniki, B.S., Hsueh-Fen W. Young, B.S., Real Time Data Acquistion: Experience With the Medical Information Bus (MIB), LDS Hospital, University of Utah, Salt Lake City, UT.

Eric F. Lepage, MD, Reed M. Gardner, PHD, R. Myron Laub, MD, Julie T. Jacobson, MT(ASCP), Assessing The Effectiveness Of A Computerized Blood Order Consultation System, LDS Hospital, 1992, 33-37, AMIA, Inc.

R. Scott Evans, PH.D., Stanley L. Pestotnik, R.PH., David C. Classen, M.D., Sheron B. Bass, B.S.N. Ronald L. Menlove, PH.D., Reed M. Gardner, PH.D., and John P. Burke, M.D., Development Of A Computerized Adverse Drug Event Monitor, LDS Hospital and University of Utah, Salt Lake City, UT.

E. Lepage, R. Traineau, PH. Marchetti, M. Benbunan, R. M. Gardner, Development Of A Computerized Knowledge Based System Integrated To A Medical Workstation: Application To Blood Transfusion, MEDINFO, 1992, 585-590, Elsevier Science Publishers B.V.

Reed M. Gardner, Ph.D. and R. Scott Evans, Ph.D., Computer-Assisted Quality Assurance, Group Practice Journal, May/Jun. 1992, 41(3), 8-11.

Thomas D. East, Ph.D., W. Hsueh-Fen Young, M.S., and Reed M. Gardner, Ph.D., Digital Electronic Communication between ICU Ventilators and Computers and Printers, Respiratory Care, Sep. 1992, vol. 37 No. 9, 1113-1123.

Reed M. Gardner, Computers in Critical Care, Wellcome Trends in Hospital Pharmacy, Jul. 1992.

T. Allan Pryor, Reed M. Gardner and W. Clinton Day, Computer System for Research and Clinical Application to Medicine, AFIPS—Conference Proceedings, vol. 33, 1968, 809-816.

Homer R. Warner, M.D., Reed M. Gardner and Alan F. Toronto, M.D., Computer-Based Monitoring of Cardiovascular Functions in Postoperative Patients, Supplement II to Circulation, Apr. 1968, vols. 37 & 38, 68-74.

Russell M. Nelson, Homer R. Warner, Reed E. Gardner and J. D. Mortensen, Computer Based Monitoring of Patients Following Cardiac Surgery, Computers in Cardiology, Jul.-Aug. 1969, vol. 5, No. 4, 926-930.

Reed M. Gardner, Computerized Patient Monitoring at LDS Hospital—An Evaluation, Proceedings of the San Diego Biomedical Symposium, 1971, vol. 10, 151-159.

Reed M. Gardner, Monitoring of Physiological Data in a Clinical Environment, Annual Review of Biophysics and Bioengineering, 1972, vol. 1, 211-224.

Reed M. Gardner, Computerized Intensive Care Monitoring at LDS Hospital—Progress and Development, 97-105.

Reed M. Gardner, Donald R. Bennet, and Richard B Vorce, Eight-Channel Data Set for Clinical EEG Transmission Over Dial-Up Telephone Network, IEEE Transactions on Biomedical Engineering, May 1974, vol. BME-21, No. 3, 246-249.

Reed M. Gardner, George H. Cannon, Alan H. Morris, Kenneth R. Olsen, W. Gary Price, Computerized Blood Gas Interpretation and Reporting System, Computer Magazine, Jan. 1975, 39-45.

Russell K. Hulse, Stephen J. Clark, J. Craig Jackson, Homer R. Warner and Reed M. Gardner, Computerized Medication Monitoring System, American Journal of Hospital Pharmacy 33, Oct. 1976, 1061-1064.

Reed M. Gardner, Ph.D., Computers in the ICU, Medical Electronics, Jun. 1984, 129-135.

Robert D. Andrews, M.S., M.T., Reed M. Gardner, Ph.D., Sandy M. Metcalf, R.R.T., and Deon Simmons, R.R.T., Computer Charting: An Evaluation of a Respiratory Care Computer System, Respiratory Care, Aug. 1985, vol. 30, No. 8, 695-707.

Reed M. Gardner, Ph.D., Computerized Data Management and Decision Making in Critical Care, Symposium on Critical Care, Aug. 1985, vol. 65, No. 4, 1041-1051.

Reed M. Gardner, David P. Scoville, Blair J. West, Beth Bateman, Robert M. Cundick, Jr., Terry P. Clemmer, Integrated Computer Systems for Monitoring of the Critically Ill, 1977, 301-307.

T. Allan Pryor, Reed M. Gardner, Paul D. Clayton, Homer R. Warner, A Distributed Processing System for Patient Management, Computers in Cardiology, Sep. 1978, 325-328.

Reed M. Gardner, Ph.D., Terry P. Clemmer, M.D., Keith G. Larsen, R.Ph., and Dickey S. Johnson, R.N., Computerized Alert System Use in Clinical Medicine, IEEE Session 6, 1979, 136-140.

T. Allan Pryor, Homer R. Warner, Reed M. Gardner, HELP—A Total Hospital Information System.

T. P. Clemmer, R. M. Gardner, J. F. Orme, Jr., Computer Support in Critical Care Medicine, 1980.

Scott R. Cannon, and Reed M. Gardner, Experience with a Computerized Interactive Protocol System Using HELP, Computers and Biomedical Research 13, 1980, 399-409, Academic Press, Inc.

T. Allan Pryor, Paul D. Clayton, Reed M. Gardner, Randy Waki, and Homer R. Warner, HELP—A Hospital-Wide System for Computer-Based Support of Decision-Making, Jan. 1981.

T. A. Pryor, R. M. Gardner, P. D. Clayton and H. R. Warner, The HELP System, Proceedings of the Sixth Annual Symposium on Computer Applications in Medical Care, Oct.-Nov. 1982, 19-27, IEEE.

Reed M. Gardner, Information Management—Hemodynamic Monitoring, Seminars in Anesthesia, Dec. 1983, vol. 2, No. 4, 287-299.

T. A. Pryor, R. M. Gardner, P. D. Clayton, H. R. Warner, The HELP System, Journal of Medical Systems, 1983, vol. 7, No. 2, 87-102.

Reed M. Gardner, Blair J. West, T. Allan Pryor, Distributed Data Base and Network for ICU Monitoring, IEEE Computers in Cardiology, Sep. 18-24, 1984, 305-307.

Reed M. Gardner, T. Allan Pryor, Paul D. Clayton, and R. Scott Evans, Integrated Computer Network for Acute Patient Care, Symposium on Computer Applications in Medical Care, Nov. 4-7, 1984.

Reed M. Gardner, Tomorrow's Electronic Hospital is Here Today, IEEE Spectrum, Jun. 1984, 101-103.

Karen E. Bradshaw, Reed M. Gardner, Terry P. Clemmer, Jams F. Orme, Frank Thomas, and Blair J. West, Physician Decision Making—Evaluation of Data Used in a Computerized ICU, International Journal of Clinical Monitoring and Computing 1, 1984, 81-91.

Terry P. Clemmer, M.D., and Reed M. Gardner, Ph.D., Data Gathering, Analysis, and Display in Critical Care Medicine, Respiratory Care, Jul. 1985, vol. 30, No. 7, 586-601.

Reed M. Gardner, Ph.D., and William L. Hawley, Standardizing Communications and Networks in the ICU, Patient Monitoring and Data Management, 1985, 59-63.

R. Scott Evans, Reed M. Gardner, Allan R. Bush, John P. Burke, Jay A. Jacobson, Robert A. Larsen, Fred A. Meier, and Homer R. Warner, Development of a Computerized Infectious Disease Monitor (CIDM), Computers and Biomedical Research 18, 1985, 103-113.

Reed M. Gardner, Ph.D., Susan M. Monis, Paul Oehler, Monitoring Direct Blood Pressure: Algorithm Enhancements, 607-610.

R. Scott Evans, PHD, Robert A. Larsen, MD, John P. Burke, MD, Reed M. Gardner, PHD, Frederick A. Meier, MD, Jay A. Jacobson, MD, Marlyn T. Conti, BSN, Julie T. Jacobson, MT, Russell K. Hulse, RPH, Computer Surveillance of Hospital-Acquired Infections and Antibiotic Use, Journal of the American Medical Association, Aug. 22-29, 1986, vol. 256, No. 8, 1007-1011.

Reed M. Gardner, Computerized Management of Intensive Care Patients, Images, Signals, and Devices, 1986, vol. 3, No. 1.

R. Whiting, L. Hayes, The Practice of Telemedicine—The TARDIS Perspective, Informatics in Healthcare—Australia, Jul./Aug. 1997, vol. 6, No. 3, 103-106.

Monique Frize, Robin Walker, Clinical Decision-Support Systems for Intensive Care Units Using Case-Based Reasoning.

Ho Sung Lee, Seung Hun Park, and Eung Je Woo, Remote Patient Monitoring Service Through World-Wide Web, Proceedings—19th International Conference—IEEE/EMBS, Oct. 30-Nov. 2, 1997, 928-931.

Betty L. Grundy, M.D., Pauline Crawford, R.N., Paul K. Jones, Ph.D., May Lou Kiley, Ph.D., Arnold Reisman, Ph.D., Yoh-Han Pao, Ph.D., Edward L. Wilkerson, M.D., J. S. Gravenstein, M.D., Telemedicine in Critical Care: An Experiment in Health Care Delivery, Oct. 1977, 6:10.

Betty Lou Grundy, M.D., Paul K. Jones, Ph.D., and Ann Lovitt, M.D., Telemedicine in Critical Care: Problems in Design, Implementation, and Assessment, Critical Care Medicine, Jul. 1982, vol. 10, No. 7, 471-475.

Geraldine Fitzpatrick, TARDIS Evaluation: Report on Final Usage Evaluation of the TARDIS Telehealth System, Jul. 24, 1998, Issue No. 1.0.

Abstract Marie Delima, R.N., M. Michael Shabot, M.D., FACS, FCCM, FACMI, Karen Morris, R.N, Janet Mould, R.N., Eden Torre-Javier, R.N., Mark Lobue, B.A. and Jeannie Chen, Pharm.D., Successful Implementation of a Multiple-ICU Clinical Information System in a Tertiary Care Medical Center.

Xin Li, Daniel J. Valentino, George J. So, Robert Lufkin, Ricky K. Taira, A World Wide Web Telemedicine System, SPIE vol. 2711, 427-439.

Stephen M. Ayres, M.D., F.C.C.M., Ake Grenvik, M.D., Ph.D., F.C.C.M., Peter R. Holbrook, M.D., F.C.C.M., William C. Shoemaker, M.D., F.C.C.M., Textbook of Critical Care, 3rd Edition, 1995, Harcourt Brace & Company.

Karen B. Tate, PH.D., Reed M. Gardner, PH.D., Kurt Scherting, Nurses, Pagers, and Patient-Specific Criteria; Three Keys to Improved Critical Value Reporting, 1995, 164-168, AMIA, Inc.

Karen E. Tate, Ph.D., Reed M. Gardner, Ph.D., Computers, Quality, and the Clinical Laboratory: A Look at Critical Value Reporting, 17th Annual Symposium on Computer Applications in Medical Care, Oct. 30-Nov. 3, 1993, 193-197.

Peter J. Haug, Reed M. Gardner, Karen E. Tate, R. Scott Evans, Thomas D. East, Gilad Kuperman, T. Allan Pryor, Stanley M. Huff, and Homer R. Warner, Decision Support in Medicine: Examples from the HELP System, Computers and Biomedical Research 27, 1994, 396-418.

Thomas D. East, Ph.D., C. Jane Wallace, R.N., M.S., Alan H. Morris, M.D., Reed M. Gardner, Ph.D., and Dwayne R. Westenskow, Ph.D., Computers in Critical Care, New Technologies in Critical Care, Jun. 1995, vol. 7, No. 2, 203-216.

Reed M. Gardner, Ph.D., Bette B. Maack, R.R.A., R. Scott Evans, Ph.D., and Stanley M. Huff, M.D., Computerized Medical Care: The HELP System at LDS Hospital, Journal of AHIMA, Jun. 1992, 63(6):68-78.

Reed M. Gardner, Ph.D., Integrated Computerized Records Provide Improved Quality of Care with Little Loss of Privacy, Journal of the AMIA, Jul./Aug. 1994, vol. 1, No. 4, 320-322.

S Reddy, M Niewiadomska-Bugaj, Y V Reddy, H C Galfalvy, V Jagannathan, R Raman, K. Srinivas, R. Shank, T. Davis, S. Friedman, MD, B. Merkin, MD, M. Kilkenny,MD, Experience with ARTEMIS—An Internet-Based Telemedicine System, AMIA, 1997, 759-763.

Patrick R. Norris, M.S., Benoit M Dawant, Ph.D., Antoine Geissbuhler, M.D., Web-Based Data Integration and Annotation in the Intensive Care Unit, 1997.

H. C. Galfalvy, M.S., S. M. Reddy, Ph.D., M. Niewiadomska-Bugaj, Ph.D., S. Friedman, M.D., Evaluation of Community Care Network (CNN) System in a Rural Health Care Setting, 1995, AMIA Inc., 698-702.

K. Major, M. Shabot, S. Cunneen, Wireless Critical Alerts and Patient Outcomes in the Surgical Intensive Care Unit; The American Surgeon, 2000; p. 1057-1060.

M. Shabot, M. Lobue, Cedars-Sinai Medical Center Critical Alerting System, Feb. 2004; p. 1-16.

Shabot MM, LoBue M, Leyerle BJ, Dubin SB. Inferencing strategies for automated ALERTS on critically abnormal laboratory and blood gas data, SCAMC 1989; 13:54-57.

APACHE® III Equation Update (Version III-J) 2002, pp. 1-22.

APACHE® III Equation Update (Version III-I) 2003, pp. 1-13.

O. Kostopoulau, M. Wildman, Sources of Variability in Uncertain Medical Decisions In the ICU: A Process Tracing Study, Qual. Saf. Health Care 2004, 13:272-280.

A. Seiver, Critical Care Computing: Past, Present, and Future; Critical Care Clinics, vol. 16, No. 4, Oct. 2000, pp. 1-17.

J. Fisher, S. Harbarth, A. Agthe, A. Benn, S. Ringer, D. Goldmann, and S. Fancani, Quantifying Uncertainty: Physicians'Estimates of Infection in Critically Ill Neonates and Children; Clinical Infection Diseases 2004:38, pp. 1383-1390.

N. Halpern, S. Pastores, R. Greenstein, Critical Care Medicine in the United States 1985-2000: An Analysis of Bed Numbers, Use, and Cost; Critical Care Medicine 2004, vol. 32, No. 6, pp. 1254-1259.

J.MRUS, Getting Beyond Diagnostic Accuracy: Moving Toward Approaches That Can Be Used in Practice; Clinical Infectious Diseases 2004:38, pp. 1391-1393.

B. Leyerle, M. Shabot, Integrated Computerized Databases for Medical Data Management Beyond the Bedside, International Journal of Clinical Monitoring and Clinical Computing 1990:7, pp. 83-89.

M.Shabot, M. Lobue, B. Leyerle, S. Dubin, Decision Support Alerts For Clinical Laboratory and Blood Gas Data, Int. J. Clinical Monitoring and Computing 1990:7, pp. 27-31.

M. Shabot, M. Lobue, Real-Time Wireless Decision Support Alerts on a Palmtop PDA; Proc. Ann. Symp. Compt Appl. Med Care 1995, pp. 174-179.

G. Kuperman, D. Sittig, M. Shabot, J.Teich, Clinical Decision Support for Hospital and Critical Care, pp. 174-179.

W. Bates, M. Cohen, L. Leape, J. Overhage, M. Shabot, T. Sheridan, Reducing the Frequency of Errors In Medicine, J. American Medical Informatics Assn. 2001:8 pp. 299-308.

M. Shabot, B. Leyerle, M. Lobue, Automatic Extraction of Intensity Intervention Scores From A Computerized Surgical ICU Flowsheet, Am. J. Surg 1987:154:1, pp. 72-76.

Grundy, Betty Lou; Jones, Paul; Lovitt, Ann; "Telemedicine in critical care: Problems in design, implementation and assessment" Jul. 1982. Critical Care Medicine vol. 10, No. 7.

Terry Ann Capuano, et al., Remote Telemetry, Nursing Management, Vo. 26, No. 7, Jul. 1995, p. 26.

Valeriy Nenov and John Klopp, Remote Access to Neurosurgical ICU Physiological Data using the World Wide web, health Care in the Information Age, 1996, pp. 242-249.

Betty L. Grundy, et al., Telemedicine in Critical Care: An Experiment in Health Care Delivery, JACEP, vol. 6, Oct. 1977, pp. 439-444.

Susan L. Mabry, et al., Integrated Medical Analysis System, Proceedings of the 1997 Winter Simlation Conferece,, 1997, pp. 1167-1168.

Simon M. Kaplan and Geraldine Fitzpatrick, Designing Support for Remote Intensive-Care Telehealth Using the Locales Framework, ACM, 1997, pp. 173-184.

Douglas A. Perednia, Telemedine Technology and Clinical Applications, JAMA, vol. 6, Feb. 8, 1995, p.

Silvia Miksch,Artificial Intelligence for Decision Support: Needs, Possibilities, and Limitations in ICU, 10th Postgraduate Cousre in Critical Care Medicine A.P.I.C.E. '95, Springer 1995 pp. 1-11.

Ho Sung Lee, et al., Remote Patient Monitoring Service through World-Wide Web, Proceedings—19th Int.

Silvia Miksch, Artificial Intelligence for Decision Support: Needs Possibilities, and Limitations in ICU, 10th Postgraduate Course in Critical Care Medicine APICE '95, Springer, 1995.

Doctors use 'remote control' to monitor ICU patients, CNN.com. technology>computing, Aug. 21, 2000, http://www.cnn.com/2000/TECH/computing/08/21/icu.t_t/.

Finding Value in Intensive Care, From Afar, The New York Times on the Web, Jul. 27, 1999, www.Visicu.com/companynews/0799_nytimes.htm.

Remote Monitoring of ICU Patients Lowers Mortality Rates, Complications, Johns Hopkins Newsrelease, Mar. 20, 2001, http://www.newswise.com/areticles/2001/3/ICU.JHM.html.

Brian A. Rosenfeld, M.D., FCCM, FCCP, et al., Intensive care unit telemedicine: Alternate paradigm for providing continuous intensivist care, Critical Care Medicine, vol. 28, No. 12, 2000 p. 3925.

Benjamin Berg, Dale Vincent, and Donald Hudson, Remote Critical Care Consultation: Telehealth Projection of Clinical Specialty Expertise, Tripler Army Medical Center, Honolulu.

Xin Li, et al., A World Wide Web Telemedicine System, SPIE vol. 2711 p. 427-439.

Guidelines for Intensive Care Unit Design, Critical Care Medicine, Mar. 1995; 23(3):582-588.

Michael Breslow, et al., Effect of a Multiple-Site Intensive Care Unit Telemedicine Program on clinical and Economic Outcomes: An Alternative Paradigm for Intensivist Staffing, Critical Care Medicine 2004 vol. 32, No. 1.

Richard Brilli, et al., Critical care Delivery in the Intensive Care Unit: Defining Clinical Roles and the Best Practice Model, Critical Care Medicine 2001 vol. 29, No. 10.

M. Michael Shabot, et al., Decision Support Systems in Critical Care, 1994, Springer-Verlag Publishing, New York.

Rosenfeld, et al. Intensive care unit telemedicine: alternate paradigm for providing continuous intensivist care, Dec. 28, 2000, www.ncbi.nlm.nih.gov.

Definitions of Intensive Care Unit (ICU) on the Web, Apr. 2004, www.google.com and other websites.

Tsien, C.L. and Fackler, J.C., "Poor prognosis for existing monitors in the intensive care unit," Critical Care Medical Journal, vol. 25, No. 4 (1997) (p. 614-619).

Tsien, C.L. "Reducing False Alarms in the Intensive Care Unit: A Systematic Comparison of Four Algorithms," Proceedings Annual AMIA Fall Symposium (1997).

Kohane, I.S. and Haimowitz, I.J., "Hypothesis-Driven Data Abstraction with Trend Templates," Proceedings Annual AMIA Symposium on Computer Applications in Medical Care (1994), (p. 444-448).

Summary of iMDSoft, LTD's Counterclaims-Filed Dec. 10, 2007.

Response to Summary of iMDSoft, LTD's Counterclaims - Filed Dec. 28, 2007.

Clayton, Paul D.; Hripcsak, George. "Decision Support in Healthcare." *Intl. Journal of Bio-Medical Computing* 39 (1995), pp. 59-66.

Kuperman, Gilad J., et al. "Detecting Alerts, Notifying the Physician, and Offering Action Items: A Comprehensive Alerting System." Proceedings fo the AMIA Annual Fall Symposium, 1996. Philadelphia: Hanley and Belfun, Inc. 1996; 20:704-708.

* cited by examiner

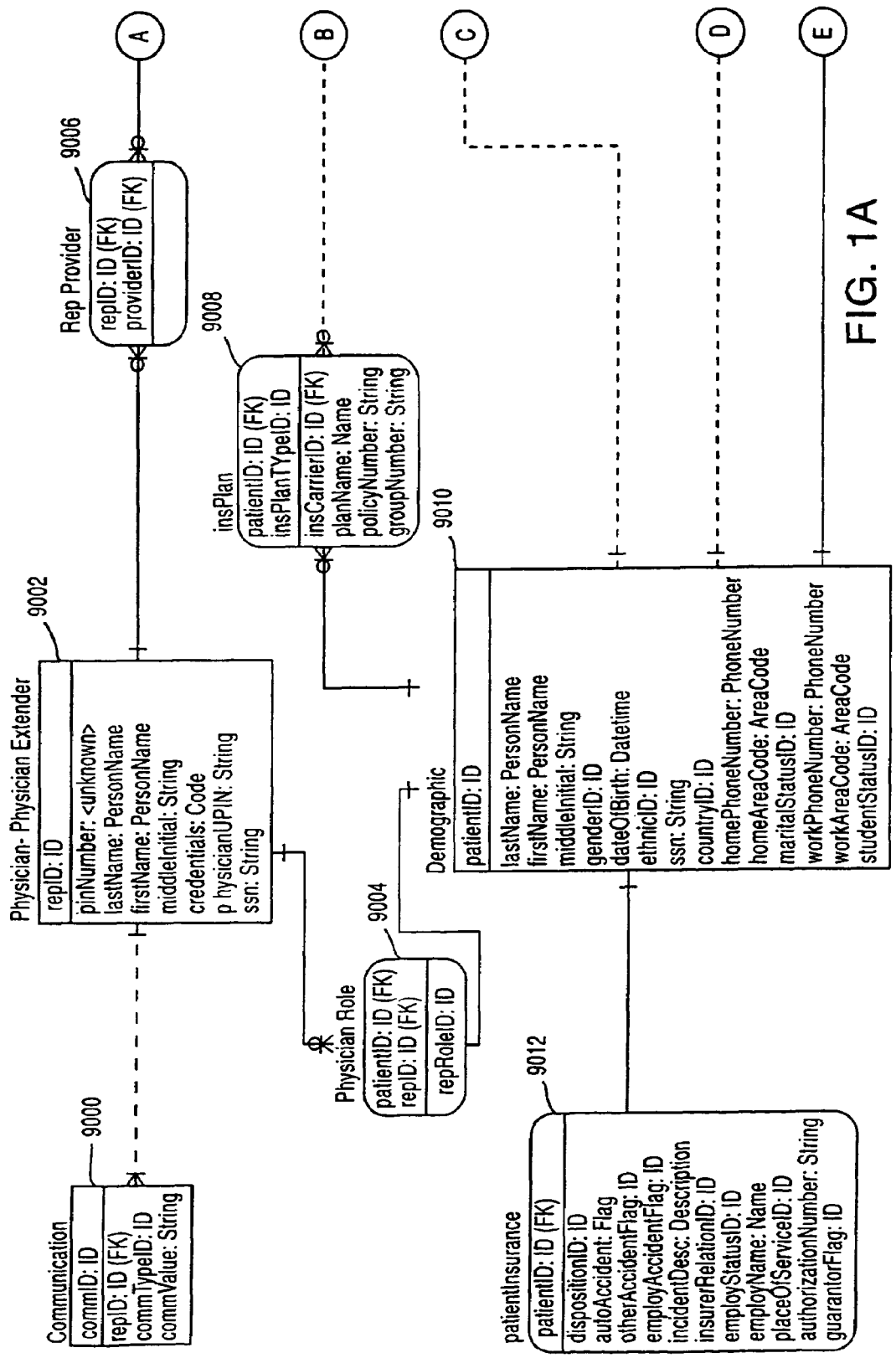

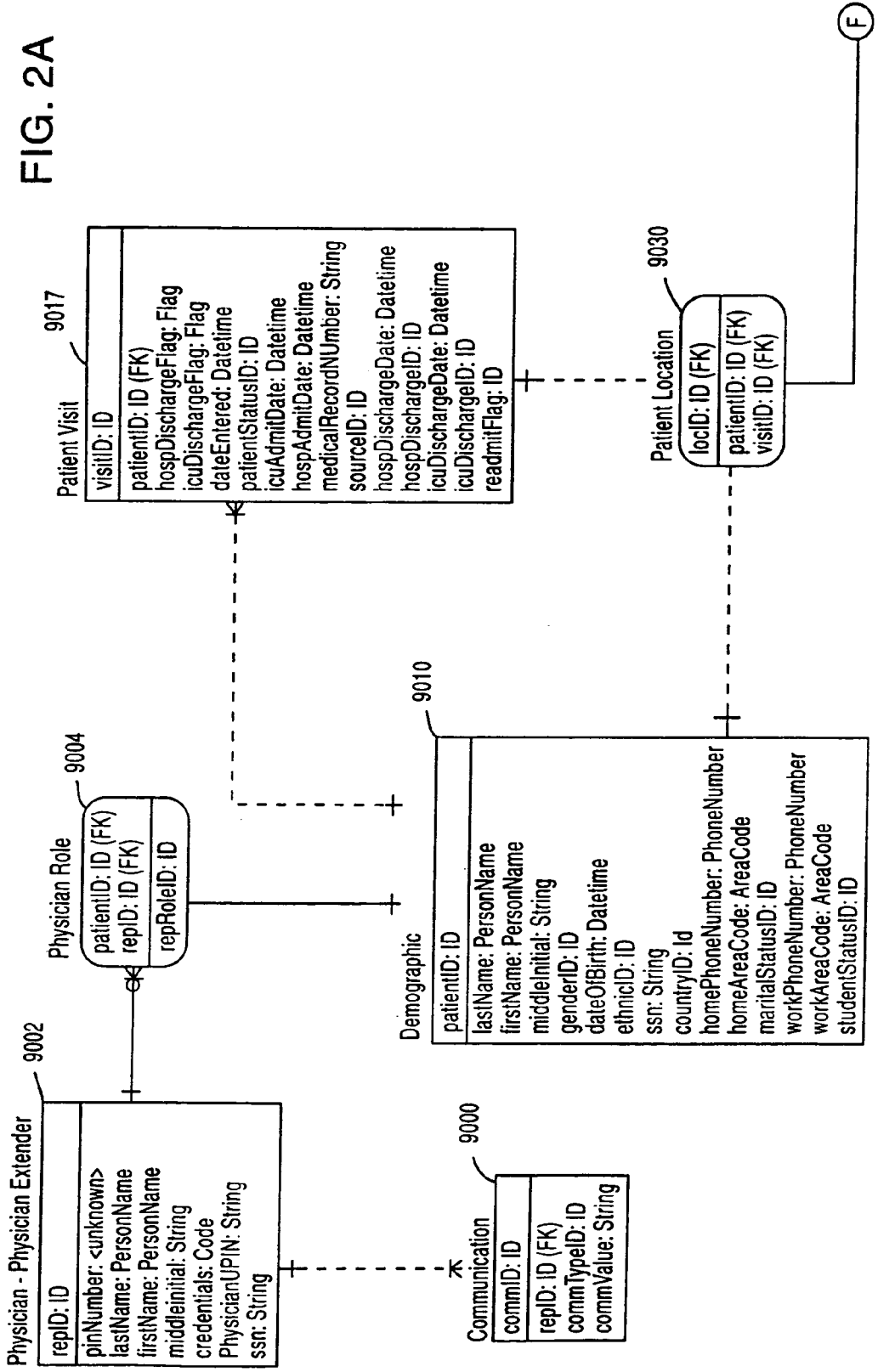

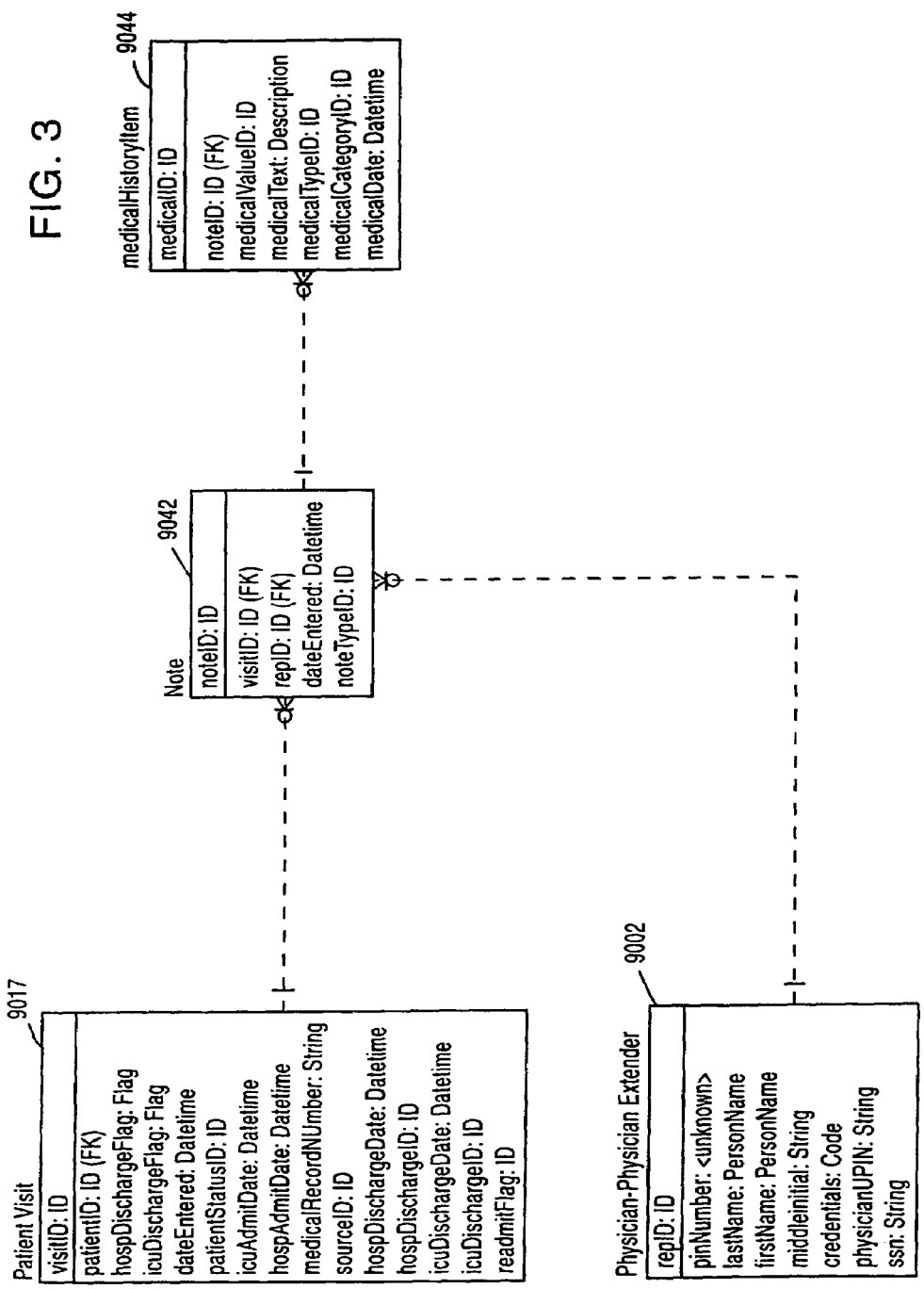

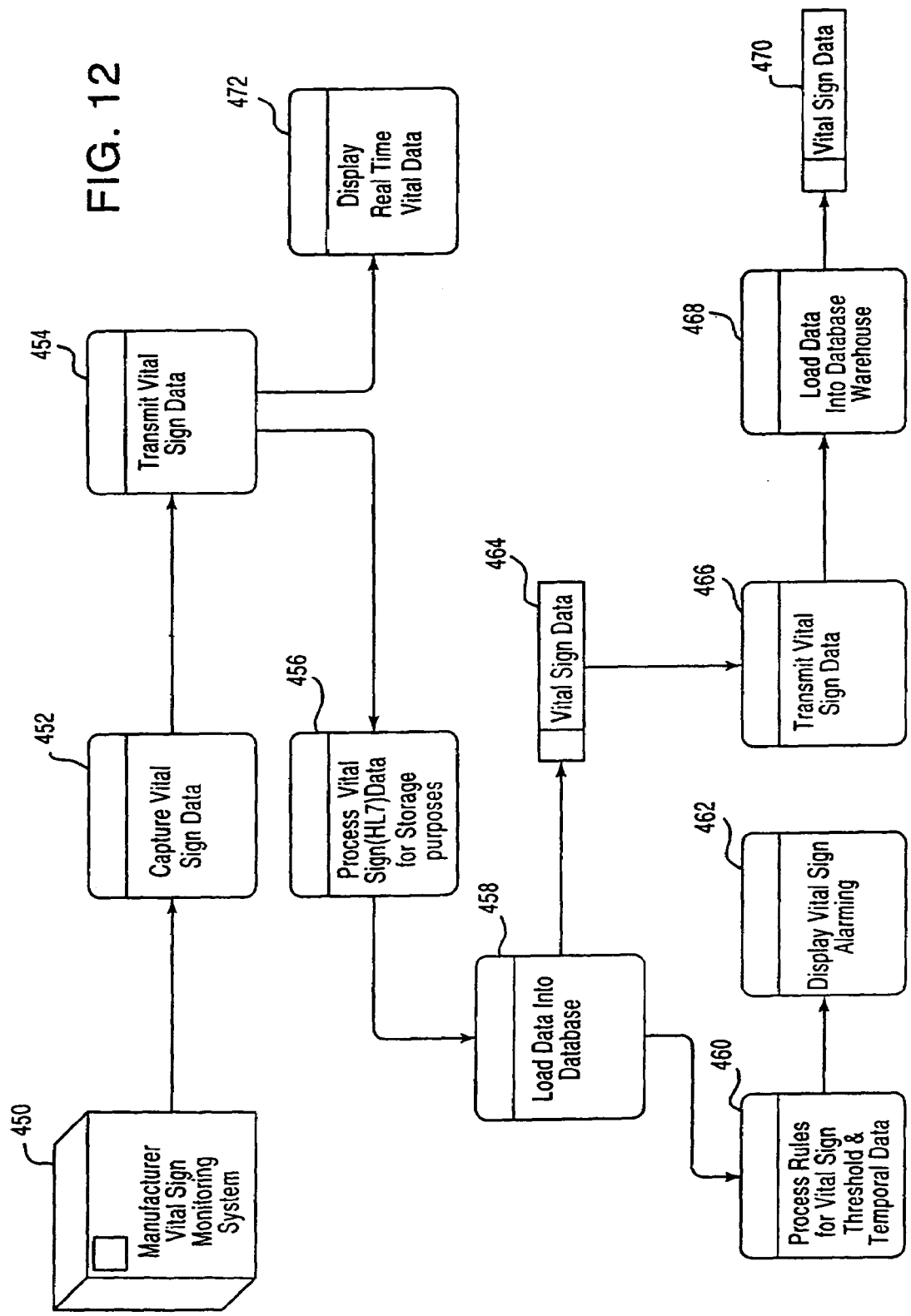

SYSTEM AND METHOD FOR DISPLAYING A HEALTH STATUS OF HOSPITALIZED PATIENTS

RELATIONSHIP TO OTHER APPLICATIONS

This application is a continuation in part of application Ser. No. 10/654,668 filed Sep. 4, 2003 and a continuation in part of application Ser. No. 10/946,548 filed Sep. 21, 2004, now U.S. Pat. No. 7,256,708 both of which are continuations in part of application Ser. No. 09/443,072 filed Nov. 18, 1999, now U.S. Pat. No. 6,804,656 issued Oct. 12, 2004, which claims the benefit of U.S. Provisional Application No. 60/141,520, filed Jun. 23, 1999. The Ser. No. 09/443,072 application is hereby incorporated by reference in its entirety for all purposes.

FIELD OF THE INVENTION

This invention relates generally to the care of patients in Intensive Care Units (ICUs). More particularly this invention is a system and method for care of the critically ill that combines a real-time, multi-node telemedicine network and an integrated, patient care management system to enable specially-trained Intensivists to provide 24-hour/7-day-per-week patient monitoring and management to multiple, geographically dispersed ICUs from both on-site and remote locations.

BACKGROUND OF THE INVENTION

While the severity of illness of ICU patients over the past 15 years has increased dramatically, the level of and type of physician coverage in most ICUs has remained constant. Most ICU patients receive brief minutes of attention during morning rounds from physicians with limited critical care experience. During the remainder of the day and night, nurses are the primary caregivers, with specialists called only after patient conditions have started to deteriorate. The result of this mismatch between severity of illness and physician coverage is an unacceptably high ICU mortality rate (10% nationwide), and a high prevalence of avoidable errors that result in clinical complications. In 1998, an Institute of Medicine Roundtable determined that avoidable patient complications were the single largest problem in medical care delivery. In another prominent 1998 study of 1000 patients, 46% experienced an avoidable adverse event in care, with 40% of these errors resulting in serious disability or death.

The physicians who can remedy this situation are in critically short supply. Numerous studies have shown that Intensivists (physicians who have trained and board certified in Critical Care Medicine) can markedly improve patient outcomes. However, only one-third of all ICU patients ever has an Intensivist involved in their care, and the number of Intensivists would need to increase tenfold (nationally) to provide 24-hour coverage to all ICU patients. With the rapid aging of the population, this shortfall of expertise is going to increase dramatically.

Even where Intensivists are present (and especially where they are not), patients suffer from unnecessary variation in practice. There is little incentive for physicians to develop and conform to evidence-based best practices (it takes significant work and a change in behavior to develop and implement them). This variation contributes to sub-optimal outcomes, in both the quality and cost of care delivered to ICU patients.

What is needed is a redesigning of the critical care regimen offered to patients in an ICU. Rather than the consultative model where a periodic visit takes place and the doctor then goes away, a more active 24-hour intensivist managed care is required. Further, technology that leverages the intensivists' expertise and standardizes the care afforded to patients in an ICU is required. Further, continuous feedback to improve the practice of intensivists in an ICU is necessary to provide the intervention required to minimize adverse events. This invention seeks to provide new methods for managing and delivering care to the critically ill.

Attempts to automate various aspects of patient care have been the subject of various inventions. For example, U.S. Pat. No. 5,868,669 to Iliff was issued for "Medical Diagnostic and Treatment Advice System." The disclosed invention is for a system and method for providing knowledge based medical diagnostic and treatment advice to the general public over a telephone network.

U.S. Pat. No. 5,823,948 to Ross, Jr. et al was issued for "Medical Records Documentation, Tracking and Order Entry System". The disclosed invention is for a system and method that computerizes medical records, documentation, tracking and order entries. A teleconferencing system is employed to allow patient and medical personnel to communicate with each other. A video system can be employed to videotape a patient's consent.

U.S. Pat. No. 4,878,175 to Norden-Paul et al. was issued for "Method for Generating Patient-Specific Flowsheets By Adding/Deleting Parameters." The disclosed invention is for an automated clinical records system for automated entry of bedside equipment results, such as an EKG monitor, respirator, etc. The system allows for information to be entered at the bedside using a terminal having input means and a video display.

U.S. Pat. No. 5,544,649 to David et al. was issued for "Ambulatory Patient Health Monitoring Techniques Utilizing Interactive Visual Communications." The disclosed invention is for an interactive visual system, which allows monitoring of patients at remote sites, such as the patient's home. Electronic equipment and sensors are used at the remote site to obtain data from the patient, which is sent to the monitoring site. The monitoring site can display and save the video, audio and patient's data.

U.S. Pat. No. 5,867,821 to Ballantyne et al. was issued for "Method and Apparatus for Electronically Accessing and Distributing Personal Health Care Information and Services in Hospitals and Homes." The disclosed invention is for an automated system and method for distribution and administration of medical services, entertainment services, and electronic health records for health care facilities.

U.S. Pat. No. 5,832,450 to Myers et al. issued for "Electronic Medical Record Using Text Database." The disclosed invention is for an electronic medical record system, which stores data about patient encounters arising from a content generator in freeform text.

U.S. Pat. No. 5,812,983 to Kumagai was issued for "Computer Medical File and Chart System." The disclosed invention is for a system and method which integrates and displays medical data in which a computer program links a flow sheet of a medical record to medical charts.

U.S. Pat. No. 4,489,387 to Lamb et al. was issued for "Method and Apparatus for Coordinating Medical Procedures." The disclosed invention is for a method and apparatus that coordinates two or more medical teams to evaluate and treat a patient at the same time without repeating the same steps.

U.S. Pat. No. 4,731,725 to Suto et al. issued for "Data Processing System which Suggests a Pattern of Medical Tests to Reduce the Number of Tests Necessary to Confirm or Deny a Diagnosis." The disclosed invention is for a data processing system that uses decision trees for diagnosing a patient's symptoms to confirm or deny the patient's ailment.

U.S. Pat. No. 5,255,187 to Sorensen issued for "Computer Aided Medical Diagnostic Method and Apparatus." The disclosed invention is for an interactive diagnostic system which relies on color codes which signify the presence or absence of the possibility of a disease based on the symptoms a physician provides the system.

U.S. Pat. No. 5,553,609 to Chen et al. issued for "Intelligent Remote Visual Monitoring System for Home Health Care Service." The disclosed invention is for a computer-based remote visual monitoring system, which provides in-home patient health care from a remote location via ordinary telephone lines.

U.S. Pat. No. 5,842,978 to Levy was issued for "Supplemental Audio Visual Emergency Reviewing Apparatus and Method." The disclosed invention is for a system which videotapes a patient and superimposes the patient's vital statistics onto the videotape.

While these inventions provide useful records management and diagnostic tools, none of them provides a comprehensive method for monitoring and providing real time critical care at disparate ICUs. In short, they are NOT designed for critical care. Further, none of these inventions provide for the care of a full time intensivist backed by appropriate database and decision support assistance in the intensive care environment. What would be useful is a system and method for providing care for the critically ill that maximizes the presence of an intensivist trained in the care of the critically ill. Further such a system would standardize the care in ICUs at a high level and reduce the mortality rate of patients being cared for in ICUs.

SUMMARY OF THE INVENTION

The present invention provides a core business of Continuous Expert Care Network (CXCN) solution for hospital intensive care units (ICUs). This e-solution uses network, database, and decision support technologies to provide 24-hour connectivity between Intensivists and ICUs. The improved access to clinical information and continuous expert oversight leads to reduced clinical complications, fewer medical errors, reduced mortality, reduced length of stay, and reduced overall cost per case.

The technology of the present invention as explained below can be implemented all at once or in stages. Thus the technology, as more fully explained below is available in separate components to allow for the fact that hospitals may not be able to implement all of the technology at once. Thus modular pieces (e.g. videoconferencing, vital sign monitoring with smart alarms, hand-held physician productivity tools, etc.) can be implemented, all of which can add value in a stand-alone capacity. First amongst these offerings will be an Intensivist Decision Support System, a stand-alone software application that codifies evidence-based, best practice medicine for 150 common ICU clinical scenarios. These support algorithms are explained more fully below.

The "Command Center" model, again as more fully set forth below, will ultimately give way to a more distributed remote management model where Intensivists and other physicians can access ICU patients and clinicians (voice, video, data) from their office or home. In this scenario, the present invention will be available in hospital applications that centralize ICU information, and offer physicians web-based applications that provide them with real-time connectivity to this information and to the ICUs. This access and connectivity will enable physicians to monitor and care for their patients remotely. These products will be natural extensions and adaptations of the present invention and the existing applications disclosed herein that those skilled in the art will appreciate and which do not depart from the scope of the invention as disclosed herein.

The present invention addresses these issues and shortcomings of the existing situation in intensive care, and its shortfalls via two major thrusts. First, an integrated video/voice/data network application enables continuous real-time management of ICU patients from a remote setting. Second, a client-server database application—integrated to the remote care network—provides the data analysis, data presentation, productivity tools and expert knowledge base that enables a single Intensivist to manage the care of up to 40 patients simultaneously. The combination of these two thrusts—care management from a remote location and new, technology-enhanced efficiency of Intensivist efforts—allows health care systems to economically raise the standard of care in their ICUs to one of 24.times.7 continuous Intensivist oversight.

It is therefore an object of the present invention to reduce avoidable complications in an ICU.

It is a further object of the present invention to reduce unexplained variations in resource utilization in an ICU.

It is a further objective of the present invention to mitigate the serious shortage of intensivists.

It is yet another objective of the present invention to reduce the occurrence of adverse events in an ICU.

It is a further objective of the present invention to standardize the care at a high level among ICUs.

It is yet another objective of the present invention to reduce the cost of ICU care.

It is yet another objective of the present invention to dramatically decrease the mortality in an ICU.

It is yet another objective of the present invention to bring information from the ICU to the intensivist, rather than bring the intensivist to the ICU.

It is a further objective of the present invention to combine tele-medical systems comprising two-way audio/video communication with a continuous real time feed of clinical information to enable the intensivist to oversee care within the ICU.

It is a further objective of the present invention to allow intensivists to monitor ICUs from a site remote from each individual ICU.

It is a further objective of the present invention to bring organized detailed clinical information to the intensivist, thereby providing standardized care in the ICU.

It is yet another objective of the present invention to utilize knowledge-based software to use rules, logic, and expertise to provide preliminary analysis and warnings for the intensivists.

The present invention comprises a command center/remote location, which is electronically linked to ICUs remote from the command center/remote location. The command center/remote location is manned by intensivists 24 hours a day, seven days per week. Each ICU comprises a nurse's station, to which data flows from individual beds in the ICU. Each patient in the ICU is monitored by a video camera, as well as by clinical monitors typical for the intensive care unit. These monitors provide constant real time patient information to the nurse's station, which in turn provides that information over a dedicated T-1 (high bandwidth) line to the ICU command center/remote location. As noted earlier, the command center/remote location is remote from the ICU, thereby allowing the command center/remote location to simultaneously monitor a number of patients in different ICUs remote from the command center/remote location.

At each command center/remote location, video monitors exist so that the intensivist can visually monitor patients within the ICU. Further, the intensivist can steer and zoom the video camera near each patient so that specific views of the patient may be obtained, both up close and generally. Audio links allow intensivists to talk to patients and staff at an ICU bed location and allow those individuals to converse with the intensivist.

Clinical data is constantly monitored and presented to the command center/remote location in real time so that the intensivist can not only monitor the video of the patient but also see the vital signs as transmitted from the bedside. The signals from the clinical data and video data are submitted to a relational database, which comprises 1) standardized guidelines for the care of the critically ill, 2) various algorithms to support the intensive care regimen, 3) order writing software so that knowledge-based recommendations and prescriptions for medication can be made based upon the clinical data, and 4) knowledge-based vital-sign/hemodynamic algorithms that key the intensivist to engage in early intervention to minimize adverse events.

The advantage of the present invention is that intensivists see all patients at a plurality of ICU's at all times. Further, there is a continuous proactive intensivist care of all patients within the ICU, thereby minimizing adverse events. Intervention is triggered by evidence-based data-driven feedback to the intensivist so that standardized care can be provided across a plurality of ICUs.

The economic benefits of the present invention are manifold. For the first time, 24-hour a day, seven day a week intensivist care for patients in an ICU can be obtained. Further, more timely interventions in the care of the patients can be created by the knowledge-based guidelines of the present invention, thereby minimizing complications and adverse events. This in turn will lead to a reduced mortality within the ICU, and hence, a reduced liability cost due to the dramatic reduction in avoidable errors in health care.

By providing timely interventions, the length of stay within the ICU can be greatly reduced, thereby allowing more critically ill patients to be cared for in the ICU.

In addition, by reviewing and standardizing the care afforded to patients in an ICU, a more standardized practice across a variety of ICUs can be achieved. This will lead to more cost-effective care within the ICU, and reduced ancillary cost for the care of the critically ill.

The overall architecture of the present invention comprises a "pod." The pod comprises a tele-medicine command center/remote location connected to a plurality multiple ICUs at various locations. The connection between the command center/remote location and the ICUs is via a dedicated wide-area network linking the ICUs to the command center/remote location and a team of intensivists who integrate their services to provide 24-hour, seven day a week care to all of the pod ICUs.

The pod is connected via a wide-area network using dedicated T-1 lines, for example, with redundant backup. This network provides reliable, high speed secure transmission of clinical data and video/audio signals between each patient room and the command center/remote location. The use of a T-1 line is not meant as a limitation. It is expected that more and higher bandwidth networks will become available. Such high bandwidth networks would come within the scope of the invention as well.

Each patient room is equipped with a pan/tilt/zoom video camera with audio and speaker to enable full videoconferencing capability. In addition, computer workstations are dedicated for exclusive physician use in each ICU, preferably at the nurse's station. Intensivists use the workstations to view patient information, consult decision support information, record their notes, and generate patient orders.

The patient management software used by intensivists is provided across the pod. Updates and changes made to the record are available at both the ICU and the command center/remote location for any given patient.

Each command center/remote location contains at least three workstations: one for the intensivist, one for the critical care registered nurse, and one for a clerk/administrative person.

The intensivist workstation comprises separate monitors for displaying ICU video images of patients and/or ICU personnel, output from bedside monitoring equipment, patient clinical data comprising history, notes, lab reports, etc., and decision support information. The staff at the command center/remote location are able to activate and control the cameras in each patient's room so that appropriate visual views of the patient can be generated.

Intensivists are able to switch between rooms and patients and can monitor at least two rooms simultaneously via the video screens. Patient data such as X-ray and ECG images are scanned and transmitted to the command center/remote location upon request of the intensivist.

Remote patient management is utilized in the present invention's critical care program to supplement traditional onsite care. The rationale underlying the remote patient management of the present invention is that critically ill patients are inherently unstable and require continuous expert care that is not now offered in existing ICU monitoring regimens. Further, remote monitoring allows a single intensivist to care for patients in multiple ICU locations, thereby creating an efficiency that makes continuous care feasible.

Remote intensivist care of the present invention is proactive. Intensivists will order needed therapies and check results of tests and monitor modalities in a more timely fashion than is currently offered. Patients can be observed visually when needed using the ceiling-mounted cameras in each room.

Command center/remote location personnel communicate with ICU staff through videoconferencing and through "hot phones," which are dedicated telephones directly linked between the command center/remote location and the ICU. These communications links are used to discuss patient care issues and to communicate when a new order has been generated.

Intensivists document important events occurring during their shift in progress notes generated on the command center/remote location computer terminal.

Intensivists detect impending problems by intermittently screening patient data, including both real time and continuously stored vital sign data. Patient severity of illness determines the frequency with which each patient's data is reviewed by the intensivists.

Embodiments of the present invention provide a system for providing continuous, expert network health care services from a remote location. The system comprises a plurality of health care locations, at least one remote command center for managing healthcare at said plurality of health care locations, and at least one network. The plurality of health care locations are electronically connected to said at least one remote command center by the network. The at least one remote command center provides intensivist monitoring of the plurality of health care locations 24 hours per days seven days per week.

The remote command center further comprises a patient care management system for monitoring and treating individual patients at any of said plurality of healthcare locations.

The patient care management system further comprises a data server/data warehouse for storing and analyzing data from the at least one remote command center.

Each of the plurality of health care locations further comprises patient monitoring equipment electronically connected to the at least one remote command center over the network. In another embodiment of the present invention each health care location further comprises a nurses' station electronically connected to said monitoring equipment and to the at least one remote command center over the network. In still another embodiment of the present invention, the healthcare locations comprise intensive care units (ICU's).

Optionally, the patient care management system further comprises a relational database for storing a plurality of decision support algorithms and for prompting intensivists to provide care to patients based upon any of the decision support algorithms. The algorithms are selected from the group consisting of algorithms for treating Acalculous Cholecystitis, Acute Pancreatitis Algorithms, Acute Renal Failure-Diagnosis, Acute Renal Failure-Management & Treatment, Adrenal Insufficiency. Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hyperglycemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complication, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Post-Op Management of Carotid, Post-Op Management of Open Heart, Post-Op Management of Thoracotomy, Post-Op Myocardial Ischemia (Non-Cardiac Arrhythmias after Cardiac Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrhythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding, Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoietic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

In yet another embodiment of the present invention, the patient care management system further comprises order writing software for providing knowledge-based recommendations and prescriptions for medication based upon the clinical data. In another embodiment of the present invention, the patient care management system further comprises knowledge-based vital sign/hemodynamic algorithms that prompt said intensivist to engage in early intervention.

Embodiments of the present invention provide methods for continuous expert critical care. Patients are monitored in a plurality of ICU's. Information from the patient monitoring is communicated to at least one command center over a first network. The information from the patient monitoring is received and analyzed at the command center over the first network; and guidance is provided from the command center to the plurality of ICU's to take actions regarding patient care. In another embodiment of the present invention, providing guidance from the command center further comprises an intensivist reviewing decision support algorithms that provide guidance for treating a plurality of critical care conditions. The algorithms are taken from the group consisting of algorithms for treating Acalculous Cholecystitis, Acute Pancreatitis Algorithm, Acute Renal Failure-Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hyperglycemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complications, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal, Post-Op Management of Carotid, Post-Op Management of Open Heart, Post-Op Management of Thoracotomy, Post-Op Myocardial Ischemia, (Non-Cardiac Arrhythmias after Cardiac Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrhythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoietic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

In another embodiment, a method further comprises a data server/data warehouse storing and analyzing patient data from the at least one command center and providing analysis in results over a second network to the at least one command center.

In an embodiment, a system for displaying a health status of hospitalized patients comprises a database and a display module. In this embodiment, the database receives patient data associated with hospitalized patients, applies a decision support algorithm to patient data, and identifies condition-indicating patient data according to the decision support algorithm. The display module selects condition-indicating patient data to be displayed according to display rules and displays the selected patient data. The patient data may, for example, comprise a monitored data element generated by a patient monitoring device. By way of illustration and not as a limitation, a monitored data element may be indicative of heart rate, systolic pressure, diastolic pressure, pulmonary artery wedge pressure, central venous pressure, oxygen saturation, tidal volume, inspiratory pressure, positive end expiratory pressure, respiration rate, electroencephalography cardiac output. In another example, the patient data may also comprise a clinical data element. By way of illustration and not as a limitation, a clinical data element may be indicative of patient history, caregiver notes, laboratory reports, venous pressure, and urine output.

In an embodiment, a display rule comprises criteria indicative of the severity of a hospitalized patient's current status. By way of illustration and not as a limitation, criteria indicative of the severity of a hospitalized patient's current status may be an acuity rating, a disease severity score, a diagnosis, a history of present illness (HPI) score; a review of systems (ROS) score; a past, family, and social history (PFSH) score; a physical exam score; and a modality prediction model (MPM) score.

In yet another embodiment, a display rule comprises displaying selected patient data ranked by the severity of the hospitalized patients' current status or by time, grouped by a location of the hospitalized patients, grouped by a diagnosis of the hospitalized patients, and grouped by a demographic parameter.

In yet another embodiment, patient data comprises a patient task schedule. In this embodiment, the display rule comprises criteria indicative of a scheduled time for performing a task on the patient task schedule. By way of illustration and not as a limitation, a task may be intubating the hospitalized patient, extubating the hospitalized patient, medicating the hospitalized patient, performing a laboratory procedure on a hospitalized patient, performing a surgical procedure on a hospitalized patient, and performing a radiological procedure on a hospitalized patient.

In still another embodiment, a system for displaying a health status of hospitalized patients comprises a smart alert module. The smart alert module establishes patient-specific rules associated with each hospitalized patient and applies the patient-specific rules continuously using a rules engine. The rules engine selects one or more data elements from the patient data associated with a hospitalized patient, applies the patient-specific rule associated with the hospitalized patient to the selected one or more data elements, and determines whether the patient-specific rule for the hospitalized patient has been contravened. In an embodiment, the patient-specific rule is an algorithm. If the patient-specific rule for the hospitalized patient has been contravened, a smart alert is issued for the hospitalized patient. In an embodiment, the smart alert comprises patient data for the hospitalized patient.

By way of illustration and not as a limitation, the one or more selected data elements may be selected from physiological data elements, medication data elements, laboratory data elements, and clinical data elements.

In even another embodiment of the present invention, a display rule comprises criteria indicative of the issuance of the smart alert, and the display module is further adapted to select patient data associated with the smart alert. In yet another embodiment, the selected data element is a physiological data element and if the patient-specific rule for the hospitalized patient has been contravened, the smart alert module assigns the physiological data element a graphical attribute. By way of illustration and not as a limitation, the graphical attribute is a selected display color of the physiological data element and the selected display color is indicative of the degree to which the physiological data element falls outside an acceptable range. Other graphical attributes can be used, such as display intensity and blinking, to indicate information relating to a displayed data element.

BRIEF DESCRIPTION OF THE FIGURES

FIG. 1A illustrates the logical data structure for billing, insurance and demographic information.

FIG. 2A illustrates the command center logical data structure.

FIG. 3 illustrates the logical data structure for creating a medical history.

FIG. 12 illustrates the vital signs data flow.

DEFINITIONS OF TERMS AND DATA

Figure 1B:
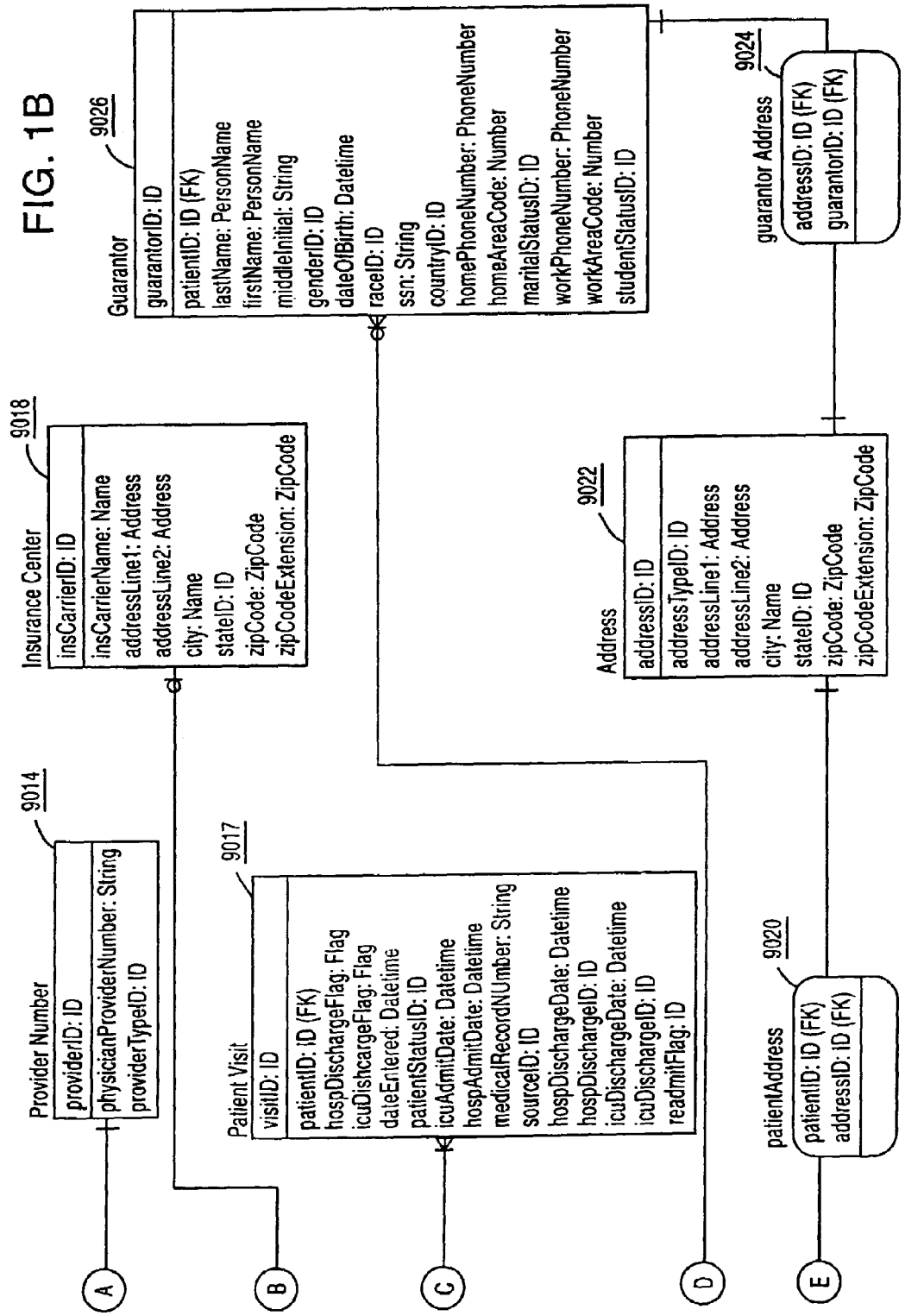
FIG. 1B illustrates the logical data structure for billing, insurance and demographic information (cont).

In the following Detailed Description of the Invention, a number of modules and procedures are described. For purposes of definitions, the following module definitions apply and are more fully amplified in the descriptions of the figures that follow.

Term Definitions

Following are a series of definitions for certain terms used in this specification:

Insurance carrier: This is a table of all the valid insurance carriers listed in the system of the present invention.

Patient guarantor: Provides the insurance guarantor information for a given patient.

Patient information: Provides demographic information for each patient.

Medical event date history: This contains the various disorders of the patient and the dates associated with major medical events relating to those disorders.

Medical history: Contains non-major system medical history of a patient.

Drug: Contains what medication and allergies have been identified for a patient at admission.

Address: Contains the address or addresses for a given patient.

Patient visit: There may be multiple records for any given patient, since the patient may visit the ICU on more than one occasion. This file contains a record of each visit to an ICU by a patient.

Physician-patient task: Contains the task that had been defined for each patient.

Present illness: This contains a textural description of the patient illness for the specific ICU visit.

Physical exam: This contains the information gathered as a result of a physical examination of the patient during the admission to the ICU.

Surgical fluids: This provides all the information related to the fluids provided during surgery.

Surgery: This contains all information pertaining to any surgical procedure performed on a patient while the patient is at the ICU.

Patient admit: This provides general information that needs to be gathered when a patient is admitted into the ICU.

Medical orders: This provides the general information for all types of medical orders associated with a given patient.

Daily treatment: This contains the treatment provided for a given patient on a given day.

Daily diagnosis: This contains the daily diagnosis for a given patient, which includes neurological, cardiological, pulmonary, renal, endocrinological, and any other diagnosis that may be associated with a patient.

Vital sign information is also critical to the administration of care in the ICU. A number of different modules collect information relating to patient vital signs. For example:

Patient admit: This provides the general information that needs to be gathered when a patient is admitted to the ICU Patient visit: This contains a record of each visit to an ICU by a patient.

Patient: Provides demographic information for each patient.

Vital sign header: This contains general information related to the vital sign data for the particular patient.

Vital sign: Contains the vital sign data taken at specific intervals for a given patient.

Hospital: This contains identifying information for a particular hospital where the care is given.

ICU bed: Contains the association for identifying which beds are in a given ICU

Command center/remote location definitions and modules have also been created for the present invention to allow for the orderly storage and retrieval and entering of data. For example:

Physician-physician (such as nurses and LPN and the like): Contains the names of all of the physicians and physician extenders for the command center/remote location as well as for ICUs associated with the command center/remote location.

Communication: Contains all of the various types of communication vehicles used to contact an individual physician or physician extender.

Physician role: Contains the role a physician is playing for a given patient, (i.e., primary care, consultant, etc.)

Patient: Provides demographic information for each patient.

Command center/remote location: Provides identifying information for a particular command center/remote location.

Hospital: Contains identifying information for a particular hospital wherein an ICU is located.

ICU: Contains identifying information for an ICU at a hospital.

ICU bed: Contains the association for identifying which beds are in a given hospital.

ICU patient location: Provides the association between an ICU and a patient and identifies where a patient is located within an ICU in a particular hospital.

The order entry functionality of the present invention provides a critical service for obtaining information on the patient during admission, medical orders, and procedures provided to the patient during the ICU stay. For example:

Radiology: Contains all radiology performed on a particular patient.

Radiology results: Contains the results of each radiology test performed on the particular patient.

Drugs: Contains all relevant information for all the drugs that a patient has been administered.

Laboratory: Contains all laboratory tests ordered for a patient.

Microbiology result: Contains the results of microbiology organisms taken on a patient.

Laboratory result: Contains the results for a laboratory test ordered for a particular patient.

DETAILED DESCRIPTION OF THE INVENTION

The present invention is a system and method for remote monitoring of ICU's from a distant command center/remote location. By monitoring a plurality of ICU's remotely, intensivists can better spread their expertise over more ICU beds that heretofore achievable. The presence of 24-hour a day/7 day-per-week intensivist care dramatically decreases the mortality rates associated with ICU care.

Referring to FIGS. 1A and 1B, the Billing and Demographic data structure of the present invention is illustrated. Patient demographic information 9010 is collected on the particular patient. This information comprises all the typical kinds of information one would normally gather on a patient such as first name, last name, telephone number, marital status, and other types of information. Patient insurance information 9012 is collected and associated with the patient demographic information 9010. Patient insurance information 9012 relates to information on the type of accident and related information such as employment, employer name, place of service, and other information that would relate to the accident that actually occurred (if at all) and which would have to be reported to an insurance agency. This information is associated with the patient demographic information which assigns the unique patient ID to the particular patient.

Insurance plan information 9008 is also created and stored and comprises insurance carrier ID's, the plan name, policy number, and group number. This information on the insurance plan 9008 is also associated with the patient ID and demographic information 9010.

Physician information 9002 is also created and stored for each physician associated with the system of the present invention. Information such as first and last name, credentials, and other information concerning the physician is saved. In addition, the physician's role is identified 9004 and information concerning the physician and the physician's role is associated with the particular patient via the patient ID stored in the demographic information 9010.

Patients are entered into the hospital by a hospital representative 9006 who has a representative ID which also is ultimately associated with the patient ID. In addition, communications data 9000 is stored concerning how a representative can be reached (cell phone, home phone etc.).

Referring now to FIG. 1B, the Overall Billing and Insurance data structure is illustrated. An insurance provider number 9014 is also stored in the system. Each physician is given a provider number and provider ID by each insurance company. Thus data must be stored regarding the ID that is given to a particular physician by each insurance provider. This information is also stored and can be associated ultimately with treatment of the patient.

Each patient admitted to the hospital and to the ICU has a patient visit ID associated with the patient 9017. This visit ID has patient ID information, ICU information, admission date, and other information relevant to the specific visit. This information is illustrated in FIG. 1B. The visit ID 9017 is associated with the patient ID 9010 so that each visit can be tracked by patient.

Insurance carrier information 9018 is stored by the system and is associated with the insurance plan information 9008 as appropriate. Thus the particular insurance carrier with its name, address, and other identifying information 9018 is associated with the type of plan 9008 carried by the patient. The insurance carrier information 9018 together with the insurance plan information 9008 is associated with the patient via the patient ID information 9010.

Patient address information 9020 and 9022 are collected for each individual patient and associated with the patient demographic information 9010. If there is a patient guarantor, this information is obtained and stored with information on the guarantor 9026. Such information as the guarantor's first and last name, date of birth, and other information is stored and is illustrated in FIG. 1B. Further, the guarantor's address 9024 is also collected and ultimately associated with the patient demographic information 9010.

Figure 2B:
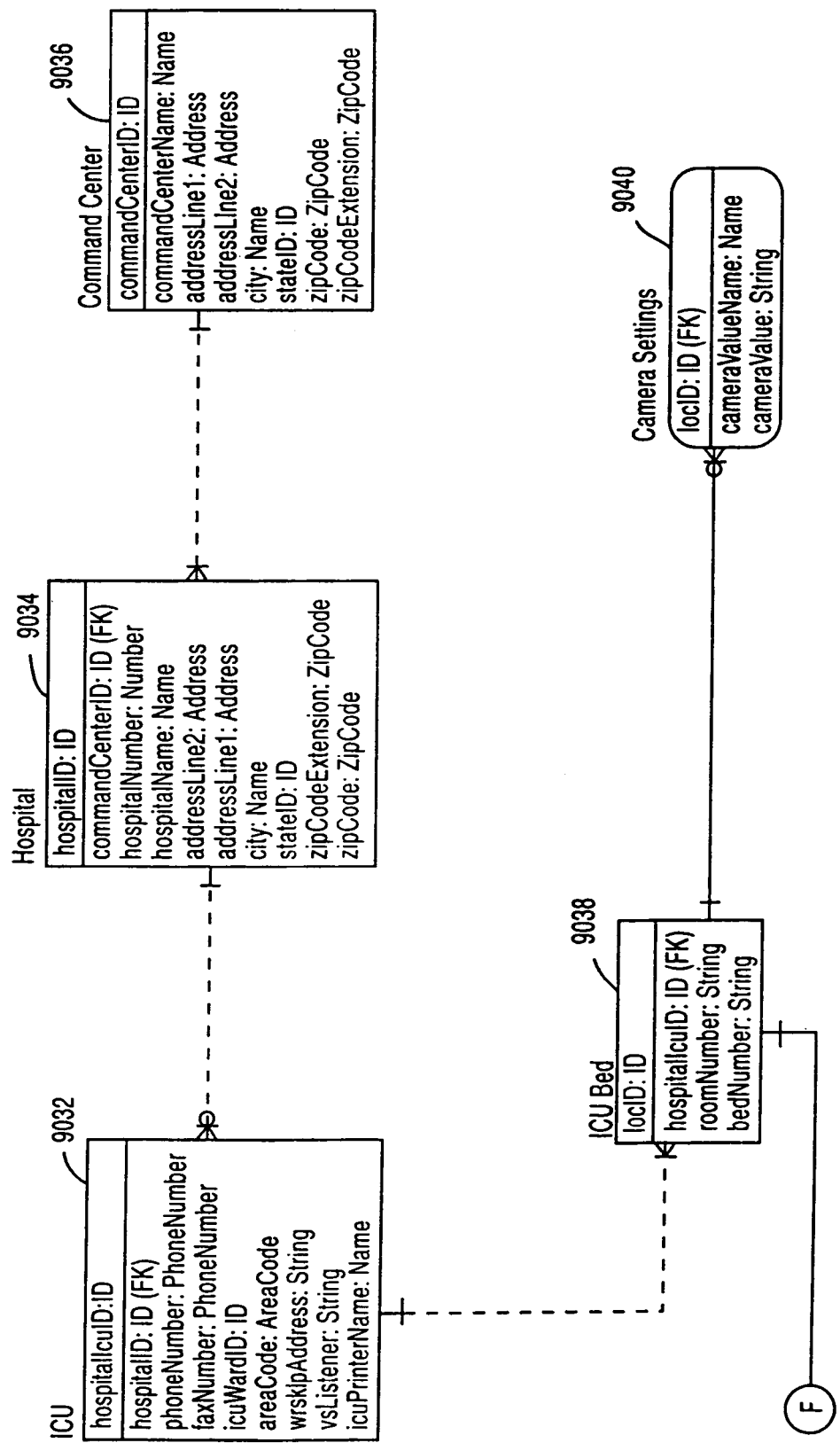
FIG. 2B illustrates the command center logical data structure (cont).

Referring to FIGS. 2A and 2B, the Command Center logical data structure is illustrated. The various information associated with demographic and insurance information is again used to manage the care and operations of the command center. Therefore, communications information 9000 is combined with physician and physician extender (i.e. nurse, LPN and the like) information 9002 and physician role 9004 to be associated with the demographic information 9010. The patient visit information 9017 together with this information is associated with the patient's location which has a unique identifier 9030. Each location ID has patient ID information and visit ID information associated with it.

Referring now to FIG. 2B, the Command Center logical data structure illustration continues. Each ICU bed has an associated location ID which comprises hospital ICU information, room number, and bed number 9038. In addition, and as described earlier, instrumentation such as cameras are also associated with the particular patient. Therefore the camera setting 9040 will have a location ID relating to the ICU bed as well as have camera value settings and associated camera identifier information.

Each ICU bed 9038 is associated with an ICU 9032. Each ICU has information associated with it that uniquely identifies the ICU as being associated with the particular hospital, and having particular phone numbers, fax numbers, work space addresses, and other information, that help to identify the ICU.

As noted above, each ICU is associated with a hospital 9034. Each hospital has a unique identifier, as well as its own name, address, and other identifying information. Further, since each hospital ICU is to be coordinated through a remote command center, information on the remote command center 9036 is associated with the hospital information. Each command center has a unique ID and has associated address information stored as well.

Thus in the Command Center logical data structure, patient ID information 9010 is linked to a patient location 9030 which in turn is associated with an ICU bed 9038 each of which beds are uniquely associated an ICU 9032 which is associated with a hospital 9034 which in turn has the ICU managed by a command center 9036.

An integral part of the system of the present invention is the recording of medical history. Referring to FIG. 3, the logical relationship among data elements for medial history is illustrated. Patient visit information 9017 combined with the physician-physician extender information 9002 is combined with specific note-taking information 9042. The note information comprises the date and time the notes are taken as well as the note type. The note ID is fed information from the medical history item 9044, which has its own unique medical ID associated with it. This information comprises medical text, category of information, and other information relevant to the medical history. As noted, this information for medical history 9044 is associated with a note ID 9042, which in turn is associated with the patient visit and physician information 9017 and 9002.

Figure 4A:
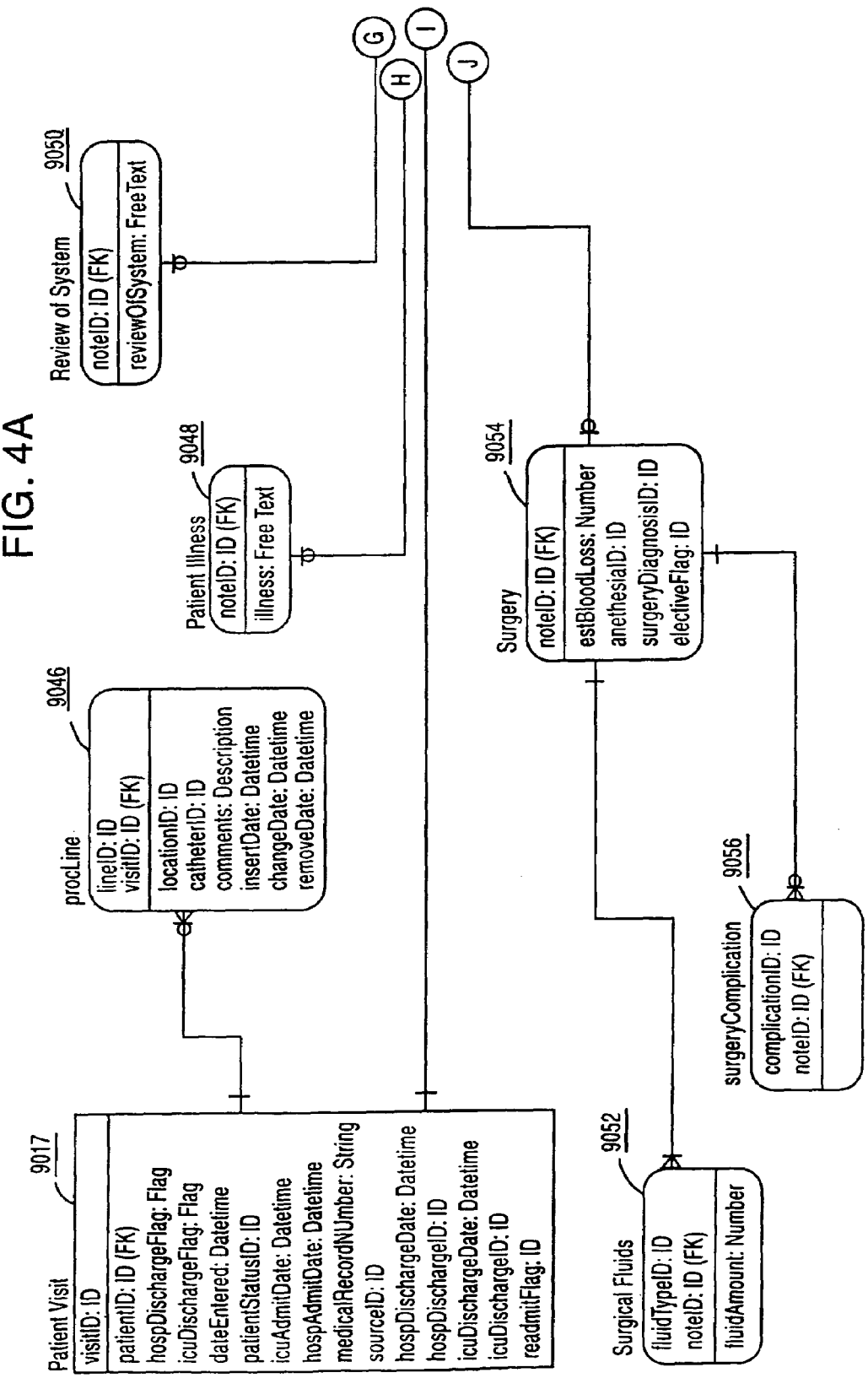
FIG. 4A illustrates the logical data structure for creating notes relating to patient treatment and diagnosis.
Figure 4B:
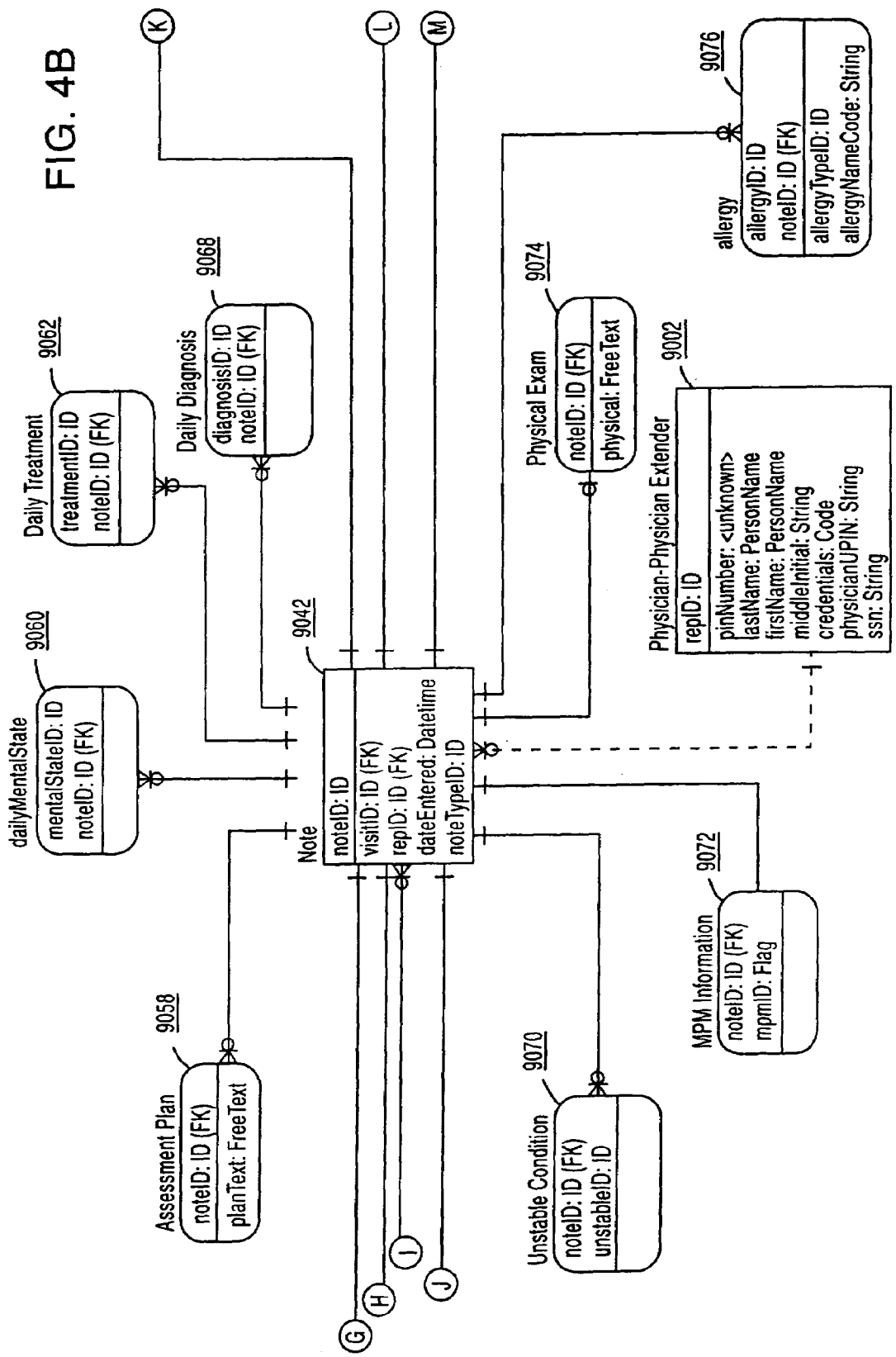
FIG. 4B illustrates the logical data structure for creating notes relating to patient treatment and diagnosis (cont).
Figure 4C:
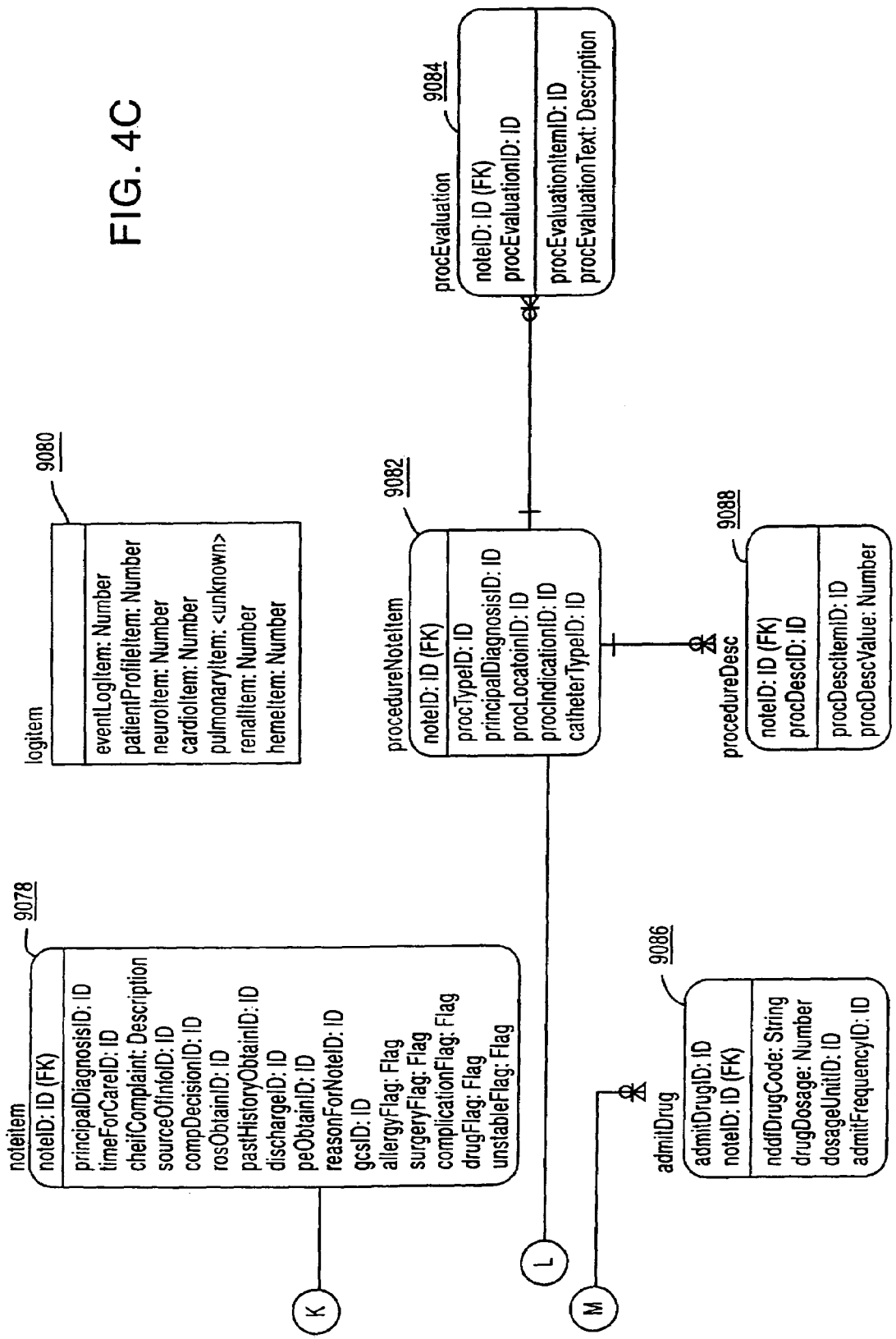
FIG. 4C illustrates the logical data structure for creating notes relating to patient treatment and diagnosis (cont).

Referring to FIGS. 4A, 4B, and 4C, the note-keeping logical data structure of the present invention is illustrated. As noted earlier, the note ID 9042 combines information from visit ID, treating physician, and other information relating to the time the note was entered. Other information is associated with the note ID. Referring first to FIG. 4A, the patient visit information 9017, is associated with the note ID 9042. Various procedural information 9046 is kept by the system of the present invention and is associated with the visit ID 9017. Physicians are able to create free text patient illness notations 9048 and associate them with the note 9042. Similarly, free text information regarding functioning of the system 9050 is permitted and also associated with notes regarding the particular patient and procedure 9042.

Specific notes regarding, for example, surgical procedures are also kept. Surgery notes 9054 are associated with a particular note ID and have such information as anesthesia, surgical diagnosis, elective information, and other related surgical information. Surgical fluids 9052 administered during the course of surgery are associated with the surgery information 9054. Additionally, any surgical complications 9056 are noted and also associated with the surgery which in turn has an associated note ID.

Referring now to FIG. 4B, the logical data structure for notes and its description is continued. An assessment plan 9058 is created and associated with the same note ID for the particular patient. The plan has a free text field that allows a physician to create the appropriate assessment plan and associate it with a note ID 9042.

Various daily notes are also kept and associated with the individual note ID 9042. For example, the daily mental state 9060 is recorded to document the mental state of the patient. The daily treatment 9062 administered to the patient is associated with the unique note ID. The daily diagnosis 9068 is also created and associated with unique note ID 9042.

Any unstable conditions are also noted 9070 and records kept of those conditions. Similarly mortality performance measures (MPM) information 9072 is kept and associated with the unique note ID. To the extent that any physical exam 9074 is administered, that physical exam and any free text created by the physician is associated with the unique ID and records kept. Allergy information 9076 for the particular patient is also created and stored along with the allergy type, and allergy name. This information is uniquely associated with the note ID. Referring now to FIG. 4C, the Logical Data Structure for the Notes Creation and Storage description is continued. A specific note item record 9078 is also kept and associated with unique note ID. This note item comprises the principal diagnosis, the chief complaint, the past history of the patient, the reason for the note, and various other identifications and flags of information which help in documenting the patient's condition.

Any drugs that are administered to the patient, including dosage, type, and number 9086 is kept and associated with the unique note ID 9042.

Procedural note items are also documented 9082. Procedural notes involve the procedural type, the principal diagnosis, the procedural location, procedural indications, and other information of a procedural nature. Procedural description information 9088 is kept as input to the procedural note item. This information is also associated with a procedural evaluation 9084 which comprises text describing the procedural evaluation that occurred, These three items, the procedural description 9088, procedural evaluation 9084, and procedural note items 9082, are all uniquely associated with the note ID 9042.

Figure 5:
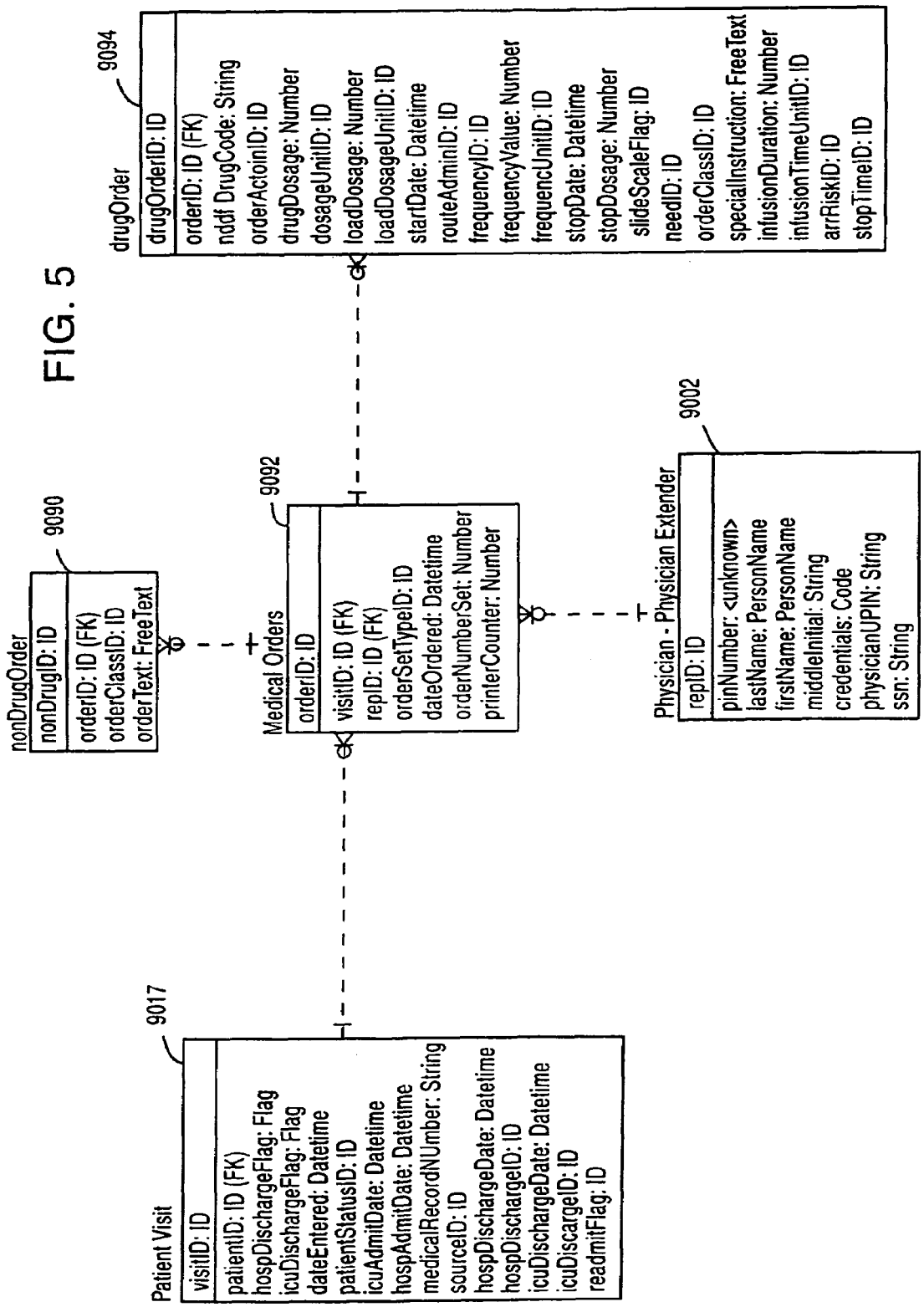
FIG. 5 illustrates the logical data structure for entry of medical orders.

Referring now to FIG. 5, the Logical Data Structure of the Medical Order Functionality of the Present Invention is illustrated. Each medical order 9092 has a unique order ID associated with it. This information derives its uniqueness from the visit ID, the representative ID, and various information about the date in which the order was created and other such relevant information. Any non-drug orders 9090 are associated with a unique non-drug order ID. The order is classified, identified, and free text can be created by the physician to describe the order. This information in the non-drug order 9090 is associated with the unique medical order for that particular patient 9092.

Again physician and physician extender identification information 9002 is also uniquely associated with the medical order to identify the physician involved in creating the particular order in question.

Drug orders 9094 are created each with its own unique drug order ID. Various information is collected as part of the drug order including the type of drug, the dosage, start date, frequency, stop date, to name but a few elements typical of a drug order. The drug order information 9094 is associated with the unique medical order ID 9092 assigned to that particular patient. All of the medical order information is associated with patient visit information 9017 which allows that information to be uniquely identified with a particular patient for a particular visit.

Referring again to FIG. 4C, the system is also capable of annotating and storing various log items 9080. For example, an event log item is given a number, a patient profile item has its own number, as do neurological, cardiographic, pulmonary, renal, and other events can have log items associated with them and may be used as input to any of the note taking of the present invention.

Figure 6A:
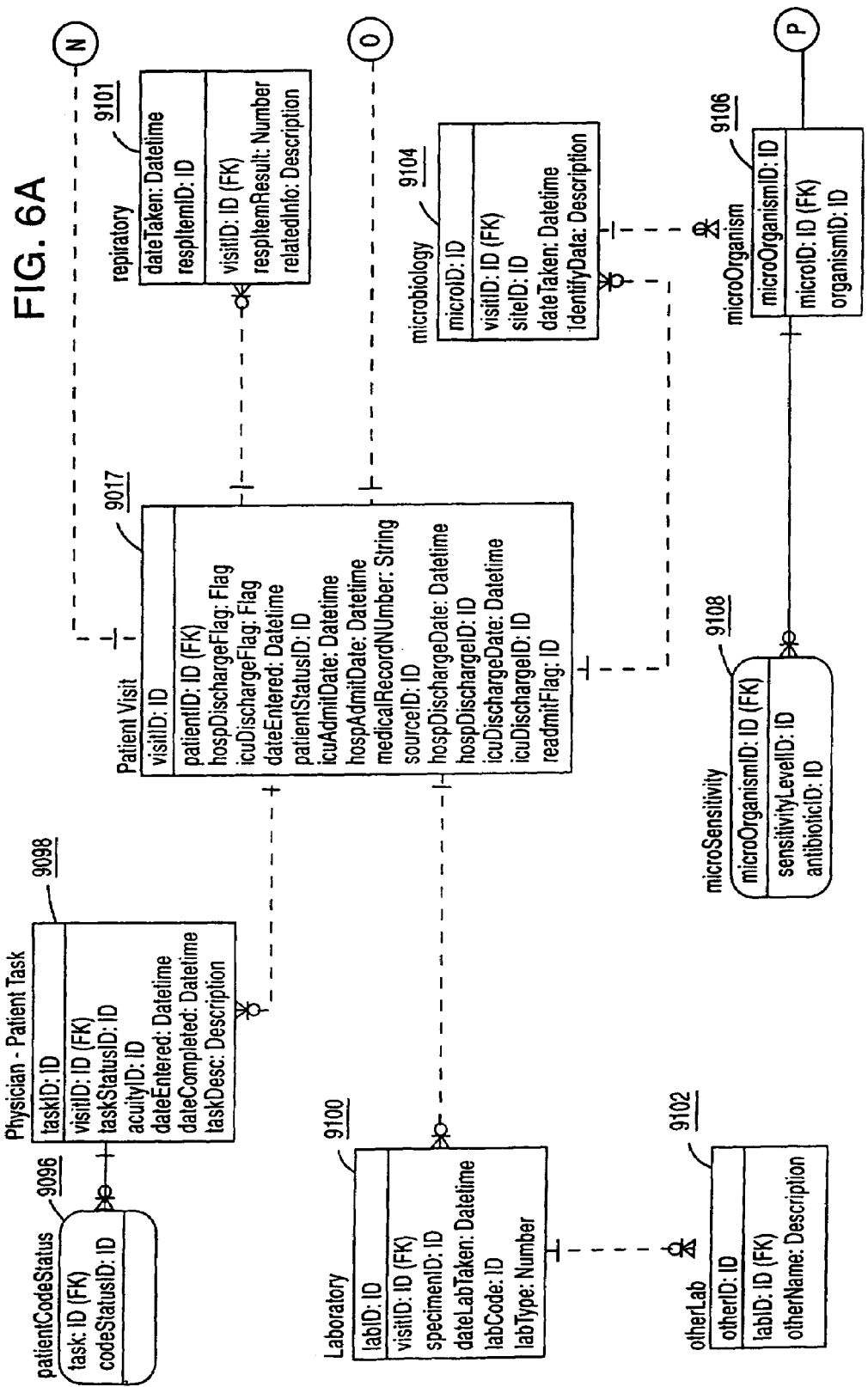
FIG. 6A illustrates the logical data structure for patient care, laboratory testing and diagnostic imaging.
Figure 6B:
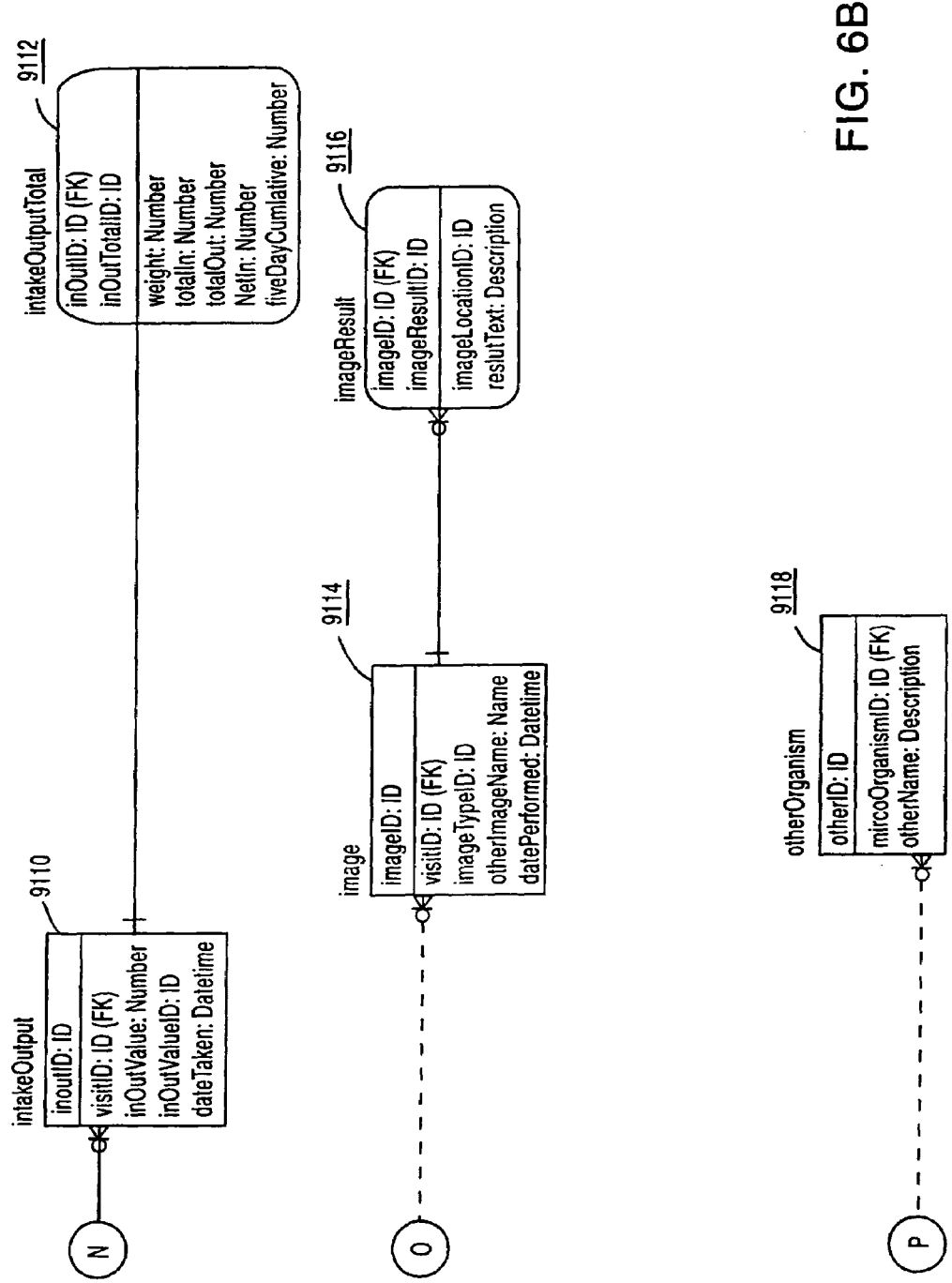
FIG. 6B illustrates the logical data structure for patient care, laboratory testing and diagnostic imaging (cont).

Referring to FIGS. 6A and 6B, the logical data structure of the patient care functionality of the present invention is illustrated. Each patient visit with its unique ID 9017 has a number of other pieced of information associated with it. For example, physician-patient tasks are tracked 9098 and have a unique task ID associated with them. The patient code status 9096 is documented and associated with the physician-patient task 9098 task ID. This information is uniquely associated with the patient visit via the the patient visit ID 9017.

Laboratory information 9100 has a unique lab ID associated with it. That information is keyed to the visit ID and records the specimen taken, the date it was taken, and various other information germaine to the laboratory procedure involved. Other lab procedures 9102 are also documented with another unique ID. "Other" lab ID is associated with the laboratory ID 9100 which again is uniquely associated with the particular patient.

Microbiological studies 9104 are documented together with the date and the date taken and the type of study involved. Any study of microorganisms 9106 is documented with a unique microorganism ID. Micro sensitivities 9108 which record the sensitivity to microorganisms and certain antibiotics is recorded and associated with the microorganism ID 9106. This information in turn is associated with a microbiological study 9104, all of which is associated with the unique patient visit ID 9107.

Respiratory studies 9101 are also recorded with unique identification numbers and a description. This information is again associated with the patient visit ID 9017.

Referring now to FIG. 6B, the logical data structure of the patient care functionality of the Present Invention is further illustrated. Other organism studies 9118 are also conducted to determine any other conditions associated with microorganisms that might exist with the particular patient. This other organism information 9118 is associated with the microorganism studies 9106 which in turn is associated with the microbiology category of information of the present invention 9104.

Various diagnostic imaging also takes place and is recorded. This image information 9114 has unique image ID associated with each image and comprises associated information such as the image type, the date performed, and other information relevant to the diagnostic imagery. The result of the image taken 9116 is also uniquely identified with the image ID and a unique image result ID. This information is associated with the image information 9114 which again is uniquely associated with the patient visit ID.

Various intake and output for the patient's biological functioning is recorded 9110. Intake and output total 9112 is recorded and uniquely associated with the intake/output identification note 9110. Intake/output totals 9112 also comprised the weight the total taken in, the total out, and five-day cumulative totals for biological functioning of the particular patient.

Figure 7:
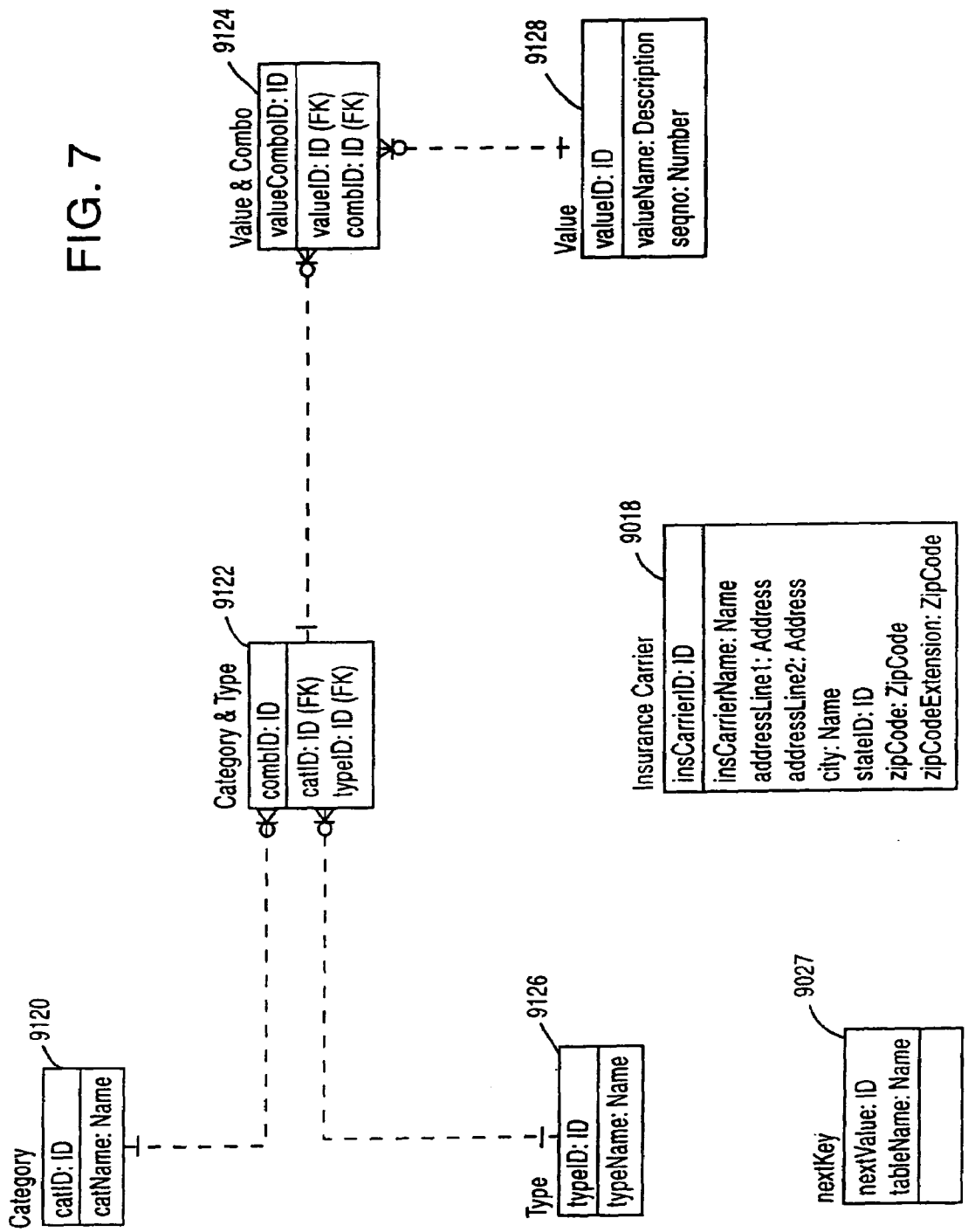
FIG. 7 illustrates the logical data structure for categories of information that are permitted to be presented to intensivists and other care givers by the system.

Referring to FIG. 7, The Logical Data Structure Concern with Reference Information for the present invention is illustrated. This data structure allows only certain ranges of data to be input by care givers into the system. This is accomplished by having categories of information 9120 each category capable of having only certain values. Similarly, each type of data 9126 associated with each category is only permitted to have certain values. This combination of Category and Type results in a Combined ID 9122 which can be used in combination with certain values 9128 to create a value and combination 9124 that can be presented to a care giver viewing and entering data. This effectively limits errors in data entry by only allowing certain values to be entered for given types of data. For example, if only milligrams of a medication are supposed to be administered, this data structure prevents a care giver from administering kilograms of material since it is not a permitted range of data entry. The "nextkey" function 9027 is the function that keeps track of the ID's that are given during the administration of the present invention. This function insures that only unique ID's are given and that no identical ID's are given to two different patients for example.

Figure 8A:
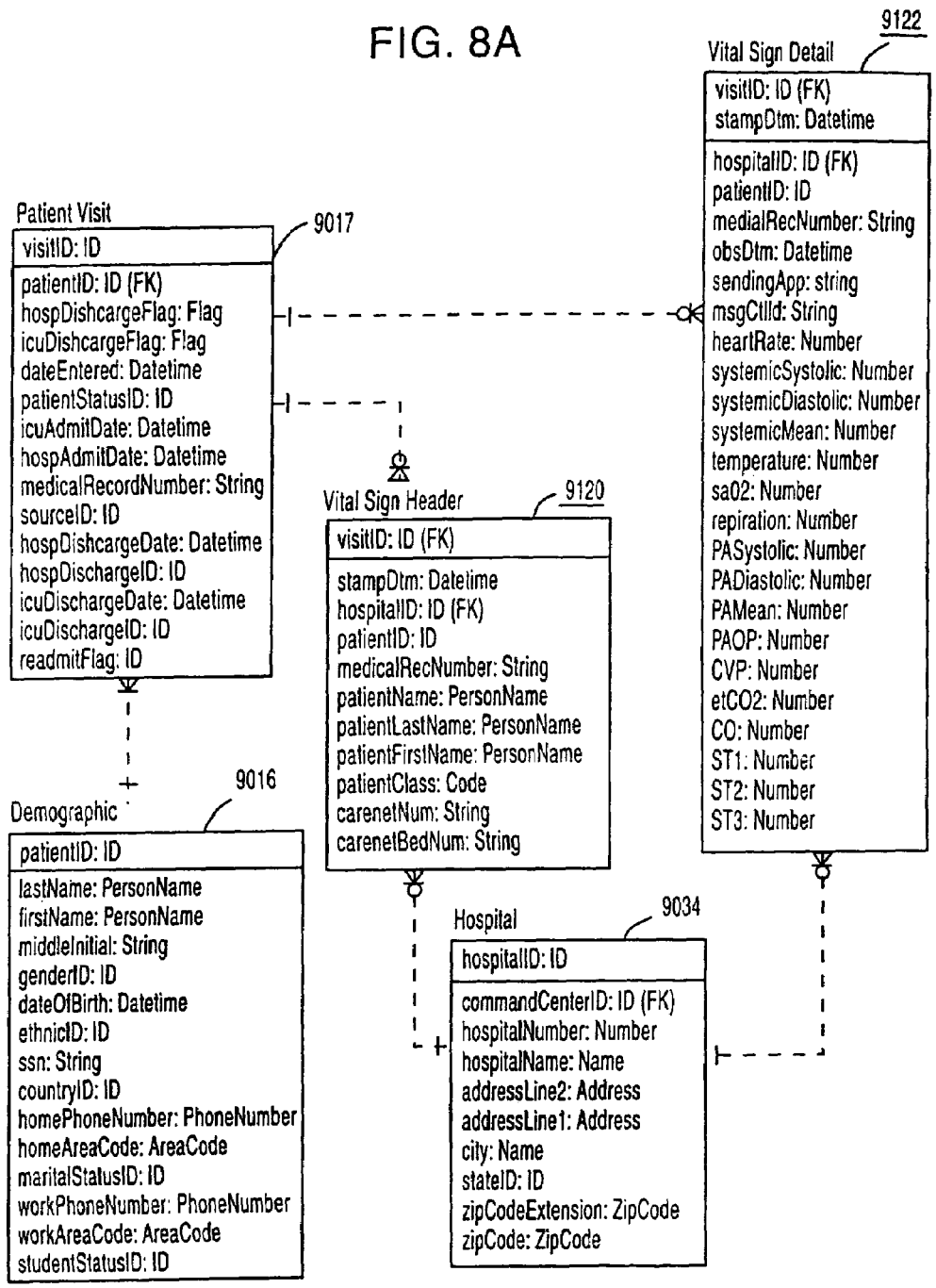
FIG. 8A illustrates the logical data structure for documenting patient vital signs.

Referring to FIG. 8A, the Logical Data Structure of the Vital Signs Functionality of the Present Invention is illustrated. Vital sign header information 9120 is created and uniquely associated with the visit ID for the particular patient. This header information comprises a date-time stamp combined with hospital information, medical reference numbers, and identification of the patient. Vital sign details 9122 are also created and uniquely date-time stamped and associated with the particular visit ID for the patient. This information comprises all manner of vital sign information relating to blood pressure, respiration, and other factors. Vital sign information is associated with the patient visit 9017 and the demographic information concerning the patient 9016. Such associations of information can be the basis for later studies.

Figure 8B:
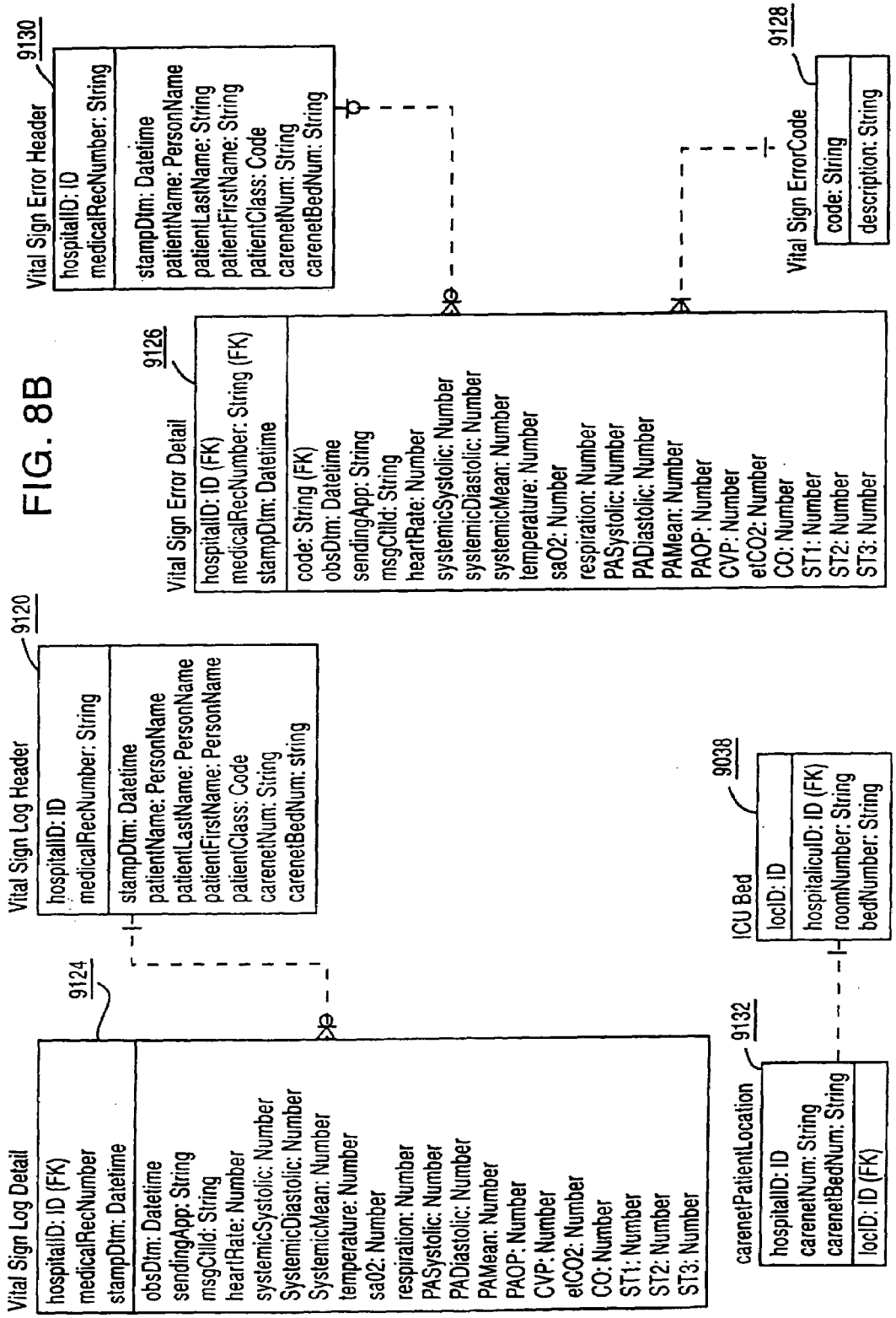
FIG. 8B illustrates the logical data structure for documenting patient vital signs (cont).

Referring to FIG. 8B, Additional Vital Sign Logical Data Structures are illustrated. For example, a vital sign log header 9120 is created using the unique hospital ID and medical record numbers. Other information such a patient name, and date-time stamp are also stored. Vital sign log details 9124 are created and associated with the vital sign log header 9120. For example, blood pressure measurements, respiration, and other factors are all detailed for a particular hospital ID. It should be noted that all vital sign data is logged in and kept by the systems of the present invention. Where vital sign information is received but cannot be associated with a particular patient, such communications are noted as errors.

Vital sign error details 9126 are also recorded and associated with a particular hospital. Information and the vital sign error detail also comprises heart rate, blood pressure, and other information. This information is associated with a vital sign error header 9130 which is associated with the hospital identifier and the patient first and last name and other information. Various vital sign error codes 9128 exist with the present invention and are used in association with the vital sign error detail 9126. This information however relates to communications of vital sign data that are deemed "errors" as noted above.

Care Net patient location 9132 is recorded and associated with a particular hospital ID and location ID for the particular patient. Carenet is a proprietary product designation of Hewlett-Packard and is kept by the system of the present invention since it identifies the equipment from which measurements come. The ICU bed information 9038 is associated with the Care Net patient location 9132.

Figure 9:
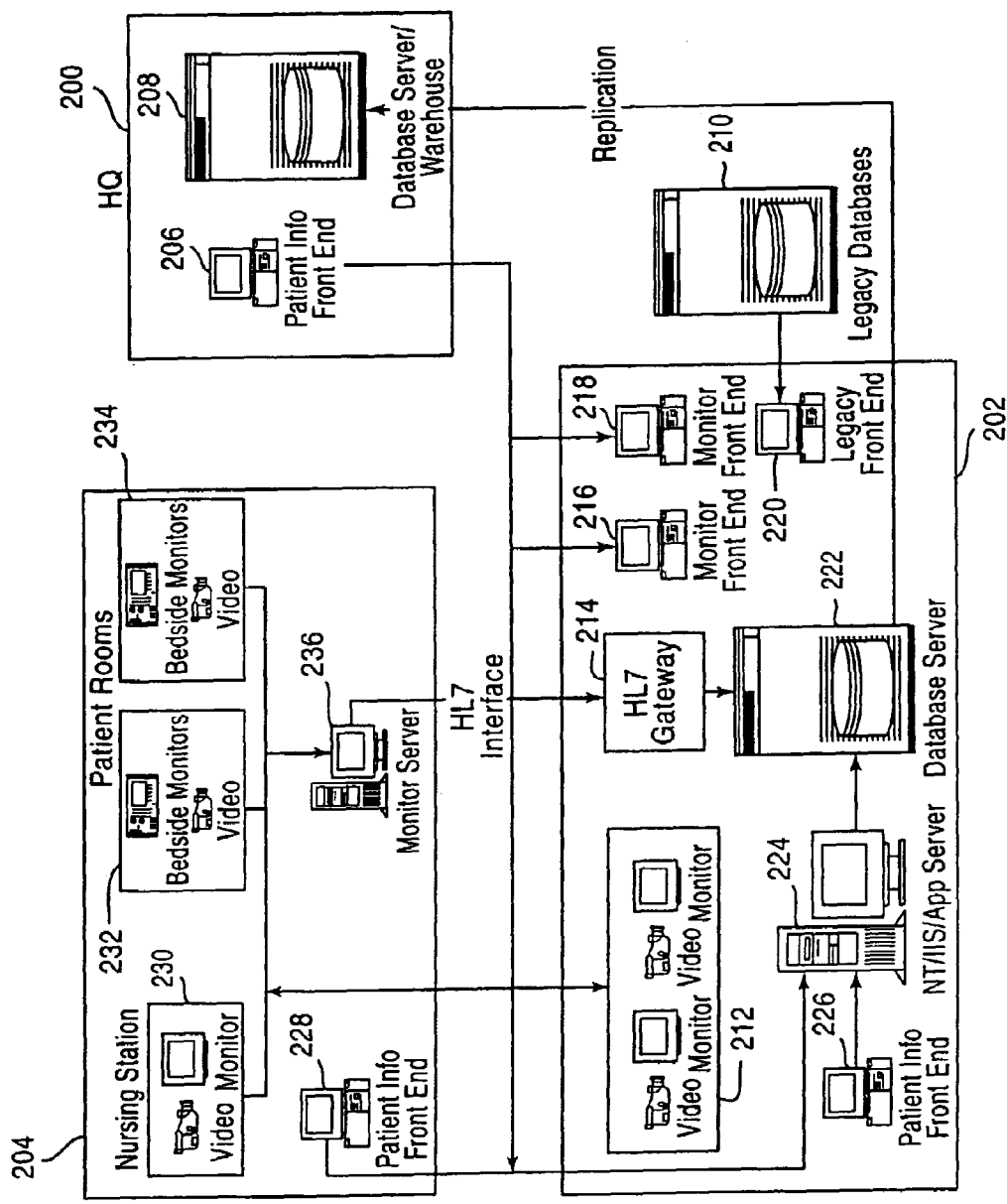
FIG. 9 illustrates the distributed architecture of the present invention.

Referring to FIG. 9, the distributed architecture of the present invention is shown. In concept, the distributed architecture comprises a headquarters component 200, a command center/remote location 202, and a hospital ICU 204, which, while represented as a single hospital in this illustration, in the preferred embodiment comprises several hospital ICUs at different locations. The headquarters unit 200 comprises a database server and data warehouse functionality, together with a patient information front end. The patient information front end 206 provides patient specific information to the command center/remote location. The database server/warehouse function 208 comprises the amassed information of a wide variety of patients, in their various conditions, treatments, outcomes, and other information of a statistical nature that will assist clinicians and intensivists in treating patients in the ICU. The headquarters' function also serves to allow centralized creation of decision support algorithms and a wide variety of other treatment information that can be centrally managed and thereby standardized across a variety of command center/remote locations. Further, the database server/data warehousing functionality 208 serves to store information coming from command center/remote locations replicating that data so that, in the event of a catastrophic loss of information at the command center/remote location, the information can be duplicated at the command center/remote location once all systems are up and running.

At the hospital ICU 204, each patient room 232, 234 has a series of bedside monitors and both video and audio monitoring of each patient in the patient room. Each ICU further has a nurse's station with a video camera and monitor 230 so that videoconferencing can go on between the nurses and doctors at the nursing station and those intensivists at the command center/remote location. The monitoring equipment at the ICU is served by a monitor server 236, which receives and coordinates the transmission of all bedside monitoring and nurses station communication with the command center/remote location. Finally, each ICU has a patient information front end 228, which receives and transmits to the command center/remote location information concerning the identity and other characteristics of the patient.

Command center/remote location 202 comprises its own video capture and monitoring capability 212 in order to allow the intensivists to view the patients and information from the bedside monitoring as well as to have videoconferencing with the nursing station and with patients as the need arises. Information from the monitor server 236 at the hospital ICU is served to an HL7 (the language for transmitting hospital/patient/diagnostic data) gateway 214 to a database server 222. In this fashion, information from the bedside monitors can be stored for current and historical analysis. Monitor front ends 216 and 218 allow technicians and command center/remote location personnel to monitor the incoming data from the patient rooms in the ICU. Information from the patient information front end 228 is provided to an application server 224, having its own patient information front end 226 for aggregating and assembling information in the database 222 that is associated with individual patients in the ICU.

It is expected that there will be a great deal of concurrent hospital data that is necessary to the implementation of the present invention. It is therefore expected that there will be a legacy database system 210 having a front end 220 from which intensivists and command center/remote location personnel can retrieve legacy database information.

Figure 10:
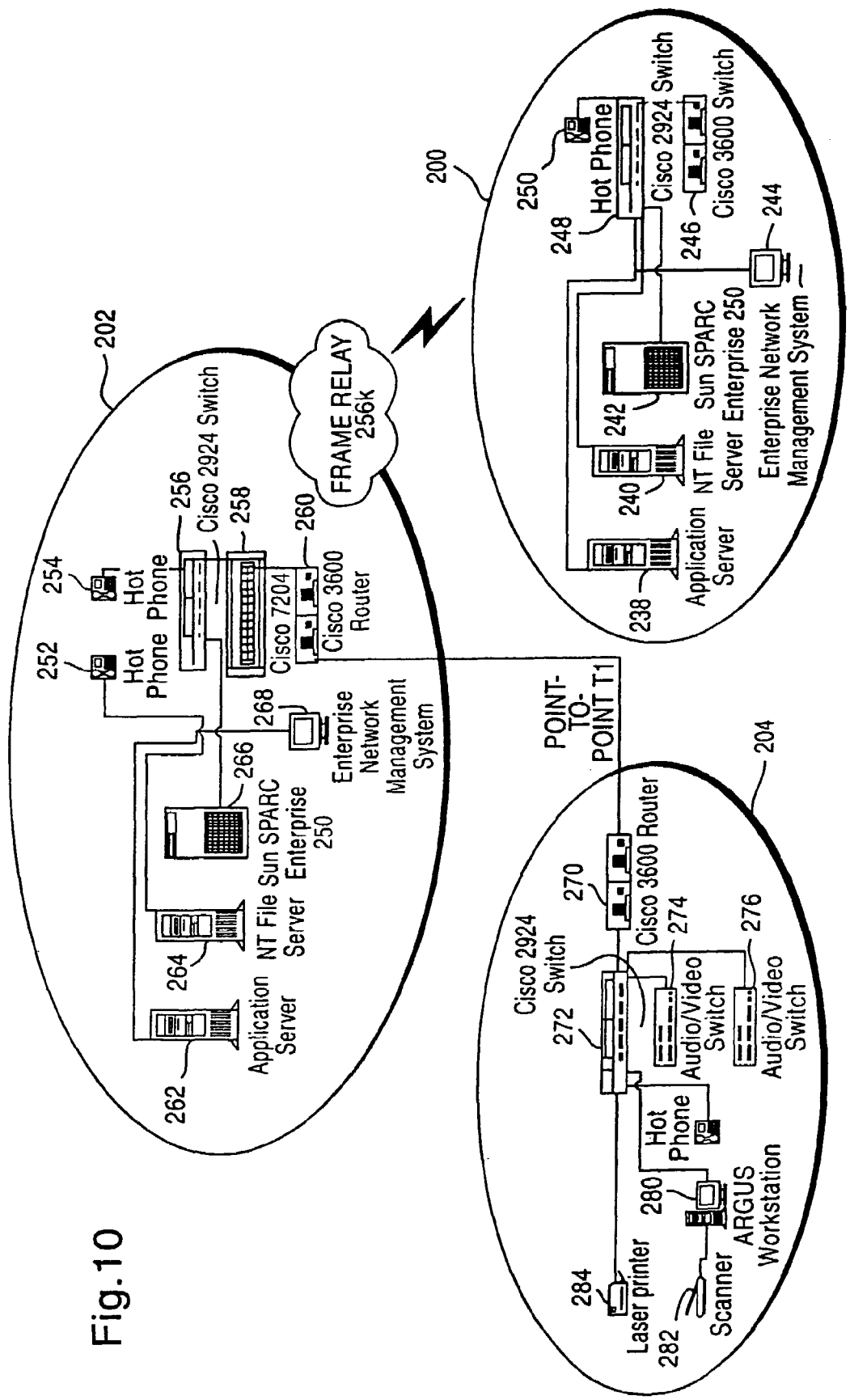
FIG. 10 illustrates the system architecture of the present invention.

Referring to FIG. 10, a system architecture of one embodiment of the present invention is illustrated. Headquarters 200 comprises an application server 238, an NT file server 240, and Sun SPARC Enterprise 250242 and Enterprise network management system 244, a Cisco 3600 router 246, a Cisco 2924 switch 248, and a hot phone 250. The application server 238 is designed to monitor and update those applications used at the command center/remote location. The NT file server serves to monitor, store, and replicate information coming from the command center/remote locations. The SPARC Enterprise 250 server 242 is a disc storage server, for storing and serving information, such as practice guidelines, algorithms, patient information, and all matter of other information records that must be stored in order to support the present invention. As explained below, the SPARC Enterprise 250 server and other components are such as routers and switches are commonly used in the ICU, the command center/remote location, and the headquarters. For example:

The Cisco 3600 router is a multi-function device that combines dial access, routing, and local area network (LAN) to LAN services, as well as the multi-service integration of voice, video, and data in the same device. This is necessary, since the various command center/remote locations, headquarters, and intensive care units all must integrate and transmit video, audio, and data among the various entities.

The Cisco 7204 is a router which provides high speed LAN interconnect, virtual private networks, and Internet access, all of which is required for providing the communication in the network of the present invention; and The Cisco 2924 switch is an autosensing fast ethernet switch, allowing networked multimedia and virtual LAN support. Multi-level security is also offered in the switch to prevent unauthorized users from gaining access and altering switch configuration. These components are also identified in the figures (below).

The particular commercial systems named here are given as but some examples of equipment available today. The function of these equipment is the important factor. Other similar or improved equipment can also be utilized.

The network management system 244 allows the entire traffic and condition of the network to be monitored and to allow maintenance to take place. The router 246 and switch 248 is used for communication with the various command center/remote locations that are served by the Headquarters component. The Headquarters component interacts via frame relay with the command center/remote location 202.

Command center/remote location 202 comprises an applications server 262 for the purpose of running various applications for the intensivists and command center/remote location staff. The NT file server 264 at the command center/remote location allows patient files, historical files, algorithms, practice standards, and guidelines, to be served to the clinicians and intensivists to assist in monitoring the patients. The Sun SPARC Enterprise 250266 is used to for storage purposes as noted above. The Enterprise network management system 268 monitors the overall health of the network of command center/remote locations and intensive care units as well as the functionality of the individual pieces of equipment within the command center/remote location. A Cisco 2924 switch 256 and Cisco 7204 router 258, combined with the Cisco 3600 router 260 allows for point to point communication over a T1 line, with a plurality of intensive care units located remotely from the command center/remote location. Hot phones 252 and 254 allow communication with the headquarters and the intensive care unit.

Figure 11:
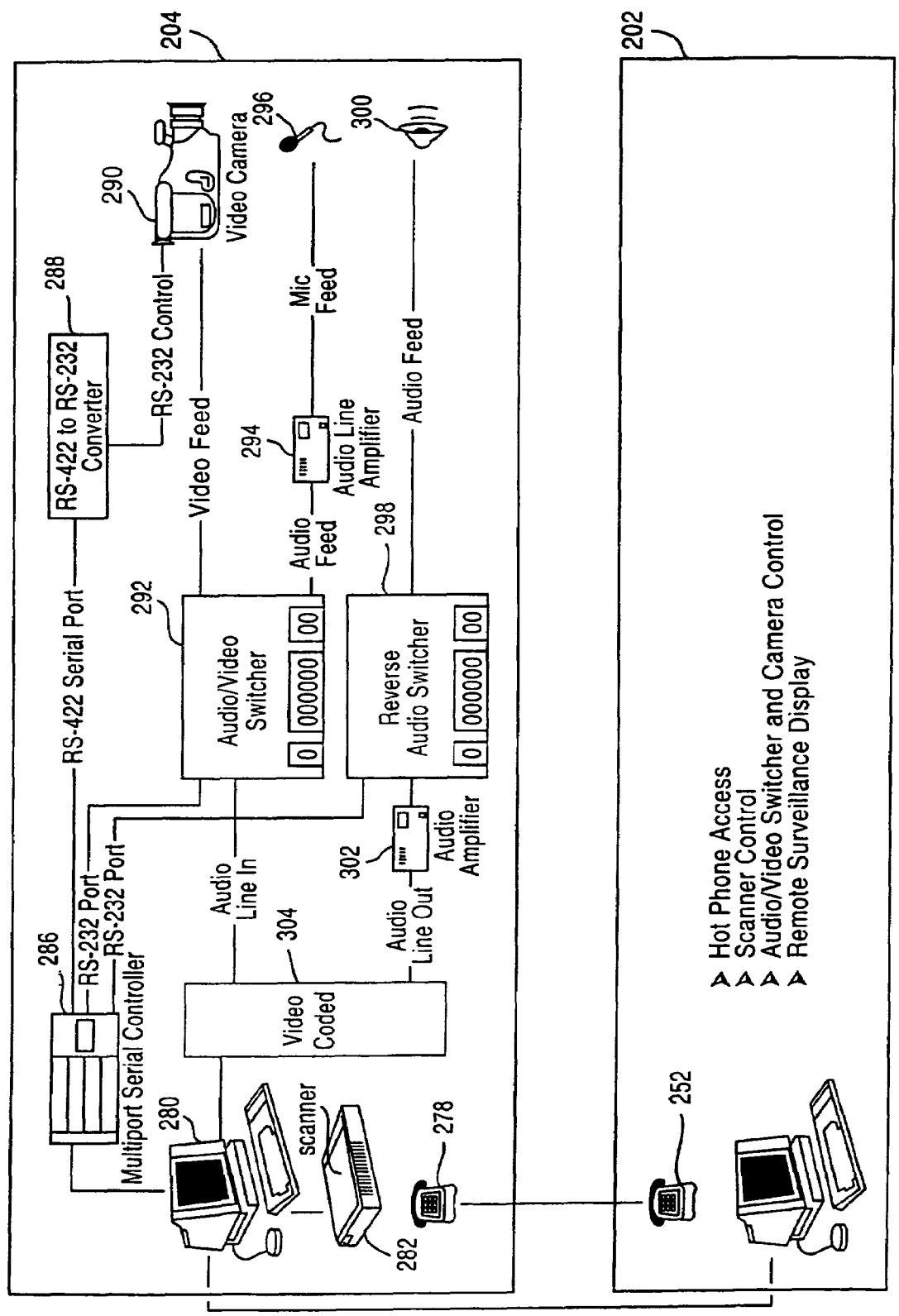
FIG. 11 illustrates the decision support algorithm for diagnosis and treatment of pancreatitis.

Intensive care unit 204 comprises a Cisco 2924 switch 272 for the purpose of interfacing with the various audio-video feeds 274, 276 from the various patient rooms and the nursing station. A local work station 280 is connected to a scanner 282 which allows data to be input, scanned, and communicated via the point to point TI communications to the command center/remote location. Further, the workstation 280 provides for textual advice and patient orders to be delivered to the intensive care unit for execution. The intensive care unit also comprises a laser printer 284 for the printing of patient orders and other information relevant to the care of intensive care patients. Referring to FIG. 11, the videoconferencing/surveillance/imaging components of the present invention are illustrated. The hospital ICU 204 comprises a series of video cameras 290, which are located in patient rooms and at the nurse's station. Control for the cameras is provided through an RS424 to RS232 converter 288, with instructions for imaging emanating from the workstation at the command center/remote location 252 through the ICU workstation 280 through a multi-port serial controller 286. Video feed from the video cameras 290 is provided to an audio-video switcher 292, which in turn provides its output to the multi-port serial controller 286 for subsequent viewing at the nurse's station and at the command center/remote location. Of equal importance is a microphone feed from the patient and from the nurses. That microphone 296 provides its signal to an audio line amplifier 294, which in turn provides an audio feed to the audio-video switcher 292. In this way, a patient can provide information, as can nurses who are visiting the patient during the course of patient care. It is also important that information of an audio nature be fed to the intensive care unit, both to the patient rooms and to the nurse's station. To do this, the multi-port serial controller 286 provides an audio signal to a reverse audio switcher 298, which in turn provides information to speakers 300 that are located at the nurse's station as well as at the bedside of the patients. Information to the reverse audio switcher is provided an audio amplifier 302 from information from a video code 304, which in turn is connected to the workstation at the ICU. As noted earlier, a scanner 282 is provided, so that information can be scanned and provided to the command center/remote location 202 and a hot telephone 278 communicates with a telephone 252 at the command center/remote location.

Referring to FIG. 12 the vital signs data flow is illustrated. The monitoring system at each ICU bedside comprises a monitoring system for monitoring the vital signs for the patient. The vital sign monitoring system 450 captures vital sign data 452 and transmits that vital sign data 454 using the HL7 language (the standard processing language for hospital data and information). The processor at the ICU processes the vital sign data for transmission and storage purposes and transmits that information to the remote location. Vital sign data is then loaded into the data base 458. The data base for each individual patient is then reviewed and process rules are applied 460 to the vital sign data. These process rules relate to certain alarming conditions which, if a certain threshold is reached, provides an alarm to the intensivist on duty. The vital sign alarm 462 is then displaced to the intensivist who can then take appropriate action. A typical type of rule processing of the vital sign data might be if blood pressure remains at a certain low level for an extended period of time, or if heart rate remains high for an extended period of time. In addition a wide range of other rules are provided which will provide an audible alarm to the intensivist before a critical situation is reached.

In addition to the information being provided to the alarming system for the intensivist, the vital sign data 464 is also transmitted 466 into a database warehouse 468 comprising vital sign data 470 from not only the individual patient but from all of the patients being cared for in the ICU. This database warehouse provides the ability to do data mining for trends that can give rise to additional process rules and vital sign thresholding. In addition to the transmission of vital sign data 454 to the remote site, the vital sign data is displayed in real time at the ICU 472.

Figure 13A:
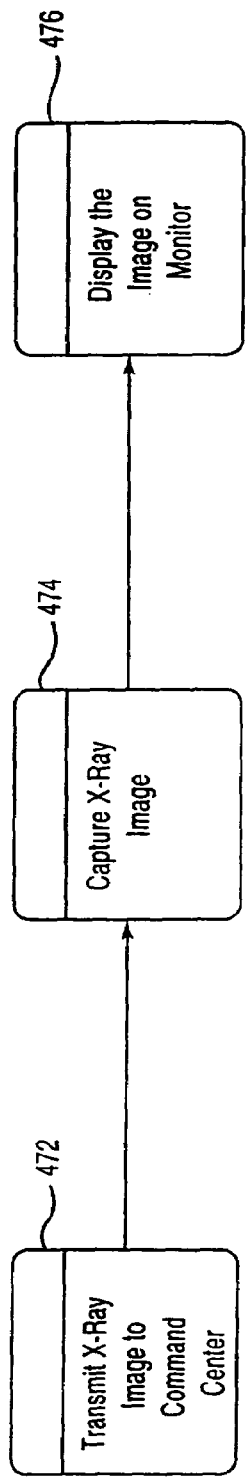
FIG. 13A illustrates capture and display of diagnostic imaging.

Referring to FIG. 13A the diagnostic imaging interaction is illustrated. X-rays for example, are created and transmitted to the command center 472. Additionally, the information could be ACT scan, MRI, or any other method of medical diagnostic imaging. The x-ray image is captured at the command center 474 where it is stored and in addition displayed on the image monitor 476 for the intensivist to review.

Figure 13B:
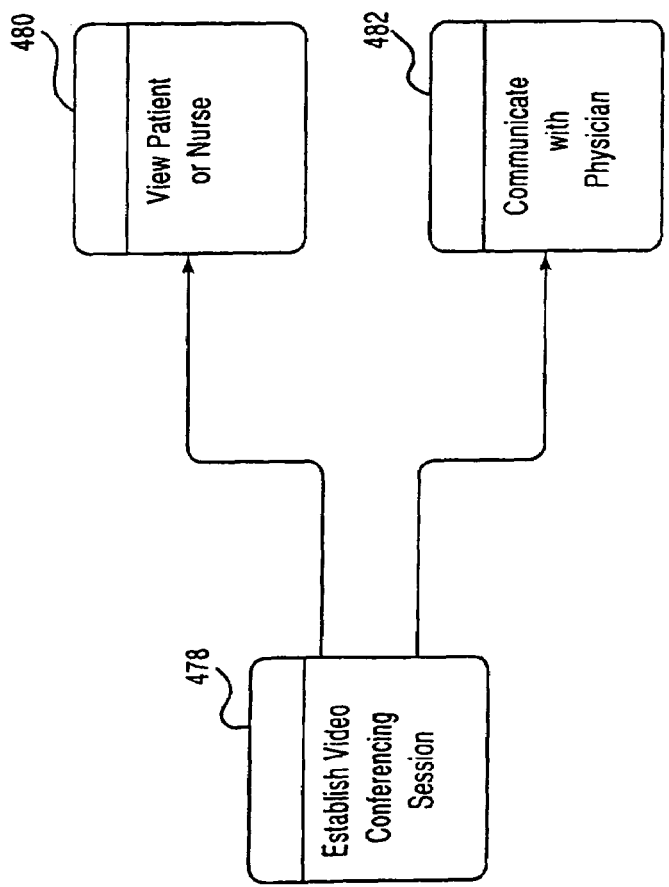
FIG. 13B illustrates establishing videoconferencing in the present invention.

Referring to FIG. 13B the interactive video session is illustrated. A video conferencing session is established 478 regarding a particular patient in an ICU bed. Using the video cameras in each room and/or at the nurses station at the ICU, the patient and/or the nurse can be viewed 480. On the other end of the video conferencing session is the intensivist who can then both visually and orally communicate with the patient and/or nurse 482.

Figure 14:
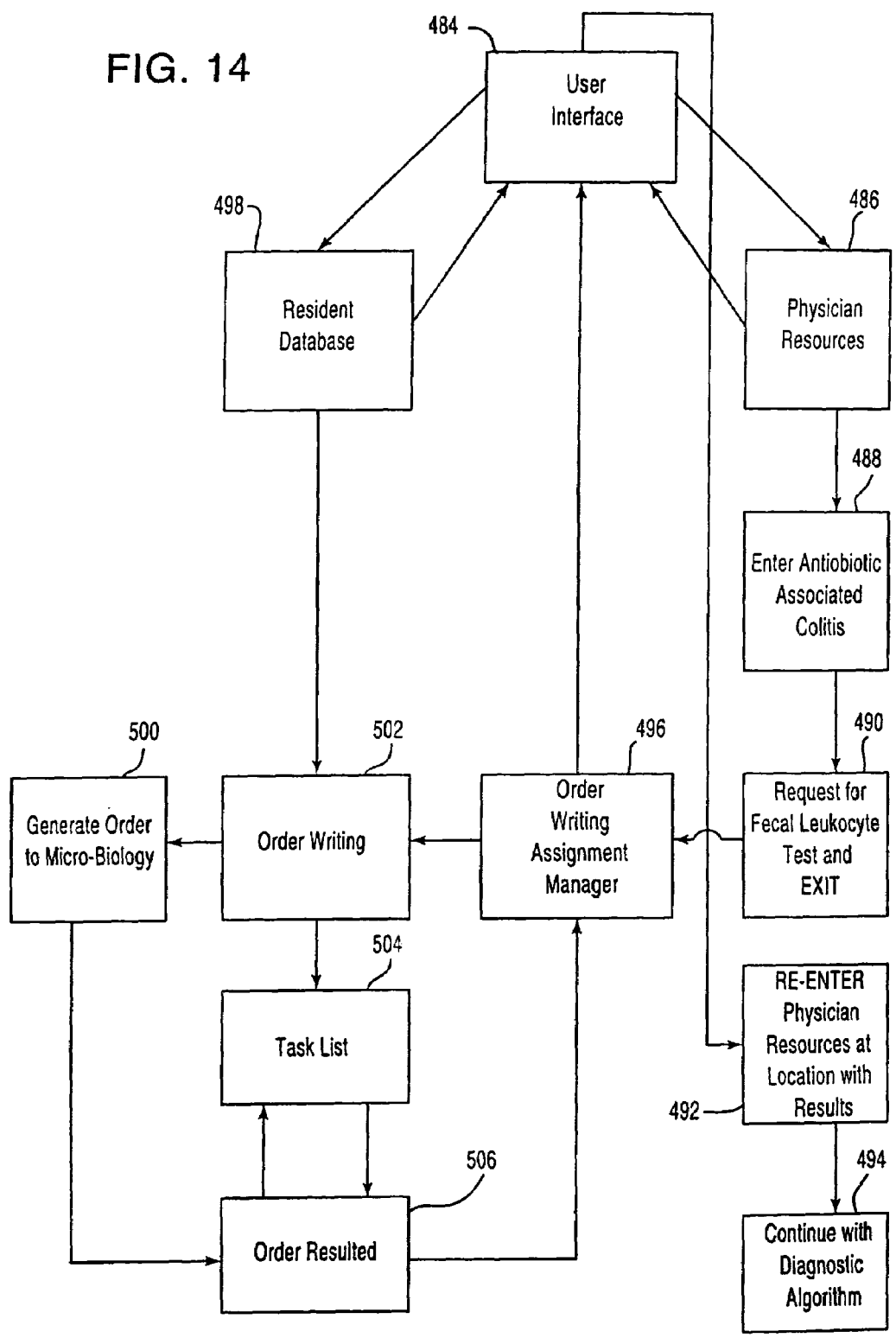
FIG. 14 illustrates the physician resources order writing data interface of the present invention.

Referring to FIG. 14 the physician resources and order writing data interface is illustrated. The user interface 484 allows the physicians to access physician resources 486. These resources provide guidelines for the treatment of the critically ill. In this example the intensivist is requested to enter the antibiotic associated with colitis 488. The system then generates a request for a fecal leukocyte test 490. This request is translated into an order writing module 496 which results in the actual order for the test 502. Since the order needs to be transmitted to the appropriate organization for execution, an appropriate order is generated to the microbiology laboratory 500 in this instance. The order results are then achieved 506 and the completion of the order is reported to the order writing assignment manager 496. In addition, the order writing module 502 also results in a task list 504 of orders for various other individuals in laboratories. In addition, user interface 484 allows the physician to re-enter the physician resources module at any particular location with results of the tests. These tests are then fed into the system to continue with the diagnostic algorithm processing of the patient test results 494. The user interface also allows interaction with the resident database 498.

Figure 15:
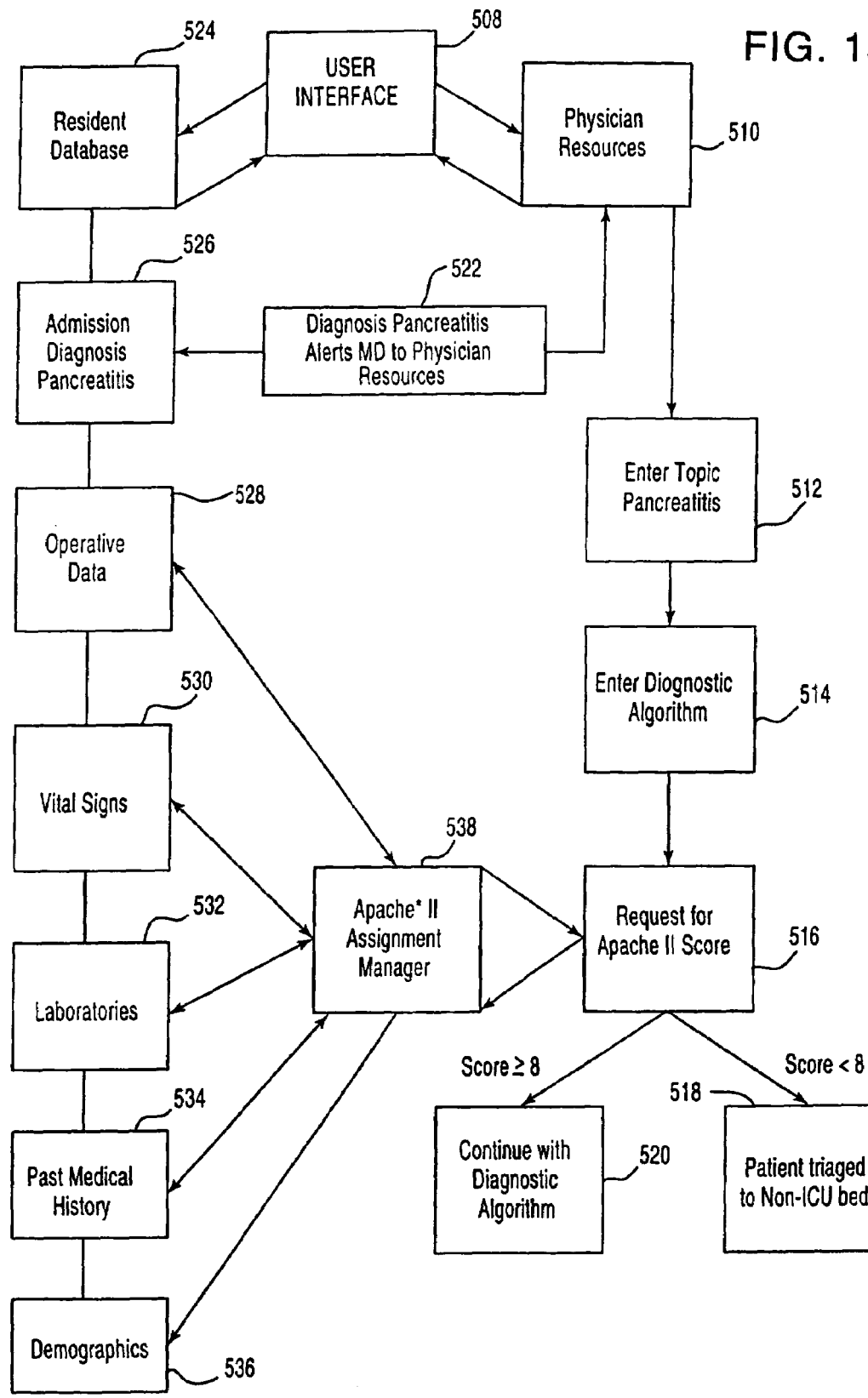
FIG. 15 illustrates the physician resources database data interface of the present invention.

Referring to FIG. 15 the physician resources database data interface is illustrated. User interface 508 allows the intensivist to interact with the physician resources data base 510. In this example, resident data base 524 which comprises the identification and background of the resident admitting the patient causes an admission diagnosis 526 to be created. In this example a diagnosis of pancreatitis is illustrated. This diagnosis of pancreatitis 522 alerts the physician resources module 510 which causes an entry for the topic pancreatitis 512. The diagnosis algorithm for pancreatitis 514 is then retrieved and a request for an Apache II score 516 is requested. The system also requests information for operative data 528 describing what if any operations have taken place with respect to this patient, vital sign data 530, request for laboratory information 532, past medical history for the patient 534 and patient demographics 536. All this information is provided to the Apache II score assignment manager 538 which assigns an Apache II score based upon weighted composite up to twenty five different variables. This Apache II score is provided to the Apache II score request module 516. If the severity based Apache II score is greater than or equal to eight the diagnostic of the system continue 520. If the Apache II score is less than eight, the patient is triaged to a none ICU bed 518 since the patient will not necessarily require intensive care thereby saving relatively scarce resources of the ICU for those who are truly critically ill.

Figure 16:
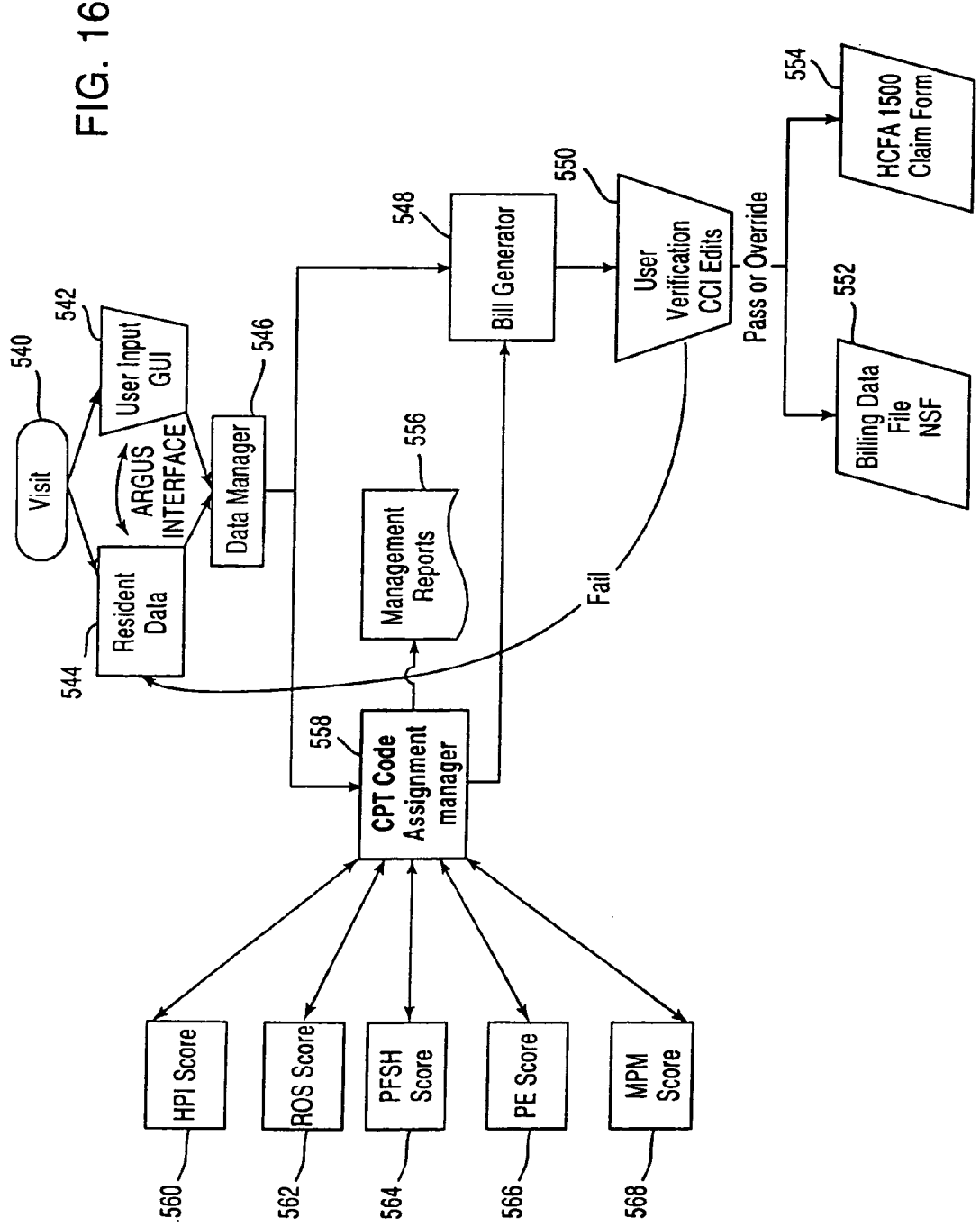
FIG. 16 illustrates the automated coding and billing system integrated with the workflow and dataflow of the present invention.

Referring to FIG. 16 the automated coding/billing work flow and data flow is illustrated. Clearly ICUs must be paid for the care that they give. At the outset of the visit 540 the user interface 542 allows for the input of International Classification of Diseases, Ninth Revision (ICD 9) diagnosis code information concerning complexity of the case, whether the patient is stable, whether the physician involved is the attending physician or consulting physician and all other manner of information required for billing purposes. In addition, resident data 544 is input such as patient demographics, insurance information, physician, guarantor, the date that the service is provided. All this information is provided to the data manager 546 which assembles the required data element for subsequent processing. The data manager sends the demographic, physician, guarantor, insurance and related information to a bill generator 548 which begins to assemble of the information to subsequently generate a bill. Clinical information is provided to the current procedural terminology (CPT) code assignment manager which assigns codes based upon the scores and user input for bill generation purposes. A history of present illness (HPI) score 560 is generated along with a review of systems (ROS) score 562. A past, family, and/or social history (PFSH) score 564 is generated along with a score relating to the physical exam 566. A mortality prediction model (MPM) score 568 which is a score relating to the severity of the illness is also generated. All of these various scores are provided to the CPT assignment manager 558. Periodically information is downloaded for management reports 556. Once all of the information for the CPT code assignment is generated that information is provided to the bill generator 548 which assembles all the data elements needed to generate a Health Care Financing Administration (HCFA) 1500 claim form. The input for the bill generator is then verified 550 where the physician can disagree with code assignments return progress notes and generally review the bill. This smart processing of the HCFA 1500 claim form allows for fewer mistakes to be made. If there is any error or additional information that is required, the verification process fails the proposed claim form and information regarding that failure is provided back to the resident data for completion of any missing items. Once an invoice has been verified as having the appropriate information to be submitted the HCFA 1500 claim form is generated 554. Additional information is written to a billing data file 552 for importation to the patient accounting system of the present invention.

Figure 17:
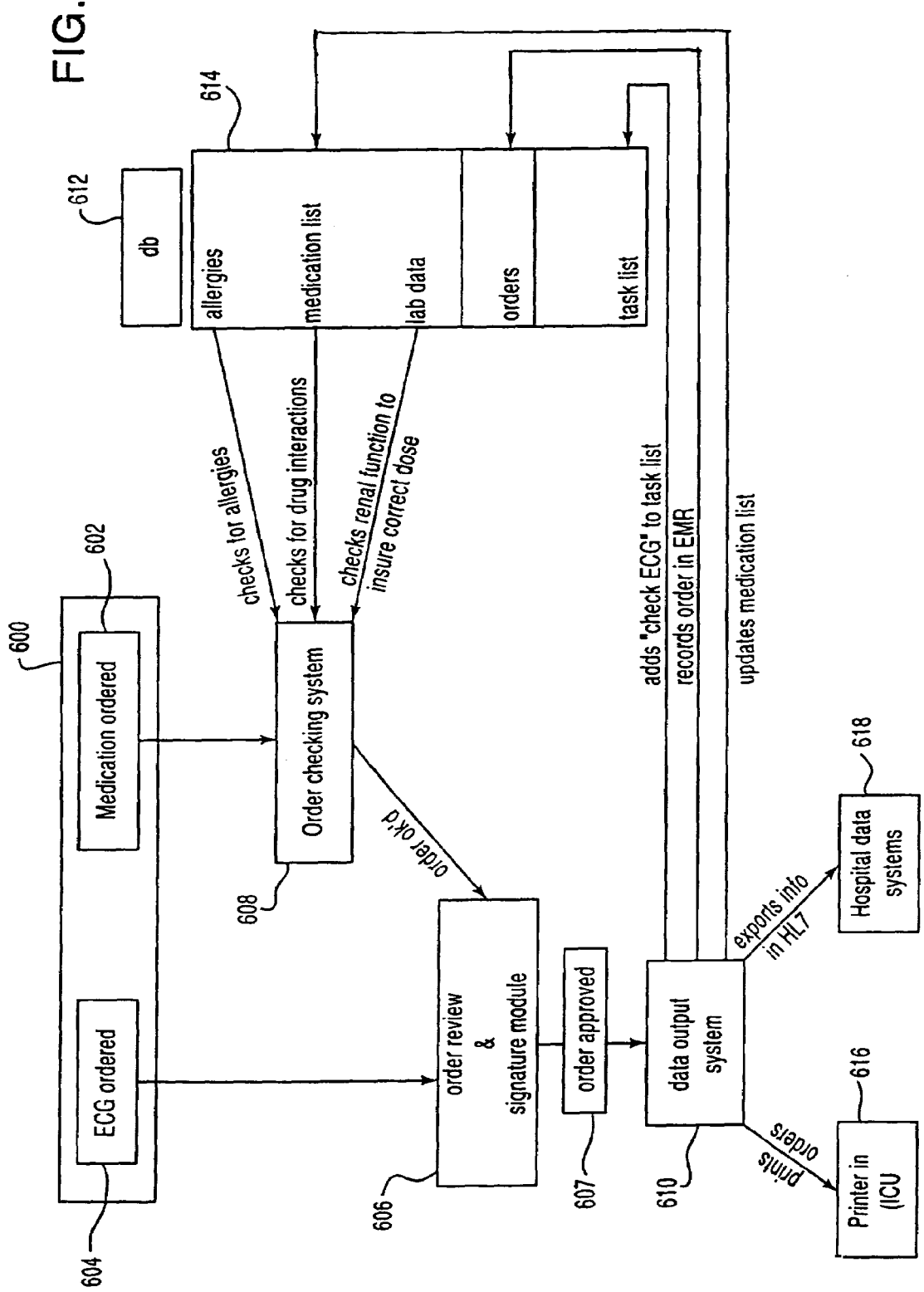
FIG. 17 illustrates the order writing data flow of the present invention.

Referring to FIG. 17 the order writing data flow is illustrated. Order entry user interface 600 allows the intensivist to order procedures and medication to assist the patients in the ICU. For example, the intensivist can order an ECG 604. Thereafter the order is reviewed and a digital signature relating to the intensivist is supplied 606. Once reviewed and signed off, the order is approved 607 and sent to the data output system 610. Thereafter the data output system prints the order to the printer in the ICU 616. For record keeping purposes the order is exported in the HL7 language to the hospital data system 618. In addition the data output system adds an item to the data base that will subsequently cause an intensivist to check the ECG results. This notification to the task list is provided to the database 614. In addition, as part of the database an orders file relating to the specific patient is also kept. The fact that and ECG has been ordered is entered in the orders file for that patient.

In a similar fashion using the order entry user interface 600 the intensivist can order medications 602 for a patient. The medication order then is provided to an order checking system 608. The order checking system retrieves information from the database 614 relating to allergies of the patient and medication list which includes medications which are already being administered to the patient. This allows for the order checking system to check for drug interactions. Further laboratory data is extracted from the database 614 and the order checking system checks to insure that there will be no adverse impact of the recommended dosage upon the renal function of the patient. Once the order checking system 608 is completed, the order is okayed and provided to the order review and signature module 606. In this module the digital signature of the intensivist is affixed to the order electronically and the order is approved 607. Thereafter it is provided to the data output system 610 where again the orders are printed for ICU and 616 and for the hospital data system. In this case, any medications that are ordered are then provided to the medications list file in the database 614 so that the complete list of all medications that are being administered to the ICU patient is current.

Figure 18:
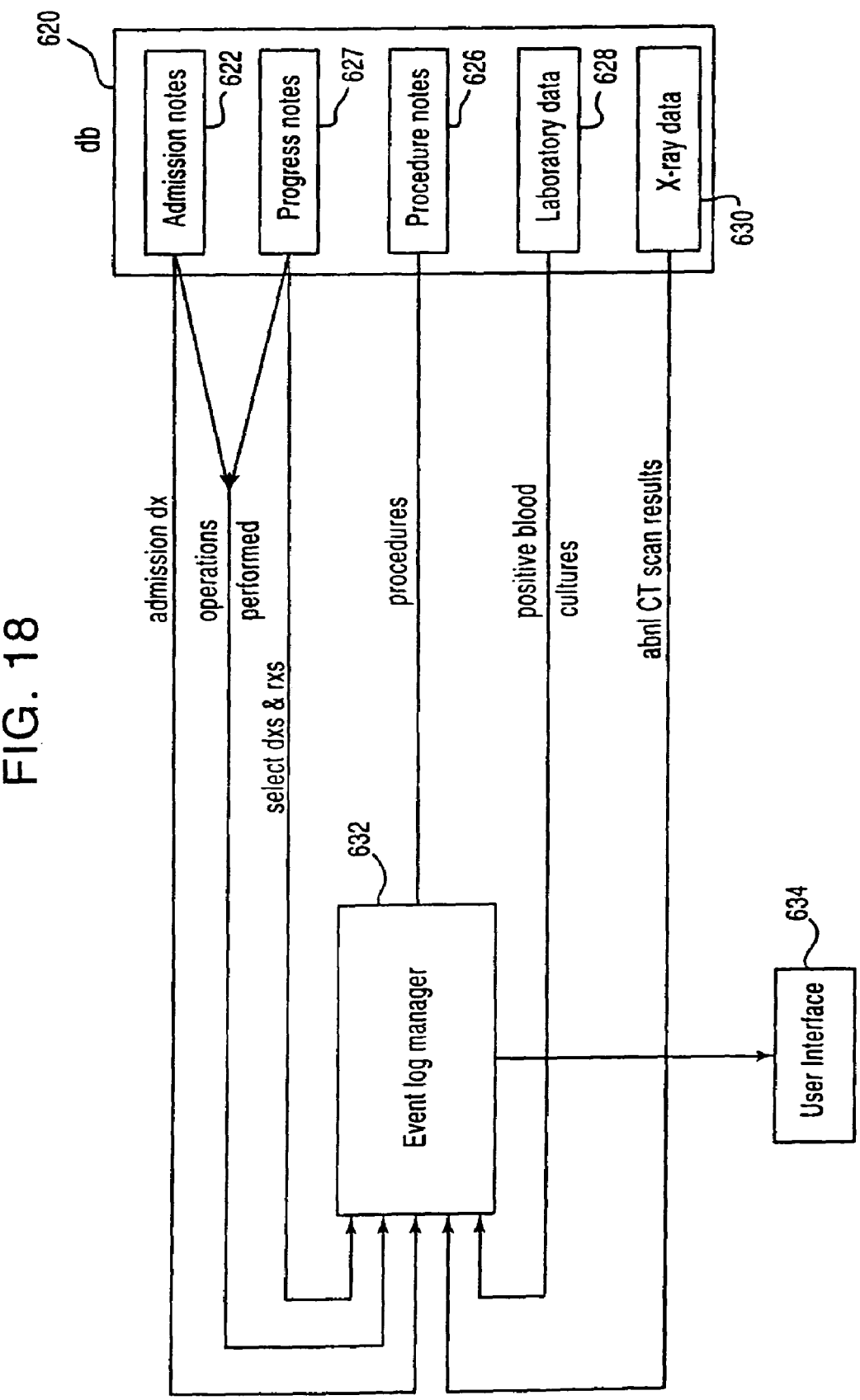
FIG. 18 illustrates the event log flow of the present invention.

Referring to FIG. 18 the event log is illustrated. The database 620 contains all manner of notes and data relating to the particular patient that is admitted to the ICU. For example, admission notes 622 are taken upon admission of the patient and stored in the file that is specific to that patient. Progress notes 624 are created during the patients stay within the ICU to note the progress the patient is making giving the various treatments. Procedural notes 626 are also created by the intensivist to note what procedures have taken place and what if any events have occurred associated with those procedures. Laboratory data such as positive blood cultures are also stored in the file 628 in the database 620. Further x-ray data 630 and abnormal CT Scan results are stored in the database.

The result of these individual files are then provided to an event log manager 632. For example, admission notes might contain operations performed. Progress notes 624 might relate to the operations preformed. This information is provided to the event log manager 632. Admission information is also input to the event log manager as are a listing of the procedures administered to the patient. To the extent there are positive blood cultures in the laboratory data 628 those are provided to the event log manager 632 as are abnormal CT scan results. All of this information is made available through the user interface 634. Thus the event log presents in a single location key clinical information from throughout a patients stay in the ICU. The event log user interface provides caregivers with a snapshot view of all salient events since admission. All relevant data on procedures and laboratory tests, etc. are presented chronologically.

Figure 19:
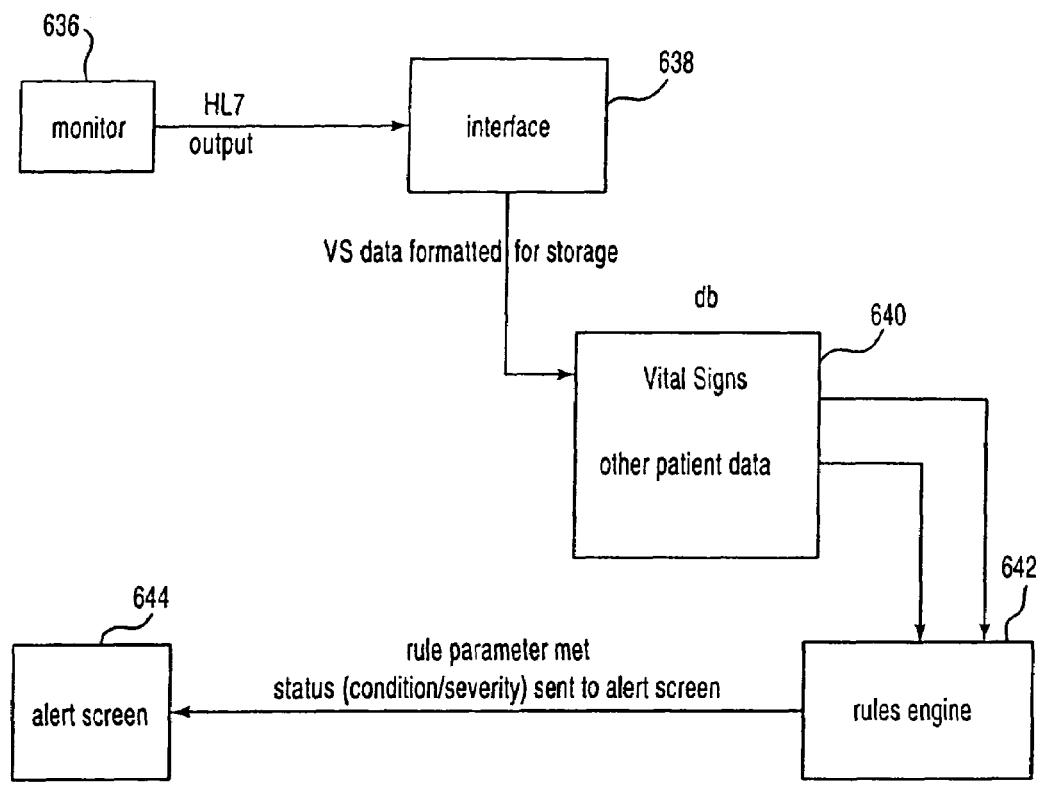
FIG. 19 illustrates the smart alarms implementation of the present invention.

Referring to FIG. 19 the smart alarms of the present invention are illustrated. The smart alarm system constantly monitors physiologic data (collected once per minute from the bedside monitors) and all other clinical information stored in the database (labs, medications, etc). The periodicity of the collection of data is stated for illustrative purposes only. It is well within the scope of the present invention to collect physiological data at more frequent time intervals. Thus, monitor 636 provides information in HL7 form to the interface engine 638. The physiological data is then formatted by the interface engine for storage in the database 640 where all patient information is maintained. The rules engine 642 searches for patterns of data indicative of clinical deterioration.

One family of alarms looks for changes in vital signs over time, using pre-configured thresholds. These thresholds are patient-specific and setting/disease-specific. For example, patients with coronary artery disease can develop myocardial ischemia with relatively minor increases in heart rate. Heart rate thresholds for patients with active ischemia (e.g. those with unstable angina in a coronary care unit) are set to detect an absolute heart rate of 75 beats per minute. In contrast, patients with known coronary artery disease in a surgical ICU have alarms set to detect either an absolute heart rate of 95 beats per minute or a 20% increase in heart rate over the baseline. For this alarm, current heart rate, calculated each minute based on the median value over the preceding 5 minutes, is compared each minute to the baseline value (the median value over the preceding 4 hours). Physiologic alarms can be based on multiple variables. For example, one alarm looks for a simultaneous increase in heart rate of 25% and a decrease in blood pressure of 20%, occurring over a time interval of 2 hours. For this alarm, thresholds were initially selected based on the known association between changes in these two variables and adverse clinical events. Actual patient data were then evaluated to determine the magnitude of change in each variable that yielded the best balance between sensitivity and specificity. This process was used to set the final thresholds for the rules engine.

Alarms also track additional clinical data in the patient database. One alarm tracks central venous pressure and urine output, because simultaneous decreases in these two variables can indicate that a patient is developing hypovolemia. Other rules follow laboratory data (e.g. looking for need to exclude active bleeding and possibly to administer blood).

The purpose of the rules engine is to facilitate detection of impending problems and to automate problem detection thereby allowing for intervention before a condition reaches a crisis state.

Figure 20:
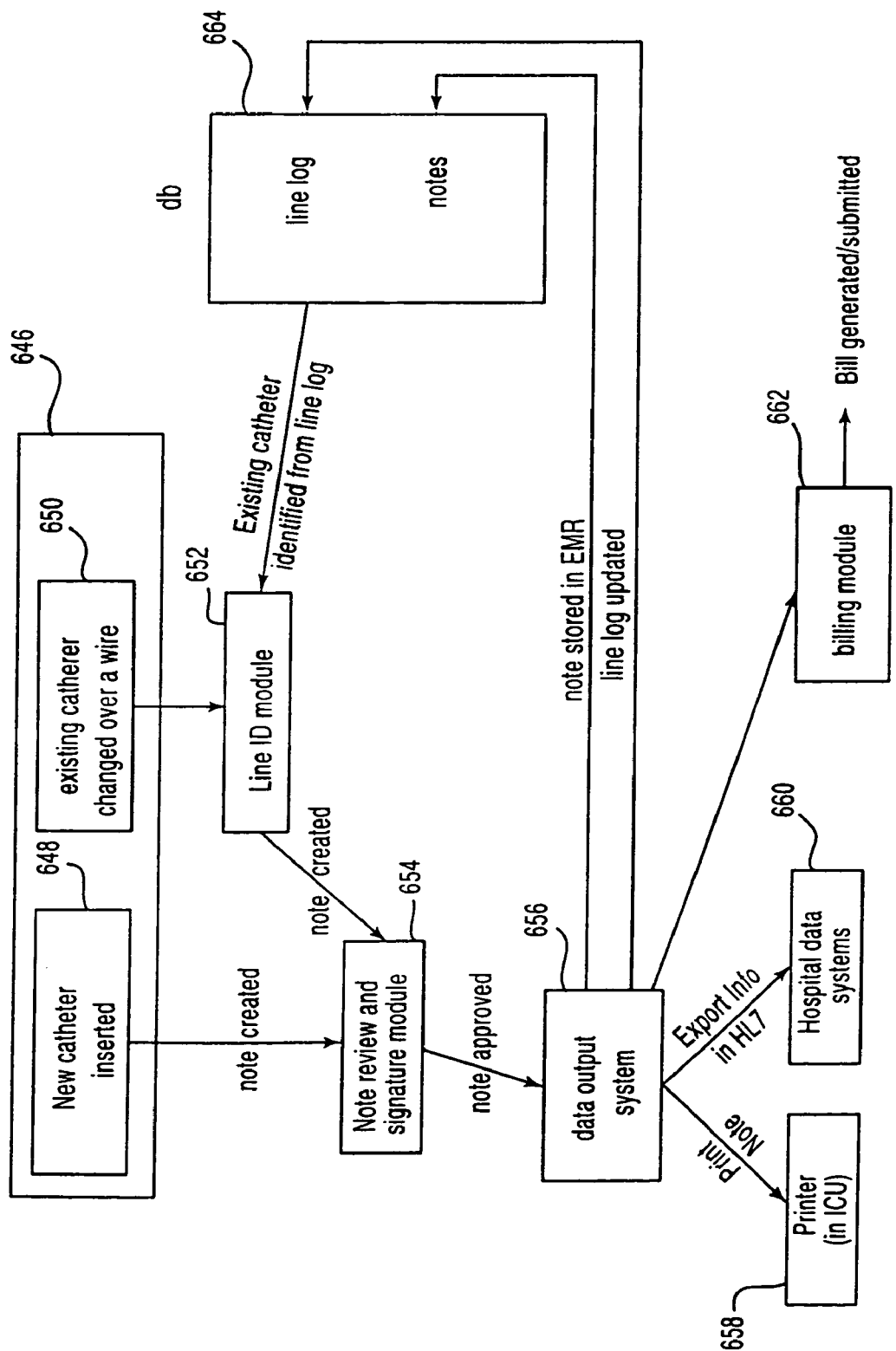
FIG. 20 illustrates the procedure note creation and line log for the present invention.

Referring to FIG. 20 the procedural note-line log is illustrated. This log allows clinicians to evaluate the likelihood that a given procedure might result in further complications. In this example presented in this FIG. 20 a catheter removal is illustrated. When a new catheter is inserted in a patient 648 a procedural note is created on the procedure note creation user interface 646. The note is reviewed and a digital signature is attached to the note to associate the note with a particular intensivist 654. The procedure is then approved and is provided to the data output system 656. The procedural note is then printed on the printer in the ICU 658 and is exported in HL7 language to the hospital data system 660. In addition, this also triggers a billing event and the data output system provides appropriate output to the billing module 662 to generate an invoice line item. In addition, the note is stored in the emergency medical record associated with the patient in the database 664. In addition, the line log is updated in the database 664 to show what procedure was administrated to a patient at what time. If there is an existing catheter, that is displayed to the intensivist at the procedure note creation user interface 646. This would show an existing catheter changed over a wire 650. That information is provided to the line id module 652 which extracts information from the line log in the database 664. This information results in a note being created and provided to the note review and signature module 664. Thus the line log contains, for each patient, relevant information about all in-dwelling catheters, including type and location of the catheter, insertion date, the most recent date that the catheter was changed over a wire, and the date the catheter was removed. This information helps clinicians evaluate the likelihood that a given catheter is infected and guides its subsequent management of that procedure.

Evidence-Based Guidelines, Algorithms, and Practice Standards Decision Support Algorithms In order to standardize treatment across ICUs at the highest possible level, decision support algorithms are used in the present invention. These include textural material describing the topic, scientific treatments and possible complications. This information is available in real time to assist in all types of clinical decisions from diagnosis to treatment to triage.

All connections among components of the present invention are presently with a high bandwidth T-1 line although this is not meant as a limitation. It is anticipated that other existing and future high bandwidth communication capabilities, both wired and wireless, as well as satellite communications will be suitable for the communications anticipated for the present invention.

As noted earlier, a key objective of the present invention is to standardize care and treatment across ICUs. This is effective in the present invention by providing decision support to intensivists as well as information concerning the latest care and practice standards for any given condition. As noted in Table I below, a wide variety of conditions is noted. Each of the conditions has an associated guideline of practice standard that can be presented to the intensivist who might be faced with that particular condition in a patient. These guidelines of practice standards can be accessed at the command center/remote location or at the ICU to assist in the treatment of the patient. Thus, the general categories of cardiovascular, endocrinology, general, gastrointestinal, hematology, infectious diseases, neurology, pharmacology, pulmonary, renal, surgery, toxicology, trauma all have guidelines and practice standards associated with them.

TABLE 1

**EVIDENCE-BASED GUIDELINES
ALGORITHMS & PRACTICE STANDARDS
DECISION SUPPORT**

CARDIOVASCULAR

BRADYARRHYTHMIAS
CARDIOGENIC SHOCK
CARDIO-PULMONARY RESUSCITATION GUIDELINES
CONGESTIVE HEART FAILURE
EMERGENCY CARDIAC PACING
FLUID RESUSCITATION
HYPERTENSIVE CRISIS
IMPLANTABLE CARDIO-DEFIBRILLATORS
INTRA-AORTIC BALLOON DEVICES
MAGNESIUM ADMINISTRATION IN PATIENTS
MANAGEMENT OF HYPOTENSION, INOTROPES
MYOCARDIAL INFARCTION
MI WITH LEFT BUNDLE BRANCH BLOCK
PA CATHETER GUIDELINES & TROUBLE-SHOOTING
PERMANENT PACEMAKERS & INDICATIONS
PULMONARY EMBOLISM DIAGNOSIS
PULMONARY EMBOLISM TREATMENT
SUPRA-VENTRICULAR TACHYARRHYTHMIAS
UNSTABLE ANGINA
VENOUS THROMBOEMBOLISM PROPHYLAXIS
VENOUS THROMBOSIS: DIAGNOSIS & TREATMENT
VENTRICULAR ARRHYTHMIAS
ENDOCRINOLOGY

ADRENAL INSUFFICIENCY
DIABETIC KETOACIDOSIS
HYPERCALCEMIA: DIAGNOSIS & TREATMENT
HYPERGLYCEMIA: INSULIN TREATMENT
STEROID REPLACEMENT STRATEGIES
THYROID DISEASE
GENERAL

DEALING WITH DIFFICULT PATIENTS AND FAMILIES
END OF LIFE DECISIONS
ETHICAL GUIDELINES
PRESSURE ULCERS
ORGAN PROCUREMENT GUIDELINES
GASTROINTESTINAL

ANTIBIOTIC ASSOCIATED COLITIS
HEPATIC ENCEPHALOPATHY
HEPATIC FAILURE
MANAGEMENT OF PATIENTS WITH ASCITES
NUTRITIONAL MANAGEMENT
ACUTE PANCREATITIS
UPPER GI BLEEDING: STRESS PROPHYLAXIS
UPPER GI BLEEDING: NON-VARICEAL
UPPER GI BLEEDING: VARICEAL
HEMATOLOGY

HEPARIN
HEPARIN-INDUCED THROMBOCYTOPENIA
THE BLEEDING PATIENT
THROMBOCYTOPENIA
THROMBOLYTIC THERAPY
TRANSFUSION GUIDELINES
USE OF HEMATOPOETIC GROWTH FACTORS
WARFARIN
INFECTIOUS DISEASES

ACALCULUS CHOLECYSTITIS
ANTIBIOGRAMS
BLOODSTREAM INFECTIONS
CANDIDURIA
CATHETER RELATED SEPTICEMIA
CATHETER REPLACEMENT STRATEGIES
ENDOCARDITIS PROPHYLAXIS
ENDOCARDITIS DIAGNOSIS AND TREATMENT
FEBRILE NEUTROPENIA
FUO

TABLE 1-continued

**EVIDENCE-BASED GUIDELINES
ALGORITHMS & PRACTICE STANDARDS
DECISION SUPPORT**

HIV+ PATIENT INFECTIONS
MENINGITIS
NECROTIZING SOFT TISSUE INFECTIONS
NON-INFECTIOUS CAUSES OF FEVER
OPHTHALMIC INFECTIONS
PNEUMONIA, COMMUNITY ACQUIRED
PNEUMONIA, HOSPITAL ACQUIRED
SEPTIC SHOCK
SINUSITIS
SIRS
TRANSPLANT INFECTION PROPHYLAXIS
TRANSPLANT-RELATED INFECTIONS
NEUROLOGY

AGITATION, ANXIETY, DEPRESSION & WITHDRAWAL
BRAIN DEATH
GUILLAIN-BARRE SYNDROME
INTRACEREBRAL HEMORRHAGE
MYASTHENIA GRAVIS
NEUROMUSCULAR COMPLICATIONS OF CRITICAL ILLNESS
NON-TRAUMATIC COMA
SEDATION
STATUS EPILEPTICUS
STROKE
SUB-ARACHNOID HEMORRHAGE
PHARMACOLOGY

AMINOGLYCOSIDE DOSING AND THERAPEUTIC MONITORING
AMPHOTERICIN-B TREATMENT GUIDELINES
ANALGESIA
ANTIBIOTIC CLASSIFICATION & COSTS
DRUG CHANGES WITH RENAL DYSFUNCTION
PENICILLIN ALLERGY
NEUROMUSCULAR BLOCKERS
VANCOMYCIN
THERAPEUTIC DRUG MONITORING
PULMONARY

ARDS: HEMODYNAMIC MANAGEMENT
ARDS: STEROID USE
ARDS: VENTILATOR STRATEGIES
ASTHMA
BRONCHODILATOR USE IN VENTILATOR PATIENTS
BRONCHOSCOPY & THORACENTESIS GUIDELINES
COPD EXACERBATION & TREATMENT
CXR (INDICATIONS)
NONINVASIVE MODES OF VENTILATION
ENDOTRACHEAL TUBES & TRACHEOTOMY
TREATMENT OF AIRWAY OBSTRUCTION
VENTILATOR WEANING PROTOCOL
RENAL

ACUTE RENAL FAILURE: DIAGNOSIS
ACUTE RENAL FAILURE: MANAGEMENT & TREATMENT
DIALYSIS
DIURETIC USE
HYPERKALEMIA: ETIOLOGY & TREATMENT
HYPERNATREMIA: ETIOLOGY & TREATMENT
HYPOKALEMIA: ETIOLOGY & TREATMENT
HYPONATREMIA: ETIOLOGY & TREATMENT
OLIGURIA
SURGERY

OBSTETRICAL COMPLICATIONS
DISSECTING AORTIC ANEURYSM
POST-OPERATIVE HYPERTENSION
POST-OPERATIVE MYOCARDIAL ISCHEMIA (NON-CARDIAC
ARRHYTHMIAS AFTER CARDIAC SURGERY
POST-OPERATIVE BLEEDING
POST-OPERATIVE MANAGEMENT OF ABDOMINAL
POST-OPERATIVE MANAGEMENT OF OPEN HEART
POST-OPERATIVE MANAGEMENT OF THORACOTOMY
POST-OPERATIVE POWER WEANING
POST-OPERATIVE MANAGEMENT OF CAROTID
WOUND HEALING STRATEGIES

TABLE 1-continued

EVIDENCE-BASED GUIDELINES
ALGORITHMS & PRACTICE STANDARDS
DECISION SUPPORT

TOXICOLOGY

ACETAMINOPHEN OVERDOSE
ANAPHYLAXIS
COCAINE TOXICITY
ALCOHOL WITHDRAWAL
HYPERTHERMIA
LATEX ALLERGY
UNKNOWN POISONING
TRAUMA

ABDOMINAL COMPARTMENT SYNDROME
BLUNT ABDOMINAL INJURY
BLUNT AORTIC INJURY
BLUNT CARDIAC INJURY
DVT PROPHYLAXIS
EXTREMITY COMPARTMENT SYNDROME
HEAD INJURY
HYPOTHERMIA
IDENTIFICATION OF CERVICAL CORD INJURY
SPINAL CORD INJURY
OPEN FRACTURES
PENETRATING ABDOMINAL INJURY
PENETRATING CHEST INJURY

Figure 21A:
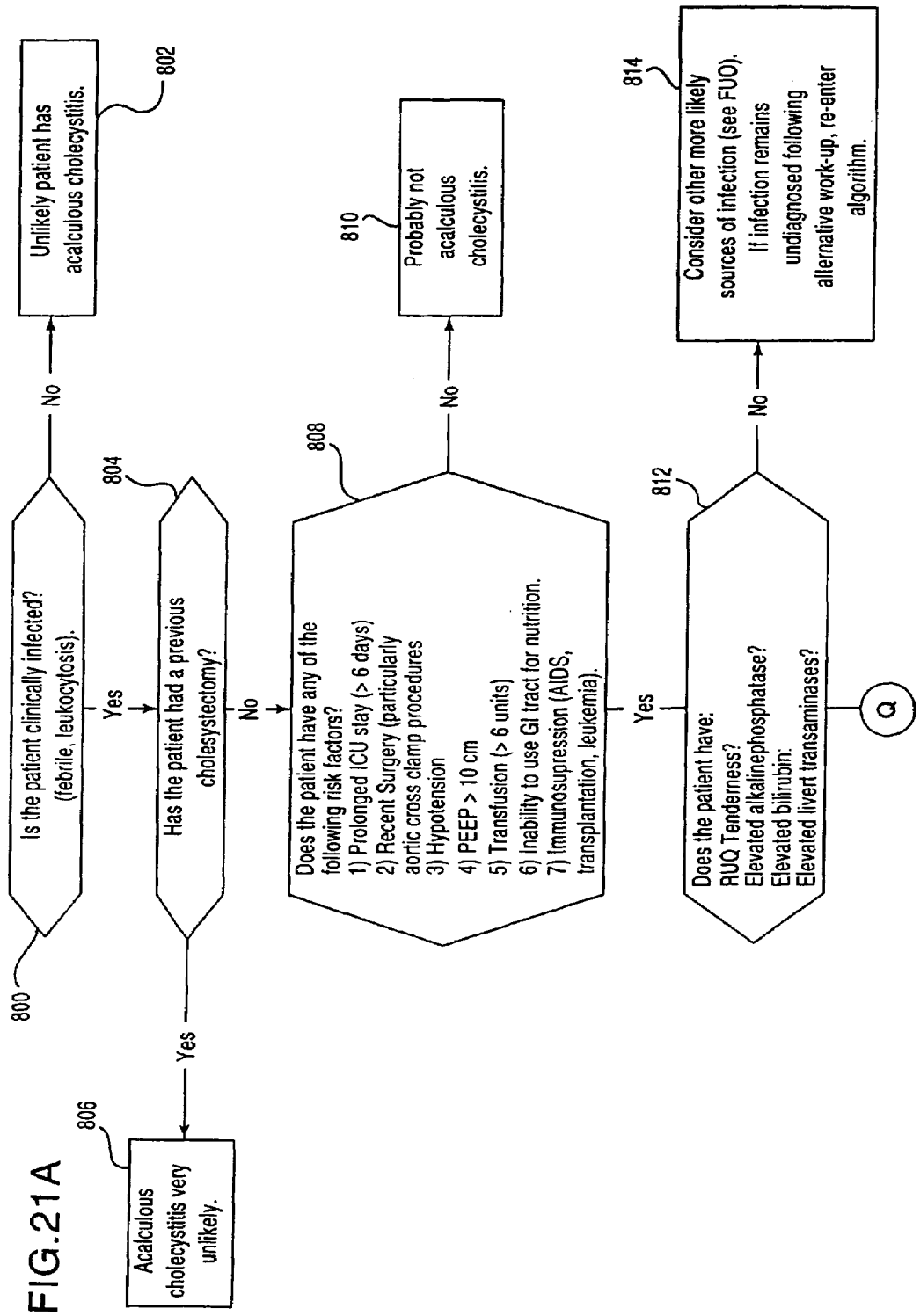
FIGS. 21A-B illustrate the acalculous cholecystitis decision support algorithm.
Figure 21B:
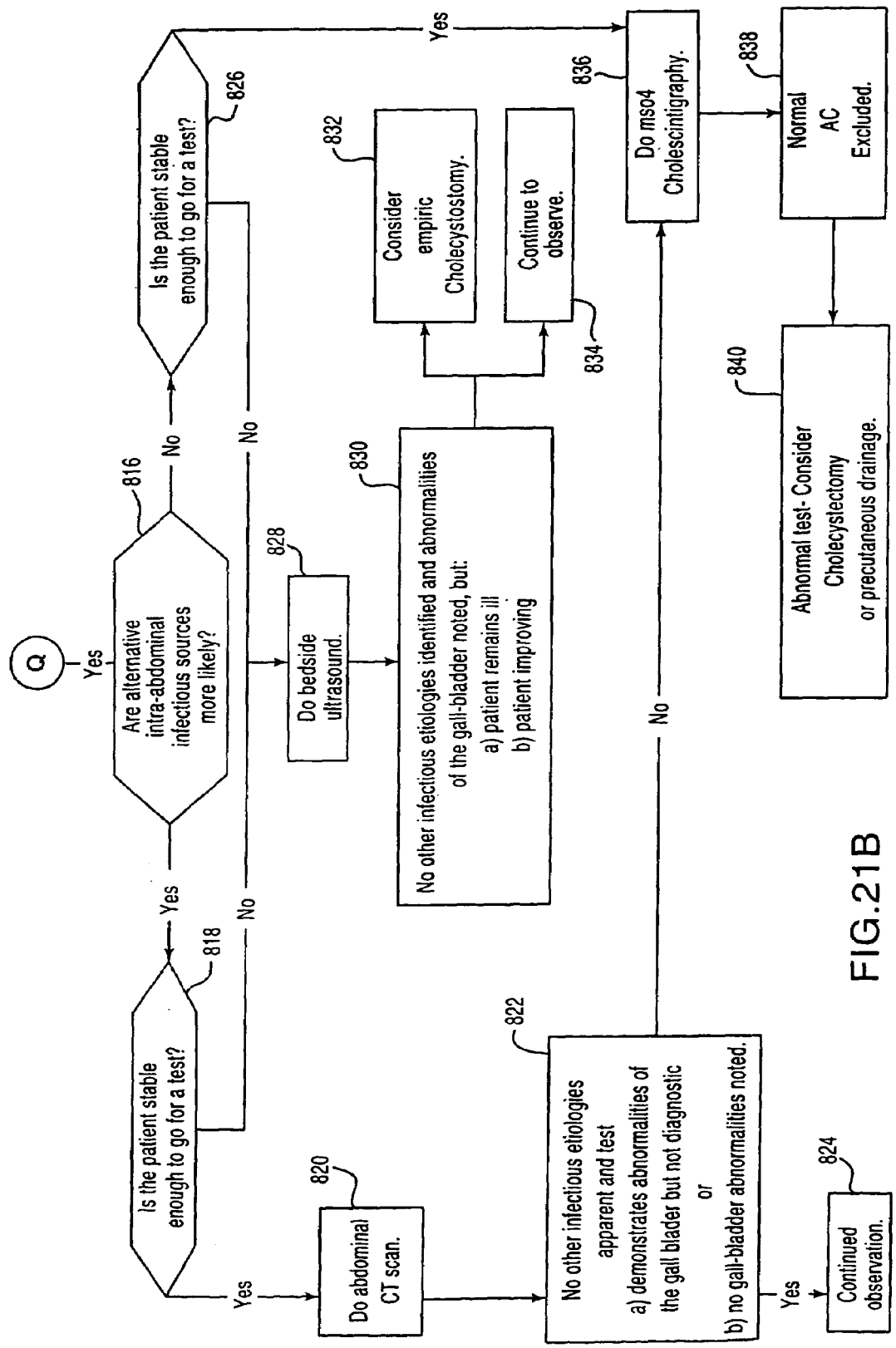

Referring to FIGS. 21A-B, the acalculous cholecystitis decision support algorithm of the present invention is illustrated. If an intensivist suspects that acalculous cholecystitis may be present, the intensivist may not be certain of all of the aspects that would be indicative of this particular condition. Therefore, the intensivist is lead through a decision support algorithm, which first causes the intensivist to determine if the patient is clinically infected, either febrile or leukocystosis 800. If this criterion is not met, the intensivist is prompted that it is unlikely that the patient has acalculous cholecystitis 802.

If the patient is clinically infected 800, the intensivist is prompted to determine whether the patient has had a previous cholesystectomy 804. If patient has had a previous cholesystectomy, the intensivist is prompted that it is very unlikely that the patient has acalculous cholecystitis 806. Alternatively, if a patient has not had a previous cholesystectomy, the intensivist is prompted to determine whether the patient has any of seven (7) risk factors, specifically: 1) Prolonged intensive care unit (ICU) stay (defined as greater than six (6) days); 2) recent surgery (particularly aortic cross clamp procedures); 3) hypotension; 4) positive end-expiratory pressure (PEEP) greater than ten (10) centimeters (cm); 5) transfusion greater than six (6) units of blood; 6) inability to use the gastrointestinal (GI) tract for nutrition; or 7) immunosuppresssion (AIDS, transplantation, or leukemia) 808. If the patient has none of these seven risk factors, the intensivist is prompted that the patient probably does not have acalculous cholecystitis 810.

If the patient has any of the seven risk factors 808, the intensivist is prompted to determine whether the patient has any of the following symptoms: right upper quadrant (RUQ) tenderness; elevated alkalinephosphatase; elevated bilirubin; or elevated livert transaminases 812. If the patient has none of these four (4) symptoms 812, the intensivist is prompted to consider other more likely sources of infection (see fever of unknown origin or FUO) 814. If the infection remains undiagnosed following an alternative work-up, the intensivist is prompted to re-enter the algorithm 814.

If the patient has any of these four (4) symptoms 812, the intensivist is prompted to determine whether alternative intra-abdominal infectious sources are more likely 816. If alternative intra-abdominal infectious sources are not more likely, the intensivist is prompted to determine whether the patient is sufficiently stable to go for a test 826. If the patient is sufficiently stable to go for a test, the intensivist is prompted to perform an mso4 Cholescintigraphy 836. The normal AC is excluded 838. If the test indicates an abnormality, the intensivist is prompted to consider a cholecystectomy or precutaneous drainage 840. If the patient is not sufficiently stable to go for a test, the intensivist is prompted to perform a bedside ultrasound 828. If no other infectious etiologies are identified and no abnormalities of the gall-bladder are noted but: a) the patient remains ill 830, the intensivist is prompted to consider empiric cholecystostomy 832. If no other infectious etiologies are identified and no abnormalities of the gall bladder are noted but: b) the patient is improving 830, the intensivist is prompted to continue to observe the patient 834.

If alternative intra-abdominal infectious sources are more likely 816, the intensivist is prompted to determine whether the patient is sufficiently stable to go for a test 818. If the patient is sufficiently stable to go for a test 818, the intensivist is prompted to perform an abdominal CT scan 820. If no other infectious etiologies are apparent and the test: a) demonstrates abnormalities of the gall-bladder but not diagnostic; or b) no gall-bladder abnormalities are noted 822, the intensivist is prompted to maintain continued observation of the patient 824. Alternatively, if neither of these criteria is met 822, the intensivist is prompted to perform an mso4 cholescintigraphy 836. Normal AC is excluded 838. If the test is abnormal, the intensivist is prompted to consider cholecystectomy or precutaneous drainage 840. If the patient is not sufficiently stable to go for a test, the intensivist is prompted to perform a bedside ultrasound 828. If no other infectious etiologies are identified and no abnormalities of the gall-bladder are noted but: a) the patient remains ill 830, the intensivist is prompted to consider empiric cholecystostomy 832. If no other infectious etiologies are identified and no abnormalities of the gall bladder are noted but: b) the patient is improving 830, the intensivist is prompted to continue to observe the patient 834.

Figure 22:
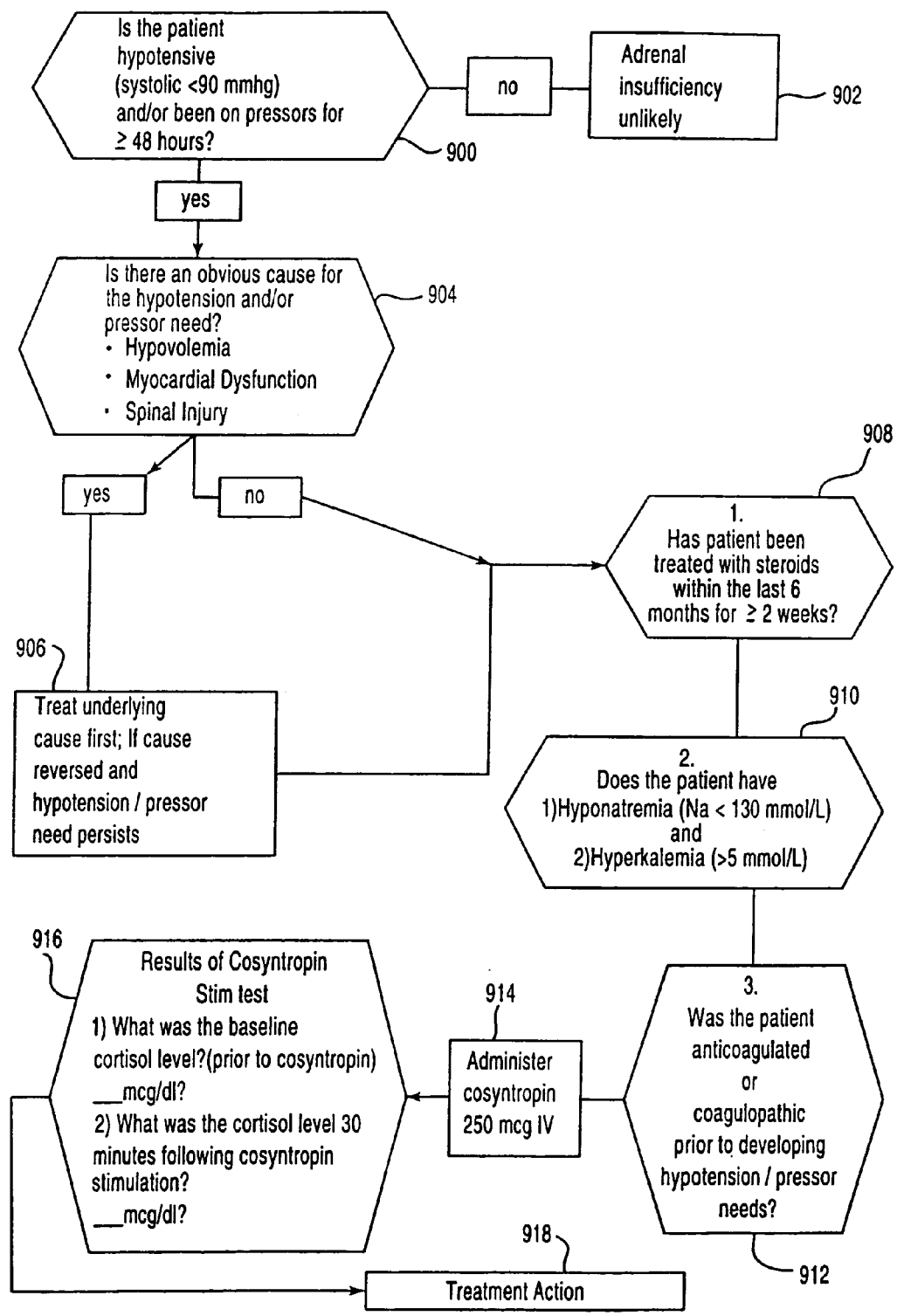
FIG. 22 illustrates the adrenal insufficiency decision support algorithm.

Referring to FIG. 22, the adrenal insufficiency decision support algorithm of the present invention is illustrated. When an intensivist suspects an adrenal problem may be presented in a patient, the intensivist may initiate the adrenal insufficiency decision support algorithm which prompts questions concerning all aspects of the condition. First the intensivist is prompted to determine whether the patient is either hypotensive and/or has been administered pressors for forty-eight hours or longer 900. If neither condition is met, the system advises the intensivist that it is unlikely that an adrenal problem is present 902.

If one or both conditions are met, the intensivist is asked whether an obvious cause for hypotensive blood pressure or treatment with pressors are manifested, such as hypovolemia or low blood volume, myocardial dysfunction, or spinal injury 904. If at least one of these obvious causes is present, the intensivist is alerted by the system that the underlying cause must first be treated 906. If treatment of a suspected underlying cause is reversed, yet the hypotension or pressor need persists, the intensivist is further directed to determine whether other adrenal problems have occurred in the patient's history 908, 910, 912.

In order to examine prior treatment issues, the intensivist is first prompted by the system to determine if the patient has been treated with steroids in the previous six months for at least a two week period 908. Next, the intensivist is prompted to determine whether the patient has hyponatremia or hyperkalemia 910. The intensivist is also prompted to determine whether the patient has experienced anticoagulation or become coagulopathic prior to the hypotension or pressor treatment 912. According to the responses provided by the intensivist to the system queries or blocks 908, 910, and 912, the system calculates a treatment action 914 as follows: The array of possible responses to diagnosis questions 908, 910, and 912 are given a Decision Code as shown in Table 1A: Adrenal Insufficiency Considerations, below.

TABLE 1A

Adrenal Insufficiency Considerations

| Question 1 908 | Question 2 910 | Question 3 912 | Decision Code |
|---|---|---|---|
| N | N | N | A |
| N | N | Y | A |
| N | Y | N | B |
| N | Y | Y | C |
| Y | Y | Y | C |
| Y | N | N | D |
| Y | Y | N | B |
| Y | N | Y | D |
| Y | Y | Y | C |

The possible decision codes of Table 1A are as follows:

| Decision Code | Treatment Action |
|---|---|
| A | Do cosyntropin stim test |
| B | Consider possible Adrenal Insufficiency. Give decadron 5 mg IV, so cosyntropin stim test and empirically treat with hydrocortione 50 mg IV every 8 hours until stim test results return. |
| C | Consider possible Adrenal Insufficiency, secondary to adrenal hemorrhage. Give decadron 5 mg IV, so cosyntropin stim test and empirically treat with hydrocortione 50 mg IV every 8 hours until stim test results return. |
| D | Do cosyntropin stim test, may empirically treat with hydrocortisone 25-50 mg IV every 8 hours until stim test results return |

Besides specialized treatment actions listed in the decision codes above, the intensivist is directed to administer a cosyntropin stimulation test 914 in order to see how much cortisone the adrenal gland is producing.

After performing the cosyntropin stimulation test, the intensivist is prompted to enter the patient's level of cortisol before administering cosyntropin and thirty minutes afterwards 916. The software analyzes the test results as follows: The results in Table 2, shown below, are shown as having certain decision codes A through F.

TABLE 2

Cosyntropin Stimulation Test Results

| basal (A) | basal (B) | basal (C) | stim (D) | stim (E) | stim (F) |
|---|---|---|---|---|---|
| <15 | 15-20 | >25 | <5 | 5-10 | >10 |

Depending upon the outcome of the analysis of Table 2, one of the treatment actions, shown below in Table 3, will be displayed 918.

TABLE 3

Cosyntropin Test Result Treatment Actions

| Decision Code | Treatment Action |
|---|---|
| A + D | Adrenal insufficiency diagnosed - treat with hydrocortisone 50 mg IV every 8 hours and consider endocrine consult |
| A + E | Probable Adrenal insufficiency - treat with hydrocortisone 25-50 mg IV every 8 hours and taper as intercurrent illness improves |
| B + D | |
| A + F | Possible Adrenal insufficiency - consider treatment with hydrocortisone 25 mg IV every 8 hours and taper as intercurrent illness improves |
| B + E | |
| A + F | Adrenal insufficiency unlikely - would not treat |
| B + F | |
| C + E | |
| C + F | |

Figure 23:
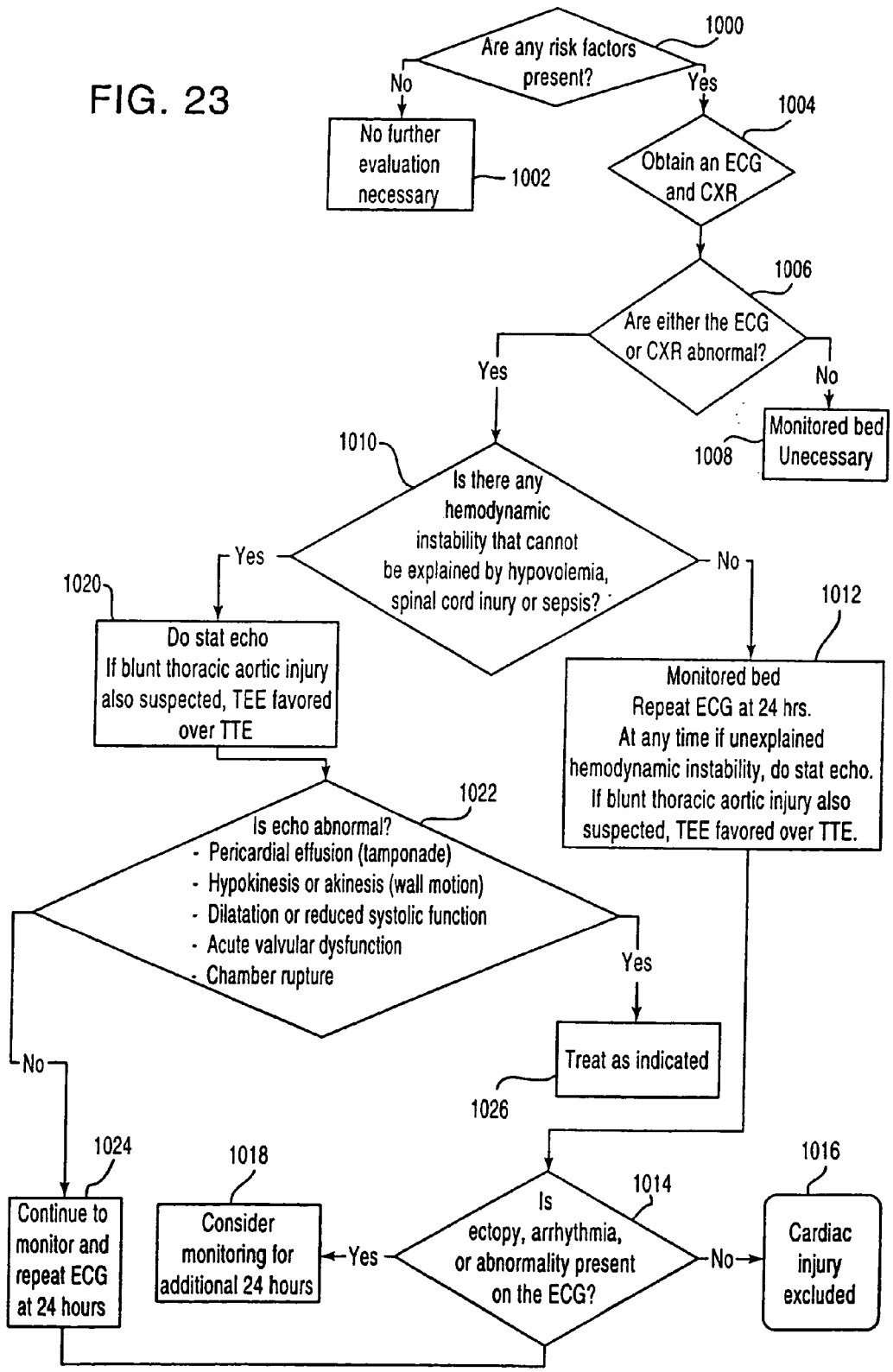
FIG. 23 illustrates the blunt cardiac injury decision support algorithm.

Referring to FIG. 23, the blunt cardiac injury decision support algorithm of the present invention is illustrated. If an intensivist suspects that blunt cardiac injury may be present, the intensivist may not be certain of all aspects that would be critical to or indicative of this particular condition. Therefore, the intensivist is lead through a decision support algorithm, which first causes the intensivist to determine whether any of seven (7) risk factors are present: 1) was thoracic impact greater than fifteen (15) mph; 2) was the steering wheel deformed; 3) was there precordial ecchymosis, contusions, or abrasions; 4) was marked precordial tenderness present; 5) was there a fractured sternum; 6) were bilateral rib/costal cartilage fractures present; 7) were thoracic spine fractures present 1000. If none of the 7 risk factors are present, the intensivist is prompted that no further evaluation is necessary 1002. If any of the 7 risk factors are present, the intensivist is prompted to obtain an electrocardiogram (ECG) and chest X-ray (CXR) 1004.

Once the results of the ECG and CXR are obtained, the intensivist is prompted to determine: whether the ECG results are abnormal, with abnormal being defined as anything other than sinus rhythm, including ectopy and unexplained sinus tachycardia (greater than 100 beats/minute); and whether the CXR results are abnormal, with abnormal being defined as any skeletal or pulmonary injury, especially cardiac enlargement 1006. If either the ECG or CXR is not abnormal, the intensivist is prompted that a monitored bed is unnecessary for the patient 1008. If either the ECG or CXR is abnormal, the intensivist is prompted to determine whether there is any hemodynamic instability (hemodynamic instability being defined as the absence of hypovolemia, spinal cord injury, or sepsis) that cannot be explained by hypovolemia, spinal cord injury, or sepsis 1010.

If this criterion is not met, the intensivist is prompted: that the patient should be in a monitored bed; that the ECG should be repeated at 24 hours; that, at any time, if unexplained hemodynamic instability is present, the intensivist should request a stat echo; and that, if blunt thoracic aortic injury is also suspected, a transesophogeal echocardiogram (TEE) is favored over a transthoracic echocardiogram (TTE) 1012. Once the results of these tests are obtained, the intensivist is prompted further to determine whether ectopy, arrhythmia, or abnormality is present on the ECG 1014. If none of these criteria are met, the intensivist is prompted that cardiac injury is excluded 1016. If any of these criteria are met, the intensivist is prompted that he should consider monitoring the patient for an additional 24 hours 1018.

If the internist determines that there is any hemodynamic instability that cannot be explained by hypovolemia, spinal cord injury, or sepsis 1010, he is prompted: to perform a stat echo; and, if blunt thoracic aortic injury is also suspected, that a transesophogeal echocardiogram (TEE) is favored over a transthoracic echocardiogram (TTE) 1020. Once the results of the stat echo are obtained, the intensivist is prompted to determine whether the echo is abnormal with possible causes for the abnormality being: pericardial effusion (tamponade; hypokineses or akinesis (wall motion); dilatation or reduced systolic function; acute valvular dysfunction; and/or chamber rupture 1022. If the stat echo is abnormal, the intensivist is prompted to treat as indicated for the particular cause of the abnormality 1026. If the stat echo is not abnormal, the intensivist is prompted to continue to monitor the patient and repeat the ECG at 24 hours 1024.

Once the results of the ECG are obtained, the intensivist is prompted to determine whether ectopy, arrhythmia, or abnormality are present on the ECG 1014. If any of these criteria are not met, the intensivist is prompted that cardiac injury is excluded 1016. If any of these criteria are met, the intensivist is prompted that he should consider monitoring the patient for an additional 24 hours 1018.

Figure 24A:
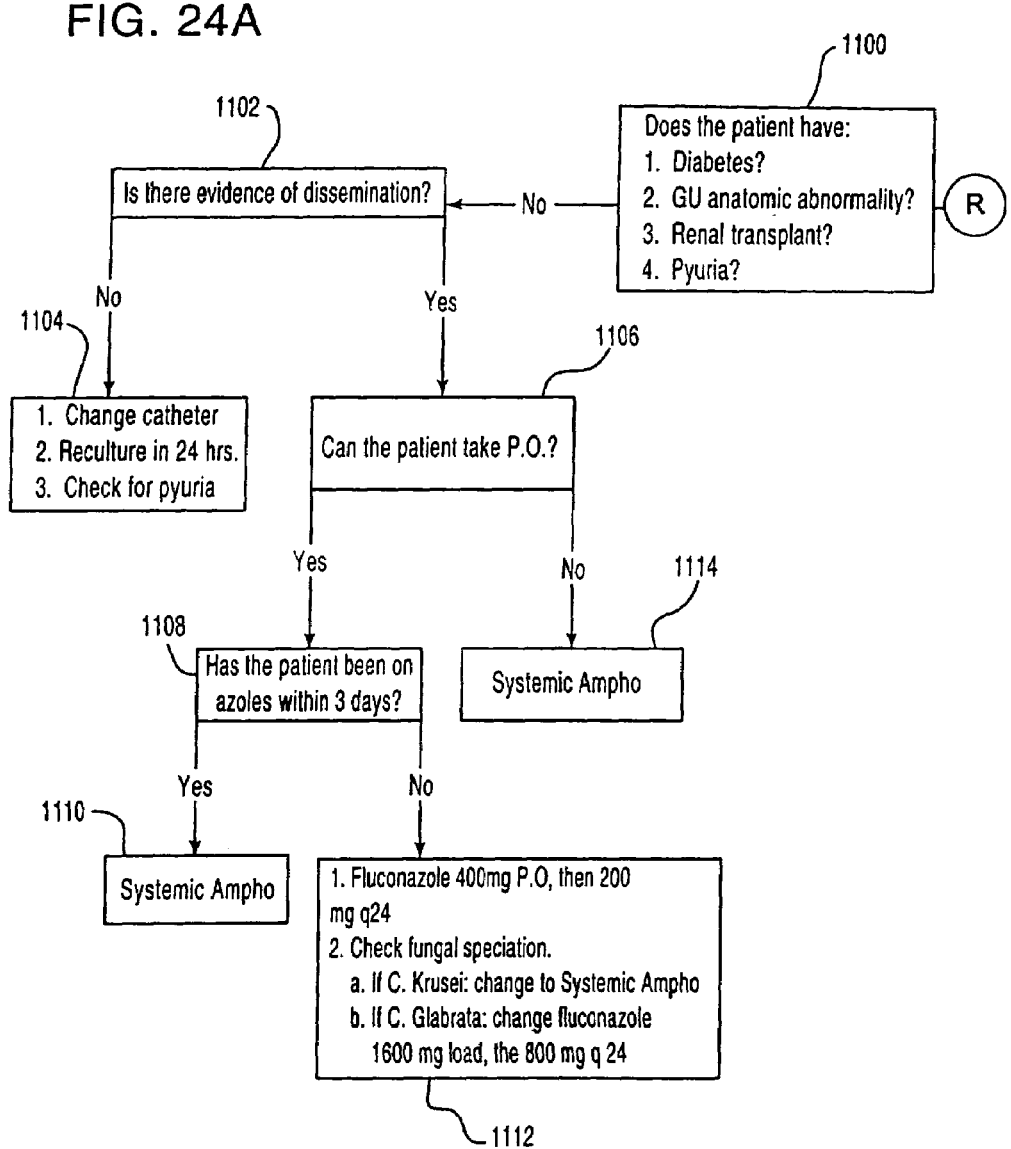
FIGS. 24A-B illustrate the candiduria decision support algorithm.
Figure 24B:
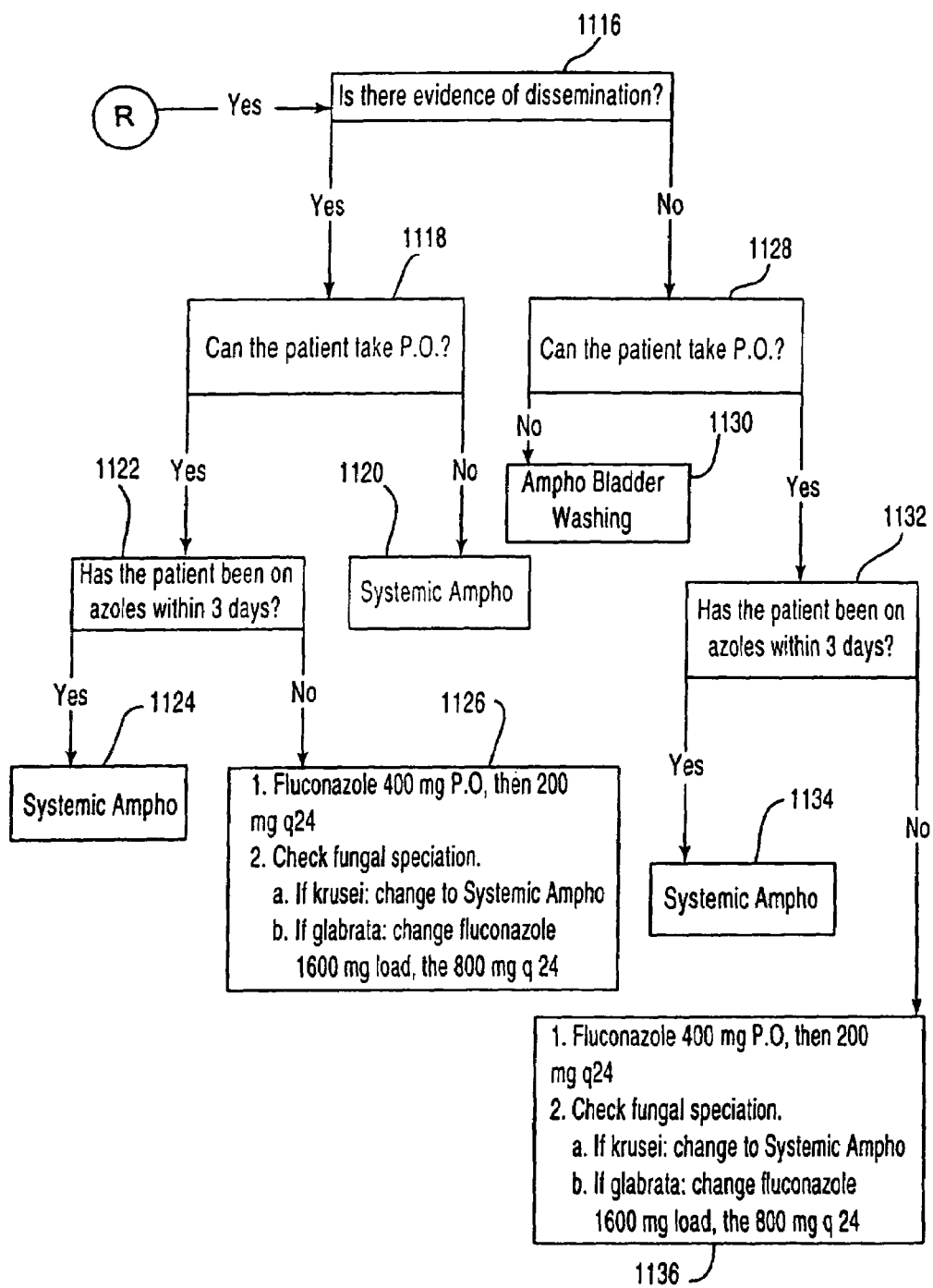

Referring to FIGS. 24A-B, the candiduria decision support algorithm, which is yet another decision support algorithm of the present invention is illustrated. In the candiduria decision support algorithm, the intensivist is presented with the criteria for diagnosing candiduria, or severe fungal infection. First, the intensivist determines whether the patient has any medical conditions that render the patient prone to fungal infections, such as diabetes, GU anatomic abnormality, renal transplant, or pyuria 1100. If there are no such conditions, the intensivist is next prompted by the system to look for dissemination or spreading of the fungal infection 1102. If the infection does not seem to have spread, the intensivist is prompted to change the patient's catheter and test for pyuria after twenty four hours have passed 1104.

The intensivist is prompted by the system to determine whether the patient can have P.O. 1106. If the patient can take P.O., the system next prompts the intensivist to determine whether azoles, an organic compound for inhibiting fungal growth, have been administered in the past three days to fight the infection 1108. If azoles have been previously administered, the systemic infection diagnosis is confirmed and the intensivist is referred to the systemic amphotericin dosing algorithm 1110. If azoles have not been previously administered, directions for the proper treatment dosage of fluconazole (a type of azole) is provided to the intensivist along with adjustments for the species of fungus found 1112. Where the patient cannot take P.O., the intensivist is again referred to the systemic amphotericin dosing algorithm 1114.

When the patient does have some condition prone to fungal infection, the intensivist is prompted to determine what other signs of dissemination are exhibited in the patient 1116. The intensivist is prompted to see if the patient can take P.O. If the patient cannot take P.O., the intensivist is referred to the systemic amphotericin dosing algorithm 1120. If the patient can take P.O., the intensivist is prompted to check whether azoles have been administered in the previous three days 1122. If azoles have been administered, the systemic infection is confirmed and the intensivist is referred to the systemic amphotericin dosing algorithm 1124. If no azoles have been administered previously, the intensivist is given instructions for administering fluconazole to treat the ftmgal infection 1126.

If there is no evidence of dissemination, the intensivist is still prompted to determine whether the patient can take P.O. 1128. Where the patient cannot take P.O., directions are provided to administer amphotericin bladder washing procedures 1130. If the patient cannot take P.O., the intensivist is prompted to determine whether azoles have been administered in the previous three days 1132. If azoles have been administered, the systemic infection is confirmed and the intensivist is referred to the systemic amphotericin dosing algorithm 1134. If no azoles have been administered previously, the intensivist is given instructions for administering fluconazole to treat the fungal infection 1136.

Figure 25A:
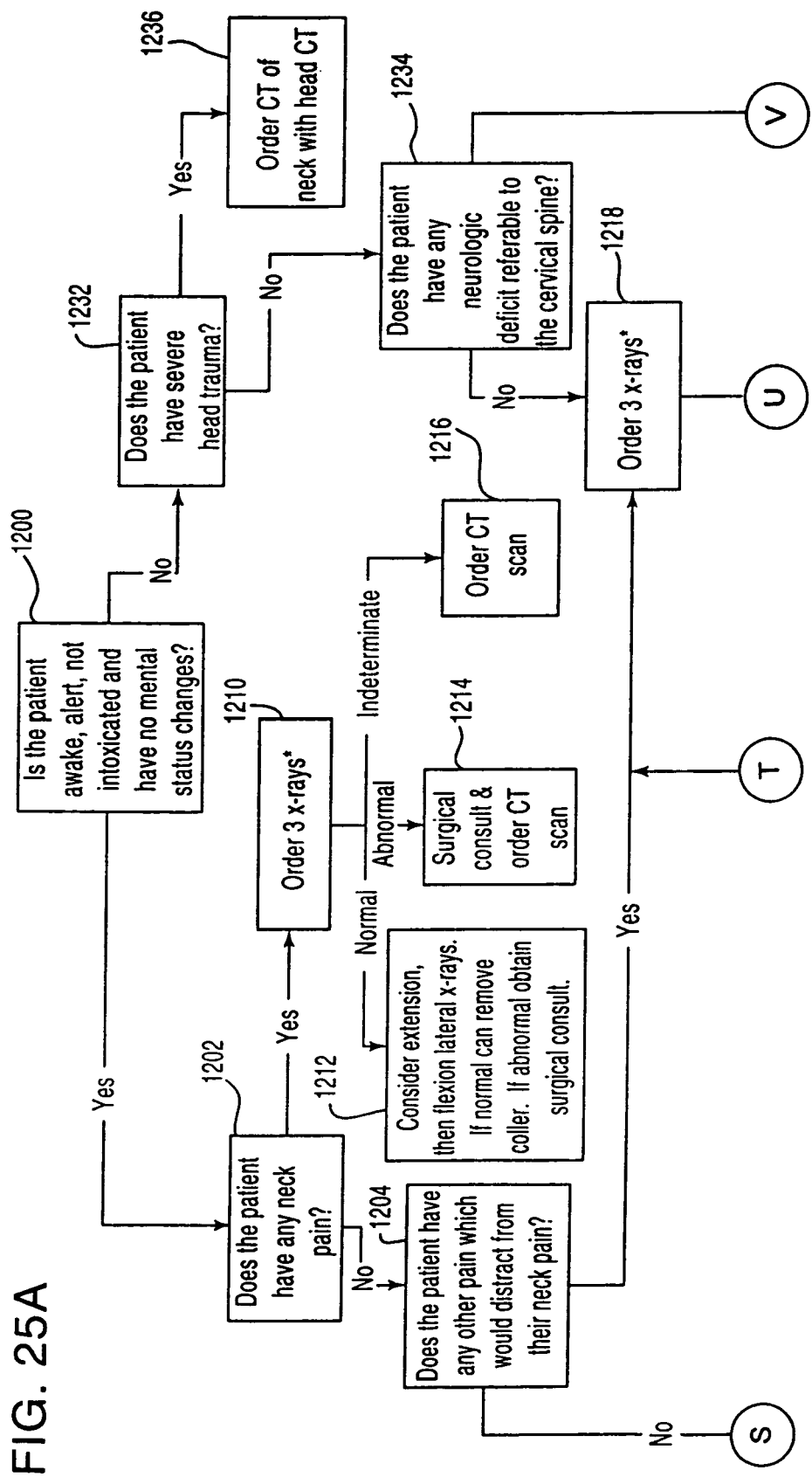
FIGS. 25A-B illustrate the cervical spine injury decision support algorithm.
Figure 25B:
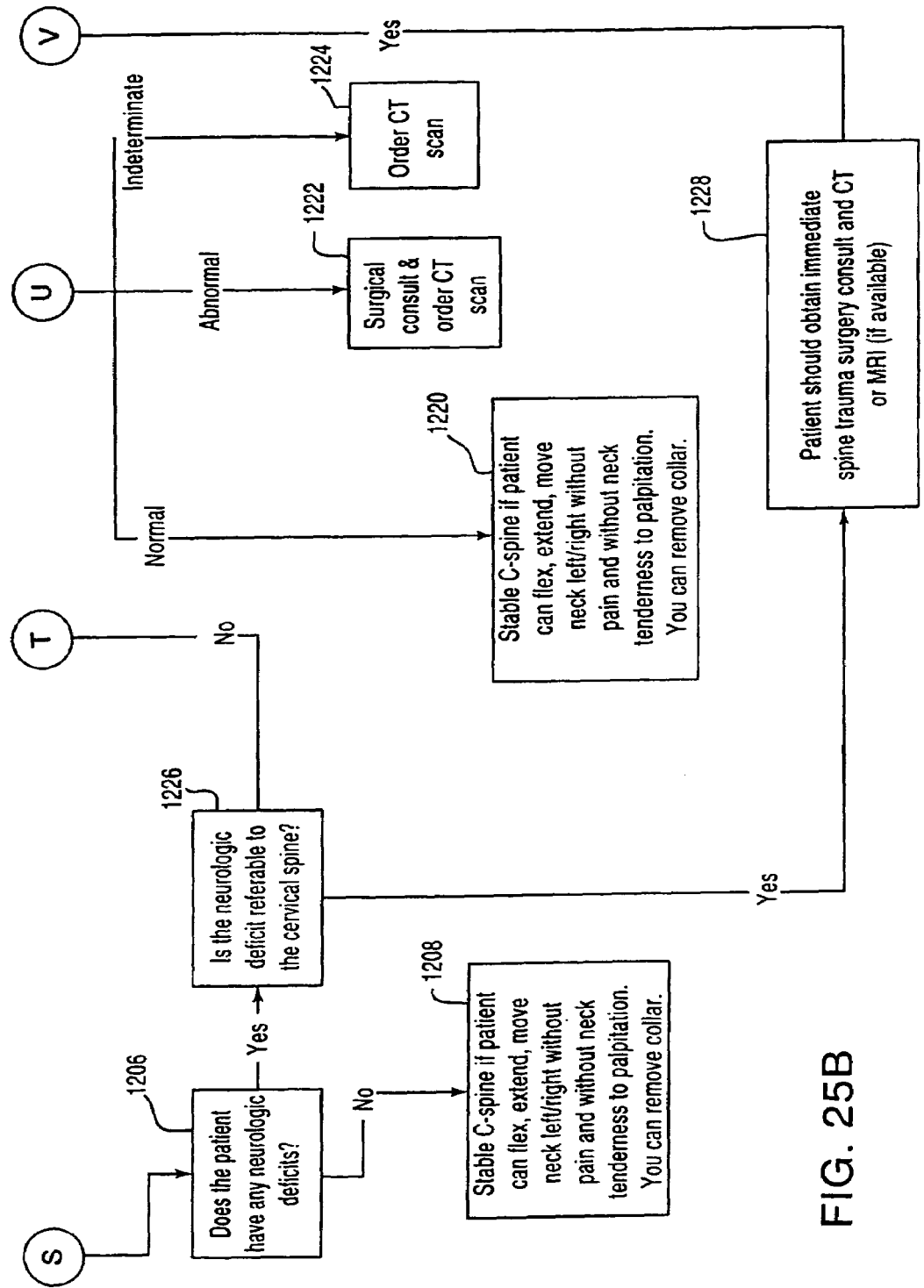

Referring to FIGS. 25A-B, the Cervical Spine Injury decision support algorithm of the present invention is illustrated. If an intensivist suspects that a cervical spine injury may be present, the intensivist may not be certain of all of the factors that would be indicative of this particular condition. Therefore, the intensivist is lead through a decision support algorithm, which first prompts the intensivist to determine if the patient is awake, alert, not intoxicated, and has no mental status changes 1200. If these criteria are met, the intensivist is prompted to determine whether the patient has any neck pain 1202. If the patient does not have any neck pain, the intensivist is prompted to determine whether the patient has any other pain which would distract from his or her neck pain 1204. If this criterion is not met, the intensivist is prompted to determine whether the patient has any neurologic deficits 1206. If this criterion is not met, the intensivist is prompted that a stable C-spine is present if the patient can flex, extend, move neck left/right without pain and without neck tenderness to palpitation 1208. The intensivist is prompted further that he can remove the collar 1208.

Alternatively, if the patient does have neck pain 1202, the intensivist is prompted to order 3 x rays 1210 consisting of: 1) lateral view revealing the base of the occiput to the upper border of the first thoracic vertebra; 2) anteroposterior view revealing spinous processes of the second cervical through the first thoracic vertebra; and 3) an open mouth odontoid view revealing the lateral masses of the first cervical vertebra and entire odontoid process 1210. If the x rays are normal the intensivist is prompted to consider extension then flexion lateral x rays; if normal he is prompted that he can remove the collar; if abnormal, he is prompted to obtain a surgical consult 1212. If the x rays are abnormal, the intensivist is prompted to obtain a surgical consult and order a CT scan 1214. If the x rays are indeterminate, the intensivist is prompted to order a CT scan 1216.

Alternatively, if the patient has no other pain which would distract from their neck pain 1204, the intensivistis prompted to order 3 x rays (the same types of x rays described in 1210 above with the same prompting based on normal, abnormal, or indeterminate x rays) 1218.

If the patient does have neurologic deficits 1206, the intensivist is prompted to determine whether the neurologic deficit is referable to the cervical spine 1226. If this criterion is not met, the intensivist is prompted to order 3 x rays (the same types of x rays described in 1210 above with the same prompting based on normal, abnormal, or indeterminate x rays) 1218. If the neurologic deficit is referable to the cervical spine 1226, the intensivist is prompted that the patient should obtain immediate spine trauma surgery consult and CT or MRI (if available) 1228.

Alternatively, if the intensivist determines that the patient does not pass the criteria of being awake, alert, not intoxicated and having no mental status changes 1200, the intensivist is prompted to determine whether the patient has severe head trauma 1232. If this criterion is met, the intensivist is prompted to order CT of the neck with head CT 1236. If this criterion is not met, the intensivist is prompted to determine whether the patient has any neurologic deficit referable to the cervicale spine 1234. If the intensivist determines that the patient does have a neurologic deficit referable to the cervical spine, the intensivist is prompted that the patient should obtain immediate spine trauma surgery consult and CT or MRI (if available) 1228. If the intensivist determines that the patient does not have a neurologic deficit referable to the cervical spine 1234, he is prompted to order 3 x rays (the same types of x rays described in 1210 above with the same prompting based on normal, abnormal, or indeterminate x rays) 1218.

Figure 26A:
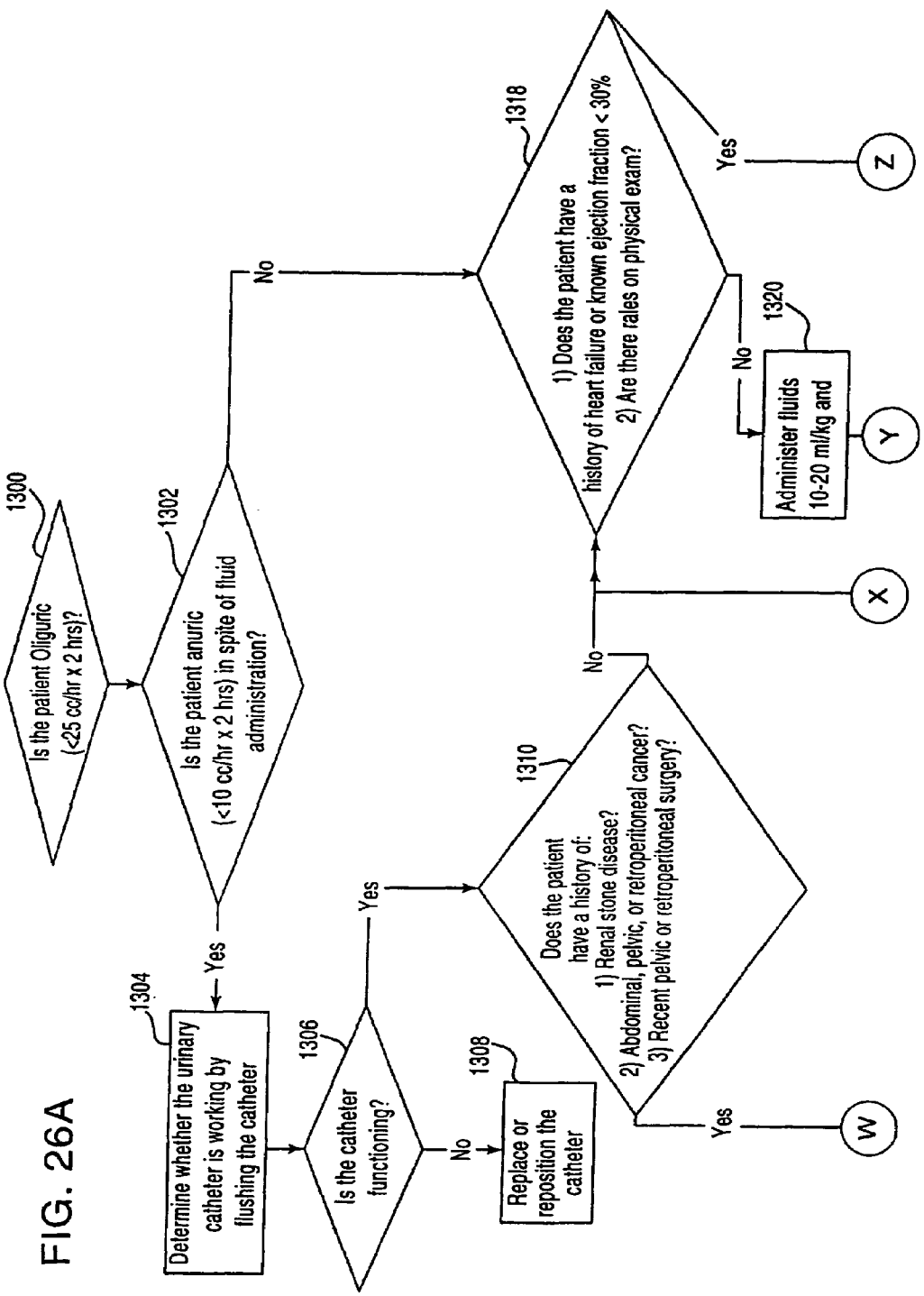
FIGS. 26A-B illustrate the oliguria decision support algorithm.
Figure 26B:
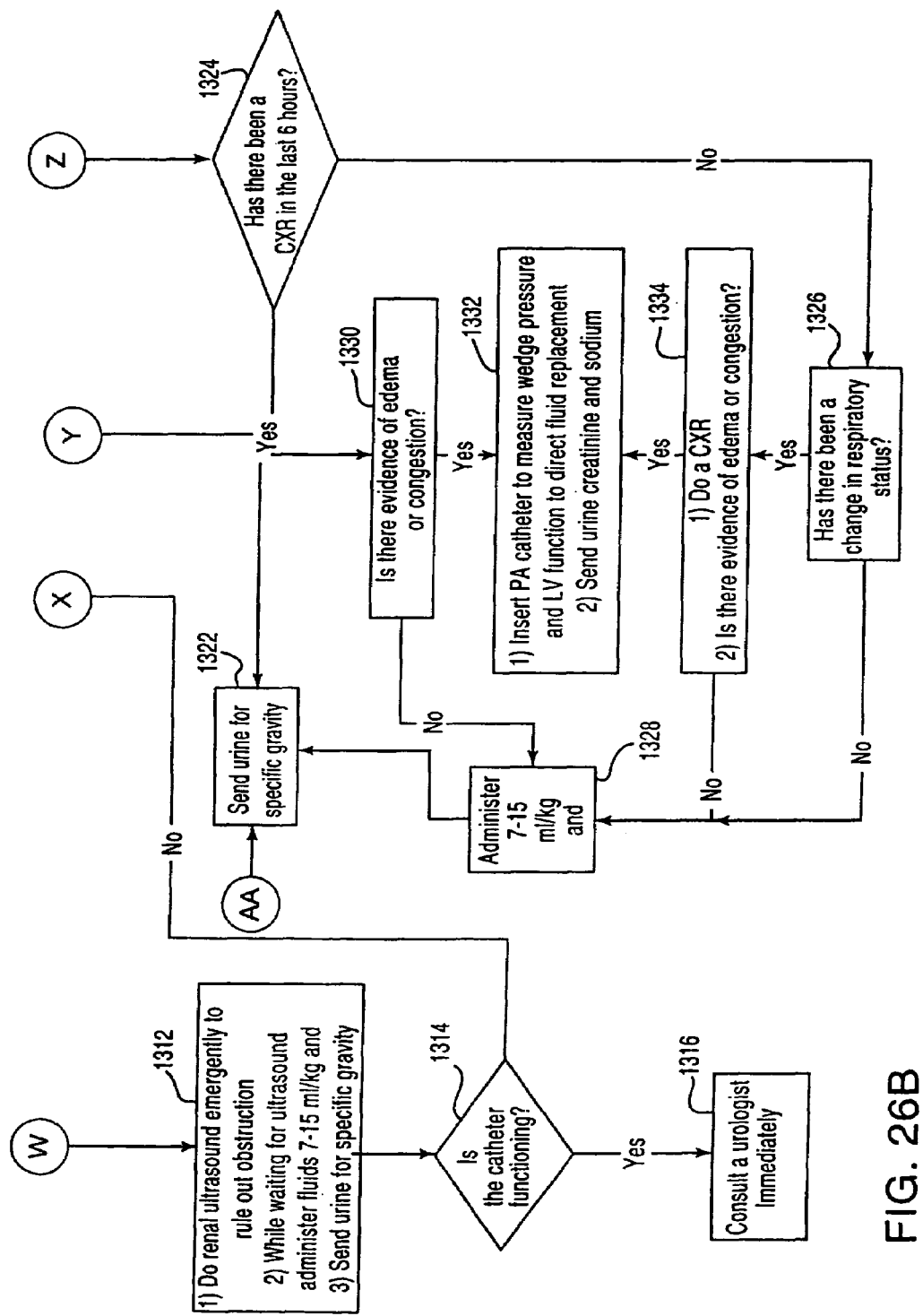

Referring to FIG. 26A-B, the Oliguria decision support algorithm of the present invention is illustrated. If an intensivist suspects that Oliguria may be present, the intensivist may not be certain of all of the aspects that would be indicative of this particular condition. Therefore, the intensivist is lead through a decision support algorithm, which first causes the intensivist to determine if the patient is oliguric, with the criterion being passage of less than 25 cc of urine in a period of 2 hours 1300. If this criterion is met the intensivist is prompted to determine whether the patient is anuric (the criterion for which is passage of less than 10 cc of urine in a 2 hour period) in spite of fluid administration 1302.

If this criterion is met, the intensivist is prompted to determine whether the urinary catheter is working by flushing the catheter 1304. The intensivist is then prompted to determine whether the catheter is functioning 1306. If the catheter is not functioning, the intensivist is prompted to replace or reposition the catheter 1308. If the catheter is functioning, the intensivist is prompted to determine whether the patient has a history of: 1) renal stone disease; 2) abdominal, pelvic, or retroperitoneal cancer; or 3) recent pelvic or retroperitoneal surgery 1310. If any of these criteria are met, the intensivist is prompted to perform the following actions: 1) do renal ultrasound emergently to rule out obstruction; 2) while waiting for ultrasound, administer fluid at the rate of 7-15 ml/kg of bodyweight; and 3) send urine for specific gravity determination 1312. Based on the renal ultrasound test results, the intensivist is prompted to determine whether an obstruction is present 1314. If an obstruction is determined to be present, the intensivist is prompted to consult a urologist immediately 1316.

Alternatively, if the intensivist determines that the patient does not have a history of: 1) renal stone disease; 2) abdominal, pelvic, or retroperitoneal cancer; or 3) recent pelvic or retroperitoneal surgery 1310, the intensivist is prompted to determine whether: 1) the patient has a history of heart failure or known ejection fraction of less than 30 percent; or 2) there are rales on the physical exam 1318.

Alternatively, if following the renal ultrasound test, the intensivist determines that there is no obstruction the intensivist is prompted to determine whether: 1) the patient has a history of heart failure or known ejection fraction of less than 30 percent; or 2) there are rales on the physical exam 1318.

If the intensivist determines that the patient is not anuric 1302, then the intensivist is prompted to determine whether: 1) the patient has a history of heart failure or known ejection fraction of less than 30 percent; or 2) whether there are rales on the physical examination 1318. If neither of these criteria is met, the intensivist is prompted to administer fluids to the patient at the rate of 10-20 ml/kg of bodyweight 1320 and send the patient's urine sample for a specific gravity test 1322 as more fully described in FIGS. 26B-C.

Alternatively, if the patient does: 1) have a history of heart failure or known ejection fraction less than 30 percent; or 2) there are rales on the physical exam 1318, the intensivist is prompted to determine whether there has been a chest x-ray (CXR) in the last 6 hours 1324. If this criterion is not met, the intensivist is prompted to determine whether there has been a change in respiratory status 1326. If there has been no change in the respiratory status, the intensivist is prompted to administer 7-15 ml of fluids per kg of bodyweight 1328 and to send the patient's urine sample for a specific gravity test.

Alternatively, if the intensivist determines that there has been a change in respiratory status 1326, the intensivist is prompted to: 1) do a chest x-ray; and 2) determine whether there is evidence of edema or congestion 1334. If there is evidence of edema or congestion 1334, the intensivist is prompted to: 1) insert a PA catheter to measure wedge pressure and liver function to direct fluid replacement; and 2) send urine creatinine and sodium 1332.

If the intensivist determines that there has been a CXR in the last 6 hours 1324, the intensivist is prompted to determine whether there is evidence of edema or congestion 1330. If there is no evidence of edema or congestion, the intensivist is prompted to administer 7-15 ml of fluids per kg of bodyweight 1328 and send the patient's urine for a specific gravity test 1322.

Alternatively, if the intensivist determines there is evidence of edema or congestion 1330, the intensivist is prompted to: 1) insert a PA catheter to measure wedge pressure and liver function to direct fluid replacement; and 2) send urine creatinine and sodium 1332.

Figure 26C:
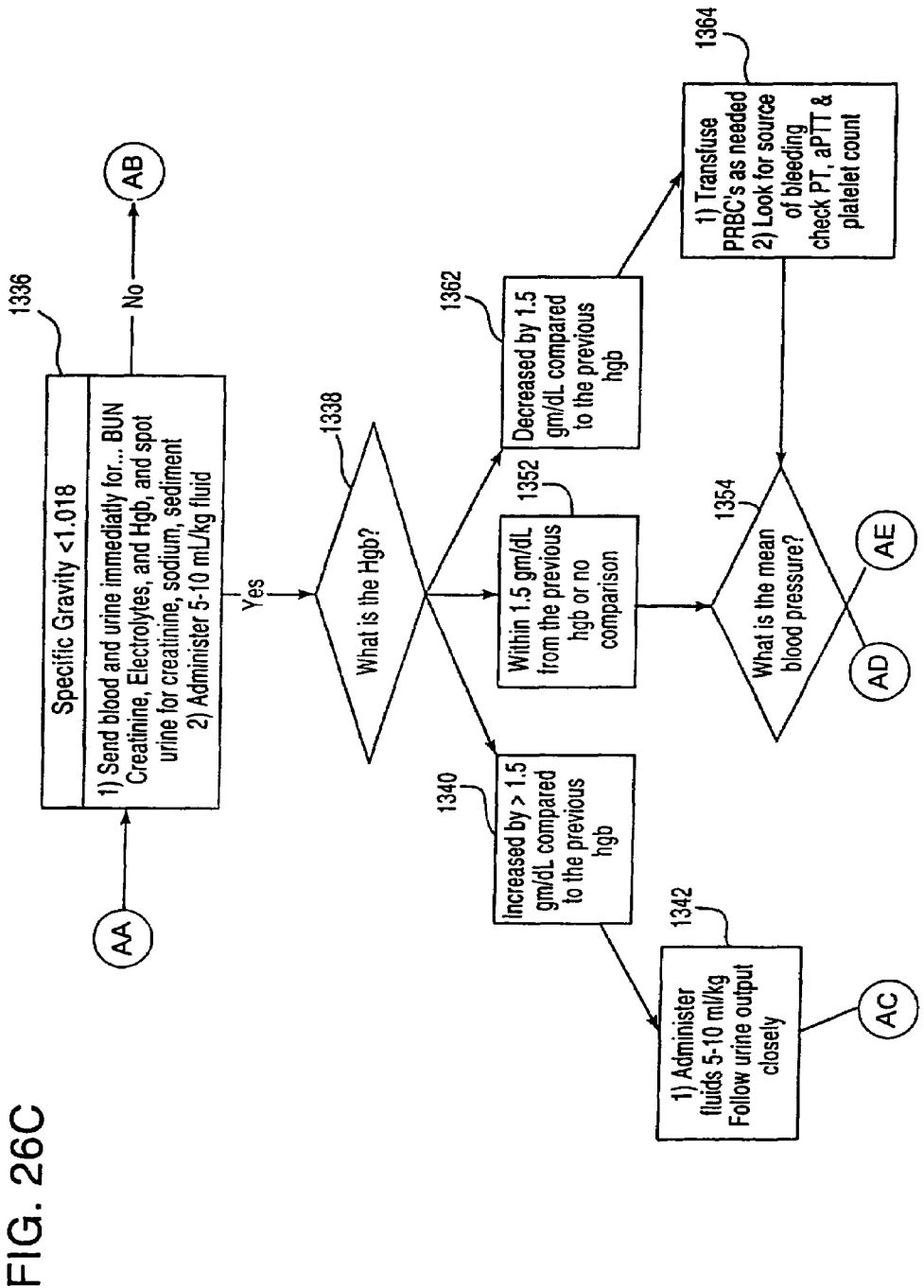
FIGS. 26C-D illustrate the oliguria decision support algorithm (cont).
Figure 26D:
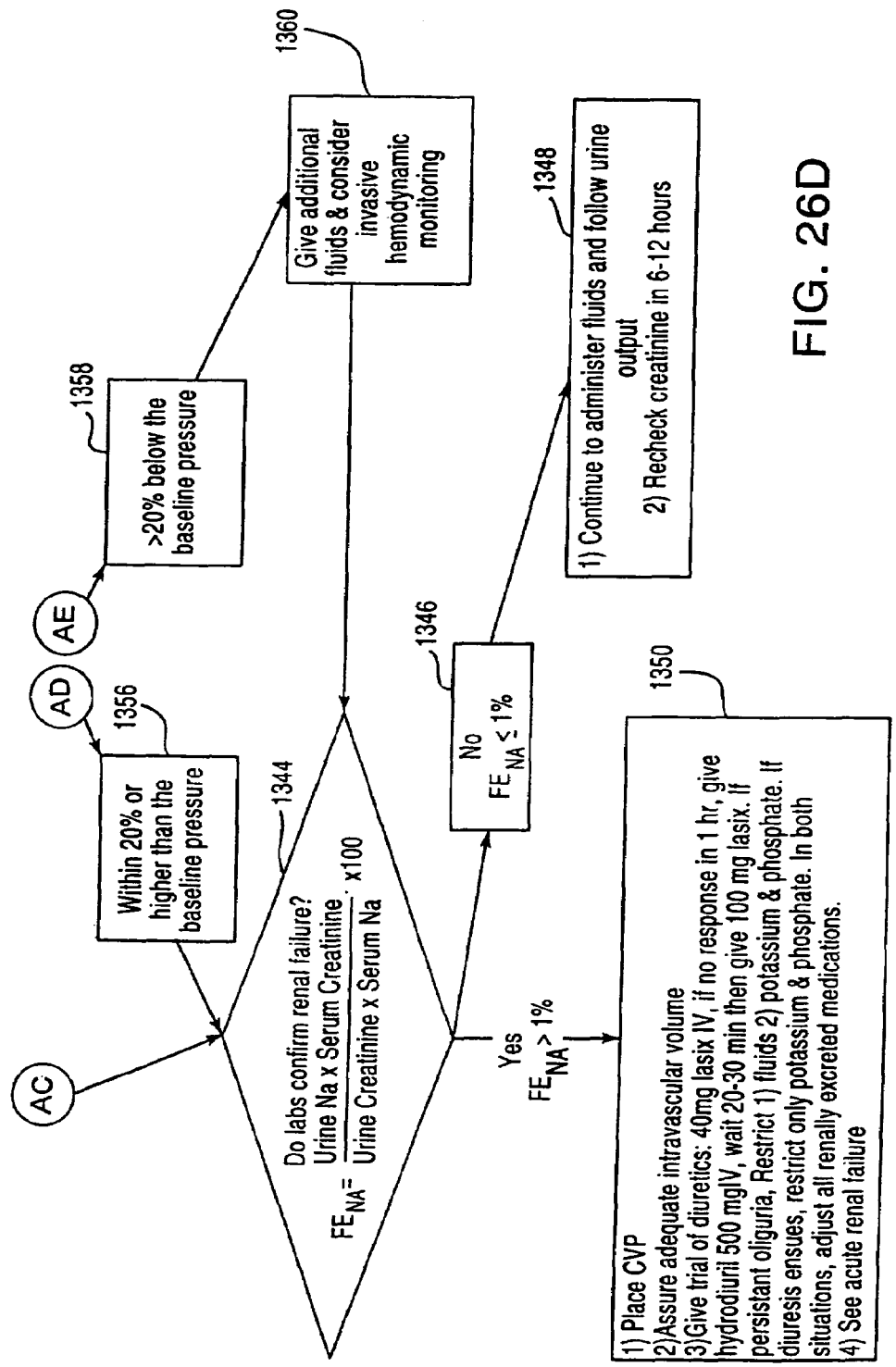

Referring now to FIG. 26C-D, the oliguria algorithm description continues. Following the specific gravity test of the patient's urine, the intensivist is prompted to determine whether the results indicate the specific gravity is less than 1.018. If this criterion is met, the intensivist is prompted to: 1) send blood and urine immediately to test for blood urea nitrogen (BUN), creatinine, electrolytes, and Hgb, and spot urine for creatinine, sodium, and sediment; and 2) administer 5-10 ml of fluid per kg of bodyweight 1356. Once the results of these tests are obtained, the intensivist is prompted to determine what is the Hgb 1338.

If the Hgb has increased by more than 1.5 gm/dl compared to the previous Hgb 1340, the intensivist is prompted to: 1) administer fluids 5-10 ml/kg of bodyweight and follow the urine output closely 1342. Following this, the intensivist is prompted to determine whether the labs confirm renal failure by use of the formula $FE_{Na} = Urine\ Na \times Serum\ Creatinine / Urine\ Creatinine \times Serum\ Na \times 100$ 1344.

If the Hgb is within 1.5 gm/dl from the previous Hgb or no comparison 1352, the intensivist is prompted to determine what is the mean blood pressure 1354. If the mean blood pressure is determined to be within 20 percent or higher than the baseline blood pressure 1356, the intensivist is prompted to determine whether the labs confirm renal failure 1344. If the mean blood pressure is determined to be greater than 20 percent below the baseline pressure 1358, the intensivist is prompted to give additional fluids and consider invasive hemodynamic monitoring 1360. Following this, the intensivist is prompted to determine whether the labs confirm renal failure by use of the formula $FE_{Na} = Urine\ Na \times Serum\ Creatinine / Urine\ Creatinine \times Serum\ Na \times 100$ 1344.

Alternatively if the Hgb has decreased by 1.5 gm/dl compared to the previous Hgb 1362, the intensivist is prompted to: 1) transfuse PRBCs as needed; 2) look for source of bleeding and check PT, aPTT, & platelet count 1364. Following this, the intensivist is prompted to determine what is the mean blood pressure 1354. If the mean blood pressure is determined to be greater than 20 percent below the baseline pressure 1358, the intensivist is prompted to give additional fluids and consider invasive hemodynamic monitoring 1360. Following this, the intensivist is prompted to determine whether the labs confirm renal failure by use of the formula FE.sub.Na=Urine Na.times.Serum Creatinine/Urine Creatinine.times.Serum Na.times.100 1344.

If the labs do not confirm renal failure, as indicated by FE.sub.Na.ltoreq.1 percent 1346, the intensivist is prompted to: 1) continue to administer fluids and follow urine output; and 2) recheck creatinine in 6-12 hours 1348.

Alternatively, if the labs do confirm renal failure, as indicated by FE.sub.Na>1 percent 1350, the intensivist is prompted to: 1) place central venous pressure (CVP); 2) Assure adequate intravascular volume; 3) give trial of diuretics: 40 mg lasix IV, if no response in 1 hour, give hydrodiuril 500 mg IV, wait 20-30 minutes then give 100 mg lasix, if persistent oliguria, restrict: 1) fluids; 2) potassium & phosphate; if diuresis ensues, restrict only potassium & phosphate; in both situations, adjust all renally excreted medications; and 4) see acute renal failure 1350.

Figure 26E:
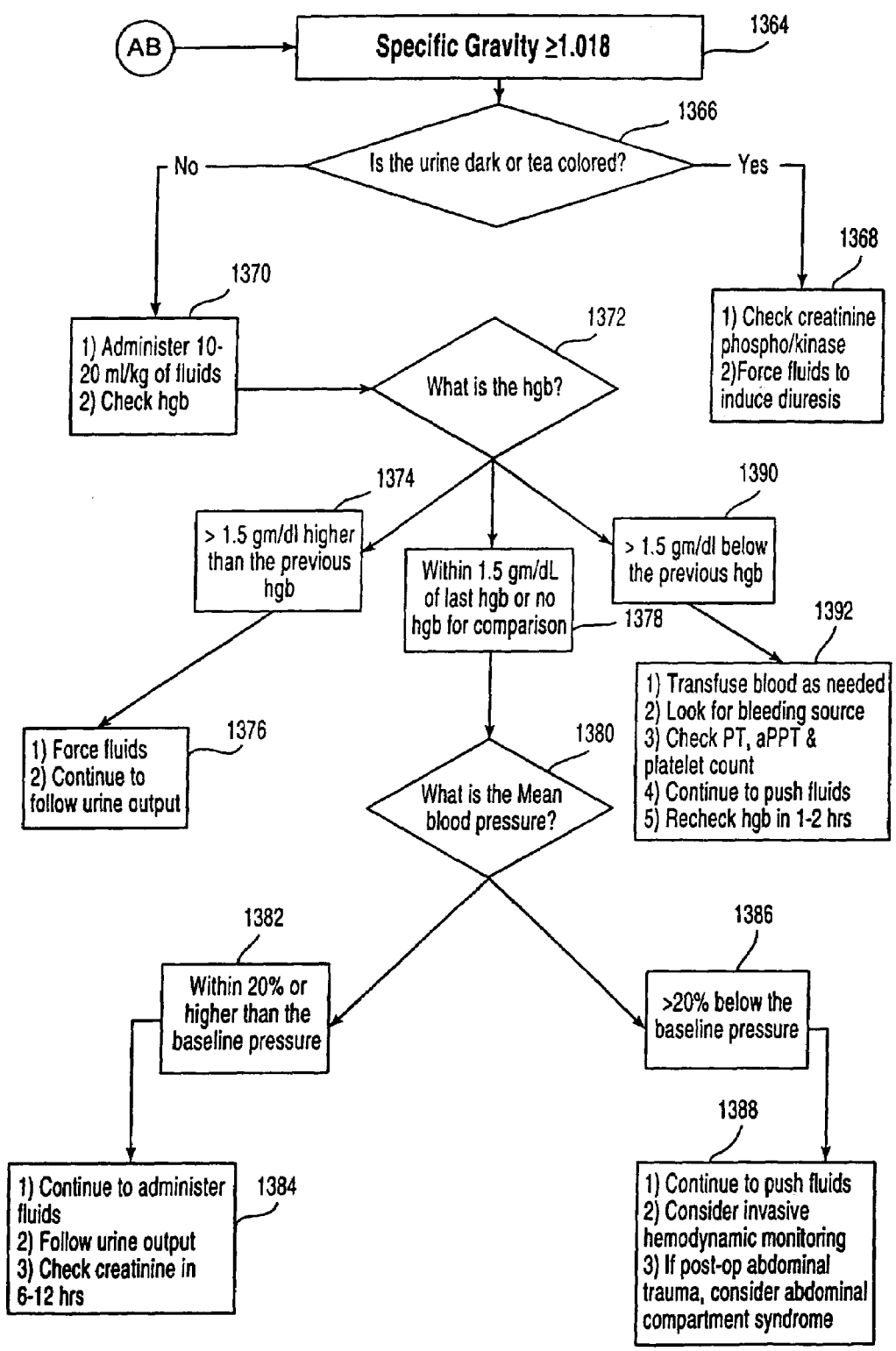
FIG. 26E illustrates the oliguria decision support algorithm (cont).

Referring now to FIG. 26E, the oliguria algorithm description continues. Alternatively, following the specific gravity test of the patient's urine, the intensivist is prompted to determine whether the results indicate the specific gravity is greater than or equal to 1.018 1336. If this criterion is not met 1364, the intensivist is prompted to determine whether the urine is dark or tea colored 1366. If this criterion is met, the intensivist is prompted to: 1) check creatinine phospho/kinase; and 2) force fluids to induce diuresis 1368.

If the intensivist determines that the urine is not dark or tea colored, the intensivist is prompted to: 1) administer 10-20 ml of fluids per kg of bodyweight; and 2) check Hgb 1370. The intensivist is then prompted to determine what is the Hgb 1372.

If the Hgb is determined to be greater than 1.5 gm/dl higher than the previous Hgb 1374, the intensivist is directed to: 1) force fluids; and 2) continue to follow the urine output 1376.

Alternatively, if the Hgb is determined to be within 1.5 gm/dl of the last Hgb or there is no Hgb for comparison 1378, the intensivist is prompted to determine what is the mean blood pressure 1380. If the mean blood pressure is determined to be 20 percent or higher than the baseline pressure 1382, the intensivist is prompted to: 1) continue to administer fluids; 2) follow urine output; and 3) check creatinine in 6-12 hours 1384. If the mean blood pressure is determined to be greater than 20 percent below the baseline pressure 1386, the intensivist is prompted to: 1) continue to push fluids; 2) consider invasive hemodynamic monitoring; and 3) if post-op abdominal trauma, consider abdominal compartment syndrome 1388.

If the Hgb is determined to be greater than 1.5 gm/dl below the previous Hgb 1390, the intensivist is prompted to: 1) transfuse blood as needed; 2) look for bleeding source; 3) check PT, aPPT & platelet count; 4) continue to push fluids; and 5) recheck Hgb in 1-2 hours 1392.

Figure 27A:
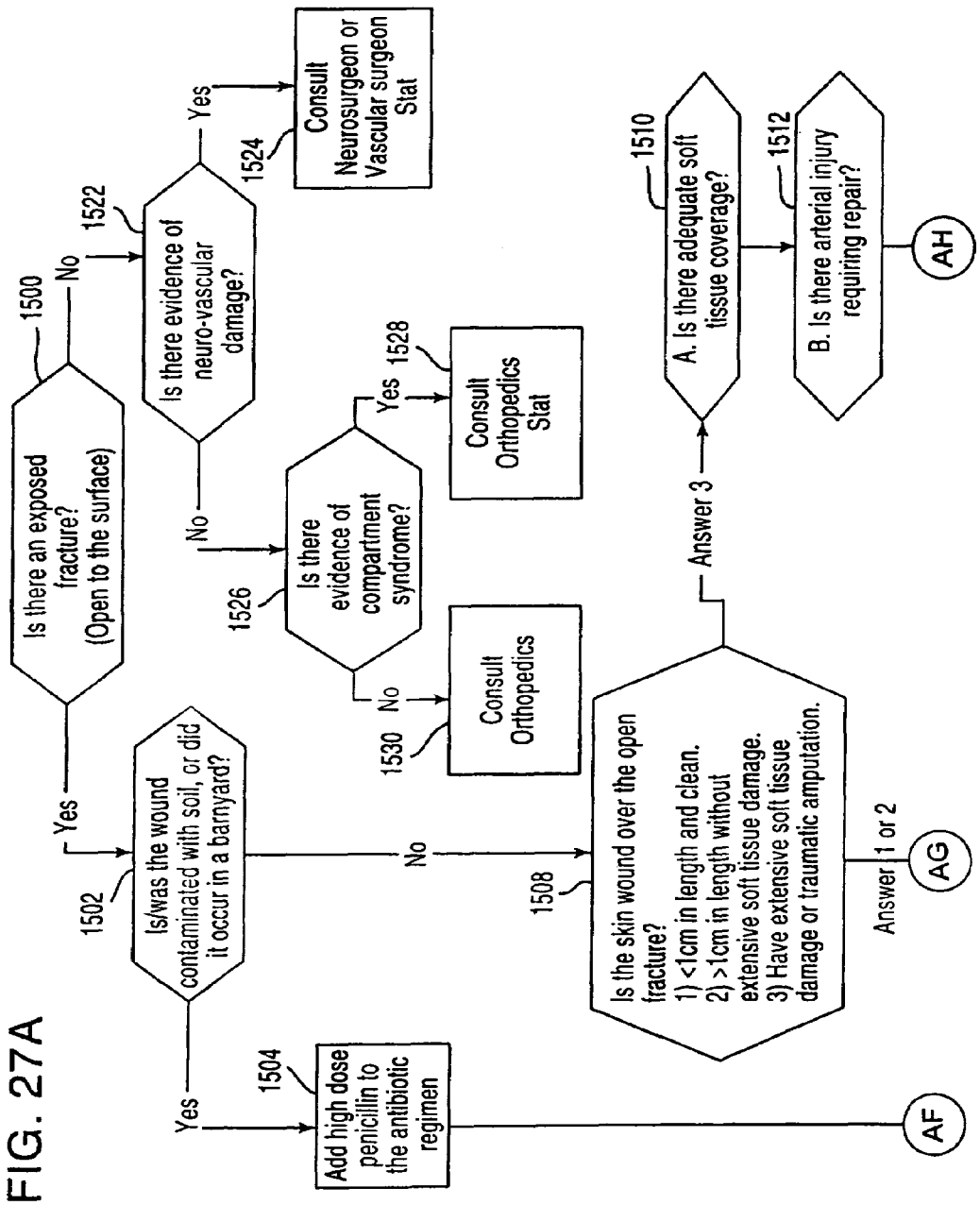
FIGS. 27A-B illustrate the open fractures decision support algorithm.
Figure 27B:
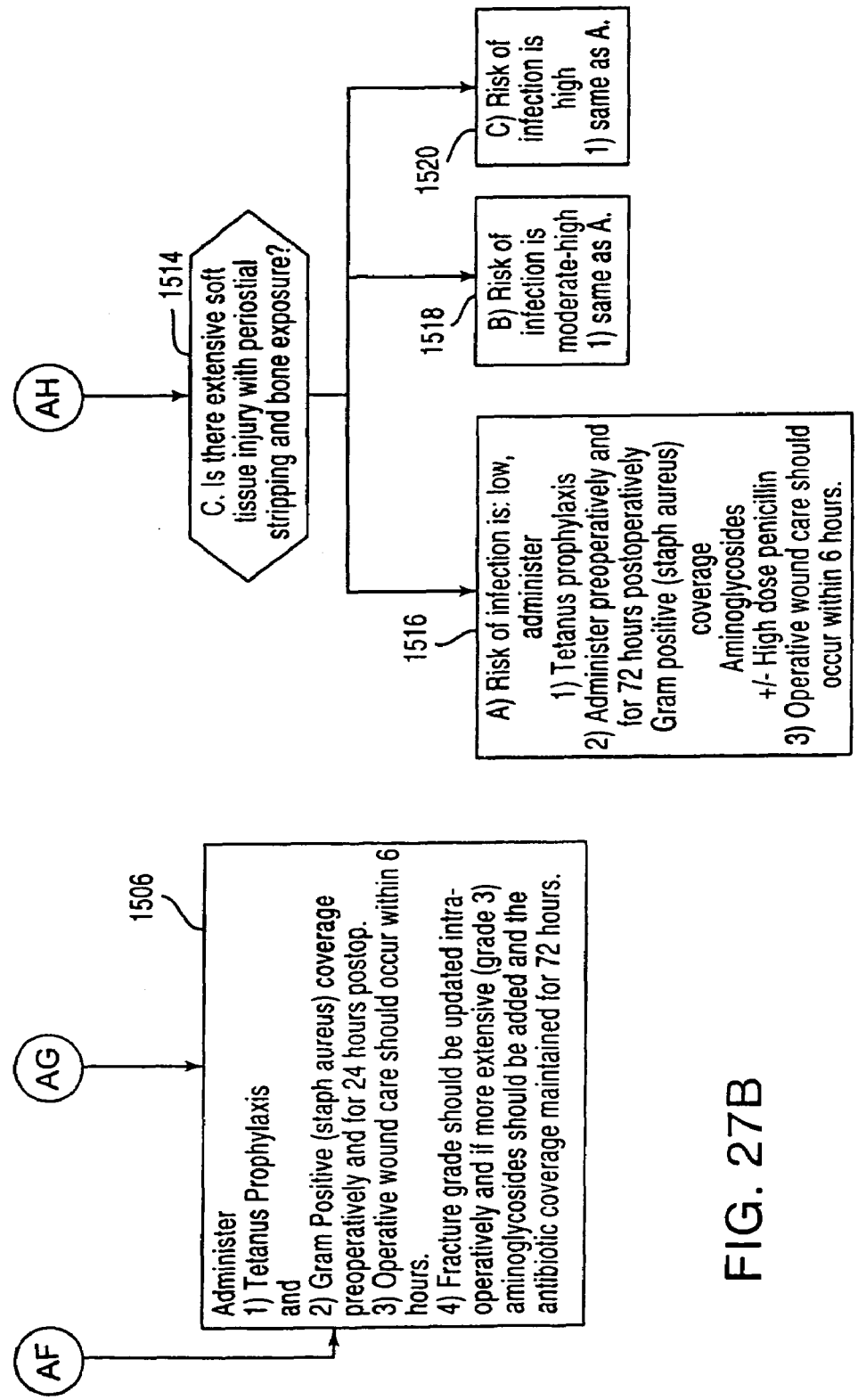

Referring to FIG. 27A-B, the open fractures decision support algorithm of the present invention is illustrated. Open fractures are where bone, cartilage, or a tooth break and push through the skin surface. The intensivist is first prompted by the system to determine whether the patient has an open fracture 1500. If one has occurred, the intensivist must then determine whether the wound is contaminated with soil, or was inflicted in a barnyard 1502 in order to address higher risk of infection. If the wound is contaminated with soil, or was inflicted in a barnyard, the intensivist is prompted to administer a high dose of penicillin to the antibiotics prescribed 1504. The intensivist is also prompted to take several treatment steps 1506. These treatment steps include administering tetanus prophylaxis, such an antitoxin injection, monitoring *staphylococcus aureus* until twenty-four hours after surgery, caring for the wound within six hours, and where the injury is found to be more severe during surgery, the intensivist is prompted to administer aminoglycosides for seventy two hours.

If the wound is not contaminated with soil, or was inflicted in a barnyard, the intensivist is next prompted to determine the severity of the wound 1508. To do so, the intensivist must determine the length of the wound and corresponding soft tissue damage. If the wound is either less than one centimeter and clean or greater than a centimeter long without extensive soft tissue damage, the intensivist is prompted to take several treatment steps 1506 as previously described. Where the soft tissue damage is extensive or amputation has occurred, the intensivist is prompted by the system to make further determinations 1510, 1512, 1514 about the wound caused by the fracture. The intensivist is prompted to determine if enough soft tissue coverage is remaining for the wound to close and heal 1510, if any arterial repair is needed 1512, and if extensive soft tissue damage with periostitial injury, and bone exposure 1514. If there is adequate soft tissue coverage, the intensivist is advised that risk of infection is low and directed to take treatment actions 1516. If arterial damage requiring repair is present, the intensivist is advised by the system that risk of infection is moderate to high and given treatment instructions 1518. Where there is soft tissue injury with periostitial stripping and bone exposure, the intensivist is alerted by the system that risk of infection is high and given treatment instructions 1520. The treatment instructions in each case 1516, 1518, 1520 include administering tetanus prophylaxis, such an antitoxin injection, caring for the wound within six hours, and performing: monitoring for *staphylococcus aureus*, and administering aminoglycosides and high doses of penicillin, all for seventy two hours before and after any operative procedures.

If the intensivist has determined that no exposed fracture has occurred, the system next prompts the intensivist to determine whether there is any evidence of neuro-vascular damage 1522. If there is evidence of neuro-vascular damage, the intensivist is prompted to consult with a nerosurgeon or vascular surgeon immediately 1524. If the intensivist determines there is no evidence of neuro-vascular damage to the patient, the system next prompts the intensivist to determine whether the patient has compartment syndrome 1526. If there is evidence of compartment syndrome seen in the patient, the intensivist is prompted to consult orthopedics right away 1528. If there is no evidence of compartment syndrome seen in the patient, the intensivist is still prompted to consult orthopedics, but without any prompt for time sensitivity 1530.

Figure 28A:
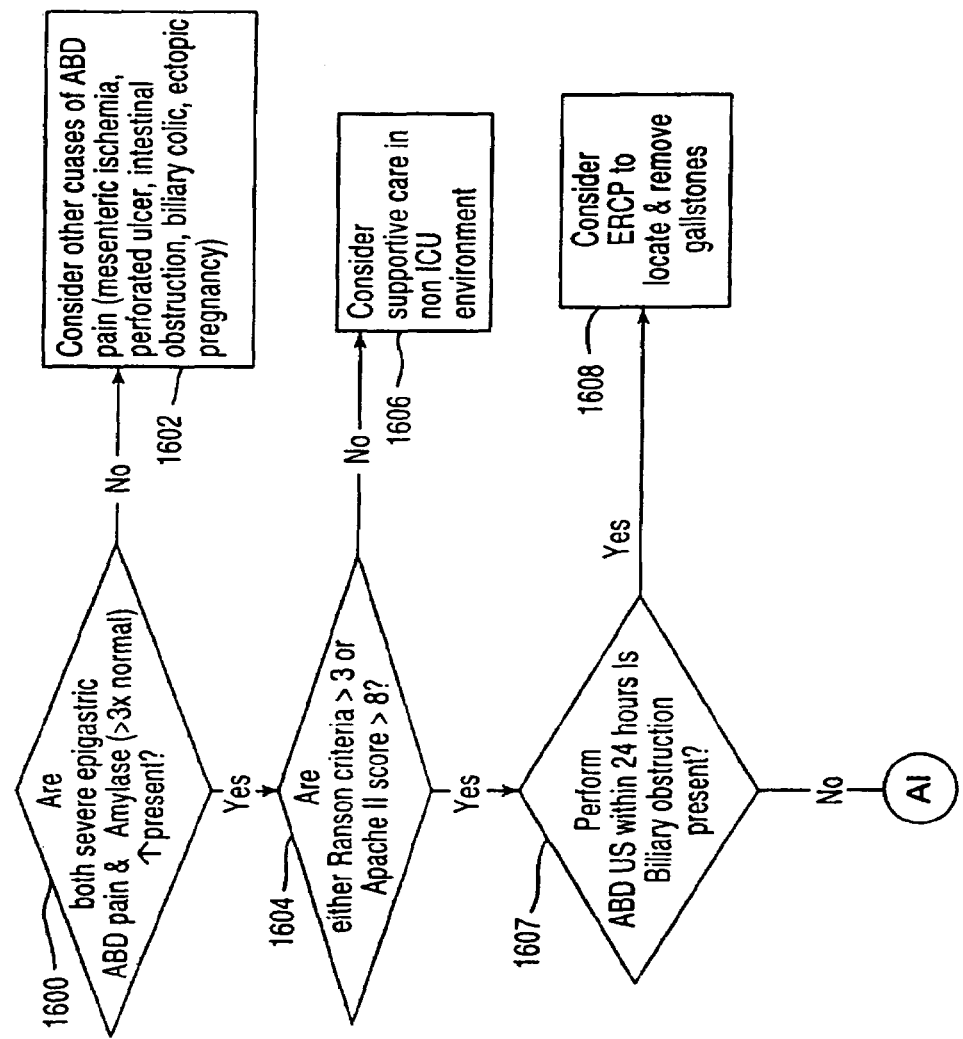
FIGS. 28A-B illustrate the pancreatitis decision support algorithm.
Figure 28B:
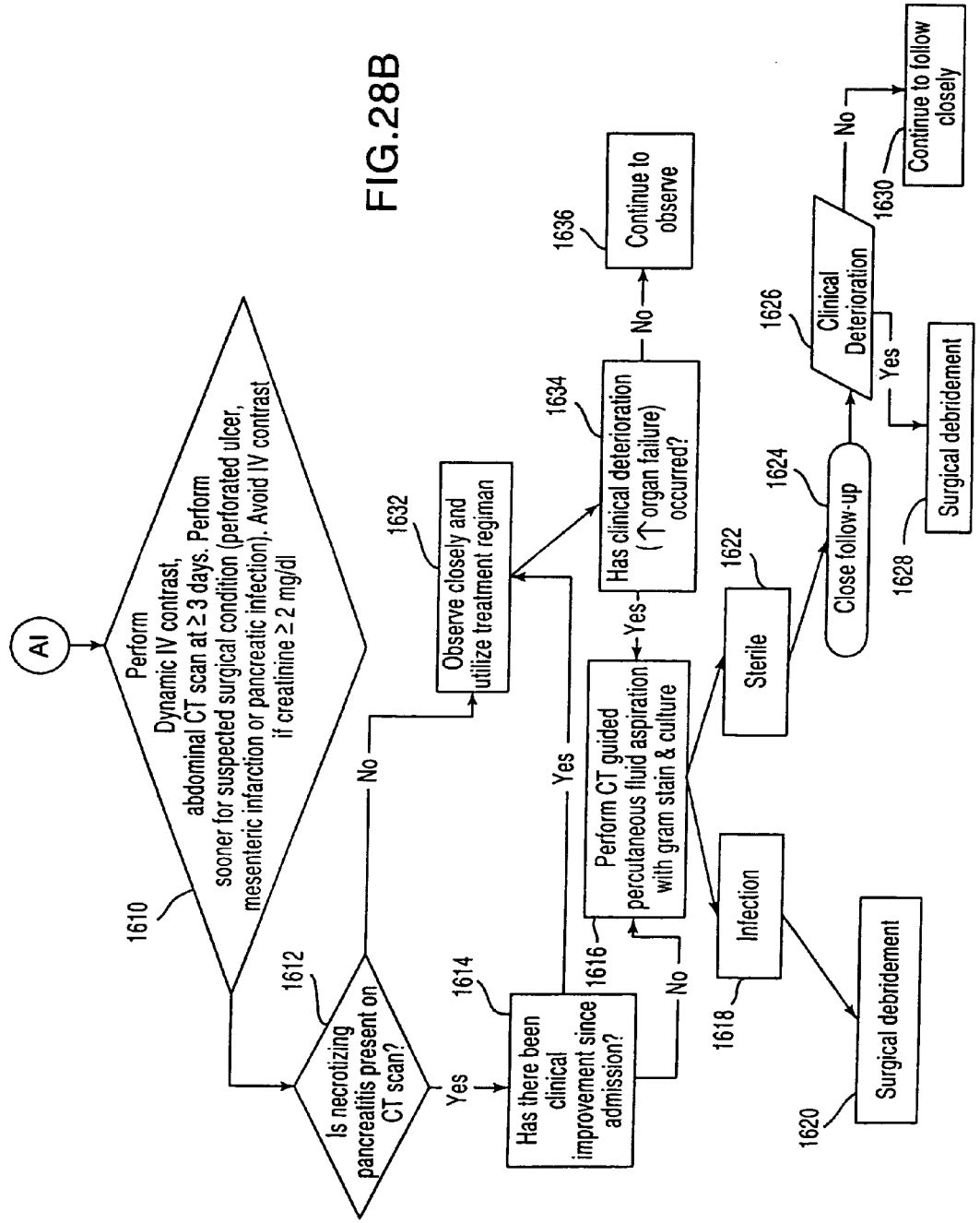

Referring to FIGS. 28A-B, the Pancreatitis diagnostic algorithm of the present invention is illustrated. To evaluate whether a patient has pancreatitis, the intensivist is first prompted to examine whether severe epigastric abdominal pains and amylase levels three times greater than normal are present in the patient 1600. If neither or one of the conditions is present, the intensivist is prompted to consider other causes of the abdominal pain, such as mesenteric ischemia, a perforated ulcer, intestinal obstruction, biliary colic, or an ectopic pregnancy 1602.

If severe epigastric abdominal pains and amylase levels three times greater than normal are present, the intensivist is next prompted to provide the Ranson Criteria which is a criteria associated with the severity of pancreatitis and the potential outcome or prognosis at that particular level of severity, or Apache II score which is also a score associated with the severity of the disease and the potential prognosis at a particular level of the patient 1604. If the patient has a Ranson Criteria less than three or an Apache II score of less than eight, the intensivist is prompted by the system to consider removing the patient from the Intensive Care Unit 1606. However, if the patient has a Ranson Criteria greater than three or an Apache II score of greater than eight, the intensivist is instructed to perform an abdominal ultrasound test within twenty-four hours 1607. If the results of the ultrasound test show a biliary obstruction, the intensivist is instructed to consider performing an ERCP to find and remove any gallstones 1608.

If the abdominal ultrasound results do not show any biliary obstruction, intensivist is next prompted to perform more diagnostic tests 1610. The intensivist is directed to perform a Dynamic IV contrast and an abdominal Tomography (CT) scan. If the intensivist does not suspect a surgical condition exists, such as a perforated ulcer, mesenteric infarction or pancreatic infection, the tests may be performed after three days have passed. If the intensivist does suspect a surgical condition exists, the tests should be performed within three days. In either case, if the patient has creatinine levels greater than or equal to 2 miligrams per dl, the intensivist should not perform the Dynamic IV contrast test.

Once the CT scan is performed, the intensivist is prompted to determine whether necrotizing pancreatitis is present 1612. The intensivist is next required to determine whether the patient has improved since admission 1614. If no improvement has been seen, the intensivist is directed to perform percutaneous fluid aspiration and do a gram stain culture the collected fluid 1616. If the culture shows infection 1618, the intensivist is directed to perform surgical debridement of the pancreas 1620. If the results of the culture are sterile 1622, the intensivist is directed to closely follow up on the patient's condition 1624 and watch for clinical deterioration 1626. If the patient does further deteriorate, the intensivist is then instructed to perform a surgical debridement of the pancreas 1628. If the patient does not deteriorate, the intensivist is still prompted to closely follow the patient's condition 1630.

Where the CT scan does not show signs of necrotizing pancreatitis 1612, the intensivist is prompted by the system to closely observe the patient 1632. The intensivist is also prompted to check whether clinical deterioration is occurring 1634. If no deterioration is observed, the intensivist continues to observe the patient's condition 1636. If clinical deterioration is occurring 1634, the intensivist is directed to perform percutaneous fluid aspiration and do a gram stain culture the collected fluid 1616. If the culture shows infection 1618, the intensivist is directed to order surgical debridement of the pancreas 1620. If the results of the culture are sterile 1622, the intensivist is directed to closely follow up on the patient's condition 1624 and watch for clinical deterioration 1626. If the patient does further deteriorate, the intensivist is then prompted to order a surgical debridement of the pancreas 1628. If the patient does not deteriorate, the intensivist is still directed by the system to closely follow the patient's condition 1630.

Figure 29A:
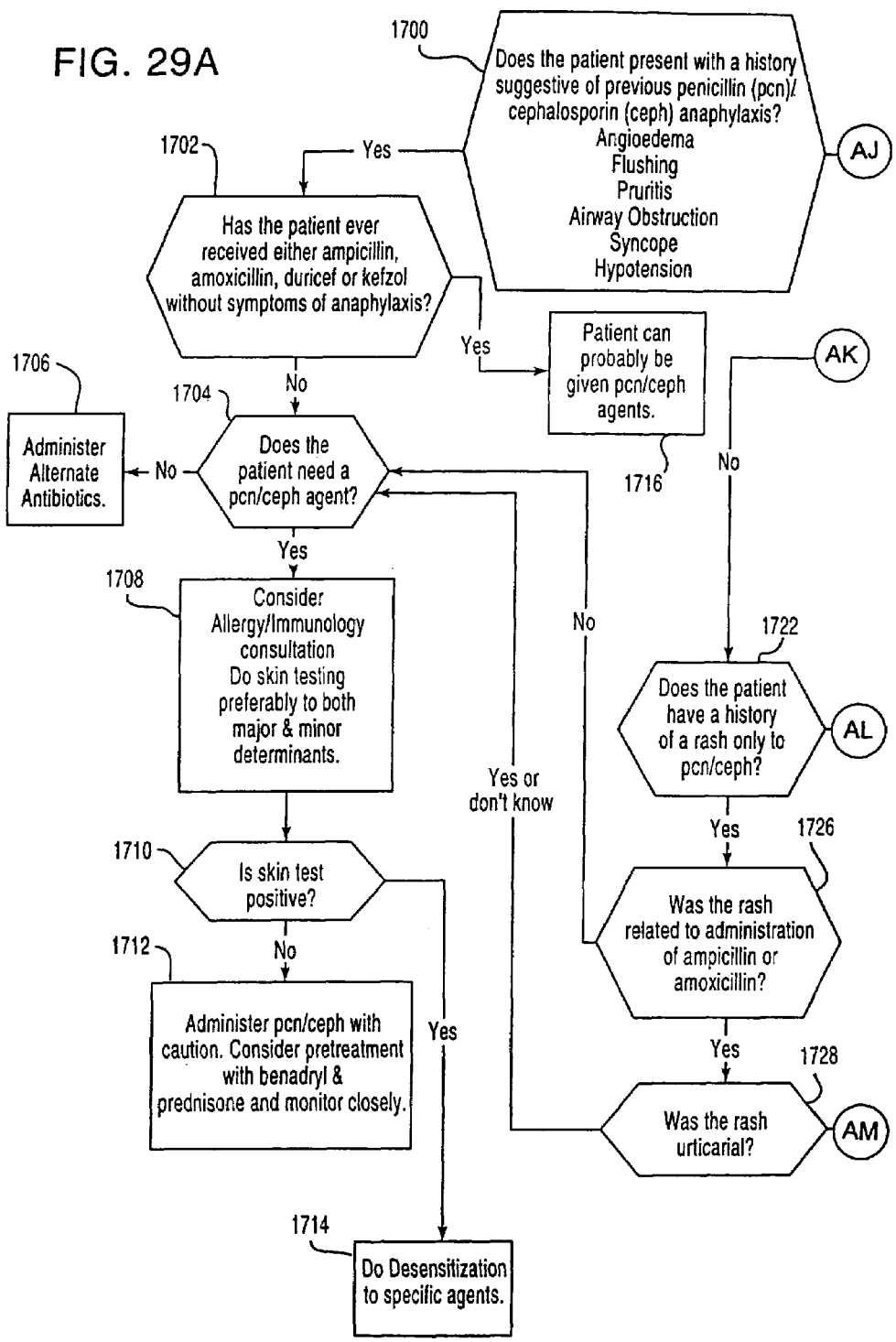
FIGS. 29A-B illustrate the penicillin allergy decision support algorithm.
Figure 29B:
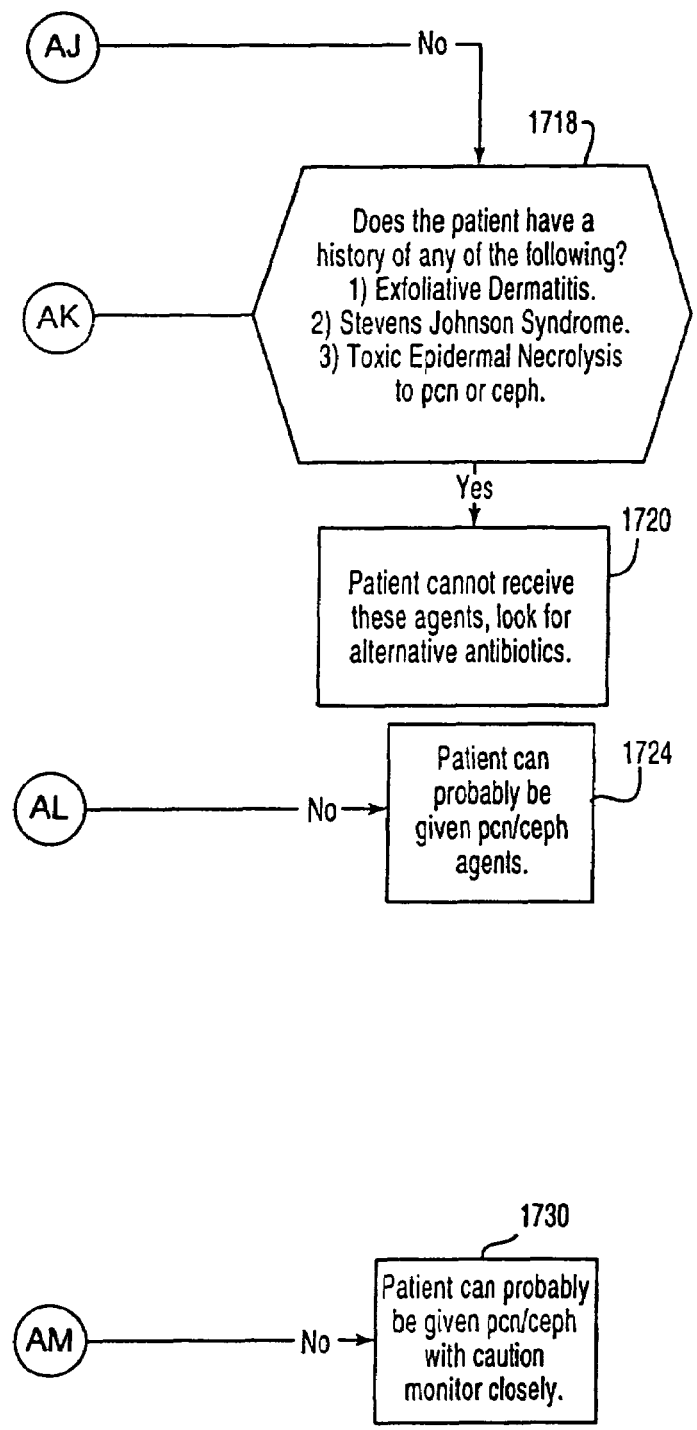

Referring to FIGS. 29A-B, the penicillin allergy diagnosis algorithm of the present invention is illustrated. In order to diagnose a penicillin allergy, the intensivist is first prompted to determine whether the patient has a history suggestive of previous penicillin or cephalosporin anaphylaxis 1700. Various known reactions, including angioedema, flushing, pruritis, airway obstruction, syncope, and hypertension, are displayed for the intensivist's review. If the patient has previously had any of these reactions, the intensivist is prompted to determine whether the patient has ever taken synthetic or partially synthetic antibiotics, such as ampicillin, amoxicillin, duricef or kefzol, without any anaphylaxis symptoms 1702. If the patient has taken synthetics without reaction, the intensivist is advised by the system that penicillin or cephalosporin may be administered 1716. If the patient has reacted to synthetic or partially synthetic antibiotics, the intensivist is next prompted to determine whether the patient needs penicillin or cephalosporin specifically 1704.

If the patient is not required to have penicillin or cephalosporin, the intensivist is prompted to administer the synthetic antibiotics 1706. If the patient does need penicillin or cephalosporin, the intensivist is directed by the system to consider consulting with an allergist or immunologist and perform skin tests for reactions 1708. Next, the intensivist is prompted to enter whether the skin test was positive 1710. If the results are negative, the intensivist is further directed by the system to administer penicillin or cephalosporin with caution, to consider pretreatment with benadryl or prednisone to counter any reaction, and to closely monitor the patient 1712. If the results of the skin test are positive, the intensivist is prompted by the system to perform desensitization procedures 1714.

If the patient does not have a history suggestive of previous penicillin or cephalosporin anaphylaxis 1700, the intensivist is prompted to determine whether the patient has previously experienced skin-level reactions, such as exfoliative dermatitis, Stevens Johnson Syndrome, or Toxic Epidernial Necrolysis, when given penicillin or cephalosporin 1718. If the patient has previously experienced one of these reactions, the intensivist is directed by the system to administer an alternative antibiotic 1720. If the patient has not experienced one of these reactions, the intensivist is prompted to determine whether there is a history of any rash when given penicillin or cephalosporin 1722. If the patient has not previously had a rash when given penicillin or cephalosporin, the intensivist is advised that the patient will most likely be able to take penicillin or cephalosporin 1724.

If the patient has previously experienced a rash when given penicillin or cephalosporin, the intensivist is prompted to determine whether the rash presented when the patient was given ampicillin or amoxycillin 1726. If the rash resulted from ampicillin or amoxycillin, the intensivist is next prompted to determine whether the rash was urticarial 1728. If the rash was not urticarial, the intensivist is advised by the system that the patient probably can take penicillin or cephalosporin, but should be closely monitored 1730. If the rash was urticarial, the intensivist is prompted to determine whether or not the patient needs penicillin or cephalosporin 1704.

If the patient is not required to have penicillin or cephalosporin, the intensivist is directed by the system to administer the synthetic antibiotics 1706. If the patient does need penicillin or cephalosporin, the intensivist is directed to consider consulting with an allergist or immunologist and perform skin tests for reactions 1708. Next, the intensivist is prompted to enter whether the skin test was positive 1710. If the results are negative, the intensivist is further directed to administer penicillin or cephalosporin with caution, to consider pretreatment with benadryl or prednisone to counter any reaction, and to closely monitor the patient 1712. If the results of the skin test are positive, the intensivist is directed to perform desensitization procedures 1714.

Figure 30A:
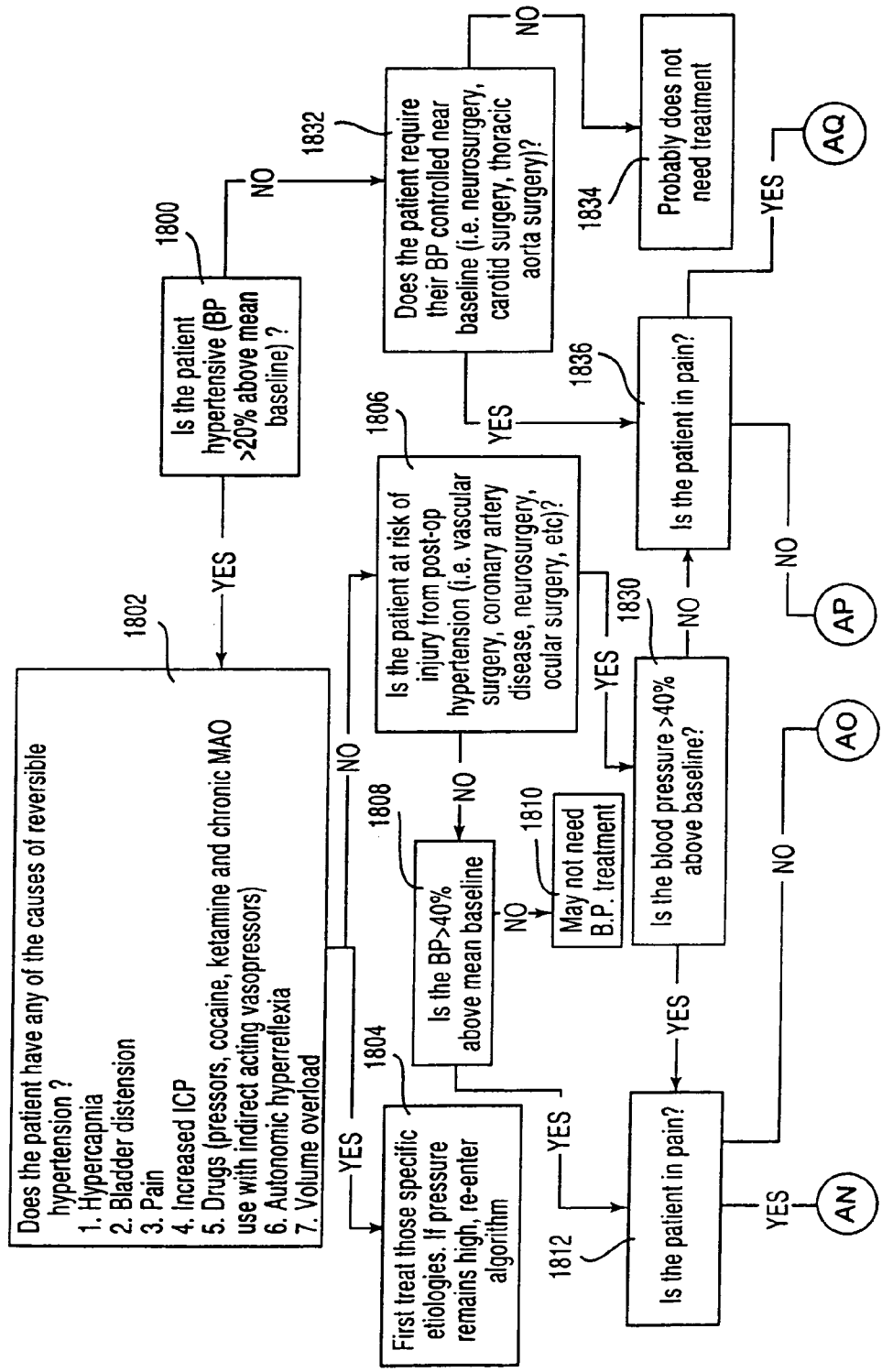
FIGS. 30A-B illustrate the post-op hypertension decision support algorithm.
Figure 30B:
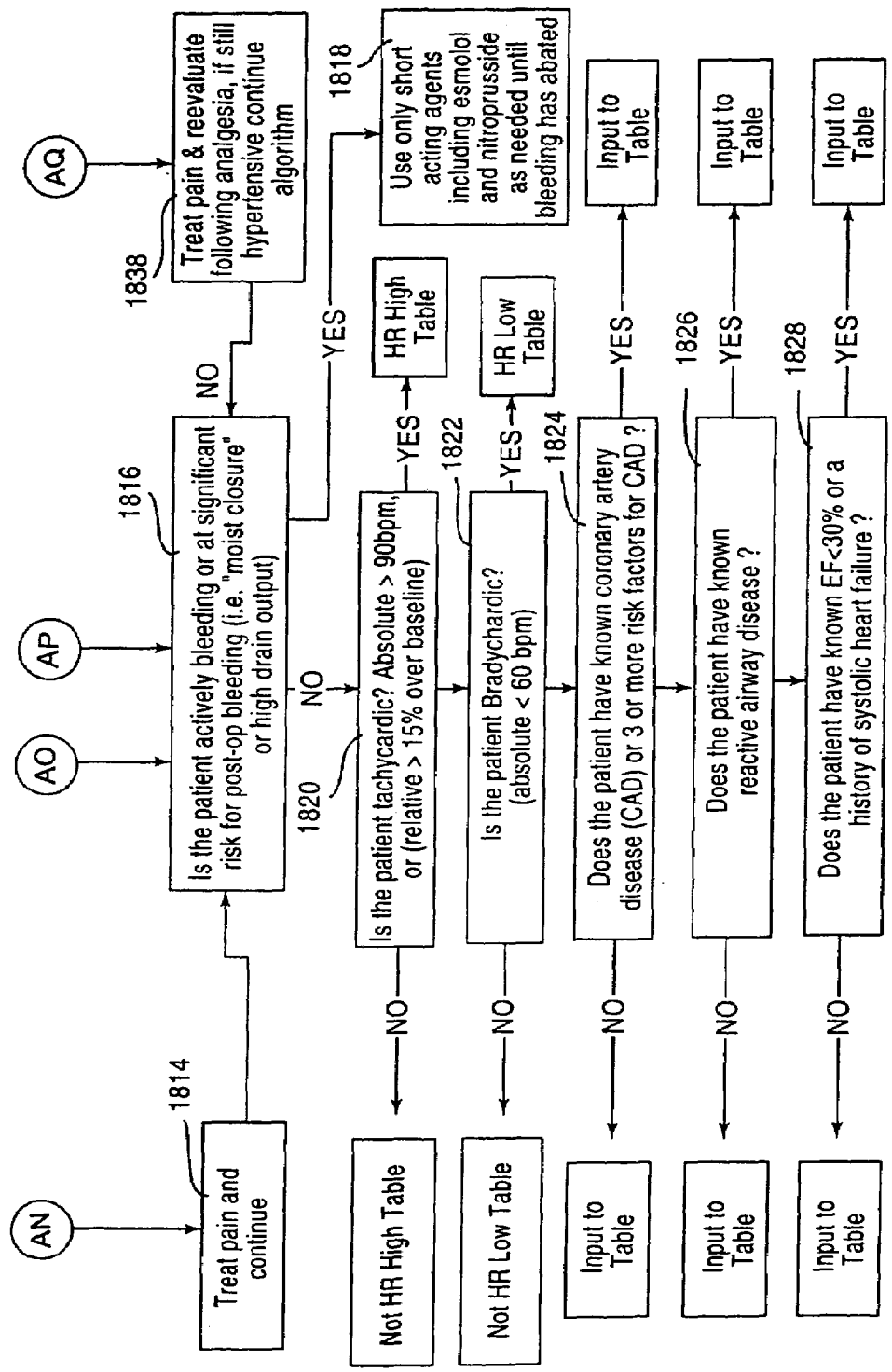

Referring to FIG. 30A-B, the Post-Op Hypertension decision support algorithm of the present invention is illustrated. If an intensivist determines that there may be a possibility of post-op hypertension, the intensivist may not be certain of all aspects that would be involved in this particular condition. Therefore, the intensivist is lead through a decision support algorithm which prompts the intensivist to determine the appropriate care to be given.

Initially, the intensivist is prompted to determine whether the patient is hypertensive (BP greater than 20 percent above mean baseline) 1800. If this criterion is met, the intensivist is prompted to determine whether the patient has any of the causes of reversible hypertension: 1) hypercapnia; 2) bladder distension; 3) pain; 4) increased ICP; 5) drugs (pressors, cocaine, ketamine and chronic MAO use with indirect acting vasopressors); 6) automatic hyperreflexia; or 7) volume overload 1802. If any of these criteria are met, the intensivist is prompted to first treat those specific etiologies and, if pressure remains high, re-enter algorithm 1804.

Alternatively, if none of these criteria are met 1802, the intensivist is prompted to determine whether the patient is at risk of injury from post-op hypertension (i.e., vascular surgery, coronary artery disease, neurosurgery, ocular surgery, etc.) 1806. If this criterion is not met 1806, the intensivist is prompted to determine whether the BP is greater than 40 percent above mean baseline 1808. If this criterion is not met, the intensivist is prompted that the patient may not need BP treatment 1810.

If the BP is greater than 40 percent above the mean baseline 1808, the intensivist is prompted to determine whether the patient is in pain 1812. If this criterion is met 1812, the intensivist is prompted to treat pain and continue 1814. Following this prompt 1814, the intensivist is prompted next to determine whether the patient is actively bleeding or at significant risk for post-op bleeding (i.e., "moist closure" or high drain output) 1816. If either of these criteria is met 1816, the intensivist is prompted to use only short acting agents including emolol and nitroprusside as needed until bleeding has abated 1818.

Alternatively, if neither of these criteria is met 1816, the intensivist is prompted to determine whether the patient is tachycardic (absolute greater than 90 bpm or ((relative greater than 15 percent over baseline)) 1820. If either of these criteria is met 1820, the intensivist is prompted to go to Decision Table C, which is programmed for the condition of a high heart rate. If neither of these criteria is met 1820, the intensivist is prompted to eliminate (NOT C) Table C and proceed to the next decision point 1820.

| HR ↑ Table C | | | | | | |
|---|---|---|---|---|---|---|
| CAD | Y | Y | Y | N | N | N |
| RAD | N | Y | Y | N | Y | N |
| ↓ EF | N | N | Y | N | Y | Y |
| Treatment | | | | | | |
| $1^{ST}$ | L | E | L | L | A | E |
| $2^{ND}$ | E | L | A | N | N | A |

The intensivist is prompted next to determine whether the patient is bradycardic (absolute less than 60 bpm) 1822. If this criterion is met, the intensivist is prompted to go to Decision Table B, which is programmed for the condition of a low heart rate.

| HR ↓ Table B | | | | | | |
|---|---|---|---|---|---|---|
| CAD | Y | Y | Y | N | N | N |
| RAD | N | Y | Y | N | Y | N |
| ↓ EF | N | N | Y | N | Y | Y |
| Treatment | | | | | | |
| $1^{ST}$ | N | N | A | N | A | A |
| $2^{ND}$ | S | S | S | H | H | H |

If this criterion is not met, the intensivist is prompted to eliminate (NOT B) Table B and proceed to the next decision point 1822. [Note: If NOT C and NOT B, the intensivist is prompted to go to Table A by default, i.e., If NOT C and NOT B Then A].

| HR (nl) Table A | | | | | | |
|---|---|---|---|---|---|---|
| CAD | Y | Y | Y | N | N | N |
| RAD | N | Y | Y | N | Y | N |
| ↓ EF | N | N | Y | N | Y | Y |
| Treatment | | | | | | |
| $1^{ST}$ | L | E | A | N | A | A |
| $2^{ND}$ | N | N | E | A | N | N |

The intensivist is prompted next to determine, sequentially, table input values for CAD, RAD, and EF.

In these decision tables, the letter references have the following meanings: L=labetalol, E=esmolol, A=enalapril, N=nicardipine, H=hyrdalazine, S=nitroprusside. The reference to 1.sup.st and 2.sup.nd means that treatment should begin with the 1.sup.st drug and add or substitute the 2.sup.nd drug as needed.

Using the above decision tables, the intensivist is prompted to determine whether the patient has known coronary artery disease (CAD) or 3 or more risk factors for CAD 1824. If either of these criteria is met 1824, the intensivist is prompted to enter a "Y" or "YES" for CAD into the table selected above in 1820 and 1822. If neither of these criteria is met, the intensivist is prompted to enter a "N" or "NO" for CAD into the table selected above in 1820 and 1822.

Next, the intensivist is prompted to determine whether the patient has known reactive airway disease (RAD)1826. If this criterion is met 1826, the intensivist is prompted to enter a "Y" or "YES" for RAD into the table selected above in 1820 and 1822. If this criterion is not met, the intensivist is prompted to enter a "N" or "NO" for RAD into the table selected above in 1820 and 1822.

Next, the intensivist is prompted to determine whether the patient has known EF less than 30 percent or a history of systolic heart failure 1828. If either of these criteria is met 1828, the intensivist is prompted to enter a "Y" or "YES" for EF into the table selected above in 1820 and 1822. If neither of these criteria is met 1828, the intensivist is prompted to enter a "N" or "NO" for EF into the table selected above in 1820 and 1822.

Based on the table selected in 1820 and 1822 above, and the table inputs determined from 1824, 1826, and 1828, the intensivist is prompted with the proper medication to administer for the 1.sup.st and 2.sup.nd treatment.

If the patient is not in pain 1812, the intensivist is prompted to employ the procedures described above in 1816.

If the patient is at risk of injury from post-op hypertension 1806, the intensivist is prompted to determine whether the blood pressure is greater than 40 percent above baseline 1830. If this criterion is met 1830, the intensivist is prompted to employ the procedures described above in 1812.

Alternatively, if this criterion is not met 1830, the intensivist is prompted to determine whether the patient is in pain 1836. If this criterion is met 1836, the intensivist is prompted to treat pain and reevaluate following analgesia and, if still hypertensive, to continue algorithm 1838. Following this action 1838, the intensivist is prompted to employ the procedures described above in 1816. If the patient is not in pain 1836, the intensivist is prompted to employ the procedures described above in 1816.

If the patient is determined not to be hypertensive 1800, the intensivist is prompted to determine whether the patient requires their BP controlled near baseline (i.e., neurosurgery, carotid surgery, thoracic aorta surgery) 1832. If this criterion is not met 1832, the intensivist is prompted that the patient probably does not need treatment 1834.

Alternatively, if this criterion is met 1832, the intensivist is prompted to employ the procedures described above in 1836.

Figure 31A:
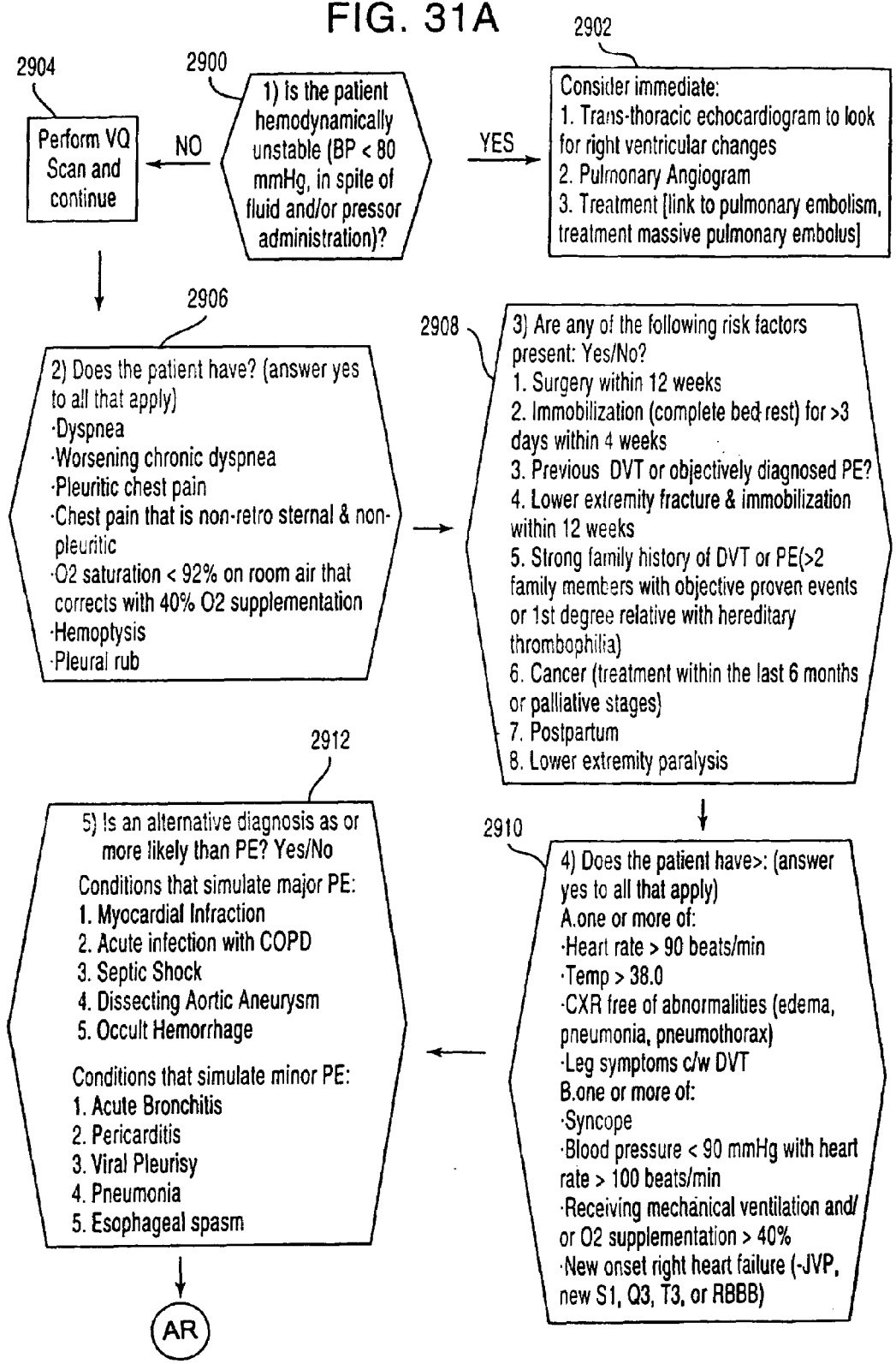
FIG. 31A illustrates the pulmonary embolism decision support algorithm.

Referring to FIG. 31A, the pulmonary embolism diagnosis algorithm is illustrated. If a pulmonary embolism is suspected, the intensivist is first prompted to determine whether the patient is hemodynamically unstable 2900. If the patient is hemodynamically unstable, the intensivist is directed by the system to consider performing an immediate transthoracic echocardiogram, pulmonary angiogram and treatment consistent with massive pulmonary embolism 2902. If the patient is not hemodynamically unstable, the intensivist is prompted to perform a VQ scan and perform further assessment of the patient 2904.

In order to further assess the patient, the intensivist is prompted to respond to a series of questions 2906, 2908, 2910, 2912. The intensivist is prompted to determine whether any of the following patient conditions are present: Dyspnea, Worsening chronic dyspnea, Pleuritic chest pain, Chest pain that is non-retro sternal & non-pleuritic, O.sub.2 saturation<92% on room air that corrects with 40% O.sub.2 supplementation, Hemoptysis, or Pleural rub 2906. The intensivist is also prompted to determine whether any risk factors are in the patient's history, such as: Surgery within 12 weeks, Immobilization (complete bed rest) for >3 days within 4 weeks, Previous DVT or objectively diagnosed PE, Lower extremity fracture & immobilization within 12 weeks, Strong family history of DVT or PE(.gtoreq.2 family members with objective proven events or 1.sup.st degree relative with hereditary thrombophilia), Cancer (treatment within the last 6 months or palliative stages), Postpartum, or Lower extremity paralysis 2908. Further, the intensivist must determine whether the patient has any of the following symptoms: Heart rate>90 beats/min, Temp.gtoreq.38.0, CXR free of abnormalities (edema, pneumonia, pneumothorax), or Leg symptoms c/w DVT, syncope, blood pressure less than 90 mm Hg with heart rate greater than 100 beats/min, receiving mechanical ventilation and/or oxygen supplementation greater than 40%, and new onset or right heart failure (-JVP, new S1, Q3, T3, or RBBB) 2910. The intensivist is also queried by the system to consider alternative diagnosis that may be more likely than pulmonary embolism. To do so, the intensivist is prompted to consider conditions that simulate major pulmonary embolism, such as myocardial infarction, acute infection with COPD, septic Shock, dissecting aortic aneurysm, or occult hemorrhage. The intensivist is additionally prompted to consider conditions that simulate minor pulmonary embolism, such as acute bronchitis, pericarditis, viral pleurisy, pneumonia, and esophageal spasm 2912.

Figure 31B:
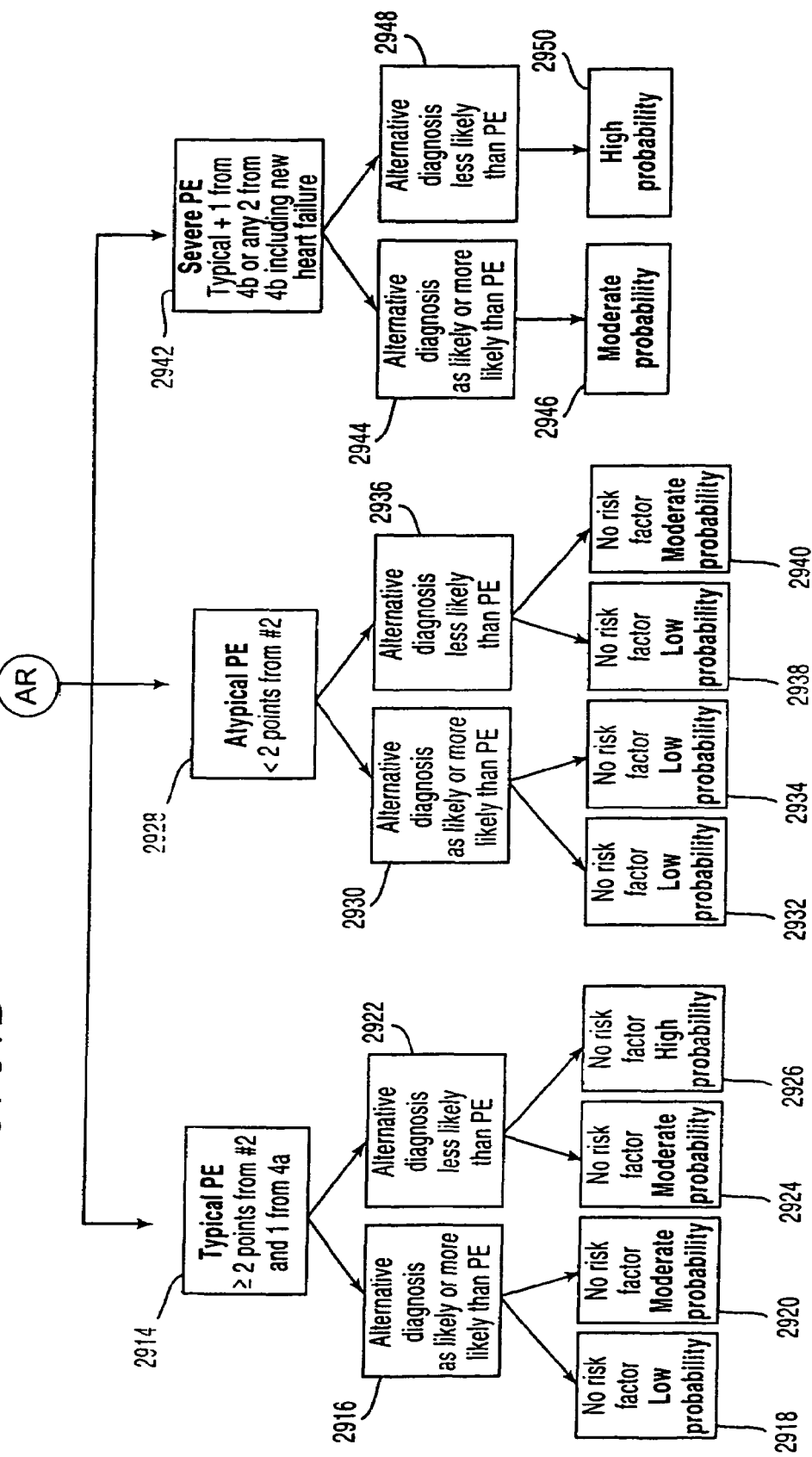
FIG. 31B illustrates the pulmonary embolism decision support algorithm (cont).

Referring to FIG. 31B, the pulmonary embolism algorithm description continues. The intensivist enters the answers to the assessment queries posed 2906, 2908, 2910, 2912 into the system. If two or more responses to the patient condition query 2906 were answered yes and one or more questions were answered yes from: Heart rate>90 beats/min, Temp.gtoreq.38.0, CXR free of abnormalities, or Leg symptoms c/w DVT of the symptoms query 2910, the intensivist is informed that a typical pulmonary embolism is present 2914. Next, the system compares this response to the answer to the alternative diagnosis query 2912. If an alternative diagnosis is at least as likely as pulmonary embolism 2916, the intensivist is also given a low probability 2918 to moderate probability 2920 risk factor. If an alternative diagnosis is less likely than pulmonary embolism 2922, the intensivist is given a moderate 2924 to high 2926 probability risk factor.

If less than two yes answers resulted from the patient conditions 2906, the intensivist is advised by the system that an atypical pulmonary embolism may be present 2928. Next, the system compares this response to the answer to the alternative diagnosis query 2912. If an alternative diagnosis is at least as likely as pulmonary embolism 2930, the intensivist is told there is no risk and low probability 2932 or some risk with a low probability 2934 risk factor. If an alternative diagnosis is less likely than pulmonary embolism 2934, the intensivist is given a no risk and low probability 2938 to risk but moderate probability 2940.

If at least one answer to the symptoms of syncope, blood pressure less than 90 mm Hg with heart rate greater than 100 beats/min, receiving mechanical ventilation and/or oxygen supplementation greater than 40%, and new onset or right heart failure 2910 is yes, the intensivist is prompted with a message that severe pulmonary embolism is occurring 2942. Next, the system compares this response to the answer to the alternative diagnosis query 2912. If an alternative diagnosis is at least as likely as pulmonary embolism 2944, the intensivist is told there is a moderate probability of pulmonary embolism 2946. If an alternative diagnosis is less likely than pulmonary embolism 2948, the intensivist is notified that a high probability of pulmonary embolism is present 2950.

Once the risk factors and probabilities are determnined the system compares this information to the VQ scan results. This comparison is performed according to the following Table 4 below.

TABLE 4

Probability table

| Input | Clinical Probability | | |
|---|---|---|---|
| V/Q Scan | High | Moderate | Low |
| High | A | A | B |
| Intermediate | B | C | C |
| Low | B | C | E |
| Normal | E | E | E |

Where the VQ scan column and the risk column intersect, a letter code is assigned to various treatment instructions. The treatment instructions are as follows.

A=Pulmonary embolus diagnosed. Begin treatment

E=Pulmonary embolus excluded

B=Proceed with the following work-up:
1) Perform spira CT (If patient has real insufficiency [creatinine>2.0], consider going directly to pulmonary angiogram to reduce the potential dye load). If positive begin treatment,
2) If negative, assess for DVT using compression ultrasound or venography. If positive begin treatment,
3) If negative, perform pulmonary angiogram. If positive begin treatment, if negative diagnosis excluded.

C=Proceed with the following work-up:
1) Perform spiral CT. If positive begin treatment,
2) If negative, assess for DVT using compression ultrasound or venography. If positive begin treatment, 3) If negative perform D-dimer assay (elisa only). If negative diagnosis excluded, If positive, perform serial ultrasound of the lower extremities.

Once the correlation is made, the instructions associated with the letter code are displayed by the system to prompt the intensivist with diagnosis and treatment instructions.

Figure 32:
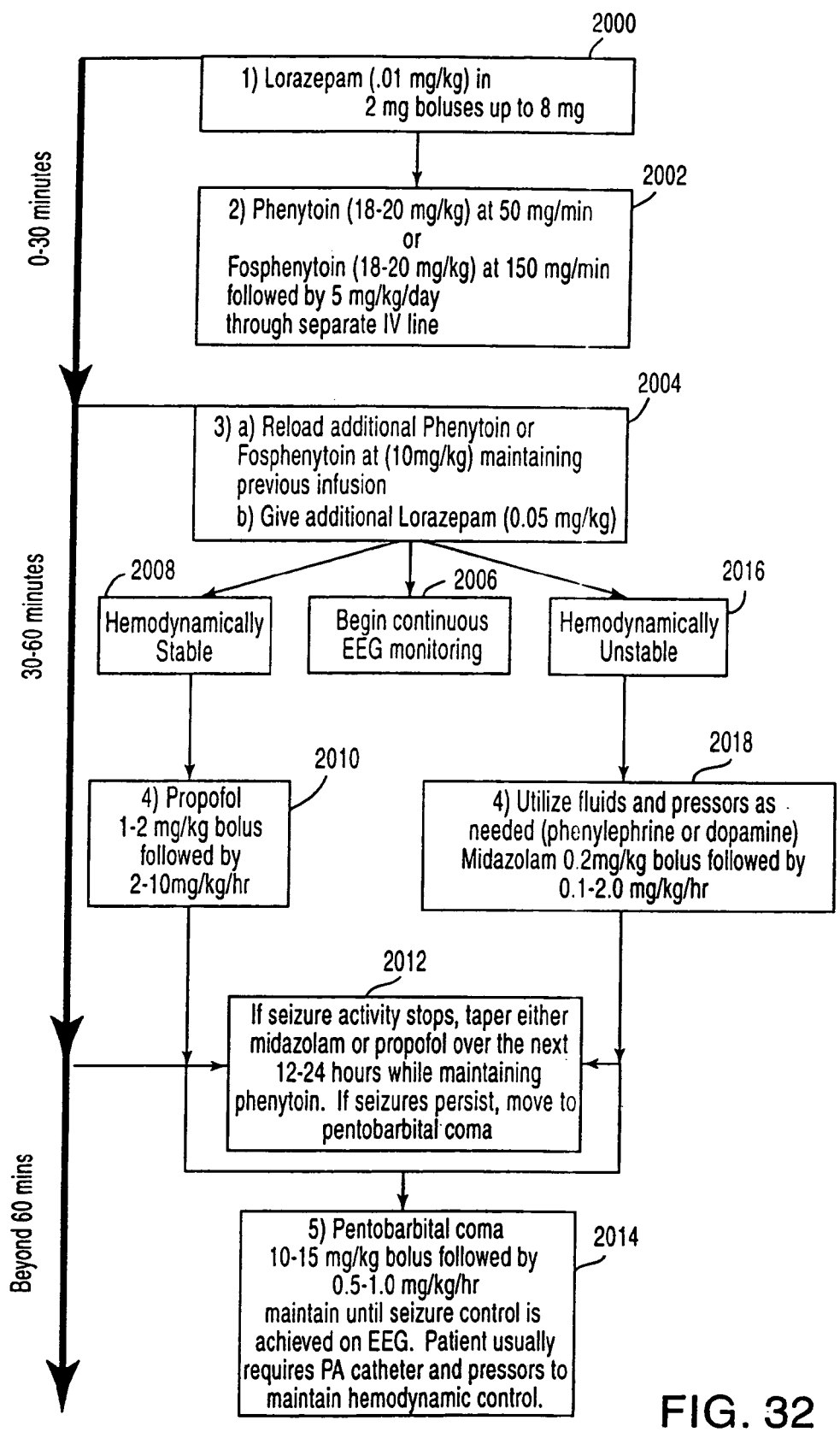
FIG. 32 illustrates the seizure decision support algorithm.

Referring to FIG. 32, the seizure decision support algorithm of the present invention is illustrated. If an intensivist encounters seizure in a patient, he may not be certain of all of the aspects and the timelines that are critical to treating this particular condition. Therefore, the intensivist is lead through a decision support algorithm, which divides the treatment sequence into three segments: 0-30 minutes; 30-60 minutes; and beyond 60 minutes.

At the onset of a seizure, in the 0-30 minute segment of the algorithm, the intensivist is prompted to give the patient lorazepam (0.1 mg/kg of bodyweight) in 2 mg boluses up to 8 mg 2000. Subsequently, the intensivist is prompted to give the patient phenyloin (18-20 mg/kg of bodyweight) at 50 mg/min of fosphenyloin (18-20 mg/kg of bodyweight) at 150 mg/min followed by 5 mg/kg of bodyweight/day through separate IV line 2002.

During the 30-60 minute segment of the algorithm, the intensivist is prompted to: reload additional phenytoin or fosphenytoin (10 mg/kg of bodyweight) maintaining previous infusion; and give additional lorazepam (0.05 mg/kg of bodyweight) 2004. Subsequently, the intensivist is prompted to begin continuous EEG monitoring 2006.

The intensivist is then prompted to determine whether the patient is hemodynamically stable 2008. If hemodynamically stable, the intensivist is prompted to administer propofol 1-2 mg/kg of bodyweight bolus followed by 2-10 mg/kg/hr 2010.

At the 60 minute segment of the algorithm, the intensivist is prompted that if seizure activity stops, he should taper either midazolam or propofol over the next 12-24 hours while maintaining phenytoin but if seizures persist, he is prompted to move to the pentobarbital coma block 2012.

Under pentobarbital coma, the intensivist is prompted to administer 10-15 mg/kg/hr and to maintain until seizure control is achieved on EEG 2014. The intensivist is prompted further that the patient usually requires PA catheter and pressors to maintain hemodynamic control 2014.

Alternatively, if the patient is determined to be hemodynamically unstable 2016, the intensivist is prompted to utilize fluids and pressors as needed (phynylephrine or dopamine) midazolam 0.2 mg/kg bolus followed by 0.1-2.0 mg/kg/hr 2018.

At the 60 minute segment of the algorithm, the intensivist is prompted that if seizure activity stops, he should taper either midazolam or propofol over the next 12-24 hours while maintain phenytoin but if seizures persist, he is prompted to move to the pentobarbital coma block 2012.

Under pentobarbital coma, the intensivist is prompted to administer 10-15 mg/kg/hr and to maintain until seizure control is achieved on EEG 2014. The intensivist is prompted further that the patient usually requires PA catheter and pressors to maintain hemodynamic control 2014.

Figure 33A:
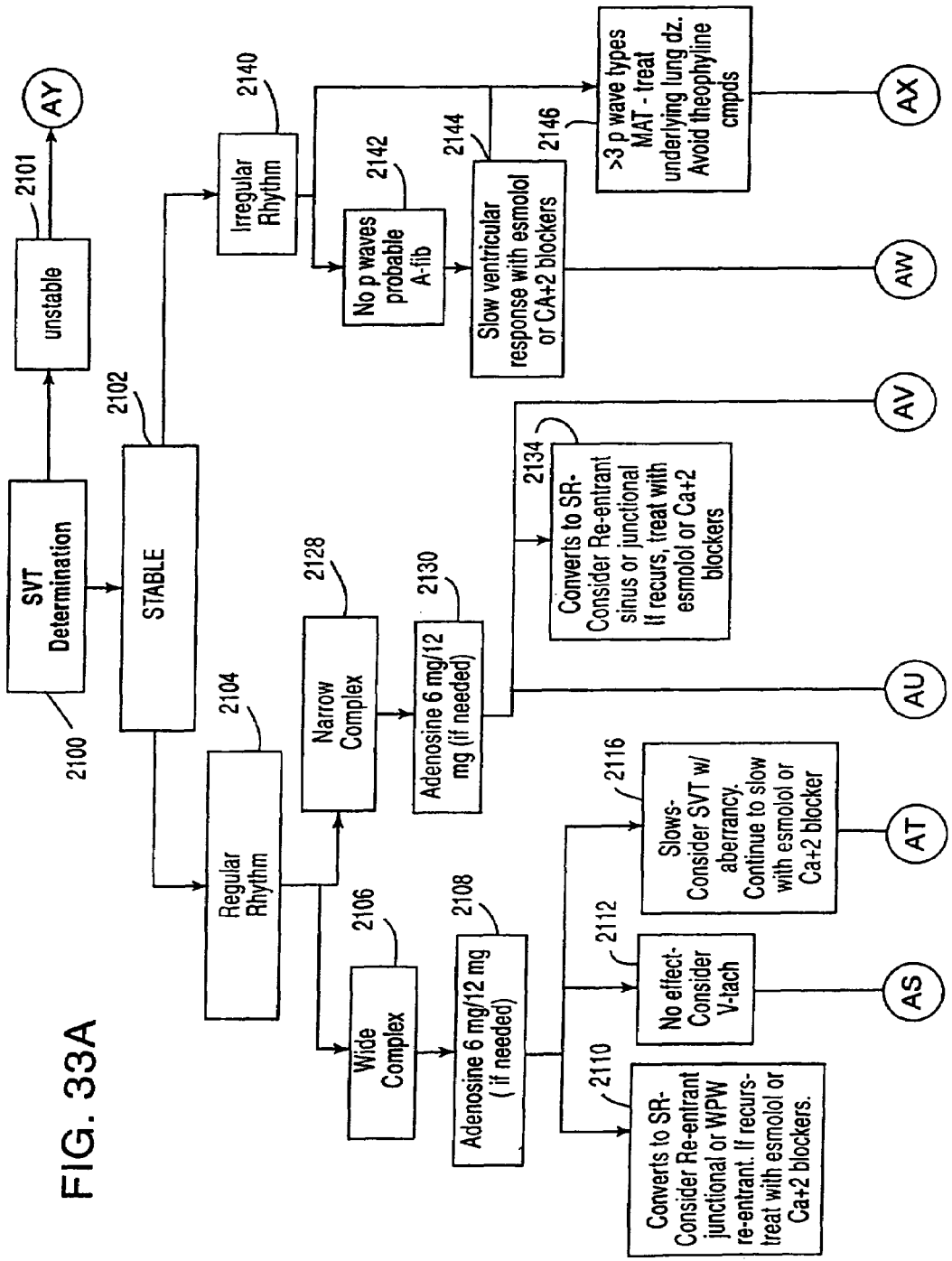
FIGS. 33A-B illustrate the SVT determination decision support algorithm.
Figure 33B:
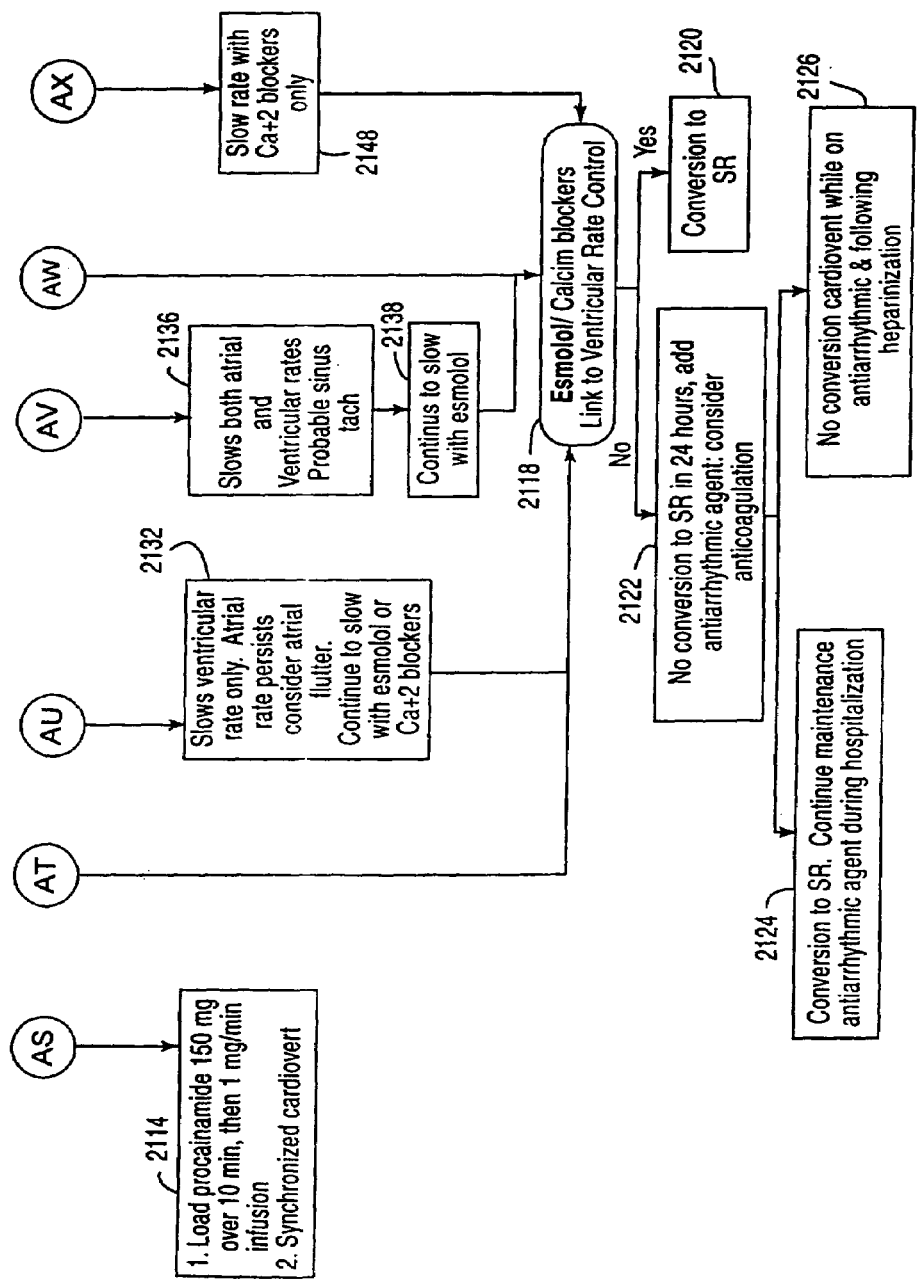

Referring to FIGS. 33A-B, the supra ventricular tachycardia (SVT) decision support algorithm of the present invention is illustrated. If an intensivist determines that SVT is present, the intensivist may not be certain of all aspects that would be involved in treating this particular condition. Therefore, the intensivist is lead through a decision support algorithm which prompts the intensivist to determine the appropriate care to be given.

Initially, the intensivist is prompted to determine whether SVT is stable or unstable 2100. If SVT is stable 2102, the intensivist is prompted to determine whether the patient has a regular or irregular rhythm 2102. If the patient has a regular rhythm 2104, the intensivist is prompted to determine whether there is a wide complex or a narrow complex 2104. If the intensivist determines that there is a wide complex 2106, the intensivist is prompted to administer adenosine 6 mg/12 mg (if needed) 2108. Following the administering of adenosine 2108, the intensivist is prompted to consider that if the patient converts to sinus rhythm (SR) to consider re-entrant junctional or WPW re-entrant. If the wide complex recurs, treat the patient with esmolol or Ca+2 blockers.

Alternatively; if no effect, the intensivist is prompted to consider V-tach 2112. Next, the intensivist is prompted to: 1) load procainamide 150 mg over 10 min, then 1 mg/min infusion; and 2) synchronized cardiovert 2114.

Alternatively, if the wide complex slows, the intensivist is prompted to consider SVT w/aberrancy and continue to slow with esmolol or Ca+2 blockers 2116.

The intensivist is prompted next to administer esmolol/calcium blockers and link to ventricular rate control 2118. The intensivist is prompted next to determine whether there has been a conversion to SR 2120. If there is no conversion to SR in 24 hours, the intensivist is prompted to add antiarrhythmic agent and consider anticoagulation 2122. The intensivist is prompted next to determine whether there has been conversion to SR. If conversion to SR, the intensivist is prompted to continue maintenance antiarrhythmic agent during hospitalization 2124. If no conversion to SR, the intensivist is prompted to cardiovert while on antiarrhythmic & following heparinization 2126.

If the patient has a regular rhythm 2104, the intensivist is prompted to determine whether there is a wide complex or a narrow complex 2104. If the intensivist determines that there is a narrow complex 2128, the intensivist is prompted to to administer adenosine 6 mg/12 mg (if needed) 2130. If administering the adenosine 2130 slows the ventricular rate only and the atrial rate persists, the intensivist is prompted to consider atrial flutter and continue to slow with esmolol or Ca+2 blockers 2132. The intensivist is prompted next to employ the procedures described above in 2118.

If administering the adenosine 2130 converts the patient to SR, the intensivist is prompted to consider re-entrant sinus or junctional and if recurs, treat with esmolol or Ca+2 blockers 2134.

If administering the adenosine 2130 slows both atrial and ventricular rates the intensivist is prompted that there is a probable sinus tachycardia 2136. The intensivist is prompted next to continue to slow with esmolol 2138. The intensivist is prompted next to employ the procedures described above in 2118.

If SVT is stable 2102, the intensivist is also prompted to determine whether the patient has a regular or irregular rhythm 2102. If the patient has an irregular rhythm 2140, the intensivist is prompted that if no p waves, there is probable Atrial fibrillation 2142. The intensivist is prompted next to slow ventricular response with esmolol or Ca+2 blockers 2144. The intensivist is prompted next to employ the procedures described above in 2118.

If the patient has an irregular rhythm 2140, the intensivist is prompted to determine whether there are more than 3 p wave types MAT—and to treat underlying lung dz. and avoid theophylline compounds 2146. The intensivist is prompted next to slow rate with Ca+2 blockers only 2148. The intensivist is prompted next to employ the procedures described above in 2118.

Figure 33C:
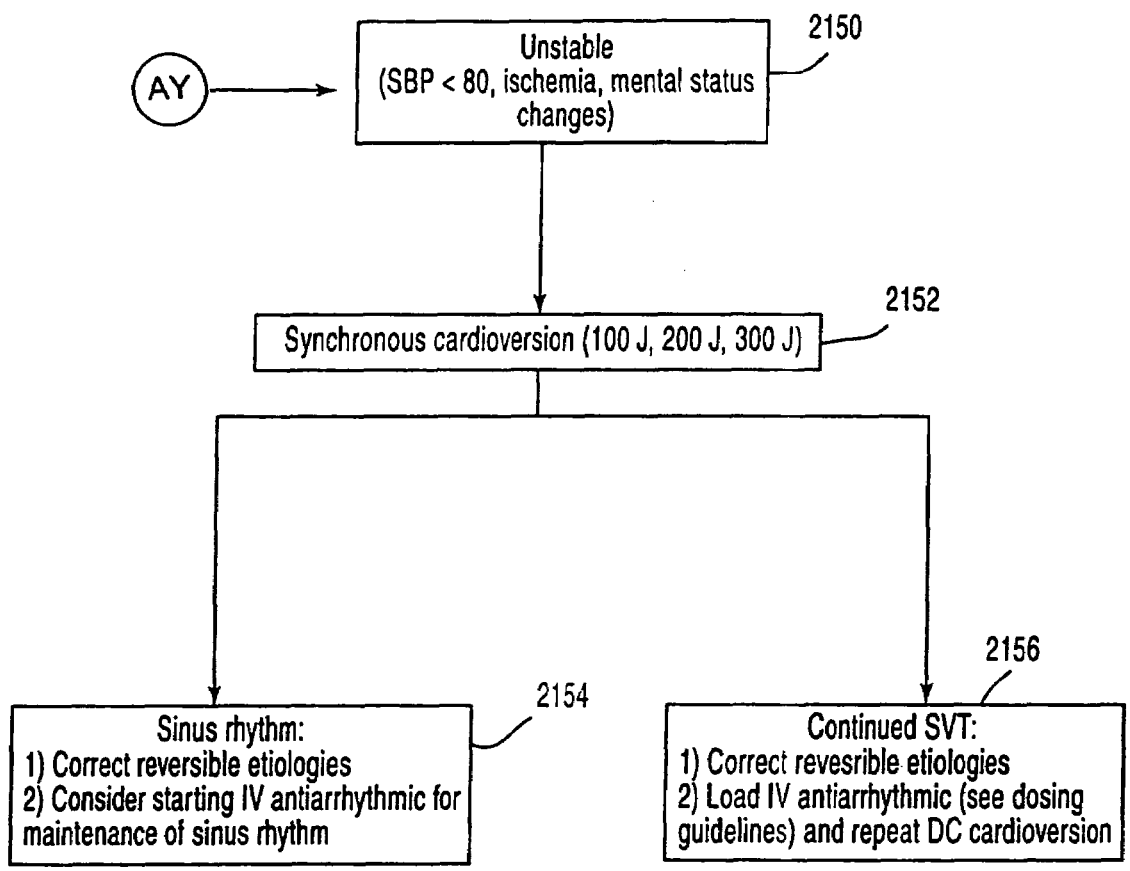
FIG. 33C illustrates the SVT unstable decision support algorithm.

Referring now to FIG. 33C, the description of the SVT decision algorithm continues. If SVT is unstable 2101, the intensivist is prompted to determine whether the patient has SBP less than 80, ischemia, mental status changes 2150. The intensivist is prompted next to perform synchronous cardioversion (100 J, 200 J, 300 J) 2152. The intensivist is prompted next that if sinus rhythm: 1) correct reversible etiologies; 2) consider starting IV antiarrhythmic for maintenance of sinus rhythm 2154. Alternatively, following 2152, the intensivist is prompted next that if continued SVT: 1) correct reversible etiologies; 2) load IV antiarrhythmic (see dosing guidelines) and repeat DC cardioversion 2156.

Figure 34A:
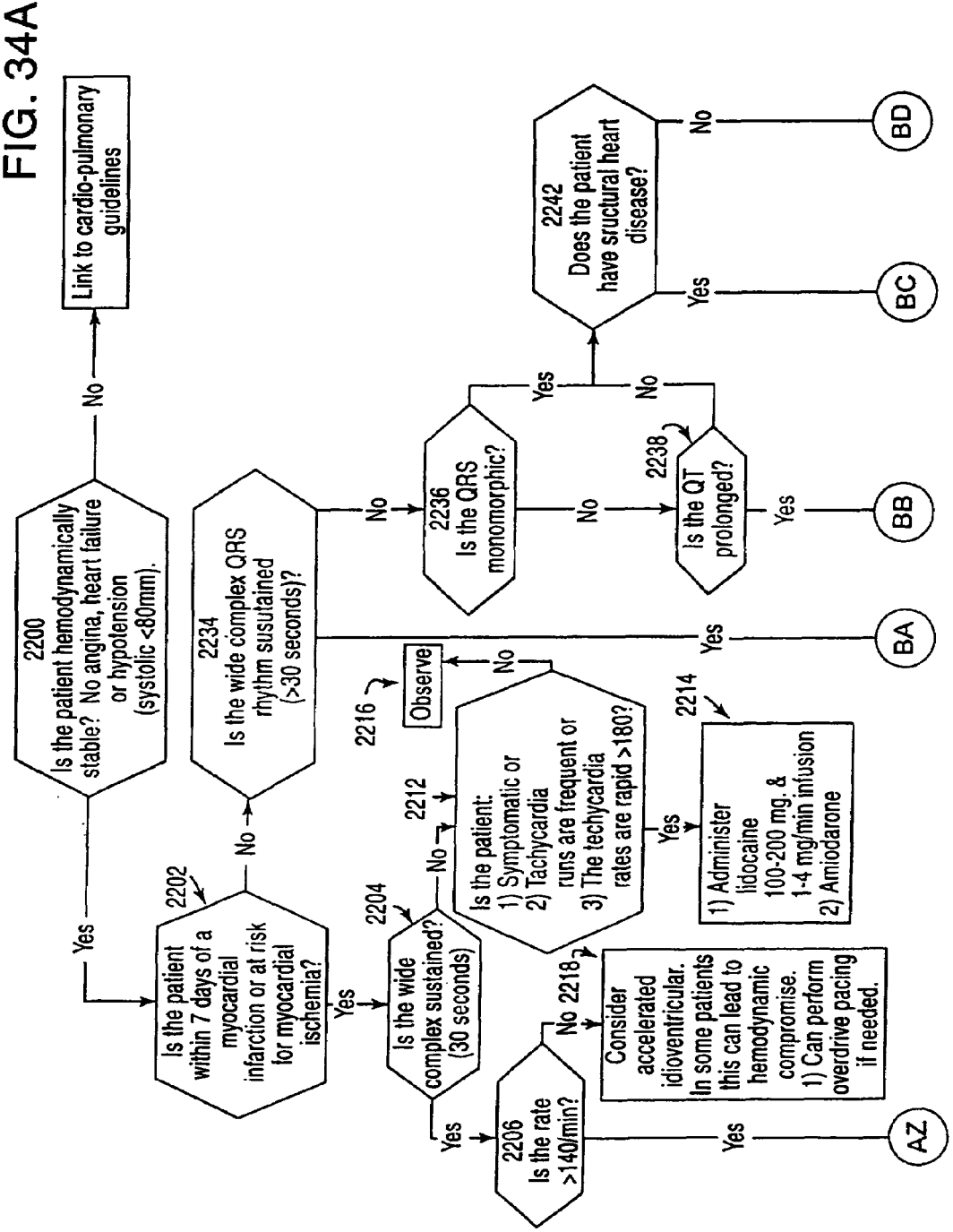
FIGS. 34A-B illustrate the wide complex QRS Tachycardia decision support algorithm.
Figure 34B:
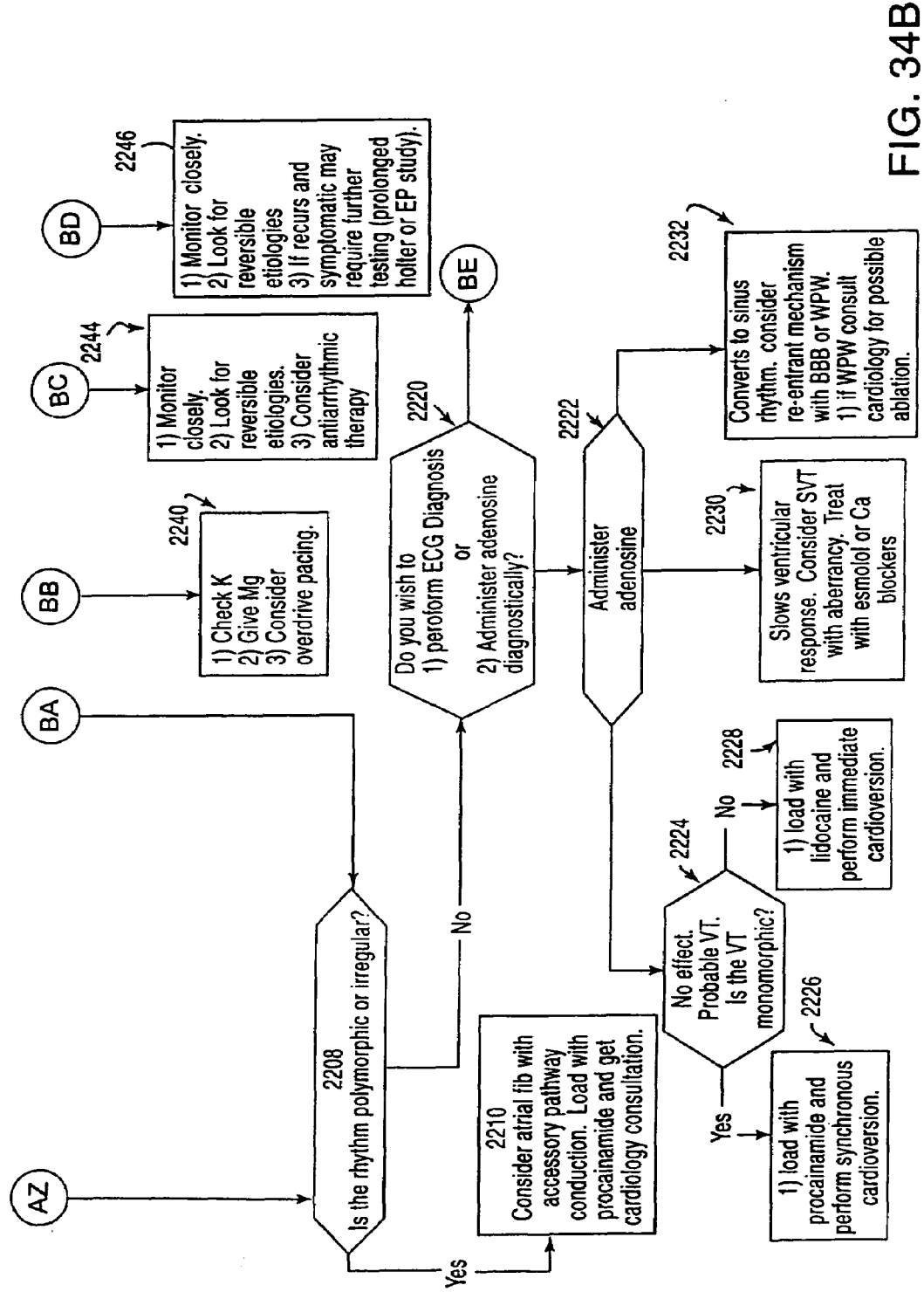

For example, and without limitations, wide complex QRS Tachycardia is also addressed in the decision support algorithm of the present invention. Referring to FIGS. 34A-B, the wide complex QRS tachycardia decision support algorithm is illustrated. If an intensivist determines that there may be a possibility of wide complex QRS tachycardia, the intensivist may not be certain of all aspects that would be involved in this particular condition. Therefore, the intensivist is lead through a decision support algorithm which prompts the intensivist to determine the appropriate care to be given.

Initially, the intensivist is prompted to determine whether the patient is hemodynamically stable (no angina, heart failure, or hypotension (systolic less than 80 mm)) 2200. If this criterion is not met, the intensivist is prompted to go to the cardiopulmonary guidelines algorithm which is generally known to those skilled in the art.

Alternatively, if this criterion is met, the intensivist is prompted to determine whether the patient is within 7 days of a myocardial infarction or at risk for myocardial ischemia 2202. If the patient is not within 7 days of a myocardial infarction or at risk for myocardial ischemia 2202, the intensivist is prompted to determine whether the wide complex QRS rhythm is sustained (greater than 30 seconds) 2234. If this criterion is not met, the intensivist is prompted to determined whether the QRS is monomorphic 2236. If the QRS is monomorphic 2236, the to intensivist is prompted to determine whether the patient has structural heart disease 2242. If the patient has structural heart disease 2242, the intensivist is prompted to: 1) monitor closely; 2) look for reversible etiologies; and 3) consider antiarrhythmic therapy 2244. If the patient does not have structural heart disease 2242, the intensivist is prompted to: 1) monitor closely; 2) look for reversible etiologies; and 3) if recurs and symptomatic may require further testing (prolonged holter or EP study) 2246.

If the QRS is not monomorphic 2236, the intensivist is prompted to determine whether the QT is prolonged 2238. If this criterion is met, the intensivist is prompted to: 1) check K; 2) give Mg; and 3) consider overdrive pacing 2240. If the intensivist determines that the QT is not prolonged, 2238, the intensivist is prompted to employ the procedures described above in 2242.

If the wide complex QRS rhythm is sustained 2234, the intensivist is prompted to determine whether the rhythm is polymorphic or irregular 2208. If the rhythm is polymorphic or irregular, the intensivist is prompted to consider atrial fibrillation with accessory pathway conduction and load with procainamide and get a cardiology consultation 2210. If the rhythm is not polymorphic or irregular, the intensivist is prompted with the question of whether he wishes to: 1) perform ECG diagnosis; or 2) administer adenosine diagnostically 2220. If the intensivist makes the determination to perform an ECG diagnosis 2220, he is prompted to go to the ECG diagnosis algorithm 2300.

If the intensivist makes the determination to administer adenosine diagnostically 2220, he is prompted to go to the administer adenosine branch of the algorithm 2222. If there is no effect, the intensivist is prompted that there is probable VT and to determine whether the VT is monomorphic 2224. If the VT is monomorphic 2224, the intensivist is prompted to load with procainamide and perform synchronous cardioversion 2226.

Alternatively, if the VT is not monomorphic 2224, the intensivist is prompted to load with lidocaine and perform immediate cardioversion 2228.

If the ventricular response is slowed after administering adenosine 2222, the intensivist is prompted to consider SVT with aberrancy and treat with esmolol or Ca blockers 2230.

If the ventricular response converts to sinus rhythm after administering adenosine 2222, the intensivist is prompted: to consider re-entrant mechanism with BBB or WPW; and, 1) if WPW consult cardiology for possible ablation 2232.

If the patient is within 7 days of a myocardial infarction or at risk for myocardial ischemia 2202, the intensivist is prompted to determine whether the wide complex is sustained (30 seconds) 2204. If the wide complex is not sustained 2204, the intensivist is prompted to determine whether the patient: 1) symptomatic; 2) tachycardia runs are frequent; or 3) the tachycardia rates are rapid (greater than 180) 2212. If none of these criteria is met, the intensivist is prompted to observe 2216. Alternatively, if any of these criteria is met 2212, the intensivist is prompted to: 1) administer lidocaine 100-200 mg & 1-4 mg/min infusion; and 2) amiodarone 2214.

If the wide complex is sustained 2204, the intensivist is prompted to determine whether the rate is greater than 140/min 2206. If this criterion is not met 2206, the intensivist is prompted: to consider accelerated idioventricular, and that in some patients this can lead to hemodynamic compromise; and that 1) he can perform overdrive pacing if needed 2218.

Alternatively, if this criterion is met, the intensivist is prompted to follow the procedures in 2208.

Figure 34C:
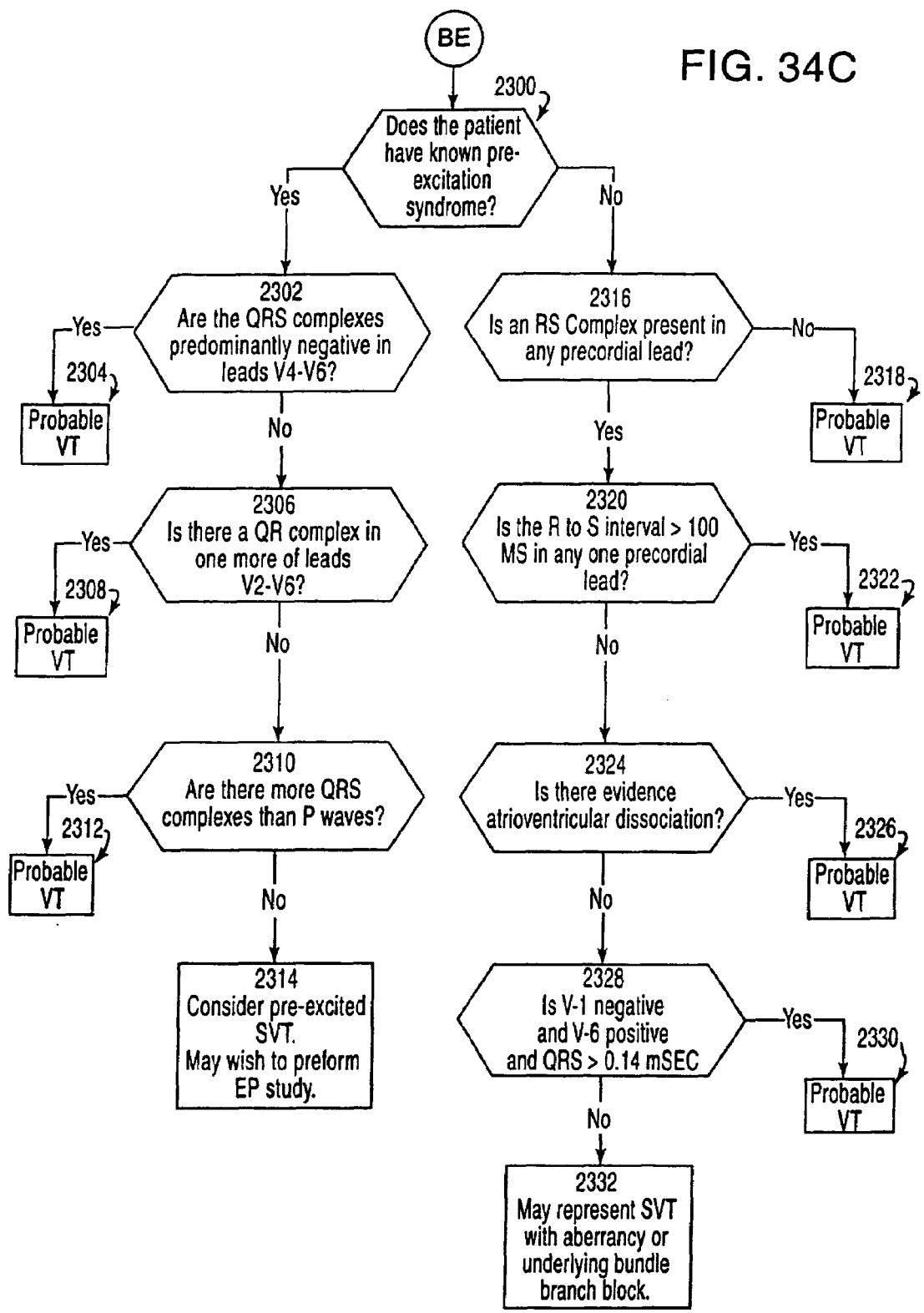
FIG. 34C illustrates the wide complex QRS Tachycardia decision support algorithm (cont).

If the intensivist makes the determination to perform ECG Diagnosis 2220, he is prompted to go to the ECG Diagnosis branch of the algorithm 2220. Referring now to FIG. 34C, in the ECG Diagnosis branch, the intensivist is prompted to determine whether the patient has known pre-excitation syndrome 2300. If this criterion is met, the intensivist is prompted to determine whether the QRS complexes are predominantly negative in leads V4-V6 2302. If the QRS complexes are predominantly negative in leads V4-V6, the intensivist is prompted that there is probable VT 2304.

If the QRS complexes are not predominantly negative in leads V4-V6 2302, the intensivist is prompted to determine whether there is a QR complex in one or more of leads V2-V6 2306. If this criterion is met, the intensivist is prompted that there is probable VT 2308.

Alternatively, if this criterion is not met 2306, the intensivist is prompted to determine whether there are more QRS complexes than P waves 2310. If there are more QRS complexes than P waves 2310, the intensivist is prompted that there is probable VT 2312. If there are not more QRS complexes than P waves 2310, the intensivist is prompted: to consider pre-excited SVT; and that he may wish to perform EP study 2314.

If the intensivist determines that the patient does not have known pre-excitation syndrome 2300, the intensivist is prompted to determine whether there is an RS complex present in any precordial lead 2316. If this criterion is not met 2316, the intensivist is prompted that there is probable VT 2318.

Alternatively, if this criterion is met 2316, the intensivist is prompted to determine whether the R to S interval is greater than 100 MS in any one precordial lead 2320. If this criterion is met, the intensivist is prompted that there is probable VT 2322.

If the R to S interval is not greater than 100 MS in any one precordial lead 2320, the intensivist is prompted to determine whether there is evidence of atrioventricular dissociation 2324. If this criterion is met, the intensivist is prompted that there is probable VT 2326.

Alternatively, if there is no evidence of atrioventricular dissociation 2324, the intensivist is prompted to determine whether V-1 is negative and V-6 positive and QRS greater than 0.14 mSEC 2328. If these criteria are met, the intensivist is prompted that there is probable VT 2330.

If none of these criteria is met 2328, the intensivist is prompted that the situation may represent SVT with aberrancy or underlying bundle branch block 2332.

Figure 35A:
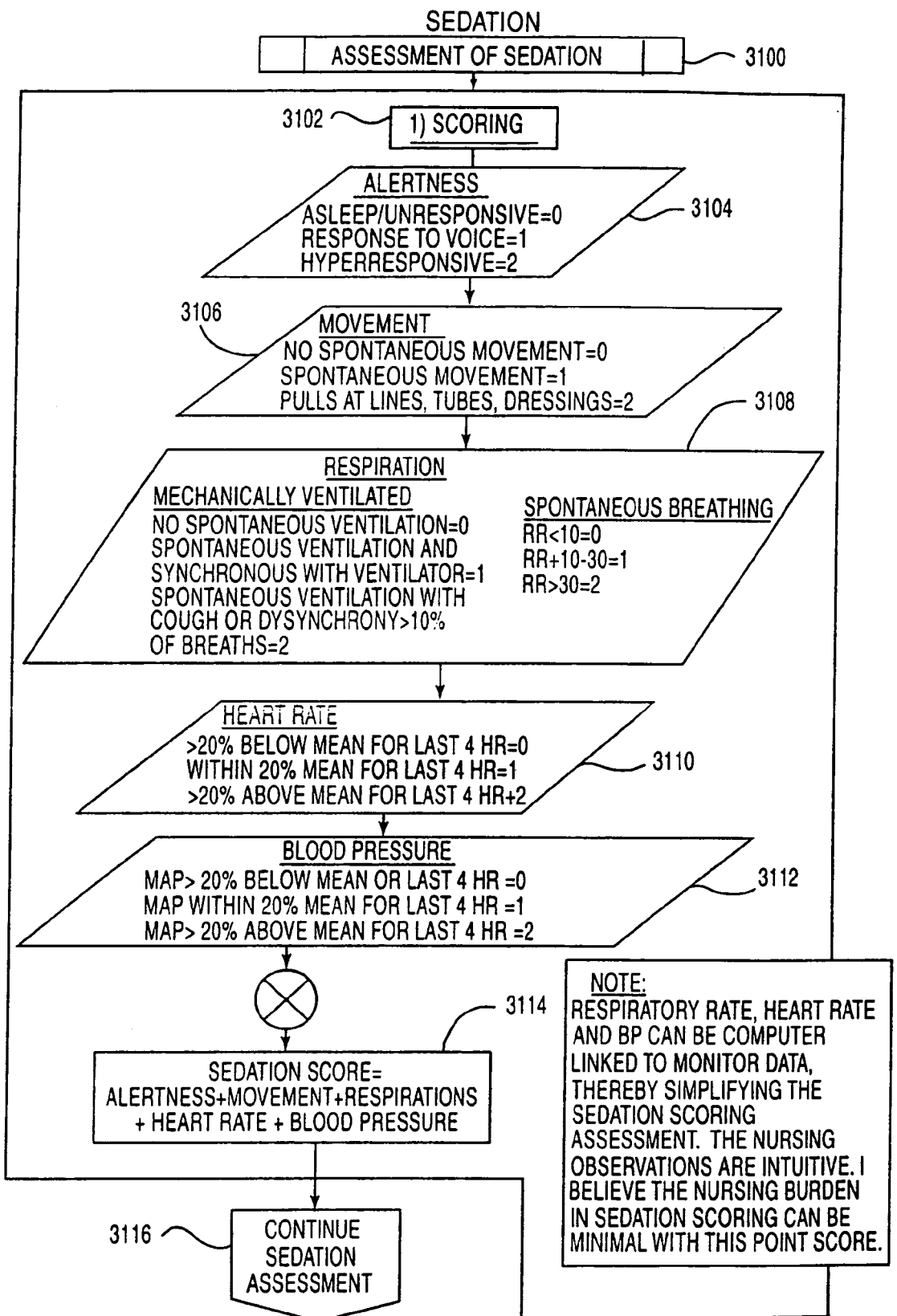
FIG. 35A illustrates the assessment of sedation decision support algorithm.

Referring to FIG. 35A, the assessment of sedation algorithm of the present invention is illustrated. If an intensivist encounters a need for sedation, he may not be certain of all of the aspects and the timelines that are critical to this particular process. Therefore, the intensivist is lead through a decision support algorithm, which prompts the intensivist to address a number of factors in the process 3100.

The intensivist is prompted initially to go to the Scoring section of the algorithm 3100. The intensivist is prompted to proceed through a number of scorings 3102 and to first score the patient's alertness with points being allocated in the following manner: asleep/unresponsive=0; responsive to voice=1; and hyperresponsive=2 3104.

The intensivist is prompted next to score the patient's movement with points being allocated in the following manner: no spontaneous movement=0; spontaneous movement=1; and pulls at lines, tubes, dressings=2 3106.

The intensivist is prompted next to score the patient's respiration based on whether the patient is mechanically ventilated or spontaneously breathing with points being allocated as subsequently discussed. If the patient is mechanically ventilated, the intensivist is prompted to allocate points in the following manner: no spontaneous ventilation=0; spontaneous ventilations and synchronous with ventilator=1; or spontaneous ventilations with cough or dysynchrony>10 percent of breaths=2 3108. Alternatively, if the patient is spontaneously breathing, the intensivist is prompted to allocate points in the following manner: respiration rate (RR)<10=0; RR=10–30=1; or RR>30=2 3108.

The intensivist is prompted next to score the patient's heart rate with points being allocated in the following manner: >20 percent below mean for last 4 hr=0; within 20 percent mean for last 4 hr=1; or >20 percent above mean for last 4 hr=2 3110.

The intensivist is prompted next to score the patient's blood pressure with points being allocated in the following manner: MAP>20 percent for last 4 hr=0; MAP within 20 percent mean for last 4 hr=1; or MAP>20 percent above mean for last 4 hr=2 3112.

The intensivist is prompted next to determine the sedation score by the following formula: SEDATION SCORE=alertness+movement+respirations+heart rate+blood pressure 3114. In one embodiment, respiratory rate, heart rate, and BP can be computer linked to monitor data thereby simplifying the sedation scoring assessment. The nursing observations are deemed intuitive and the nursing burden in sedation scoring can be minimal by using this point scoring.

Figure 35B:
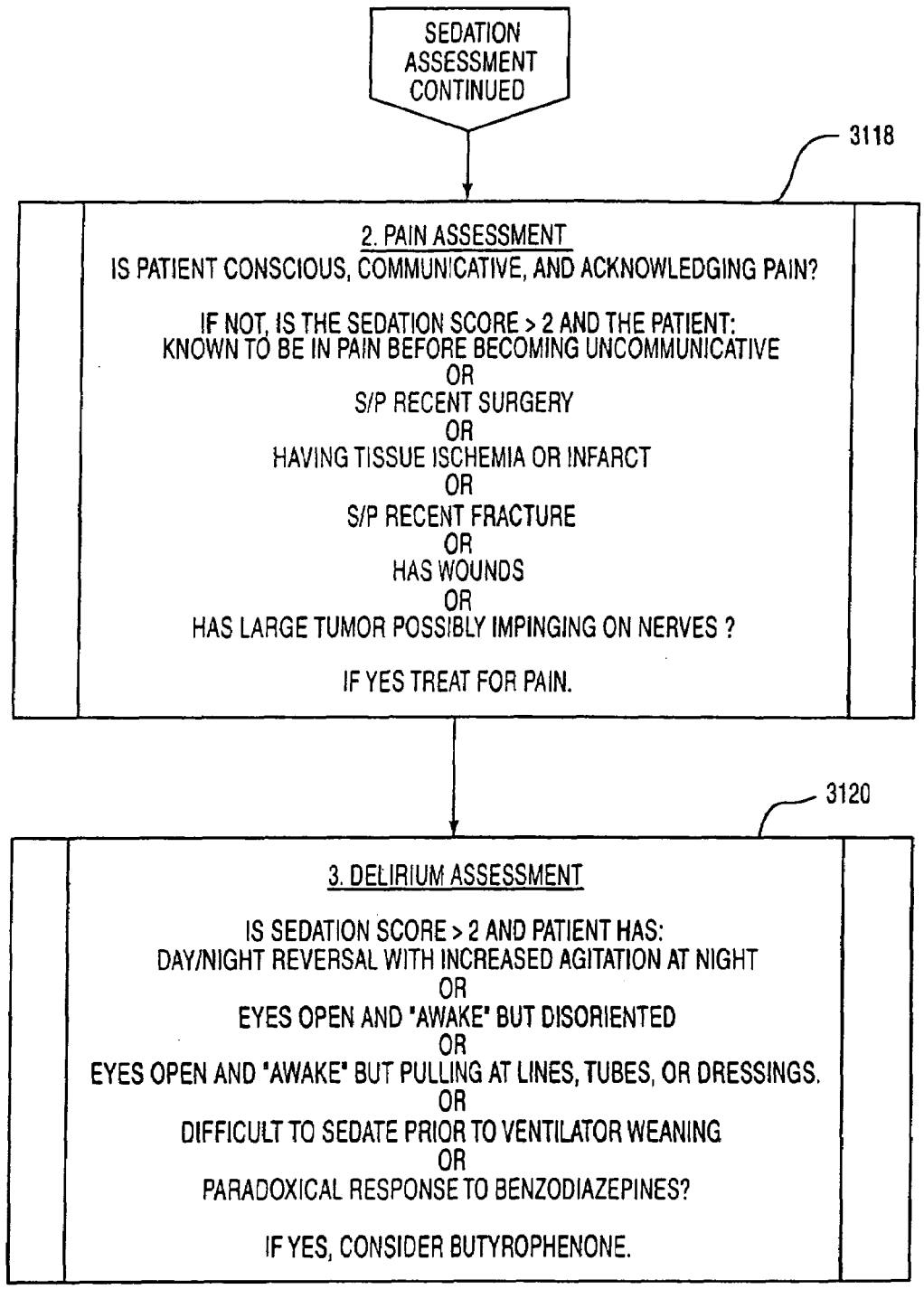
FIG. 35B illustrates the assessment of sedation decision support algorithm (cont).

Referring now to FIG. 35B, the sedation assessment algorithm description continues. The intensivist is prompted then to continue the sedation assessment by moving to the Pain Assessment section of the algorithm 3116.

In the Pain Assessment section, the intensivist is prompted to determine whether the patient is conscious, communicative, and acknowledging pain 3118. If any of these criteria is not met, the intensivist is prompted to determine: whether the sedation score is greater than 2 and the patient: is known to be in pain before becoming uncommunicative; or S/p recent surgery; or having tissue ischemia or infarct; or has wounds; or has large tumor possibly impinging on nerves. If the answer to either of these two questions is YES, the intensivist is prompted to treat for pain 3118. The intensivist is prompted then to continue the assessment by moving to the Delirium Assessment section of the algorithm 3118.

In the Delirium Assessment section, the intensivist is prompted to determine whether the sedation score is greater than 2 AND the patient has: day/night reversal with increased agitation at night OR eyes open and "awake" but disoriented; or eyes open and "awake" but pulling at lines, tubes, or dressings OR difficult to sedate prior to ventilator weaning OR paradoxical response to benzodiazepines. If these criteria is met, the intensivist is prompted to consider butyrophenone 3120.

Figure 36:
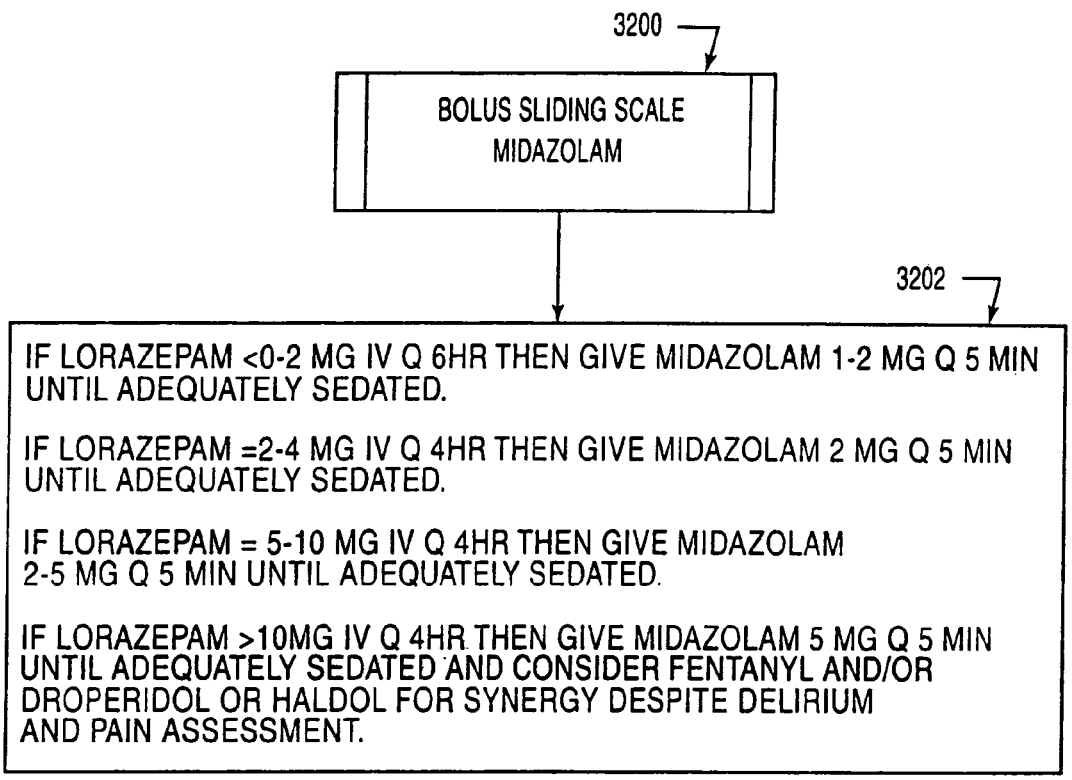
FIG. 36 illustrates the bolus sliding scale midazolam decision support algorithm.

Referring to FIG. 36, the Bolus sliding scale algorithm is illustrated. If an intensivist encounters a need for sedation, the algorithm for which may contain a reference to the bolus sliding scale for midazolam, he nay not be certain of all of the aspects which are critical to this scale. Therefore, the intensivist is lead through a decision support algorithm, which prompts the intensivist through the use of the scale 3200.

If lorazepam is less than 0-2 mg IV q 6 hr, then the intensivist is prompted to give midazolam 1-2 mg q 5 min until adequately sedated 3202.

Alternatively, if lorazepam equals 2-4 mg IV q 4 hr, then the intensivist is prompted to give midazolam 2 mg q 5 min until adequately sedated 3202.

Alternatively, if lorazapam is greater than 10 mg IV q 4 hr, then the intensivist is prompted to give midazolam 5 mg q 5 min until adequately AND consider fentanyl and/or droperidol or Haldol for synergy despite delirium and pain assessment 3202.

Figure 37:
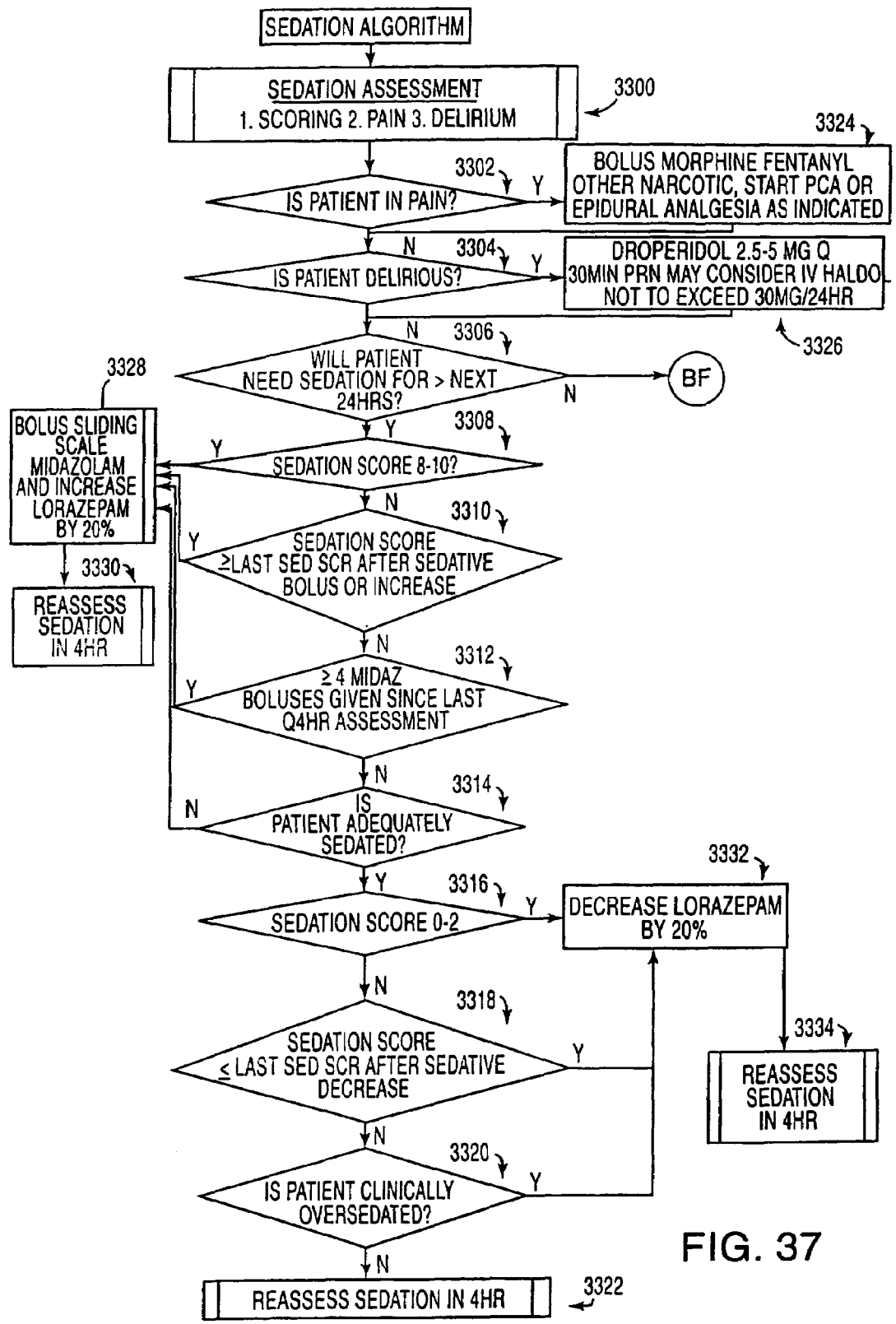
FIG. 37 illustrates the sedation assessment algorithm decision support algorithm.

Yet another decision support routine is the sedation algorithm. Referng to FIG. 37, the sedation process decision support algorithm is illustrated. If an intensivist determines that a patient will require sedation, the intensivist may not be certain of all aspects that would be involved in this particular process. Therefore, the intensivist is lead through a decision support algorithm, which prompts the intensivist to conduct a sedation assessment based on: 1) scoring; 2) pain; and 3) delirium (see Assessment of Sedation algorithm) 3300.

Following completion of the sedation assessment process 3300, the intensivist is prompted to determine whether the patient is in pain 3302. If this criterion is met, the intensivist is prompted to administer bolus morphine, fentanyl, other narcotic, start patient controlled analgesic (PCA) or epidural analgesia as indicated 3324. If the patient is not in pain 3302 or after administering bolus morphine, fentanyl, other narcotic, start patient controlled analgesic (PCA) or epidural analgesia as indicated 3324, the intensivist is prompted to determine whether the patient is delirious 3304.

If the intensivist determines that the patient is delirious 3304, he is prompted to administer droperidol 2.5-5 mg q 30 min pm and that he may consider IV Haldol not to exceed 30 mg/24 hr 3326. If the patient is not delirious or after following the procedures in 3326, the intensivist is prompted to determine whether the patient will need sedation for more than the next 24 hours 3306. If the patient will not need sedation for more than the next 24 hours 3306, the process continues as described in FIG. 38.

Alternatively, if the patient will need sedation for more than the next 24 hours 3306, the intensivist is prompted to determine whether the sedation score is 8-10 3308. If this criterion is met, the intensivist is prompted to employ the Bolus sliding scale midazolam and increase lorazepam by 20 percent 3328 (see Bolus sliding scale midazolam algorithm—FIG. 36). Subsequently, the intensivist is prompted to reassess sedation in 4 hr 3330.

Alternatively, if the patient will need sedation for more than the next 24 hours 3306, the intensivist is prompted to determine whether the sedation score is 8-10 3308. If this criterion is met, the intensivist is prompted to employ the Bolus sliding scale midazolam and increase lorazepam by 20 percent 3328 (see Bolus sliding scale midazolam algorithm—FIG. 42). Subsequently, the intensivist is prompted to reassess sedation in 4 hr 3330.

If the sedation score is not 8-10, the intensivist is prompted to determine whether the sedation score is greater than or equal to the last Sed Scr after sedative bolus or increase 3310. If this criterion is met, the intensivist is prompted to employ the procedures described above in 3328 and 3330.

If the sedation score is not greater than or equal to the last Sed Scr after sedative bolus or increase 3310, the intensivist is prompted to determine whether four (4) or more midaz boluses have been given since last q 4 hr assessment 3312. If this criterion is met, the intensivist is prompted to employ the procedures described above in 3328 and 3330.

Alternatively, if less than four (4) midaz boluses have been given since last q 4 hr assessment 3312, the intensivist is prompted to determine whether the patient is adequately sedated 3314. If this criterion is not met, the intensivist is prompted to employ the procedure described in 3328 and 3330.

If the intensivist determines that the patient is adequately sedated 3314, the intensivist is prompted to determine whether the sedation score is 0-2 3316. If this criterion is met, the intensivist is prompted to decrease lorazepam by 20 percent 3332 and reassess sedation in 4 hr 3334.

Alternatively, if the sedation score is not 0-2 3316, the intensivist is prompted to determine whether the sedation score is less than or equal to the last Sed Scr after sedative decrease 3318. If this criterion is met, the intensivist is prompted to employ the procedure described in 3332 and 3334.

If the sedation score is not less than or equal to the last Sec Scr after sedative increase 3318, the intensivist is prompted to determine whether the patient is clinically oversedated 3320. If the patient is clinically oversedated 3320, the intensivist is prompted to employ the procedure described in 3332 and 3334. If the patient is not clinically oversedated 3320, the intensivist is prompted to reassess sedation in 4 hr 3322.

Figure 38:
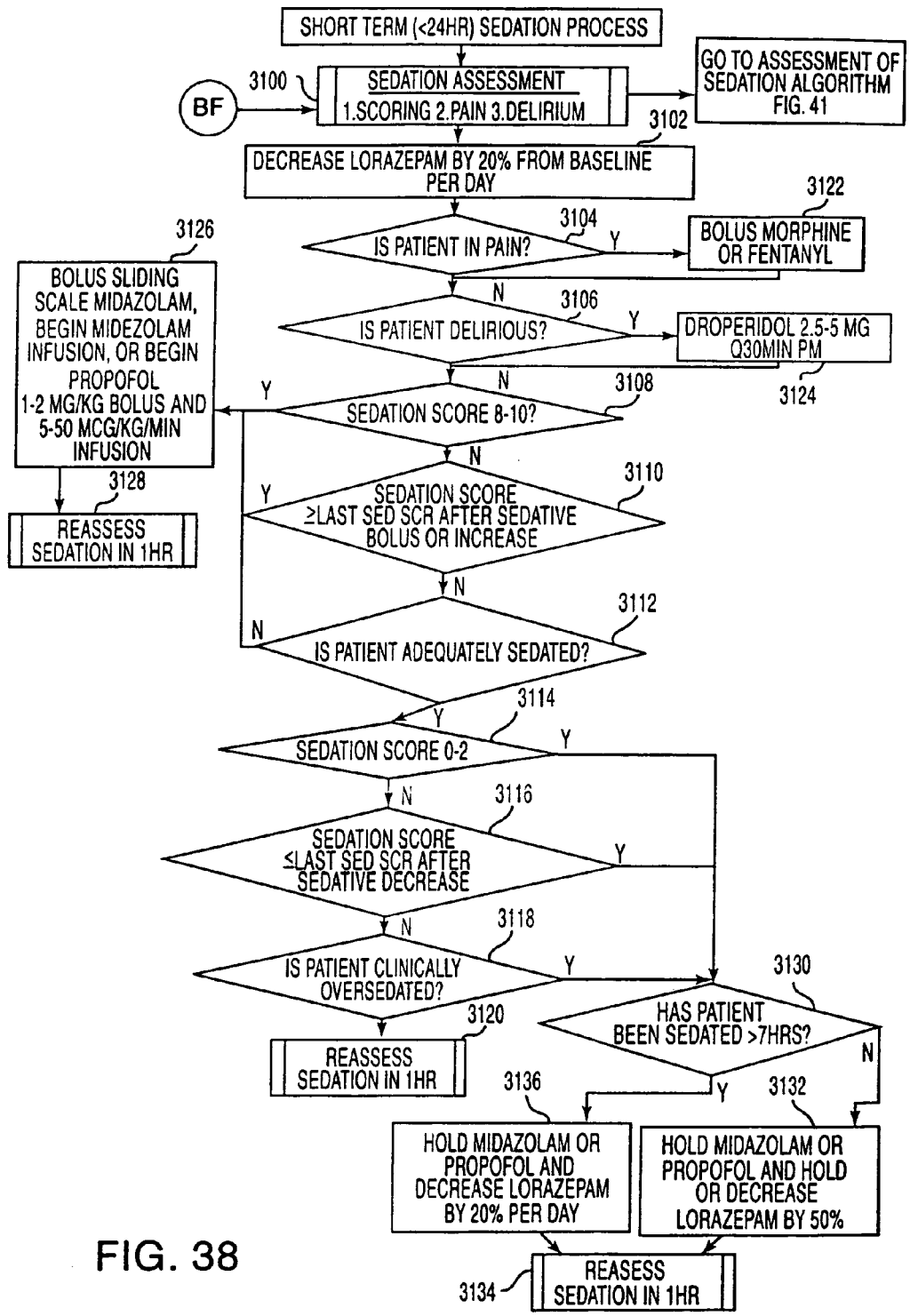
FIG. 38 illustrates the short term sedation process, decision support algorithm.

Referring to FIG. 38, the short term sedation process decision support algorithm of the present invention is illustrated. If an intensivist determines that a patient will not require sedation past the next 24 hour period, the intensivist may not be certain of all aspects that would be involved in this particular process. Therefore, the intensivist is lead through a decision support algorithm, which prompts the intensivist to conduct a sedation assessment based on: 1) scoring; 2) pain; and 3) delirium (see Assessment of Sedation algorithm) 3100.

Following completion of the sedation assessment process 3100, the intensivist is prompted to decrease lorazepam by 20 percent from baseline per day 3102. The intensivist is prompted next to determine whether the patient is in pain 3104. If this criterion is met, the intensivist is prompted to administer bolus morphine or fentanyl 3122. If the patient is not in pain or after administering bolus morphine or fentanyl 3122, the intensivist is prompted to determine whether the patient is delirious 3106.

If the intensivist determines that the patient is delirious, he is prompted to administer droperidol 2.5-5 mg q30 min prn 3124. If the patient is not delirious or after administering droperidol 3124, the intensivist is prompted to determine whether the sedation score is 8-10 3108.

If this criterion is met, the intensivist is prompted to employ the Bolus sliding scale midazolam (see Bolus sliding scale midazolam algorithm) and begin midazolam infusion or begin propofol 1-2 mg/kg bolus and 5-50 mcg/kg/min infusion 3126. Subsequently, the intensivist is prompted to reassess sedation in 1 hr 3128.

If the sedation score is not 8-10, the intensivist is prompted to determine whether the sedation score is greater than or equal to the last Sed Scr after sedative bolus or increase 3110. If this criterion is met, the intensivist is prompted to employ the procedures described above in 3126 and 3128.

If the intensivist determines that the sedation score is not greater than the last sedation score after sedative bolus or increase 3110, the intensivist is prompted to determine whether the patient is adequately sedated 3112. If this criterion is not met, the intensivist is prompted to employ the procedures described above in 3126 and 3128.

If the intensivist determines that the patient is adequately sedated 3112, he is prompted to determine whether the sedation score is 0-2 3114. If this criterion is met, the intensivist is prompted to determine if the patient has been sedated for more than 72 hours 3130. If the patient has not been sedated for more than 72 hours 3130, the intensivist is prompted to hold midazolam or propofol and hold or decrease lorazepam by 50 percent 3132. The intensivist is prompted subsequently to reassess sedation in 1 hour 3134.

Alternatively, if the intensivist determines that the patient has been sedated for more than 72 hours 3130, the intensivist is prompted to hold midazolam or propofol and decrease lorazepam by 20 percent per day 3136. The intensivist is prompted subsequently to reassess sedation in 1 hour 3134.

Alternatively, if the intensivist determines that the sedation score is not 0-2 3114, the intensivist is prompted to determine whether the sedation score is less than or equal to the last sedation screening after sedative decrease 3116. If this criterion is met, the intensivist is prompted to determine whether the patient has been sedated for more than 72 hours and to follow the procedures described above in 3130.

If the intensivist determines that the sedation score is not less than or equal to the last Sed Scr after sedative decrease 3116, the intensivist is prompted to determine whether the patient is clinically oversedated 3118. If this criterion is met, the intensivist is prompted to determine whether the patient has been sedated for more than 72 hours and to follow the procedures described above in 3130. If this criterion is not met, the intensivist is prompted to reassess sedation in 1 hr 3120.

Figure 39:
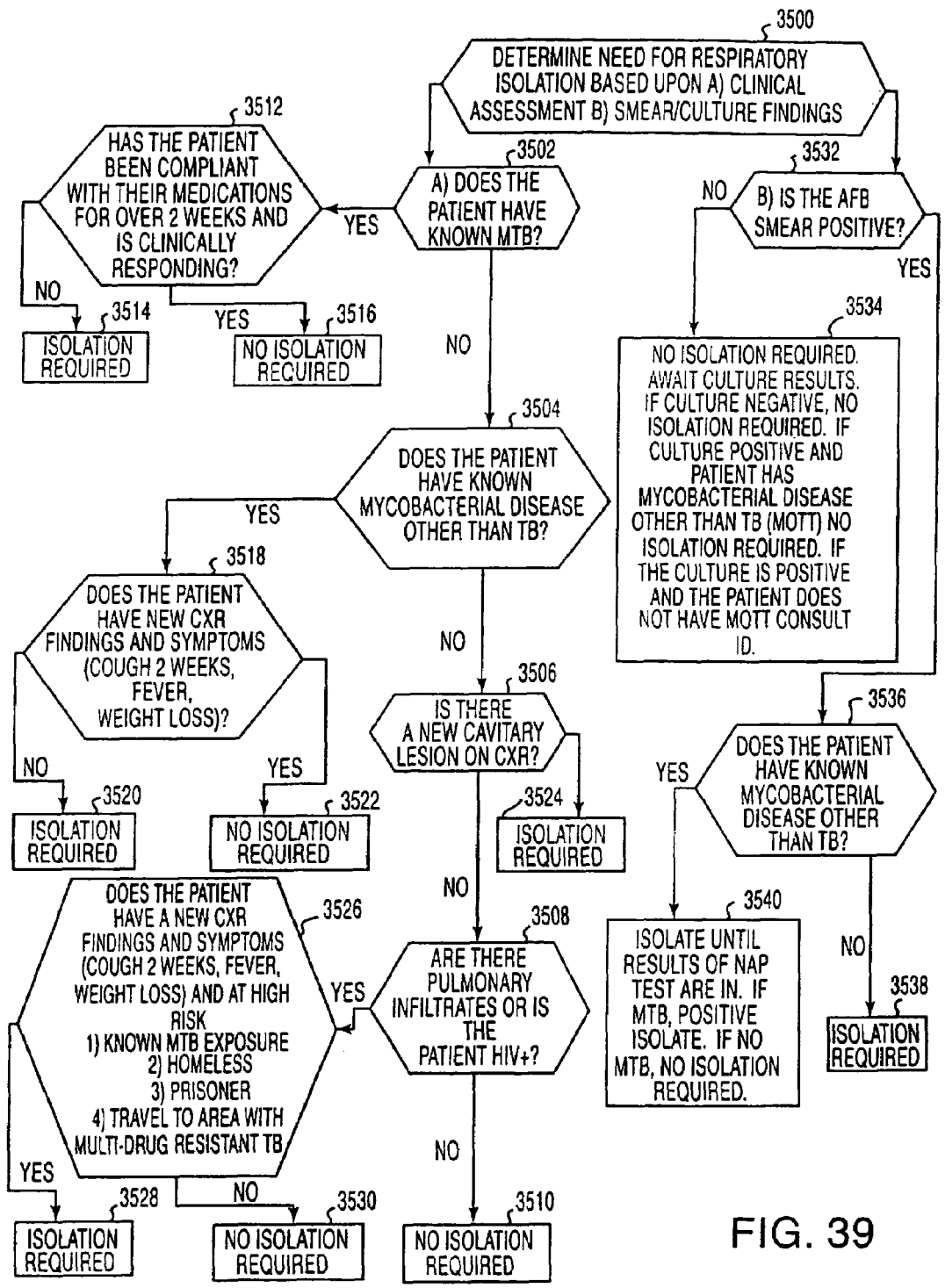
FIG. 39 illustrates the respiratory isolation decision support algorithm.

Referring to FIG. 39, the respiratory isolation decision support algorithm is illustrated. If an intensivist determines that there may be a need for respiratory isolation, the intensivist may not be certain of all aspects that would be involved in this process. Therefore, the intensivist is lead through a decision support algorithm which prompts the intensiviat to determine the need for respiratory isolation based upon: a) clinical assessment; and/or b) smear/culture findings 3500.

Pursuing the clinical assessment branch of the decision support algorithm, the intensivist is prompted to determine whether the patient has known mTB (*mycobacterium tuberculosis*) 3502. If this criterion is met, the intensivist is prompted to determine whether the patient has been compliant with their medications for over 2 weeks and is clinically responding 3512. If the patient has not been compliant with their medications for over 2 weeks and is not clinically responding 3512, the intensivist is prompted that isolation is required 3514. If the patient has been compliant with their medications and is clinically responding 3512, the intensivist is prompted that no isolation is required 3516.

Alternatively, if the patient does not have known mTB 3502, the intensivist is prompted to determine whether the patient has known mycobacterial disease other than TB 3504. If this criterion is met, the intensivist is prompted to determine whether the patient has new CXR (chest x ray) findings and symptoms (cough 2 weeks, fever, weight loss) 3518. If the patient does not have new CXR findings and symptoms 3518, the intensivist is prompted that no isolation is required 3520. If the patient does have new CXR findings and symptoms 3518, the intensivist is prompted that isolation is required 3522.

If the patient does not have known mycobacterial disease other than TB 3504, the intensivist is prompted to determine whether there is a new cavitary lesion on CXR 3506. If this criterion is met, the intensivist is prompted that isolation is required 3524.

Alternatively, if there is no new cavitary lesion on CXR 3506, the intensivist is prompted to determine whether there are pulmonary infiltrates or whether the patient is HIV (human immunodeficiency virus) positive 3508. If neither of these criteria is met, the intensivist is prompted that no isolation is required 3510. If either of these criteria is met, the intensivist is prompted to determine whether the patient has new CXR findings and symptoms (cough 2 weeks, fever, weight loss) and at high risk: 1) known mTB exposure; 2) homeless; 3) prisoner; 4) travel to area with multi-drug resistant TB 3526. If these criteria are met, the intensivist is prompted that isolation is required 3528. Alternatively, if these criteria are not met, the intensivist is prompted that no isolation is required 3530.

Pursuing the smear/culture branch of the decision support algorithm 3500, the intensivist is prompted to determine whether the AFB (acid-fast bacilli) smear is positive 3532. If the AFB smear is not positive, the intensivist is prompted that: no isolation is required; await culture results; if culture negative, no isolation required; if culture positive and patient has mycobacterial disease other than TB (MOTT no isolation is required; if the culture is positive and the patient does not have MOTT consult ID 3534.

Alternatively, if the AFB smear is positive, the intensivist is prompted to determine whether the patient has known mycobacterial disease other than TB 3536. If this criterion is not met, the intensivist is prompted that isolation is required 3538. If this criterion is met, the intensivist is prompted: to isolate until results of NAP test are in; if mTB positive isolate the patient; if no mTB, no isolation is required 3540.

Figure 40:
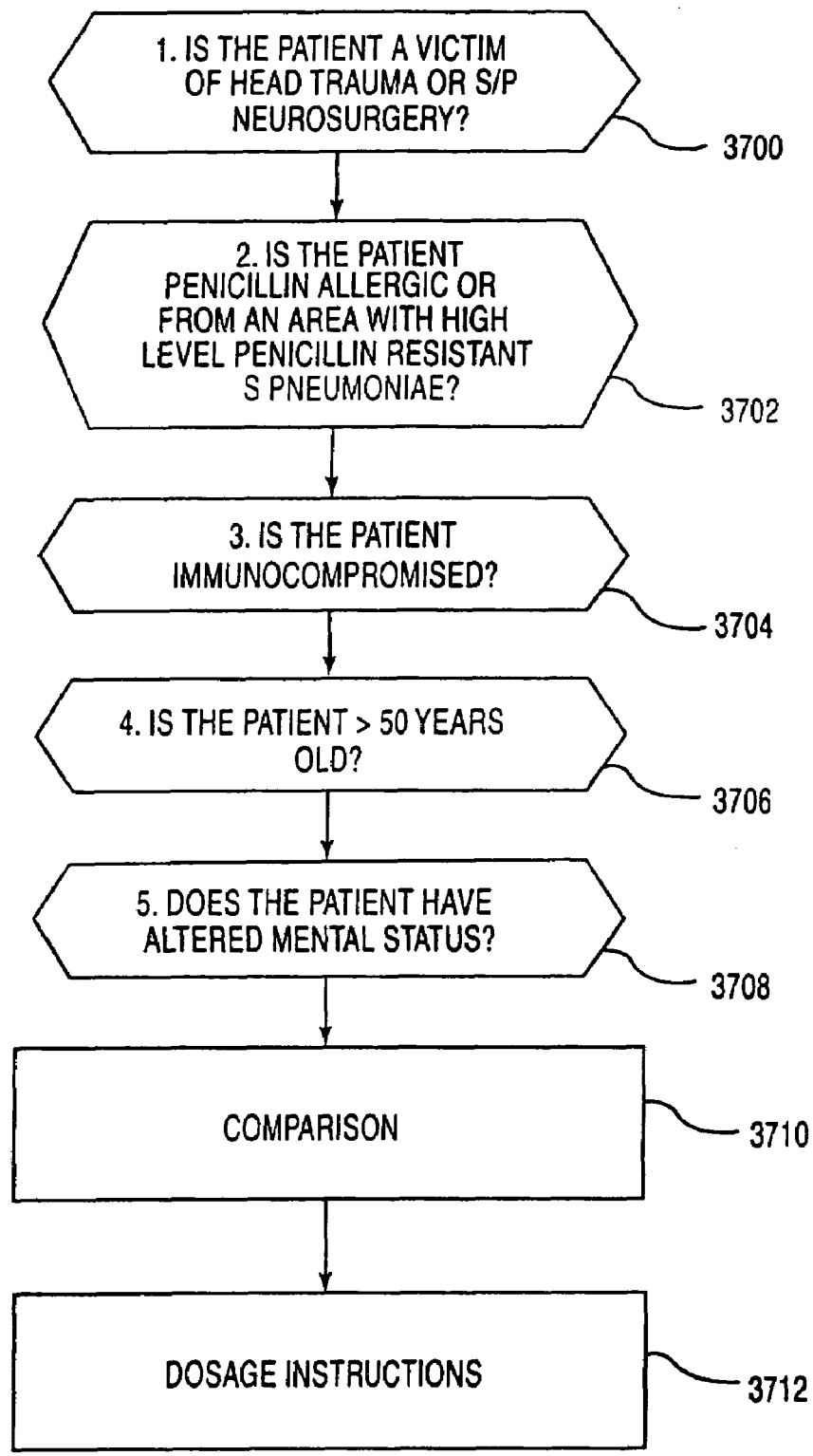
FIG. 40 illustrates the empiric meningitis treatment decision support algorithm.

Referring to FIG. 40, the empiric meningitis tratment decision support algorithm of the present invention is illustrated. If the intensivist is treating a patient for meningitis, the intensivist is prompted to answer a series of queries by the system to properly address medication and dosage. First, the intensivist is prompted to determine whether the patient has suffered a head trauma or undergone neurosurgery 3700. The answer to this question is input 1 to table x below. The intensivist is next prompted to determine whether the patient is allergic to penicillin or is from an area where penicillin resistant *staphylococcus* pneumoniae is prevalent 3702. The answer to this question becomes input 2 to table x below. The intensivist must also determine whether the patient is immunocompromised 3704, and the answer becomes input 3 to table x below. The intensivist determines if the patient is over fifty years of age 3706, with the answer being input 4 in table x below. Lastly, the intensivist is prompted to determine whether the patient has altered mental status 3708, and the answer becomes input 5 in table x below. The inputs to each of these prompts 3702, 3704, 3706, 3708 is compared to a dosage database according to the Table 5 below.

TABLE 5

Meningitis Input-Output Table

| Input | Combinations | Output |
|---|---|---|
| 1 | 1 = yes<br>2 = no | A) vancomycin<br>1.5-2 gm IV q 12 h +<br>ceftazedine 2 gm IV q 8 hr or<br>cefapime 2 gm IV q 8 hr |
| 2 | 1 = yes<br>2 = no | B) vancomycin<br>1.5-2 gm IV q 12 h +<br>aztreonam<br>0.5-2 gm IV q 6-8 hr |
| 3 | 1 = no<br>2 = no<br>3 = no<br>4 = yes | ampicillin 2 gm IV q 4 h +<br>ceftriaxone 2 gm IV q 12<br>cefotaxime 2 gm IV q 6 h |
| 4 | 1 = no<br>2 = no<br>3 = no<br>4 = no | ceftriaxone 2 gm IV q 12 hr<br>or cefotaxime 2 gm IV q 6 hr |
| 5 | 1 = no<br>2 = no<br>3 = yes | ampicillin 2 gm IV q 4 hr +<br>ceftazidime 2 gm IV q 8 hr<br>or cefipime 2 gm IV q 8 hr |
| 6 | 1 = no<br>2 = yes<br>3 = no<br>4 = yes | vancomycin 1.5-2 gm IV q 12 hr +<br>chloramphenicol 1 gm IV q 6 hr |
| 7 | 1 = no<br>2 = yes<br>3 = no<br>4 = no | |
| 8 | 1 = no<br>2 = yes<br>3 = yes | |
| 9 | 5 = yes to<br>inputs 3-8 | add to output<br>consider acyclovir<br>10 mg/kg IV q 8 h |

In the Meningitis Input-Output Table, possible combinations of the five inputs are listed. For the conditions manifested in the patient, different drugs and dosages will be required. The proper treatment for each combination is listed in the output column of Table 5. After the algorithm runs the comparison, the output is displayed on the computer screen, prompting the intensivist with the proper treatment 3712.

Figure 41A:
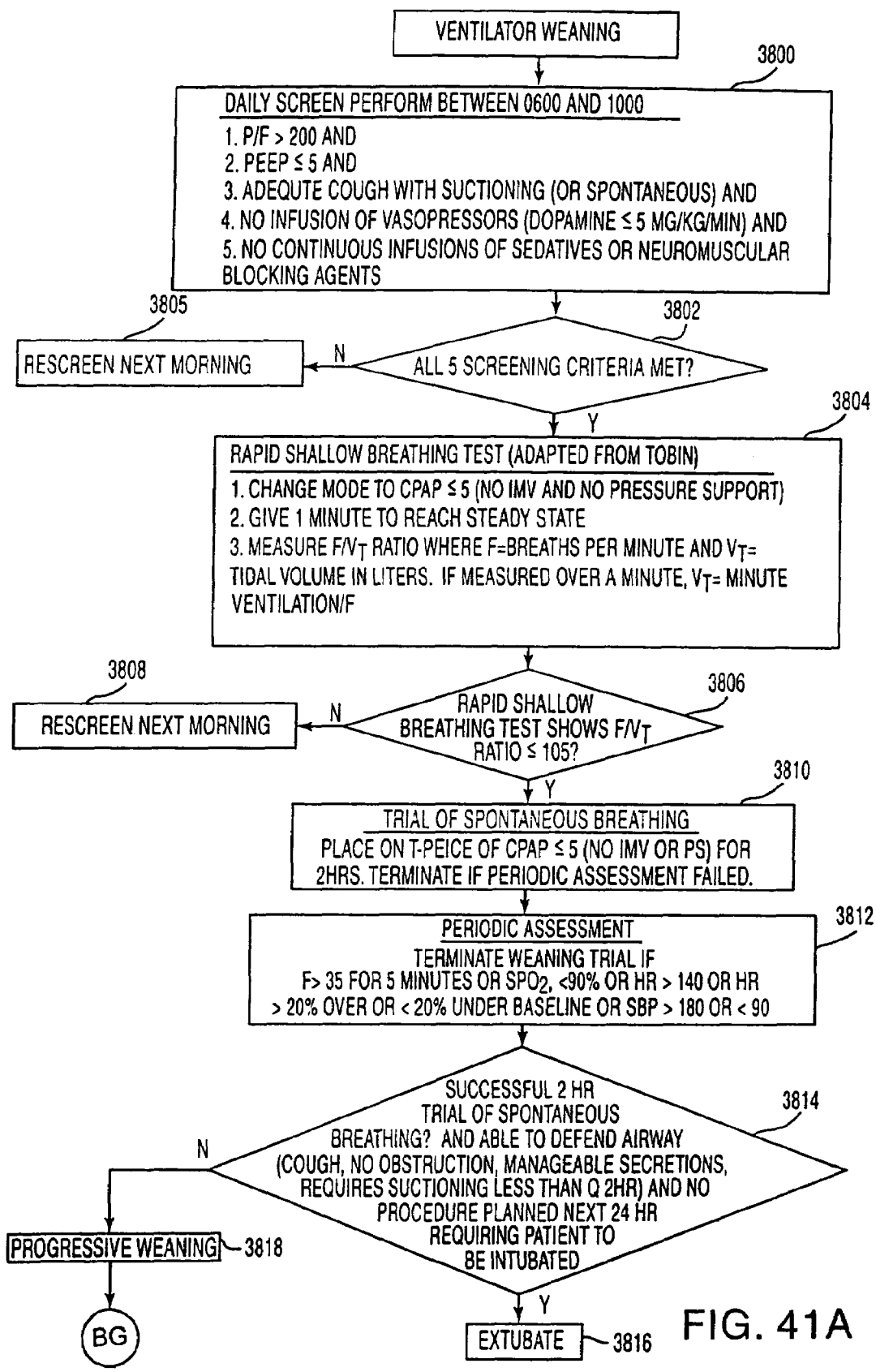
FIG. 41A illustrates the ventilator weaning decision support algorithm.

Referring to FIG. 41A, the ventilator weaning decision support algorithm of the present invention is illustrate The ventilator weaning decision support algorithm is used to determine whether an intensive care unit patient can return to breathing unassisted, and discontinue use of a ventilator. Such a determination weuires evaluation of the patient by the intensivist over the course of several days.

To begin the decision process of whether to wean a patient from ventilator use, the intensivist is prompted to conduct daily screening, preferably during the hours of 06:00 a.m. to 10:00 a.m. 3800. The daily screen prompts the intensivist to determine whether: the patients P/F ratio is greater than 200, the patient's positive end-expiratory pressure (PEEP) is less than or equal to 5, whether cough suctioning has been adequate and/or spontaneous, infusions with vasopressors have been necessary, and continuous infusions of sedatives or neuromuscular blocking agents have been necessary 3800. If all conditions 3802 are answered no, the intensivist is directed by the system to repeat the daily screen 3805 the following morning. If all the conditions of the daily screen are met 3802, the intensivist is prompted to perform additional tests.

If the patient has satisfied the daily screen, the intensivist is next directed to conduct a rapid shallow breathing test 3804. To perform the test, the intensivist is directed to change the ventilator setting to continuous positive airway pressure (CPAP) less than or equal to 5. In other words, there is no intermittent mandatory ventilation or pressure support provided for the patient. The patient is given one minute to reach a steady state of breathing. Then the intensivist measures the ratio of breaths per minute to tidal volume ($f/V_T$). The intensivist next is prompted to determine whether the patient's $f/V_T$ is less than or equal to 105 breathes per minute 3806. If the patient's $f/V_T$ is greater than 105 breathes per minute, the intensivist is prompted to return to performing daily screening the following morning 3808.

If the patient's $f/V_T$ is less than or equal to 105 breathes per minute, the intensivist is next directed to perform a trial of spontaneous breathing. Here, the intensivist can either insert a T-Piece in the patient's airway or reduce the patient's CPAP to less than or equal to 5 over the course of two hours. The intensivist is prompted to observe the patient periodically in order to evaluate if the patient is breathing without assistance 3810. The intensivist is prompted to perform a periodic assessment by determining whether: the patient's breathing characteristics are greater than 35 breaths per minute for 5 minutes, or $SpO_2$ is less than 90%, or the patient's Heart Rate (HR) is grater than 140, or HR deviates from the baseline breathing rate by more than 20%, or the patient's SBP is outside the range of 90 to 180. If any of the conditions are met, the intensivist is directed by the system to terminate ventilator weaning 3812. If the conditions are not met, the patient is further assessed.

In further assessment, the intensivist is prompted to determine whether the patient has been able to breathe spontaneously for two hours, keep a clear airway, and does not have any procedures scheduled within twenty-four hours that would require the patient to be intubated 3814. If the patient meets all of these criteria 3814, the intensivist is notified by the system that the patient may be extubated 3816. If the patient does not meet one or more of the criteria 3814, the intensivist is prompted to perform steps for progressive weaning 3818.

Figure 41B:
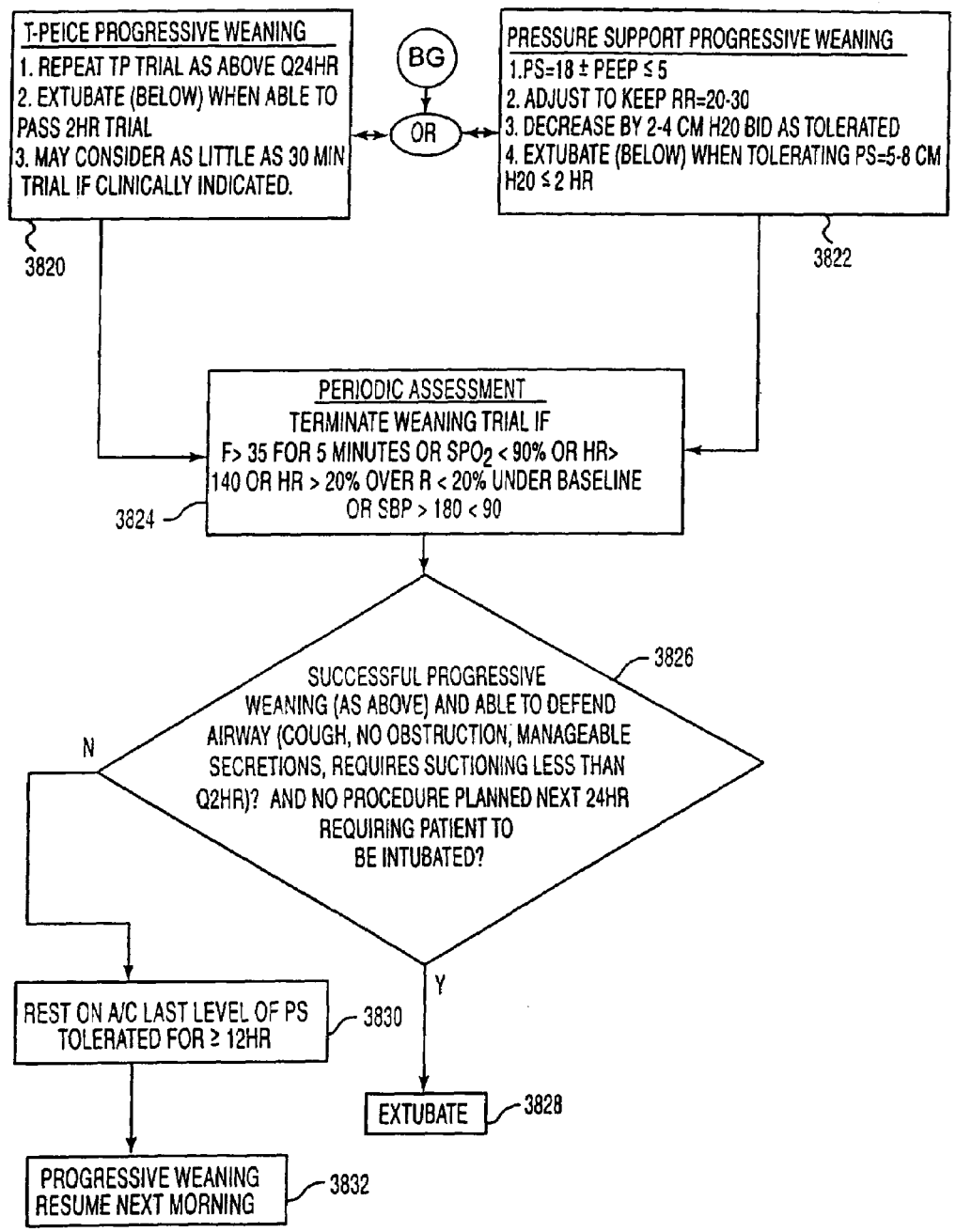
FIG. 41B illustrates the ventilator weaning decision support algorithm (cont).

Referring to FIG. 41B, the ventilator weaning decision support algorithm of the present invention is further illustrated. The intensivist, at his or her discretion may choose either T-piece progressive weaning or pressure support progressive weaning. In order to perform T-piece progressive weaning, the intensivist is directed to repeat the trial of spontaneous breathing (as previously described 3810). The intensivist can either insert a T-piece in the patient's airway or reduce the patient's CPAP to less than or equal to 5 over the course of two hours. The intensivist is prompted to perform periodic assessment of the patient by either a two hour or 30 minute trial 3820.

In order to perform pressure support progressive weaning, the intensivist is first prompted to observe whether the patient's pressure support (PS) rating is equal to eighteen plus or minus the positive end-expiratory pressure (PEEP). Next, the intensivist is directed by the system to regulate the pressure values in order to keep the patient's respiratory rate (RR) between twenty and thirty. Next, the intensivist is directed by the system to decrease the patient's pressure support by 2-4 centimeters of water two times per day. Once the patient maintains pressure support for at least two hours, the intensivist is prompted to further pursue extubating the patient 3822.

After either T-Piece progressive weaning 3820 or pressure support progressive weaning 3822, the intensivist is next prompted to perform a periodic assessment of the patient. Here, the intensivist must determine whether whether: the patient's breathing characteristics are greater than 35 breaths per minute for 5 minutes, or $SpO_2$ is less than 90%, or the patient's HR is grater than 140, or HR deviates from the baseline breathing rate by more than 20%; or the patient's SBP is outside the range of 90 to 180. Where the patient meets any of these criteria, the intensivist is prompted to terminate weaning. If the patient meets none of these criteria; the intensivist is prompted to further assess the patient's ability to breath spontaneously 3824.

In further assessment, the intensivist is prompted to determine whether the patient has been able to breathe spontaneously for two hours, keep a clear airway, and does not have any procedures scheduled within twenty-four hours that would require the patient to be intubated 3826. If the patient meets all of these criteria 3814, the intensivist is notified by the system that the patient may be extubated 3828. If the patient does not meet one or more of the criteria 3826, the intensivist is directed by the system to allow the patient to rest for at least twelve hours at A/C, the last level of pressure support the patient achieved 3830. The intensivist is prompted to resume progressive weaning the following day 3832.

Figure 42:
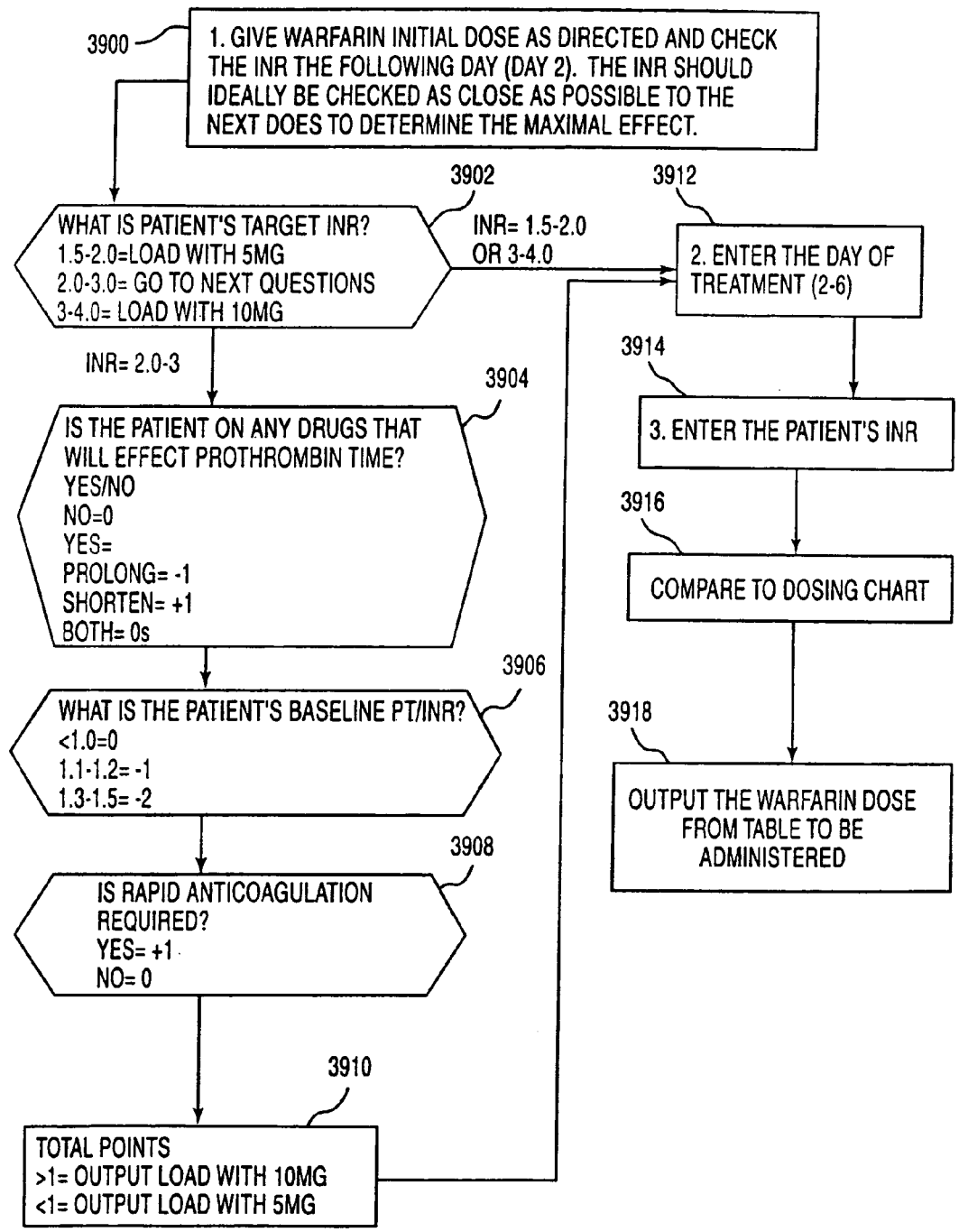
FIG. 42 illustrates the warfarin dosing decision support algorithm.

Referring to FIG. 42, the Warfarin Dosing Algorithm of the present invention is illustrated. The intensivist is first prompted to give the initial dose and determine subsequent dosage each day 3900. When the intensivist determines subsequent dosage, he is first prompted to determine the patient's target INR 3902. If the patient's target INR ranges from 2.0 to 3.0, the intensivist is prompted by the system to make further determinations relevant to dosage. The intensivist is directed by the system to determine whether the patient is taking drugs that effect prothrombin time 3904, the baseline INR value 3906, and whether rapid anticoagulation is required 3908. Each answer is assigned a point value, and the total points are tabulated. If the point value is greater than one, the system refers to the 10 milligram load target database for dosing. If the point value is less than one, the system refers to the 5 milligram load target database for dosing 3910.

At the initial INR determination 3902, if the patient's INR was initially between 1.5 and 2.0, the system refers to the 5 milligram load target database for dosing. If the patient's INR was initially between 3.0 and 4.0, the system refers to the 10 milligram load target database for dosing 3910. Next the intensivist is prompted to enter the day of treatment 3912 and the patient's INR 3914. Depending on whether the system has been directed to the 5 milligram load target or the 10 milligram load target, a comparison is run 3916 according to the following tables.

TABLE 6

5 mg Load Target INR 1.5-2.0

| Day | <1.5 | 1.5-2 | 2-2.5 | >2.5 |
|---|---|---|---|---|
| 2 | 5 | 1.25-2.5 | 0 | 0 |
| 3 | 5-7.5 | 1.25-2.5 | 0-1.25 | 0 |
| 4 | 10- (Check to see whether pt has received vit K) | 1.25-2.5 | 0-1.25 | 0 |
| 5 | 10 (Check to see whether pt Has received vit K) | 2.5-5 | 0-2.5 | 0-1.25 |
| 6 | 15 Obtain hematology consultation. | 2.5-5 | 1.25-2.5 | 0-1.25 |

TABLE 7

| Day | <1.5 | 1.5-2 | 2-2.5 | 2.5-3 | >3 |
|---|---|---|---|---|---|
| | 10 mg Load Target INR 3.0-4.0 | | | | |
| 2 | 10 | 7.5-10 | 5-7.5 | 2.5-5.0 | 0-2.5 |
| 3 | 10-15 | 7.5-10 | 5-7.5 | 2.5-5 | 2.5-5 |
| 4 | 10-15 (Check to see whether pt has received vit K) | 7.5-12.5 | 5-10 | 5-7.5 | 2.5-5 |
| 5 | 15 (Check to see whether pt has received vit K) | 10-12.5 | 7.5-10 | 5-7.5 | 2.5-5 |
| 6 | 15-20 obtain hematology consultation. | 10-15 | 7.5-12.5 | 5-10 | 5-7.5 |

The appropriate dosage and instructions is displayed on the computer screen to the intensivist 3918.

Figure 43:
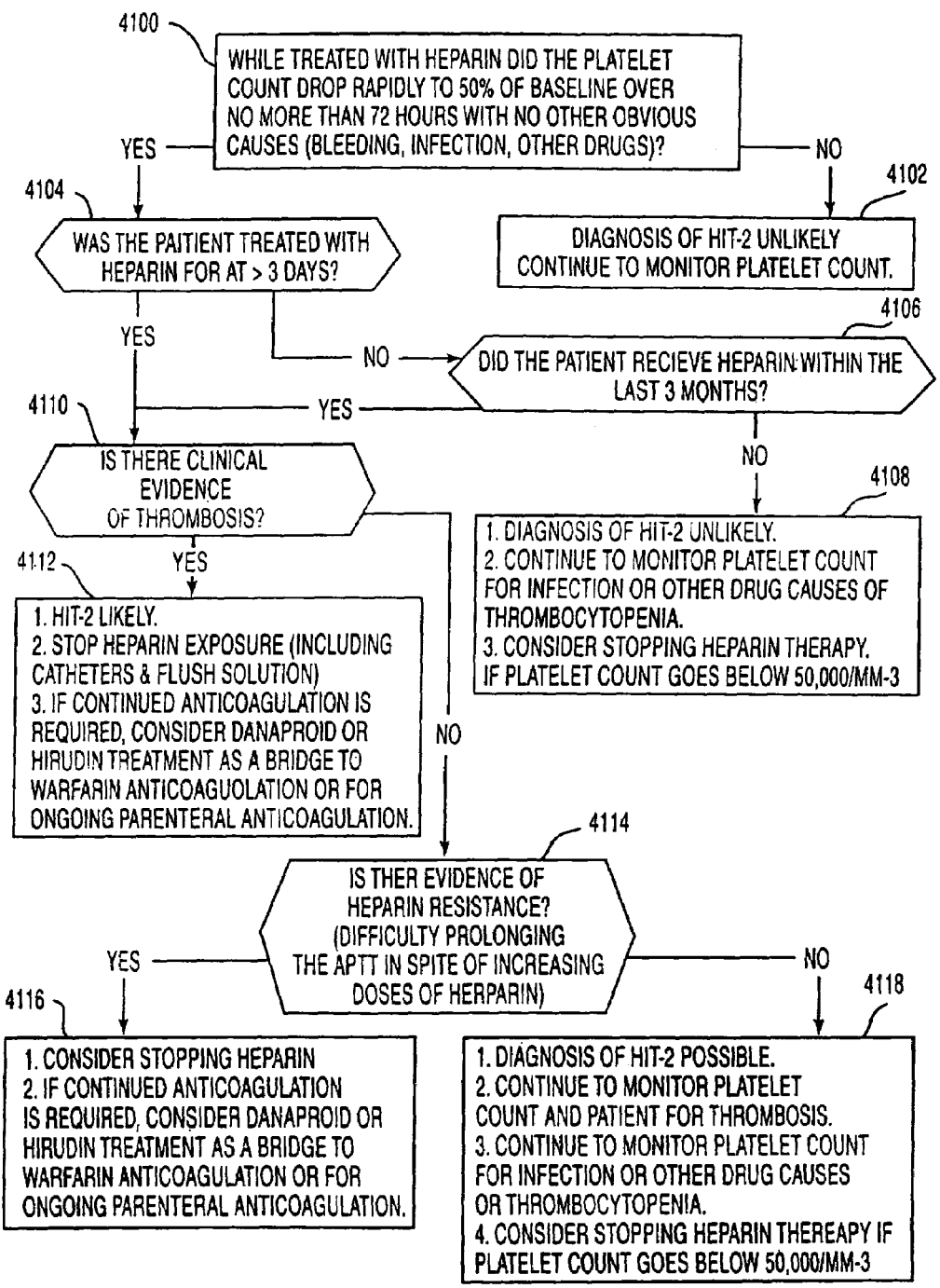
FIG. 43 illustrates the HIT-2 diagnostic decision support algorithm.

Referring to FIG. 43, the heparin-induced thrombocytopenia (HIT) decision support algorithm of the present invention is illustrated. The intensivist is prompted to observe whether the patient's platelet count has dropped 50% or more over seventy-two hours while being treated with heparin, and whether any other obvious causes of platelet reduction might be present 4100. If such a drop has not occurred, the intensivist is notified by the system that the patient most likely does not have HIT, but monitoring of the platelet count should continue 4102. If the patient's platelet count has drastically dropped, the intensivist is prompted to determine whether the patient has been treated with heparin for more than three days 4104. Regardless of the answer, the intensivist is next prompted to determine if the patient has been treated with heparin in the preceeding three months 4106. If the patient has not received heparin in the proceeding three months, the intensivist is notified by the system that HIT is not likely to be the cause of the platelet drop. The intensivist is also prompted to monitor platelet count for infection or other thronbocytopenia-causing drugs, and to consider stopping heparin therapy if the platelet count drops below 50,000 per cubic millimeter 4108.

If the patient has received heparin in the last three days 4104, the intensivist is further prompted to look for signs of thrombosis, or blood clotting 4110. If the patient shows signs of thrombosis, the intensivist is notified by the system that the patient is likely to have HIT. Accordingly, the intensivist is prompted to stop administering heparin and flush any drug administration equipment that would contain heparin traces. The intensivist is also provided instructions by the system to treat a patient still requiring anticoagulation treatment with alternate drugs and methods 4112.

Where the patient does not show signs of thrombosis 4110, the intensivist is prompted to check for heparin resistance 4114. Signs of heparin resistance include inability to hold aPTT though heparin doses have been increase. If the patient shows signs of heparin resistance, the intensivist is prompted to consider stopping heparin treatment and to consider treating a patient still requiring anticoagulation treatment with alternate drugs and methods 4116. If the patient does not show signs of heparin resistance, the intensivist is notified by the system that the patient possibly has HIT. The intensivist is accordingly prompted to continue monitoring for thrombosis, consider infection or other drugs that cause throbocytopenia, and to consider stopping heparin therapy if the platelet count drops below 50,000 per cubic millimeter 4118

RESULTS

The structure of the present invention and its efficacy have yielded striking results in practice. In a research setting, deployment of certain rudimentary aspects of the present invention designed to experimentally test the approach described and developed in detail above, yielded unprecedented improvements in clinical and economic outcomes: 50% improvement in severity adjusted mortality, 40% improvement in clinical complication rates, 30% improvement in ICU length of stay, and 30% improvement in overall ICU cost of care.

A system and method for displaying a health status of hospitalized patients has been shown. It will be apparent to those skilled in the art that other variations of the present invention are possible without departing from the scope of the invention as disclosed. For example, one can envision different ratios of command center/remote location to ICU's, other decision support algorithms that would be used by intensivists, other types of remote monitoring of not only hospitalized patients but other types of hospital functions as well as industrial functions where critical expertise is in limited supply but where that expertise must be applied to ongoing processes. In such cases a system such as that described can be employed to monitor processes and to provide standardized interventions across a number of geographically dispersed locations and operations. Further, any reference to claim elements in the singular, for example, using the articles "a," "an," or "the" is not to be construed as limiting the element to the singular.

We claim:

1. A system for displaying a health status of hospitalized patients comprising:
   a telecommunication network;
   monitoring stations comprising monitoring equipment, wherein the monitoring equipment comprises instructions for monitoring data elements from geographically dispersed hospitalized patients and for sending the monitored data elements to a remote command center via the telecommunications network, wherein the remote command center comprises instructions for:
      receiving the monitored data elements from the geographically dispersed hospitalized patients;
      accessing patient data elements indicative of a medical condition associated with each of the geographically dispersed hospitalized patients;
      selectively displaying the monitored data elements and the patient data elements of the hospitalized patients according to display rules using a display module;
      establishing patient-specific rules associated with each of the geographically dispersed hospitalized patients; and
      applying the patient-specific rules continuously and simultaneously using a rules engine comprising instructions for:
         selecting data elements from the monitored data elements and the patient data elements associated with a hospitalized patient;
         applying a patient-specific rule associated with the hospitalized patient to the selected data elements;
         determining in an automated fashion 24 hours per day 7 days per week at the remote command center whether the patient-specific rule for the hospitalized patient has been contravened; and
         in the event the patient-specific rule for the hospitalized patient has been contravened, issuing an alert from the remote command center.

2. The system of claim 1, wherein the monitoring equipment comprises physiological sensors and the monitored data elements comprise a physiological data element.

3. The system of claim 2, wherein the physiological data element is selected from the group consisting of heart rate, systolic pressure, diastolic pressure, pulmonary artery wedge pressure, central venous pressure, oxygen saturation, tidal volume, inspiratory pressure, positive end expiratory pressure, respiration rate, electroencephalography cardiac output.

4. The system of claim 1, wherein the patient data comprises a clinical data element.

5. The system of claim 4, wherein the clinical data element is selected from the group consisting of patient history, caregiver notes, laboratory reports, venous pressure, and urine output.

6. The system of claim 1, wherein the display rule comprises criteria indicative of the severity of the medical condition of the hospitalized patient.

7. The system of claim 6, wherein the criteria indicative of the severity of the medical condition of the hospitalized patient are selected from the group consisting of an acuity rating, a disease severity score, a diagnosis, a history of present illness (HPI) score; a review of systems (ROS) score; a past, family, and social history (PFSH) score; a physical exam score; and a mortality prediction model (MPM) score.

8. The system of claim 1, wherein the display rule comprises displaying selected patient data ranked by the severity of the medical condition associated with each of the hospitalized patients.

9. The system of claim 8, wherein the display rule further comprises displaying the selected patient data grouped by a location of the hospitalized patients.

10. The system of claim 8, wherein the display rule further comprises displaying the selected patient data grouped by a diagnosis of the hospitalized patients.

11. The system of claim 8, wherein the display rule further comprises displaying the selected patient data grouped by a demographic parameter.

12. The system of claim 1, wherein the patient data comprises a patient task schedule.

13. The system of claim 12, wherein a display rule comprises criteria indicative of a scheduled time for performing a task on the patient task schedule.

14. The system of claim 13, wherein the task is selected from the group consisting of intubating the hospitalized patient, extubating the hospitalized patient, medicating the hospitalized patient, performing a laboratory procedure on a hospitalized patient, performing a surgical procedure on a hospitalized patient, and performing a radiological procedure on a hospitalized patient.

15. The system of claim 1, wherein the display rule comprises displaying selected patient data ranked by time.

16. The system of claim 1, wherein the display module further comprises instructions for selecting and displaying monitored data and patient data relating to the patient specific rule associated with the hospitalized patient.

17. The system of claim 1, wherein the patient specific rule for the hospitalized patient comprises an algorithm.

18. The system of claim 1, wherein the one or more selected data elements comprise a physiological data element of the hospitalized patient and a medication data element of the hospitalized patient.

19. The system of claim 1, wherein the one or more selected data elements comprise a physiological data element of the hospitalized patient and a laboratory data element of the hospitalized patient.

20. The system of claim 1, wherein the one or more selected data elements comprise a clinical data element of the hospitalized patient and a laboratory data element of the hospitalized patient.

21. The system of claim 1, wherein the one or more selected data elements comprise a physiological data element of the hospitalized patient and another physiological data element of the hospitalized patient.

22. The system of claim 1, wherein the one or more selected data elements comprise data elements of the hospitalized patient selected from the group consisting of a physiological data element, a clinical data element of the hospitalized patient, a medication data element of the hospitalized patient, and a laboratory data element of the hospitalized patient.

23. The system of claim 1, wherein the one or more selected data element comprises a physiological data element and wherein the rules engine further comprises instructions for, if the patient-specific rule for the hospitalized patient has been contravened, assigning the physiological data element a graphical attribute.

24. The system of claim 23, wherein the graphical attribute is a selected display color of the physiological data element and wherein the selected display color is indicative of the degree to which the physiological data element falls outside an acceptable range.

25. The system of claim 23, wherein the graphical attribute is a display intensity and wherein the display intensity is indicative of the degree to which the physiological data element falls outside an acceptable range.

26. The system of claim 23, wherein the graphical attribute is blinking.

27. The system of claim 1, wherein the alert comprises a patient intervention order.

28. The system of claim 1, wherein the rules engine further comprises instructions for:
 determining whether the hospitalized patient requires monitoring by the monitoring station; and
 in the event the hospitalized patient does not require monitoring by the monitoring station, issuing a release order.

29. The system of claim 1, wherein the remote command center further comprises a patient support system further comprises instructions for:
 accessing a decision support algorithm;
 applying the decision support algorithm to selected data elements of a hospitalized patient;
 applying the decision support algorithm to user input; and
 providing patient care advice to the user.

30. The system of claim 29, wherein the decision support algorithm comprises a guideline selected from the list consisting of: Acalculous Cholecystitis, Acute Pancreatitis Algorithms, Acute Renal Failure-Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiogranis Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hyperglycemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complication, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Post-Op Management of Carotid, Post-Op Management of Open Heart, Post-Op Management of Thoracotomy, Post-Op Myocardial Ischemia (Non-Cardiac Arrhythmias after Cardiac Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrhythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding, Scale Midlazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoietic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarmn Dosing, and Wound Healing Strategies.

31. The system of claim 29, wherein the patient care advice is a diagnosis.

32. The system of claim 29, wherein the patient care advice is a method of treatment.

33. The system of claim 29, wherein the patient care advice is an order for a laboratory protocol.

34. The system of claim 29, wherein the patient support system further comprises instructions for:
   accessing an order writing module; and
   issuing an order.

35. The system of claim 34, wherein the order comprises authorization to administer medication to the hospitalized patient.

36. The system of claim 34, wherein the order comprises authorization to subject the hospitalized patient to a laboratory protocol.

37. The system of claim 34, wherein the order comprises authorization to subject the hospitalized patient to a surgical procedure.

38. The system of claim 1, wherein the telecommunications network is selected from the group consisting of a wired network, a wireless network, a cable network, a fiber optic network, and the Internet.

39. The system of claim 1, wherein the remote command center further comprises:
   an external network interface, wherein the external network interface comprises instructions for connecting to an external network; and
   instructions for providing a health care provider access to the remote command center via the external network.

40. The system of claim 39, wherein the external network is selected from the group consisting of a wired network, a wireless network, a cable network, a fiber optic network, and the Internet.

41. The system of claim 39, wherein the health care provider is selected from the group consisting of a physician, a nurse, a clinician, a diagnostician, and a intensivist.

42. The system of claim 39, wherein the remote command center further comprises instructions for sending the health care provider the alert if the patient-specific rule for the hospitalized patient has been contravened.

43. A method for displaying a health status of hospitalized patients comprising:
   receiving at a remote command center monitored data elements from geographically dispersed hospitalized patients via a telecommunications network;
   accessing patient data elements indicative of a medical condition associated with each of the geographically dispersed hospitalized patients;
   selectively displaying the monitored data elements and the patient data elements according to display rules; establishing patient-specific rules associated with each of the geographically dispersed hospitalized patients;
   selecting data elements from the monitored data elements and the patient data elements associated with a hospitalized patient;
   applying a patient-specific rule associated with the hospitalized patient to the selected data elements;
   making a determination in an automated fashion 24 hours per day 7 days per week at the remote command center whether the patient-specific rule for the hospitalized patient has been contravened; and
   in the event the patient-specific rule for the hospitalized patient has been contravened, issuing an alert from the remote command center.

44. The method for displaying a health status of hospitalized patients of claim 43, wherein the monitored data elements comprise a physiological data element generated by a patient monitoring device.

45. The method for displaying a health status of hospitalized patients of claim 44, wherein the physiological data element is selected from the group consisting of heart rate, systolic pressure, diastolic pressure, pulmonary artery wedge pressure, central venous pressure, oxygen saturation, tidal volume, inspiratory pressure, positive end expiratory pressure, respiration rate, electroencephalography and cardiac output.

46. The method for displaying a health status of hospitalized patients of claim 43, wherein the patient data comprises a clinical data element.

47. The method for displaying a health status of hospitalized patients of claim 46, wherein the clinical data element is selected from the group consisting of a patient history, caregiver notes, laboratory reports, venous pressure, and urine output.

48. The method for displaying a health status of hospitalized patients of claim 43, wherein the display rule comprises criteria indicative of the severity of the medical condition of the hospitalized patient.

49. The method for displaying a health status of hospitalized patients of claim 48, wherein displaying the selected patient data comprises displaying the selected patient data ranked by the severity of the medical condition associated with each of the hospitalized patients.

50. The method for displaying a health status of hospitalized patients of claim 49, wherein displaying the selected patient data further comprises displaying the selected patient data grouped by a location of the hospitalized patients.

51. The method for displaying a health status of hospitalized patients of claim 49, wherein displaying the selected patient data further comprises displaying the selected patient data grouped by a diagnosis of the hospitalized patients.

52. The method for displaying a health status of hospitalized patients of claim 49, wherein the displaying the selected patient data rule further comprises displaying the selected patient data grouped by a demographic parameter.

53. The method for displaying a health status of hospitalized patients of claim 48, wherein the criteria indicative of the severity of the medical condition of the hospitalized patient is selected from the group consisting of an acuity rating, a disease severity score, a diagnosis, a history of present illness (HPI) score; a review of systems (ROS) score; a past, family, and social history (PFSH) score; a physical exam score; and a mortality prediction model (MPM) score.

54. The method for displaying a health status of hospitalized patients of claim 43, wherein patient data comprises a patient task schedule.

55. The method for displaying a health status of hospitalized patients of claim 54, wherein the display rule comprises criteria indicative of a scheduled time for performing a task on the patient task schedule.

56. The method for displaying a health status of hospitalized patients of claim 55, wherein the task is selected from the group consisting of intubating the hospitalized patient, extubating the hospitalized patient, medicating the hospitalized patient, performing a laboratory procedure on a hospitalized patient, performing a surgical procedure on a hospitalized patient, and performing a radiological procedure on a hospitalized patient.

57. The method for displaying a health status of hospitalized patients of claim 43, wherein displaying the selected patient data further comprises displaying the selected patient data ranked by time.

58. The method for displaying a health status of hospitalized patients of claim 43, wherein the display rule comprises criteria indicative of the issuance of a smart alert and wherein the method further comprises selecting and displaying patient data relating to the patient specific rule associated with the hospitalized patient.

59. The method for displaying a health status of hospitalized patients of claim 43, wherein the patient specific rule for the hospitalized patient comprises an algorithm.

60. The method for displaying a health status of hospitalized patients of claim 43, wherein the one or more selected data elements comprise a physiological data element of the hospitalized patient and a medication data element of the hospitalized patient.

61. The method for displaying a health status of hospitalized patients of claim 43, wherein the one or more selected data elements comprise a physiological data element of the hospitalized patient and a laboratory data element of the hospitalized patient.

62. The method for displaying a health status of hospitalized patients of claim 43, wherein the one or more selected data elements comprise a clinical data element of the hospitalized patient and a laboratory data element of the hospitalized patient.

63. The method for displaying a health status of hospitalized patients of claim 43, wherein the one or more selected data elements comprise a physiological data element of the hospitalized patient and another physiological data element of the hospitalized patient.

64. The method for displaying a health status of hospitalized patients of claim 43, wherein the one or more selected data elements comprise data elements of the hospitalized patient selected from the group consisting of a physiological data element, a clinical data element of the hospitalized patient, a medication data element of the hospitalized patient, and a laboratory data element of the hospitalized patient.

65. The method for displaying a health status of hospitalized patients of claim 43, wherein the one or more selected data element is a physiological data element and wherein the method further comprises, if the patient-specific rule for the hospitalized patient has been contravened, assigning the physiological data element a graphical attribute.

66. The method for displaying a health status of hospitalized patients of 65, wherein the graphical attribute is a display color of the physiological data element and wherein the display color is indicative of the degree to which the physiological data element falls outside an acceptable range.

67. The method for displaying a health status of hospitalized patients of claim 65, wherein the graphical attribute is a display intensity and wherein the display intensity is indicative of the degree to which the physiological data element falls outside an acceptable range.

68. The method for displaying a health status of hospitalized patients of claim 65, wherein the graphical attribute is blinking.

69. The method for displaying a health status of hospitalized patients of claim 43, wherein issuing an alert comprises issuing a patient intervention order.

70. The method for displaying a health status of hospitalized patients of claim 43 further comprising:
  making a determination whether the hospitalized patient requires monitoring; and
  in the event the hospitalized patient does not require monitoring, issuing a release order.

71. The method for displaying a health status of hospitalized patients of claim 43 further comprising:
  accessing a decision support algorithm;
  applying the decision support algorithm to selected data elements of a hospitalized patient;
  applying the decision support algorithm to user input; and
  providing patient care advice to the user.

72. The method for displaying a health status of hospitalized patients of claim 71, wherein the decision support algorithm comprises a guideline selected from the list consisting of:
  Acalculous Cholecystitis, Acute Pancreatitis Algorithms, Acute Renal Failure-Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hyperglycemia Insulin Treatment, Hyperkalemia: Etiology & Treatment, Hypernatremia: Etiology & Treatment, Hypertensive Crisis, Hypokalenmia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complication, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Post-Op Management of Carotid, Post-Op Management of Open Heart, Post-Op Management of Thoracotomy, Post-Op Myocardial Ischemia (Non-Cardiac Arrhythmias after Cardiac Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrhythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding, Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopojetic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

73. The method for displaying a health status of hospitalized patients of claim 71, wherein providing patient care advice to the user comprises providing the user a diagnosis.

74. The method for displaying a health status of hospitalized patients of claim 71, wherein providing patient care advice to the user comprises providing the user a method of treatment.

75. The method for displaying a health status of hospitalized patients of claim 71, wherein providing patient care advice to the user comprises providing the user an order for a laboratory protocol.

76. The method for displaying a health status of hospitalized patients of claim 43 further comprising:
accessing an order writing module; and
issuing an order.

77. The method for displaying a health status of hospitalized patients of claim 76, wherein issuing an order comprises issuing an authorization to administer medication to the hospitalized patient.

78. The method for displaying a health status of hospitalized patients of claim 76, wherein issuing an order comprises issuing an authorization to subject the hospitalized patient to a laboratory protocol.

79. The method for displaying a health status of hospitalized patients of claim 76, wherein issuing an order comprises issuing an authorization to subject the hospitalized patient to a surgical procedure.

80. The method for displaying a health status of hospitalized patients of claim 43, wherein the telecommunications network is selected from the group consisting of a wired network, a wireless network, a cable network, a fiber optic network, and the Internet.

81. The method for providing services to geographically dispersed hospitalized patients from a remote command center of claim 43 further comprising:
interfacing with an external network; and
providing a health care provider access to the remote command center via the external network.

82. The method for providing services to geographically dispersed hospitalized patients from a remote command center of claim 81, wherein the external network is selected from the group consisting of a wired network, a wireless network, a cable network, a fiber optic network, and the Internet.

83. The method for providing services to geographically dispersed hospitalized patients from a remote command center of claim 81, wherein the health care provider is selected from the group consisting of a physician, a nurse, a clinician, a diagnostician, and a intensivist.

84. The method for providing services to geographically dispersed hospitalized patients from a remote command center of claim 81 further comprising sending the health care provider the alert if the patient-specific rule for the hospitalized patient has been contravened.

* * * * *